United States Patent
Shoji et al.

(10) Patent No.: US 9,862,676 B2
(45) Date of Patent: Jan. 9, 2018

(54) HYDROXAMIC ACID DERIVATIVE OR SALT THEREOF

(71) Applicant: TOYAMA CHEMICAL CO., LTD., Shinjuku-ku (JP)

(72) Inventors: Muneo Shoji, Toyama (JP); Naomi Sugaya, Toyama (JP); Naoko Yasobu, Toyama (JP)

(73) Assignee: TOYAMA CHEMICAL CO., LTD., Shinjuku-ku (JP)

( * ) Notice: Subject to any disclaimer, the term of this patent is extended or adjusted under 35 U.S.C. 154(b) by 0 days.

(21) Appl. No.: 14/777,156

(22) PCT Filed: Mar. 14, 2014

(86) PCT No.: PCT/JP2014/056864
§ 371 (c)(1),
(2) Date: Sep. 15, 2015

(87) PCT Pub. No.: WO2014/142298
PCT Pub. Date: Sep. 18, 2014

(65) Prior Publication Data
US 2016/0039751 A1    Feb. 11, 2016

(30) Foreign Application Priority Data
Mar. 15, 2013  (JP) .................. 2013-052798

(51) Int. Cl.
C07C 259/06 (2006.01)
C07D 309/12 (2006.01)
C07D 305/08 (2006.01)

(52) U.S. Cl.
CPC .......... C07C 259/06 (2013.01); C07D 305/08 (2013.01); C07D 309/12 (2013.01)

(58) Field of Classification Search
CPC .... C07C 259/06; C07D 309/12; C07D 305/08
See application file for complete search history.

(56) References Cited

U.S. PATENT DOCUMENTS 9,073,821 B2 * 7/2015 Takashima ............ C07C 259/06
2013/0072677 A1   3/2013 Takashima et al.

FOREIGN PATENT DOCUMENTS

| CN | 1777577 A | 5/2006 |
|----|-----------|--------|
| EP | 2 562 155 A1 | 2/2013 |
| WO | 2004/062601 A2 | 7/2004 |
| WO | 2007/069020 A2 | 6/2007 |
| WO | 2008/154642 A2 | 12/2008 |
| WO | 2010/017060 A1 | 2/2010 |
| WO | 2010/031750 A1 | 3/2010 |
| WO | 2010/032147 A2 | 3/2010 |
| WO | 2011/132712 A1 | 10/2011 |
| WO | WO 2012/031298 A2 | 3/2012 |
| WO | 2013/170165 A1 | 11/2013 |
| WO | WO 2015/056798 A1 | 4/2015 |
| WO | WO 2015/056800 A1 | 4/2015 |

OTHER PUBLICATIONS

Patani, G.A., "Bioisosterism: a rational approach in drug design." Chemical reviews 96.8 (1996): 3147-3176.*
David M. Livermore, "Multiple Mechanisms of Antimicrobial Resistance in *Pseudomonas aeruginosa*: Our Worst Nightmare?" Antimicrobial Resistance, vol. 34, pp. 634-640, (Mar. 1, 2002).
J. Van Eldere, "Multicentre surveillance of *Pseudomonas aeruginosa* susceptibility patterns in nosocomial infections", Journal of Antimicrobial Chemotherapy, vol. 51, pp. 347-352, (Jan. 14, 2013).
Hiroshige Mikamo, et al., "Surveillance on *Pseudomonas aeruginosa* Isolated in Gifu Prefecture (2004)" The Japanese of Antibiotics, vol. 59, No. 5, pp. 355-363, (2006) (with partial English translation).
Katherine Young, et al., "The *envA* Permeability/Cell Division Gene of *Escherichia coli* Encodes the Second Enzyme of Lipid A Biosynthesis", The Journal of Biological Chemistry, vol. 270, No. 51, pp. 30384-30391, (1995).
Bernard Beall, et al., "Sequence Analysis, Transcriptional Organization, and Insertional Mutagenesis of the *envA* Gene of *Escherichia coli*", Journal of Bacteriology, vol. 169, No. 12, pp. 5408-5415, (Dec. 1987).
International Search Report Issued May 20, 2014 in PCT/JP14/056864 Filed Mar. 14, 2014.
Chinese Search Report issued Jul. 27, 2016 in Patent Application No. 201480015562.1.

(Continued)

*Primary Examiner* — Samantha Shterengarts
*Assistant Examiner* — Matt Mauro
(74) *Attorney, Agent, or Firm* — Oblon, McClelland, Maier & Neustadt, L.L.P.

(57) ABSTRACT

A compound represented by general formula (1) (wherein $R^1$ represents a hydrogen atom, an optionally substituted $C_{1-6}$ alkyl group or the like; $R^2$ represents a hydrogen atom, an optionally substituted $C_{1-6}$ alkyl group or the like; $R^3$ represents a hydrogen atom or an optionally substituted $C_{1-6}$ alkyl group; $R^4$ represents a hydrogen atom, an optionally substituted $C_{1-6}$ alkyl group or the like; $X^1$ represents an optionally substituted $C_{2-6}$ alkynylene group or the like; A represents an optionally substituted bivalent aromatic hydrocarbon group or the like; $X^2$ represents an optionally substituted $C_{1-6}$ alkylene group or the like; $Y^1$ represents an oxygen atom or the like; and $R^5$ represents a hydrogen atom or the like) or a salt thereof is useful as an antibacterial agent.

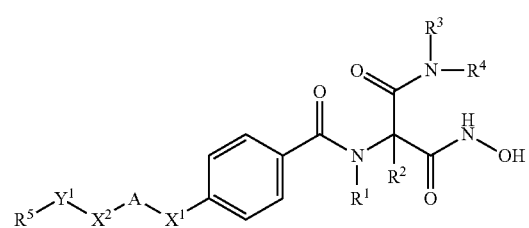

20 Claims, No Drawings

(56) References Cited

OTHER PUBLICATIONS

Extended European Search Report issued Sep. 14, 2016 in Patent Application No. 14763168.3.

* cited by examiner

HYDROXAMIC ACID DERIVATIVE OR SALT THEREOF

TECHNICAL FIELD

The present invention relates to a novel hydroxamic acid derivative or a salt thereof having inhibitory activity against uridyldiphospho (UDP)-3-O-acyl-N-acetylglucosamine deacetylase (LpxC), and an antibacterial agent comprising the same.

BACKGROUND ART

Gram-negative bacteria have an outer membrane composed of a lipid bilayer, which is not found in Gram-positive bacteria, and therefore tend to have stronger drug resistance than that of Gram-positive bacteria, in relation to problems associated with drug permeability. In addition, the Gram-negative bacteria are known to have a plurality of drug efflux proteins, which are also known to be involved in the drug resistance (Non Patent Document 1). Lipopolysaccharide (LPS), a main constituent of the outer membrane, is further largely involved as an endotoxin in toxicity.

Among the Gram-negative bacteria, particularly, *Pseudomonas aeruginosa* is known to have a strong tendency to exhibit intrinsic resistance to various antibacterial drugs. *Pseudomonas aeruginosa* resides widely in a natural environment or a living environment, but is an attenuated bacterium that usually exhibits no pathogenicity to healthy people. This bacterium, however, is a pathogen that causes serious acute infectious diseases such as sepsis for patients having a serious underlying disease, patients, so-called compromised hosts, who use an immunosuppressant as a result of transplantation or the like, and patients under medical practice such as medical catheterization, tracheal cannulation, or surgical operation. *Pseudomonas aeruginosa* is therefore a causative bacterium important for opportunistic infectious diseases or nosocomial infectious diseases. In recent years, *Pseudomonas aeruginosa* that has acquired resistance to carbapenem drugs, quinolone drugs, or aminoglycoside drugs, etc., originally expected to be effective for *Pseudomonas aeruginosa* has often been clinically isolated in medical settings (Non Patent Document 2). In addition, multidrug-resistant *Pseudomonas aeruginosa* that has acquired resistance to all of these drugs of three lineages has also been isolated (Non Patent Document 3). Since there are few therapeutic agents useful for infection by multidrug-resistant *Pseudomonas aeruginosa*, refractory infectious diseases caused thereby are major global issues. Thus, the development of a drug having a novel mechanism of action has been strongly demanded.

UDP-3-O-acyl-N-acetylglucosamine deacetylase (LpxC) is an enzyme responsible for the synthesis of lipid A (hydrophobic anchor for LPS, a constituent of the outer membrane). Lipid A biosynthesis consists of reactions of 10 stages. LpxC catalysts the second stage of the biosynthesis reactions and dissociates the acetyl group of UDP-3-O-acyl-N-acetylglucosamine (Non Patent Document 4). The lipid A is a component essential for outer membrane formation and is eventually essential for the survival of Gram-negative bacteria (Non Patent Document 5). LpxC is a rate-limiting enzyme important for the process of lipid A biosynthesis and is an enzyme essential for the lipid A biosynthesis. Thus, a drug inhibiting the activity of LpxC is strongly expected to serve as an effective antibacterial agent for Gram-negative bacteria including *Pseudomonas aeruginosa*, particularly, drug-resistant *Pseudomonas aeruginosa* because of its mechanism of action different from that of conventional drugs.

Compounds having LpxC inhibitory activity have heretofore been known (Patent Documents 1 to 7).

However, the novel hydroxamic acid derivative or a salt thereof of the present invention having LpxC inhibitory activity, and an antibacterial agent comprising the same have not been known so far.

PRIOR ART DOCUMENTS

Patent Documents

Patent Document 1: International Publication No. WO 04/062601 pamphlet
Patent Document 2: International Publication No. WO 07/069020 pamphlet
Patent Document 3: International Publication No. WO 08/154642 pamphlet
Patent Document 4: International Publication No. WO 10/031750 pamphlet
Patent Document 5: International Publication No. WO 10/017060 pamphlet
Patent Document 6: International Publication No. WO 10/032147 pamphlet
Patent Document 7: International Publication No. WO 11/132712 pamphlet

Non Patent Documents

Non Patent Document 1: Antimicrobial Resistance (2002) Mar. 1, 34, p. 634-640.
Non Patent Document 2: J. Antimicrob. Chemother. (2003) Jan. 14, 51, p. 347-352.
Non Patent Document 3: Jpn. J. Antibiotics (2006), 59 (5), p. 355-363.
Non Patent Document 4: J. Biol. Chem. (1995) Dec. 22, 270, p. 30384-30391.
Non Patent Document 5: J. Bacteriol. (1987), 169, p. 5408-5415

SUMMARY OF INVENTION

Problem to be Solved by the Invention

An object of the present invention is to provide a novel compound that exhibits strong antibacterial activity against Gram-negative bacteria including *Pseudomonas aeruginosa* and drug-resistant bacteria thereof by inhibiting LpxC, and is pharmaceutically useful.

Means for Solving the Problem

Under these circumstances, the present inventors have conducted diligent studies and consequently completed the present invention by finding that a compound represented by general formula [1]:

[Formula 1]

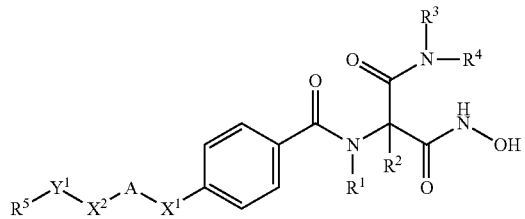

wherein
R¹ represents a hydrogen atom, an optionally substituted $C_{1-6}$ alkyl group, an optionally substituted $C_{3-8}$ cycloalkyl group or an optionally substituted $C_{1-6}$ alkoxy group;
R² represents a hydrogen atom, an optionally substituted $C_{1-6}$ alkyl group, an optionally substituted $C_{3-8}$ cycloalkyl group or an optionally substituted $C_{1-6}$ alkoxy group;
R³ represents a hydrogen atom or an optionally substituted $C_{1-6}$ alkyl group;
R⁴ represents a hydrogen atom, an optionally substituted $C_{1-6}$ alkyl group, an optionally substituted $C_{3-8}$ cycloalkyl group, an optionally substituted $C_{1-6}$ alkoxy group, an optionally substituted aromatic hydrocarbon group or an optionally substituted heterocyclic group;
X¹ represents an optionally substituted $C_{1-6}$ alkylene group, an optionally substituted $C_{2-6}$ alkenylene group or an optionally substituted $C_{2-6}$ alkynylene group;
A represents an optionally substituted $C_{2-6}$ alkynylene group, an optionally substituted $C_{3-8}$ cycloalkylene group or an optionally substituted divalent aromatic hydrocarbon group;
X² represents an optionally substituted $C_{1-6}$ alkylene group, an optionally substituted $C_{2-6}$ alkenylene group or an optionally substituted $C_{2-6}$ alkynylene group;
Y¹ represents an oxygen atom or a sulfur atom; and
R⁵ represents a hydrogen atom, an optionally substituted $C_{1-6}$ alkyl group, an optionally substituted $C_{2-6}$ alkenyl group, an optionally substituted $C_{2-6}$ alkynyl group, an optionally substituted aromatic hydrocarbon group, an optionally substituted oxygen-containing heterocyclic group, a hydroxyl-protecting group or a thiol-protecting group,
provided that when X² is CH(R⁶) wherein R⁶ represents a hydrogen atom or a methoxy group, R⁵ means a group represented by a $C_{2-6}$ alkyl group optionally substituted by one or more groups selected from substituent group α, an optionally substituted $C_{2-6}$ alkenyl group, an optionally substituted $C_{1-6}$ alkynyl group, an optionally substituted aromatic hydrocarbon group, an optionally substituted oxygen-containing heterocyclic group, a hydroxyl-protecting group or a thiol-protecting group, wherein the substituent group α consists of: a halogen atom; a cyano group; a nitro group; an oxo group; an optionally substituted carbamoyl group; an optionally substituted $C_{2-6}$ alkenyl group; an optionally substituted $C_{2-6}$ alkynyl group; an optionally substituted $C_{3-8}$ cycloalkyl group; an optionally substituted $C_{1-6}$ alkoxy group; an optionally substituted aromatic hydrocarbon group; an optionally substituted aryloxy group; an optionally substituted arylthio group; an optionally substituted heterocyclic group; an optionally substituted heterocyclic oxy group; an optionally protected hydroxyl group; and an optionally protected carboxyl group, or a salt thereof, has a strong LpxC inhibitory effect and has strong antibacterial activity against Gram-negative bacteria including *Pseudomonas aeruginosa*.

Advantageous Effects of the Invention

A compound represented by general formula [1] or a salt thereof has a strong LpxC inhibitory effect and has strong antibacterial activity against Gram-negative bacteria including *Pseudomonas aeruginosa*. The compound represented by general formula [1] or the salt thereof is therefore useful as an antibacterial agent. In another aspect, the compound represented by general formula [1] or the salt thereof is excellent in safety and pharmacokinetics and is useful as an antibacterial agent.

MODE FOR CARRYING OUT THE INVENTION

The present invention will be described below in detail.
In the present specification, each term is as defined below unless otherwise specified.
The halogen atom means a fluorine atom, a chlorine atom, a bromine atom or an iodine atom.
The $C_{1-6}$ alkyl group means a straight chain or branched chain $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group and a hexyl group, for example.
The $C_{2-6}$ alkyl group means a straight chain or branched chain $C_{1-6}$ alkyl group such as an ethyl group, a propyl group, an isopropyl group, a butyl group, a sec-butyl group, an isobutyl group, a tert-butyl group, a pentyl group, an isopentyl group and a hexyl group, for example.
The $C_{2-6}$ alkenyl group means a straight chain or branched chain $C_{2-6}$ alkenyl group such as a vinyl group, an allyl group, a propenyl group, an isopropenyl group, a butenyl group, an isobutenyl group, a 1,3-butadienyl group, a pentenyl group and a hexenyl group, for example.
The $C_{2-6}$ alkynyl group means a straight chain or branched chain $C_{2-6}$ alkynyl group such as an ethynyl group, a propynyl group, a butynyl group, a pentynyl group and a hexynyl group, for example.
The $C_{3-8}$ cycloalkyl group means a $C_{3-8}$ cycloalkyl group such as a cyclopropyl group, a cyclobutyl group, a cyclopentyl group and a cyclohexyl group, for example.
The aromatic hydrocarbon group means such as a phenyl group, a naphthyl group, an indanyl group, an indenyl group, a tetrahydronaphthyl group, a dihydronaphthyl group, a benzocycloheptyl group, a dihydro-5H-benzocycloheptenyl group or a 5H-benzocycloheptenyl group, for example.
The ar-$C_{1-6}$ alkyl group means an ar-$C_{1-6}$ alkyl group such as a benzyl group, a diphenylmethyl group, a trityl group, a phenethyl group or a naphthylmethyl group, for example.
The $C_{1-6}$ alkylene group means a straight chain or branched chain $C_{1-6}$ alkylene group such as a methylene group, an ethylene group, a propylene group, a butylene group, a pentylene group or a hexylene group.
The $C_{1-5}$ alkylene group means a straight chain or branched chain $C_{1-5}$ alkylene group such as a methylene group, an ethylene group, a propylene group, a butylene group or a pentylene group.
The $C_{2-6}$ alkenylene group means a straight chain or branched chain $C_{2-6}$ alkenylene group such as a vinylene group, a propenylene group, a 1-butenylene group, a 2-butenylene group, a 1-pentenylene group or a 1-hexenylene group.

The $C_{2-6}$ alkynylene group means a straight chain or branched chain $C_{2-6}$ alkynylene group such as an ethynylene group, a propynylene group, a 1-butynylene group, a 2-butynylene group, a 1-pentenylene group or a 1-hexenylene group.

The $C_{3-8}$ cycloalkylene group means a $C_{3-8}$ cycloalkylene group such as a 1,1-cyclopropylene group, a 1,2-cyclopropylene group, a 1,1-cyclobutylene group, a 1,2-cyclobutylene group, a 1,3-cyclobutylene group, a 1,2-cyclopentylene group, a 1,3-cyclopentylene group, a 1,1-cyclohexylene group, a 1,2-cyclohexylene group and a 1,4-cyclohexylene group, for example.

The $C_{1-6}$ alkoxy group means a straight chain or branched chain $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group and a hexyloxy group, for example.

The ar-$C_{1-6}$ alkoxy group means an ar-$C_{1-6}$ alkyloxy group such as a benzyloxy group, a phenethyloxy group and a naphthylmethyloxy group, for example.

The aryloxy group means a phenoxy group or a naphthyloxy group, for example.

The $C_{1-6}$ alkoxy-$C_{1-6}$ alkyl group means a $C_{1-6}$ alkyloxy-$C_{1-6}$ alkyl group such as a methoxymethyl group and a 1-ethoxyethyl group, for example.

The ar-$C_{1-6}$ alkoxy-$C_{1-6}$ alkyl group means an ar-$C_{1-6}$ alkyloxy-$C_{1-6}$ alkyl group such as a benzoyloxymethyl group and a phenethyloxymethyl group, for example.

The $C_{2-12}$ alkanoyl group means a straight chain or branched chain $C_{2-12}$ alkanoyl group such as an acetyl group, a propionyl group, a valeryl group, an isovaleryl group and a pivaloyl group, for example.

The aroyl group means a benzoyl group or a naphthoyl group, for example.

The heterocyclic carbonyl group means a nicotinoyl group, a thenoyl group, a pyrrolidinocarbonyl group or a furoyl group, for example.

The ($\alpha$-substituted) aminoacetyl group means an optionally N-terminally protected ($\alpha$-substituted) aminoacetyl group derived from an amino acid (examples of the amino acid include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, hydroxyproline etc.), for example.

The acyl group means a formyl group, a succinyl group, a glutaryl group, a maleoyl group, a phthaloyl group, a $C_{2-12}$ alkanoyl group, an aroyl group, a heterocyclic carbonyl group or an ($\alpha$-substituted) aminoacetyl group, for example.

The acyl-$C_{1-6}$ alkyl group means an acyl-$C_{1-6}$ alkyl group such as an acetylmethyl group, a benzoylmethyl group and a 1-benzoylethyl group, for example.

The acyloxy-$C_{1-6}$ alkyl group means an acyloxy-$C_{1-6}$ alkyl group such as an acetoxymethyl group, a propionyloxymethyl group, a pivaloyloxymethyl group, a benzoyloxymethyl group and a 1-(benzoyloxy)ethyl group, for example.

The $C_{1-6}$ alkoxycarbonyl group means a straight chain or branched chain $C_{1-6}$ alkyloxycarbonyl group such as a methoxycarbonyl group, an ethoxycarbonyl group, an isopropoxycarbonyl group, a tert-butoxycarbonyl group and a 1,1-dimethylpropoxycarbonyl group, for example.

The ar-$C_{1-6}$ alkoxycarbonyl group means an ar-$C_{1-6}$ alkyloxycarbonyl group such as a benzyloxycarbonyl group and a phenethyloxycarbonyl group, for example.

The aryloxycarbonyl group means a phenyloxycarbonyl group or a naphthyloxycarbonyl group, for example.

The $C_{1-6}$ alkylamino group means a straight chain or branched chain $C_{1-6}$ alkylamino group such as a methylamino group, an ethylamino group, a propylamino group, an isopropylamino group, a butylamino group, a sec-butylamino group, a tert-butylamino group, a pentylamino group and a hexylamino group, for example.

The di($C_{1-6}$ alkyl)amino group means a straight chain or branched chain di($C_{1-6}$ alkyl)amino group such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group and a (methyl)(propyl)amino group, for example.

The $C_{1-6}$ alkylthio group means a $C_{1-6}$ alkylthio group such as a methylthio group, an ethylthio group and a propylthio group, for example.

The arylthio group means a phenylthio group or a naphthylthio group, for example.

The $C_{1-6}$ alkylsulfonyl group means a $C_{1-6}$ alkylsulfonyl group such as a methylsulfonyl group, an ethylsulfonyl group and a propylsulfonyl group, for example.

The arylsulfonyl group means a benzenesulfonyl group, a p-toluenesulfonyl group or a naphthalenesulfonyl group, for example.

The $C_{1-6}$ alkylsulfonyloxy group means a $C_{1-6}$ alkylsulfonyloxy group such as a methylsulfonyloxy group, a trifluoromethylsulfonyloxy group and an ethylsulfonyloxy group, for example.

The arylsulfonyloxy group means a benzenesulfonyloxy group or a p-toluenesulfonyloxy group, for example.

The silyl group means a trimethylsilyl group, a triethylsilyl group or a tributylsilyl group, for example.

The monocyclic nitrogen-containing heterocyclic group means a monocyclic nitrogen-containing heterocyclic group containing only a nitrogen atom as a heteroatom forming the ring, such as an azetidinyl group, a pyrrolidinyl group, a pyrrolinyl group, a pyrrolyl group, a dihydropyrrolyl group, a piperidyl group, a tetrahydropyridyl group, a pyridyl group, a homopiperidinyl group, an octahydroazocinyl group, an imidazolidinyl group, an imidazolinyl group, an imidazolyl group, a pyrazolidinyl group, a pyrazolinyl group, a pyrazolyl group, a piperazinyl group, a pyrazinyl group, a pyridazinyl group, a pyrimidinyl group, a homopiperazinyl group, a triazinyl group, a triazolyl group and a tetrazolyl group, for example.

The monocyclic oxygen-containing heterocyclic group means a monocyclic oxygen-containing heterocyclic group containing only an oxygen atom as a heteroatom forming the ring, such as a tetrahydrofuranyl group, a furanyl group, a tetrahydropyranyl group and a pyranyl group, for example.

The monocyclic sulfur-containing heterocyclic group means a thienyl group, for example.

The monocyclic nitrogen- and oxygen-containing heterocyclic group means a monocyclic nitrogen- and oxygen-containing heterocyclic group containing only a nitrogen atom and an oxygen atom as heteroatoms forming the ring, such as an oxazolyl group, an isoxazolyl group, an oxadiazolyl group and a morpholinyl group, for example.

The monocyclic nitrogen- and sulfur-containing heterocyclic group means a monocyclic nitrogen- and sulfur-containing heterocyclic group containing only a nitrogen atom and a sulfur atom as heteroatoms forming the ring, such as a thiazolyl group, an isothiazolyl group, a thiadiazolyl group, a thiomorpholinyl group, a 1-oxidothiomorpholinyl group and a 1,1-dioxidothiomorpholinyl group, for example.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group or a monocyclic nitrogen- and sulfur-containing heterocyclic group.

The bicyclic nitrogen-containing heterocyclic group means a bicyclic nitrogen-containing heterocyclic group containing only a nitrogen atom as a heteroatom forming the ring, such as an indolinyl group, an indolyl group, an isoindolinyl group, an isoindolyl group, a benzimidazolyl group, an indazolyl group, a benzotriazolyl group, a quinolyl group, a tetrahydroquinolinyl group, a tetrahydroisoquinolinyl group, an isoquinolinyl group, a quinolizinyl group, a cinnolinyl group, a phthalazinyl group, a quinazolinyl group, a dihydroquinoxalinyl group, a quinoxalinyl group, a naphthyridinyl group, a purinyl group, a pteridinyl group and a quinuclidinyl group, for example.

The bicyclic oxygen-containing heterocyclic group means a bicyclic oxygen-containing heterocyclic group containing only an oxygen atom as a heteroatom forming the ring, such as a 2,3-dihydrobenzofuranyl group, a benzofuranyl group, an isobenzofuranyl group, a chromanyl group, a chromenyl group, an isochromanyl group, a 1,3-benzodioxolyl group, a 1,3-benzodioxanyl group and a 1,4-benzodioxanyl group, for example.

The bicyclic sulfur-containing heterocyclic group means a bicyclic sulfur-containing heterocyclic group containing only a sulfur atom as a heteroatom forming the ring, such as a 2,3-dihydrobenzothienyl group and a benzothienyl group, for example.

The bicyclic nitrogen- and oxygen-containing heterocyclic group means a bicyclic nitrogen- and oxygen-containing heterocyclic group containing only a nitrogen atom and an oxygen atom as heteroatoms forming the ring, such as a benzoxazolyl group, a benzisoxazolyl group, a benzoxadiazolyl group, a benzomorpholinyl group, a dihydropyranopyridyl group, a dihydrodioxinopyridyl group and a dihydropyridooxazinyl group, for example.

The bicyclic nitrogen- and sulfur-containing heterocyclic group means a bicyclic nitrogen- and sulfur-containing heterocyclic group containing only a nitrogen atom and a sulfur atom as heteroatoms forming the ring, such as a benzothiazolyl group, a benzisothiazolyl group and a benzothiadiazolyl group, for example.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group or a bicyclic nitrogen- and sulfur-containing heterocyclic group.

The heterocyclic group means a monocyclic heterocyclic group or a bicyclic heterocyclic group.

The oxygen-containing heterocyclic group means a monocyclic oxygen-containing heterocyclic group or a bicyclic oxygen-containing heterocyclic group.

The divalent aromatic hydrocarbon group means a divalent group formed by the removal of one arbitrary hydrogen atom from, such as a phenyl group, a naphthyl group, an indanyl group, an indenyl group, a tetrahydronaphthyl group, a dihydronaphthyl group, a benzocycloheptyl group, a dihydro-5H-benzocycloheptenyl group or a 5H-benzocycloheptenyl group, for example.

The heterocyclic oxy group means a pyrrolidinyloxy group, a piperidinyloxy group, a piperazinyloxy group, a morpholinyloxy group, a thiomorpholinyloxy group, a tetrahydrofuranyloxy group, a tetrahydropyranyloxy group, a tetrahydrothiopyranyloxy group, a pyridyloxy group or a pyrimidinyloxy group, for example.

The amino-protecting group includes all of groups that may be used as usual protecting groups for the amino group. Examples thereof include groups described in, for example, W. Greene et al., Protective Groups in Organic Synthesis, 4 ed., p. 696-926, 2007, John Wiley & Sons, Inc. Specific examples thereof include an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group.

The imino-protecting group includes all of groups that may be used as usual protecting groups for the imino group. Examples thereof include groups described in, for example, W. Greene et al., Protective Groups in Organic Synthesis, 4 ed., p. 696-868, 2007, John Wiley & Sons, Inc. Specific examples thereof include a straight chain or branched chain $C_{2-12}$ alkanoyl group such as an acetyl group, a propionyl group and an isovaleryl group.

The hydroxyl-protecting group includes all of groups that may be used as usual protecting groups for the hydroxyl group. Examples thereof include groups described in, for example, W. Greene et al., Protective Groups in Organic Synthesis, 4 ed., p. 16-299, 2007, John Wiley & Sons, Inc. Specific examples thereof include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an ar-$C_{1-6}$ alkoxy-$C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group and a tetrahydropyranyl group.

The thiol-protecting group includes all of groups that may be used as usual protecting groups for the thiol group. Examples thereof include groups described in, for example, W. Greene et al., Protective Groups in Organic Synthesis, 4 ed., p. 647-695, 2007, John Wiley & Sons, Inc. Specific examples thereof include a $C_{1-6}$ alkyl group, a $C_{2-6}$ alkenyl group, an ar-$C_{1-6}$ alkyl group, a $C_{1-6}$ alkoxy-$C_{1-6}$ alkyl group, an acyl group and a silyl group.

The carboxyl-protecting group includes all of groups that may be used as usual protecting groups for the carboxyl group. Examples thereof include groups described in, for example, W. Greene et al., Protective Groups in Organic Synthesis, 4 ed., p. 533-643, 2007, John Wiley & Sons, Inc. Specific examples thereof include a $C_{1-6}$ alkyl group, a $C_{2-6}$ alkenyl group, an aromatic hydrocarbon group, an ar-$C_{1-6}$ alkyl group, a $C_{1-6}$ alkoxy-$C_{1-6}$ alkyl group, an ar-$C_{1-6}$ alkoxy-$C_{1-6}$ alkyl group, an acyl-$C_{1-6}$ alkyl group, an acyloxy-$C_{1-6}$ alkyl group and a silyl group.

Examples of the leaving group include a halogen atom, a $C_{1-6}$ alkylsulfonyloxy group and an arylsulfonyloxy group.

Examples of the aliphatic hydrocarbons include pentane, hexane, cyclohexane and decahydronaphthalene.

Examples of the halogenated hydrocarbons include methylene chloride, chloroform and dichloroethane.

Examples of the alcohols include methanol, ethanol, propanol, 2-propanol, butanol and 2-methyl-2-propanol.

Examples of the ethers include diethyl ether, diisopropyl ether, dioxane, tetrahydrofuran, anisole, ethylene glycol dimethyl ether, diethylene glycol dimethyl ether and diethylene glycol diethyl ether.

Examples of the ketones include acetone, 2-butanone and 4-methyl-2-pentanone.

Examples of the esters include methyl acetate, ethyl acetate, propyl acetate and butyl acetate.

Examples of the amides include N,N-dimethylformamide, N,N-dimethylacetamide and 1-methyl-2-pyrrolidone.

Examples of the aromatic hydrocarbons include benzene, toluene and xylene.

In the present specification, each substituent group is as defined below.

Substituent group A: a halogen atom, a cyano group, a nitro group, an oxo group, an optionally substituted carbamoyl group, an optionally substituted $C_{3-8}$ cycloalkyl group, an optionally substituted $C_{1-6}$ alkoxy group, an optionally substituted $C_{1-6}$ alkylamino group, an optionally substituted di($C_{1-6}$ alkyl)amino group, an optionally substituted aromatic hydrocarbon group, an optionally substituted aryloxy group, an optionally substituted arylthio group, an optionally substituted heterocyclic group, an optionally substituted heterocyclic oxy group, an optionally protected amino group, an optionally protected imino group, an optionally protected hydroxyl group and an optionally protected carboxyl group.

Substituent group B: a halogen atom, a cyano group, a nitro group, an oxo group, an optionally substituted carbamoyl group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{1-6}$ alkoxy group, an optionally substituted $C_{1-6}$ alkylamino group, an optionally substituted di($C_{1-6}$ alkyl)amino group, an optionally substituted aromatic hydrocarbon group, an optionally substituted aryloxy group, an optionally substituted arylthio group, an optionally substituted heterocyclic group, an optionally substituted heterocyclic oxy group, an optionally protected amino group, an optionally protected imino group, an optionally protected hydroxyl group and an optionally protected carboxyl group.

Substituent group C: a halogen atom, a cyano group, a nitro group, a $C_{1-6}$ alkyl group, a $C_{2-6}$ alkenyl group, a $C_{2-6}$ alkynyl group, a $C_{1-6}$ alkoxy group, an acyl group, a $C_{1-6}$ alkylamino group, a di($C_{1-6}$ alkyl)amino group, a $C_{1-6}$ alkylthio group, a $C_{1-6}$ alkylsulfonyl group, an arylsulfonyl group, a $C_{3-8}$ cycloalkyl group, an aromatic hydrocarbon group, a heterocyclic group, a carbamoyl group, an amino group, a carboxyl group and a hydroxyl group.

Substituent group α: a halogen atom, a cyano group, a nitro group, an oxo group, an optionally substituted carbamoyl group, an optionally substituted $C_{2-6}$ alkenyl group, an optionally substituted $C_{2-6}$ alkynyl group, an optionally substituted $C_{3-8}$ cycloalkyl group, an optionally substituted $C_{1-6}$ alkoxy group, an optionally substituted aromatic hydrocarbon group, an optionally substituted aryloxy group, an optionally substituted arylthio group, an optionally substituted heterocyclic group, an optionally substituted heterocyclic oxy group, an optionally protected hydroxyl group and an optionally protected carboxyl group.

The $C_{1-6}$ alkyl group or the $C_{1-6}$ alkoxy group of $R^1$ is optionally substituted by one or more groups selected from substituent group A.

The $C_{3-8}$ cycloalkyl group of $R^1$ is optionally substituted by one or more groups selected from substituent group B.

The $C_{1-6}$ alkyl group or the $C_{1-6}$ alkoxy group of $R^2$ is optionally substituted by one or more groups selected from substituent group A.

The $C_{3-8}$ cycloalkyl group of $R^2$ is optionally substituted by one or more groups selected from substituent group B.

The $C_{1-6}$ alkyl group of $R^3$ is optionally substituted by one or more groups selected from substituent group A.

The $C_{1-6}$ alkyl group or the $C_{1-6}$ alkoxy group of $R^4$ is optionally substituted by one or more groups selected from substituent group A.

The $C_{3-8}$ cycloalkyl group of $R^4$ is optionally substituted by one or more groups selected from substituent group B.

The aromatic hydrocarbon group or the heterocyclic group of $R^4$ is optionally substituted by one or more groups selected from substituent group B.

The $C_{1-6}$ alkylene group, the $C_{2-6}$ alkenylene group or the $C_{2-6}$ alkynylene group of $X^1$ is optionally substituted by one or more groups selected from substituent group B.

The $C_{2-6}$ alkenylene group, the $C_{2-6}$ alkynylene group, the $C_{3-8}$ cycloalkylene group or the divalent aromatic hydrocarbon group of A is optionally substituted by one or more groups selected from substituent group B.

The $C_{1-6}$ alkylene group, the $C_{2-6}$ alkenylene group or the $C_{2-6}$ alkynylene group of $X^2$ is optionally substituted by one or more groups selected from substituent group B.

The $C_{1-6}$ alkyl group, the $C_{2-6}$ alkenyl group or the $C_{2-6}$ alkynyl group of $R^5$ is optionally substituted by one or more groups selected from substituent group A.

The aromatic hydrocarbon group or the oxygen-containing heterocyclic group of $R^5$ is optionally substituted by one or more groups selected from substituent group B.

The carbamoyl group, the $C_{3-8}$ cycloalkyl group, the $C_{1-6}$ alkoxy group, the $C_{1-6}$ alkylamino group, the di($C_{1-6}$ alkyl) amino group, the aromatic hydrocarbon group, the aryloxy group, the arylthio group, the heterocyclic group and the heterocyclic oxy group in the substituent group A are each optionally substituted by one or more groups selected from substituent group C.

The carbamoyl group, the $C_{1-6}$ alkyl group, the $C_{1-6}$ alkenyl group, the $C_{1-6}$ alkynyl group, the $C_{3-8}$ cycloalkyl group, the $C_{1-6}$ alkoxy group, the $C_{1-6}$ alkylamino group, the di($C_{1-6}$ alkyl)amino group, the aromatic hydrocarbon group, the aryloxy group, the arylthio group, the heterocyclic group and the heterocyclic oxy group in the substituent group B are each optionally substituted by one or more groups selected from substituent group C.

Preferred examples of the compound of the present invention include compounds given below.

The compound represented by general formula [1] of the present invention has asymmetric carbon. The compound of the present invention may be a racemate or may be a specific enantiomer. In this context, the specific enantiomer is preferably a compound represented by the following general formula [2]:

[2]

wherein $R^1$, $R^2$, $R^3$, $R^4$, $R^5$, $X^1$, $X^2$, $Y^1$ and A are as defined above.

A compound wherein $R^1$ and $R^2$ are the same or different and each represent a hydrogen atom or an optionally substituted $C_{1-6}$ alkyl group is preferred.

A compound wherein $R^1$ and $R^2$ are the same or different and each represent an optionally substituted $C_{1-6}$ alkyl group is more preferred.

A compound wherein each of $R^1$ and $R^2$ is a methyl group is further preferred.

A compound wherein $R^3$ is a hydrogen atom is preferred.

A compound wherein $R^4$ is a hydrogen atom or an optionally substituted $C_{1-6}$ alkyl group is preferred.

A compound wherein $R^4$ is an optionally substituted $C_{1-6}$ alkyl group is more preferred.

A compound wherein $R^4$ is a methyl group is further preferred.

A compound wherein $X^1$ is an optionally substituted $C_{2-6}$ alkynylene group is preferred.

A compound wherein $X^1$ is an ethynylene group is more preferred.

A compound wherein A is an optionally substituted divalent $C_{3-8}$ cycloalkyl group or an optionally substituted divalent aromatic hydrocarbon group is preferred.

A compound wherein A is an optionally substituted divalent aromatic hydrocarbon group is more preferred.

A compound wherein A is a phenylene group is further preferred.

A compound wherein $X^2$ is an optionally substituted $C_{1-6}$ alkylene group is preferred.

A compound wherein $X^2$ is a group represented by general formula [3]:

$$\underset{\text{OH}}{\overset{X^{2a}}{\diagup\!\!\!\diagdown}} \quad [3]$$

wherein $X^{2a}$ represents an optionally substituted $C_{1-5}$ alkylene group, provided that $X^{2a}$ is bonded to $Y^1$
is more preferred. A compound wherein $X^2$ is represented by general formula [4]:

$$\underset{\overline{\text{OH}}}{\overset{X^{2a}}{\diagup\!\!\!\diagdown}} \quad [4]$$

wherein $X^{2a}$ is as defined above
is further preferred.

A compound wherein $X^{2a}$ is an optionally substituted methylene group, an optionally substituted ethylene group or an optionally substituted propylene group is furthermore preferred.

The $C_{1-5}$ alkylene group of $X^{2a}$ is optionally substituted by one or more groups selected from substituent group B.

A compound wherein $Y^1$ is an oxygen atom is preferred.

A compound wherein $R^5$ is a hydrogen atom, an optionally substituted $C_{1-6}$ alkyl group, an optionally substituted $C_{2-6}$ alkenyl group, an optionally substituted $C_{2-6}$ alkynyl group, a hydroxyl-protecting group or a thiol-protecting group is preferred,
provided that when $X^2$ is $CH(R^6)$ wherein $R^6$ represents a hydrogen atom or a methoxy group, $R^5$ is a $C_{2-6}$ alkyl group optionally substituted by one or more groups selected from substituent group α, an optionally substituted $C_{2-6}$ alkenyl group, an optionally substituted $C_{2-6}$ alkynyl group, a hydroxyl-protecting group or a thiol-protecting group.

A compound wherein $R^5$ is a hydrogen atom, a $C_{1-6}$ alkyl group optionally substituted by one or more groups selected from an optionally substituted $C_{1-6}$ alkoxy group and an optionally protected hydroxyl group, or a hydroxyl-protecting group is more preferred, provided that when $X^2$ is $CH(R^6)$ wherein $R^6$ is as defined above, $R^5$ is a $C_{2-6}$ alkyl group optionally substituted by one or more groups selected from an optionally substituted $C_{1-6}$ alkoxy group and an optionally protected hydroxyl group, or a hydroxyl-protecting group.

Preferred examples of the compound according to the present invention include (2S)-2-((4-((4-(1,2-dihydroxyethyl)phenyl)ethynyl)benzoyl)(methyl)amino)-N-hydroxy-N',2-dimethylmalonamide, (2S)—N-hydroxy-2-((4-((4-(3-hydroxy-2-(hydroxymethyl)propyl)phenyl)ethynyl)benzoyl)(methyl)amino)-N',2-dimethylmalonamide, (2S)-2-((4-((4-((1R)-1,2-dihydroxyethyl)phenyl)ethynyl)benzoyl)(methyl)amino)-N-hydroxy-N',2-dimethylmalonamide, (2S)-2-((4-((4-((1S)-1,2-dihydroxyethyl)phenyl)ethynyl)benzoyl)(methyl)amino)-N-hydroxy-N', 2-dimethylmalonamide, (2S)—N-hydroxy-2-((4-((4-((1S)-1-hydroxy-2-methoxyethyl)phenyl)ethynyl)benzoyl)(methyl)amino)-N', 2-dimethylmalonamide, (2S)—N-hydroxy-2-((4-((4-((1S)-1-hydroxy-2-(2-hydroxyethoxy)ethyl)phenyl)ethynyl) benzoyl)(methyl)amino)-N',2-dimethylmalonamide, (2S)-2-((4-((4-((1R)-1,3-dihydroxypropyl)phenyl)ethynyl) benzoyl)(methyl)amino)-N-hydroxy-N',2-dimethylmalonamide, (2S)-2-((4-((4-((1S,2S)-1,2-dihydroxypropyl)phenyl)ethynyl)benzoyl)(methyl)amino)-N-hydroxy-N',2-dimethylmalonamide, (2S)-2-((4-((4-(1,4-dihydroxybutyl)phenyl)ethynyl)benzoyl)(methyl)amino)-N-hydroxy-N',2-dimethylmalonamide and (2S)—N-hydroxy-2-((4-((4-((1R)-1-hydroxy-3-methoxypropyl) phenyl)ethynyl)benzoyl)(methyl)amino)-N',2-dimethylmalonamide.

(2S)-2-((4-((4-((1R)-1,4-dihydroxybutyl)phenyl)ethynyl) benzoyl)(methyl)amino)-N-hydroxy-N',2-dimethylmalonamide is also included in preferred examples of the compound according to the present invention.

The compound represented by general formula [1] or a salt thereof exhibits excellent safety. The safety is evaluated by various tests and can be evaluated by various safety tests, etc., selected from, for example, cytotoxicity test, hERG test, repeated dose toxicity test, cytochrome P450 (CYP) activity inhibition test, metabolism-dependent inhibition test, in vivo mouse micronucleus test, in vivo rat liver UDS test etc.

Examples of the salt of the compound of general formula [1] can include usually known salts of basic groups such as an amino group or of acidic groups such as a hydroxyl group or a carboxyl group.

Examples of the salts of basic groups include: salts with mineral acids such as hydrochloric acid, hydrobromic acid, nitric acid and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Examples of the salts of acidic groups include: salts with alkali metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-ephenamine and N,N'-dibenzylethylenediamine.

Among these salts, preferred examples of the salt include pharmacologically acceptable salts.

The compound of general formula [1] or the salt thereof may have isomers (e.g., optical isomers, geometric isomers and tautomers). The present invention encompasses these isomers. The compound of general formula [1] or the salt thereof also includes solvates, hydrates and crystals in various forms.

Next, a method for producing the compound of the present invention will be described.

The compound of the present invention is produced by the combination of methods known per se in the art and can be produced according to, for example, production methods shown below.

[Production Method 1]

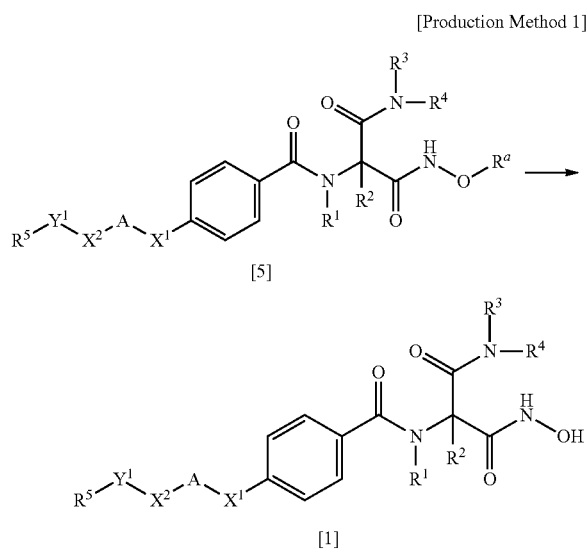

wherein $R^a$ represents a hydroxyl-protecting group; and $R^1$, $R^2$, $R^3$, $R^4$, $R^5$, $X^1$, $X^2$, $Y^1$ and A are as defined above.

The compound of general formula [1] can be produced by deprotecting a compound of general formula [5]. This reaction can be carried out by, for example, a method described in Protective Groups in Organic Synthesis, 4th edition, p. 16-299, 2007, John Wiley & Sons, Inc.

[Production Method 2]

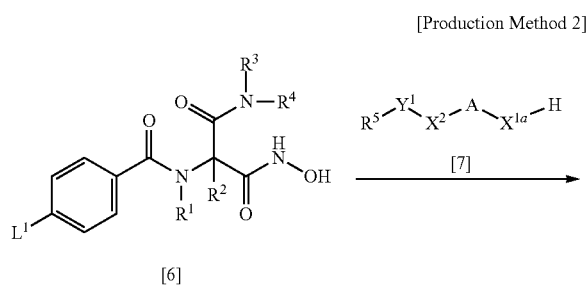

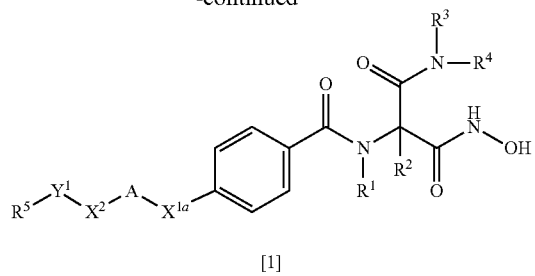

wherein $X^{1a}$ represents an optionally substituted $C_{2-6}$ alkynylene group; $L^1$ represents a bromine atom or an iodine atom; and $R^1$, $R^2$, $R^3$, $R^4$, $R^5$, $X^2$, $Y^1$ and A are as defined above.

As compounds of general formula [7], for example, 1-(4-ethynylphenyl)ethane-1,2-diol and (1R)-1-(4-ethynylphenyl)butane-1,4-diol are known.

The compound of general formula [1] can be produced by reacting a compound of general formula [6] with a compound of general formula [7] in the presence or absence of a base, in the presence or absence of a copper catalyst, in the presence or absence of a ligand and in the presence of a palladium catalyst.

This reaction can be performed by a method described in, for example, International Publication No. WO 11/132712 pamphlet or a method similar thereto.

The solvent used in this reaction is not particularly limited as long as the solvent has no adverse effect on the reaction. Examples thereof include aliphatic hydrocarbons, halogenated hydrocarbons, alcohols, ethers, ketones, esters, amides, aromatic hydrocarbons, dimethyl sulfoxide and water. These solvents may be used as a mixture. Preferred examples of the solvent include ethers.

Examples of the base used, if desired, in this reaction include: organic bases such as sodium methoxide, sodium ethoxide, potassium tert-butoxide, pyridine, dimethylaminopyridine and triethylamine; and inorganic bases such as sodium hydride, sodium hydroxide, potassium hydroxide, sodium bicarbonate, potassium carbonate and sodium carbonate. Preferred examples of the base include triethylamine.

The amount of the base used can be 1 to 50 times the mol of the compound of general formula [6] and is preferably 1 to 10 times the mol of the compound of general formula [6].

Examples of the copper catalyst used, if desired, in this reaction include copper bromide and copper iodide.

The amount of the copper catalyst used can be 0.01 to 50 times the mol of the compound of general formula [6] and is preferably 0.1 to 5 times the mol of the compound of general formula [6].

Examples of the ligand used, if desired, in this reaction include tri-t-butylphosphine, tricyclohexylphosphine, triphenylphosphine, tritolylphosphine, tributylphosphite, tricyclohexylphosphite, triphenylphosphite, 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-t-butylphosphino)-2',4',6'-triisopropylbiphenyl and 2-(di-t-butylphosphino)biphenyl. These ligands may be used in combination.

The amount of the ligand used can be 0.00001 to 1 times the mol of the compound of general formula [6] and is preferably 0.001 to 0.1 times the mol of the compound of general formula [6].

Examples of the palladium catalyst used in this reaction include: metal palladiums such as palladium-carbon and palladium black; inorganic palladium salts such as palladium chloride and palladium(II) sodium chloride trihydrate; organic palladium salts such as palladium acetate; organic palladium complexes such as tetrakis(triphenylphosphine)palladium(0), bis(triphenylphosphine)palladium(II) dichloride, bis(acetonitrile)palladium(II) dichloride, bis(benzonitrile)palladium(II) dichloride, 1,1'-bis(diphenylphosphino)ferrocene palladium(II) dichloride, tris(dibenzylideneacetone)dipalladium(0), bis(dibenzylideneacetone)palladium(0), bis(tricyclohexylphosphine)palladium(II) dichloride, bis(tri-o-tolylphosphine)palladium(II) dichloride, bis(tri-t-butylphosphine)palladium(II) dichloride, (1,3-bis(2,6-diisopropylphenyl)imidazolidene)(3-chloropyridyl)palladium(II) dichloride and bis(di-tert-butyl(4-dimethylaminophenyl)phosphine)palladium(II) dichloride; and polymer-immobilized organic palladium complexes such as polymer-supported bis(acetato)triphenylphosphinepalladium(II) and polymer-supported di(acetato)dicyclohexylphenylphosphinepalladium(II). These palladium catalysts may be used in combination.

The amount of the palladium catalyst used can be 0.00001 to 1 times the mol of the compound of general formula [6] and is preferably 0.001 to 0.1 times the mol of the compound of general formula [6].

The amount of the compound of general formula [7] used is 1 to 50 times, preferably 1 to 5 times, the mol of the compound of general formula [6].

This reaction can be carried out at −50 to 200° C., preferably −10 to 50° C., for 10 minutes to 48 hours.

This reaction can be preferably carried out under an inert gas (e.g., nitrogen or argon) atmosphere.

Next, methods for producing the compound of general formula [5] and the compound of general formula [6], which are starting materials for the production of the compound of the present invention, will be described.

[Production Method A]

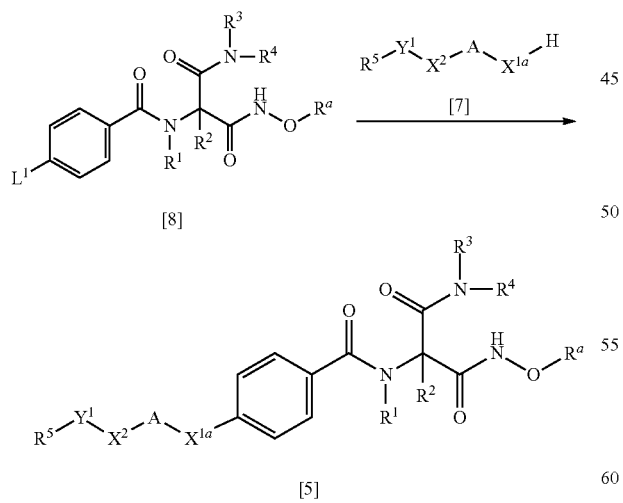

wherein $R^1$, $R^2$, $R^3$, $R^4$, $R^5$, $R^a$, $X^2$, $X^{1a}$, $Y^1$, A and $L^1$ are as defined above.

As a compound of general formula [8], for example, (2S)-2-((4-iodobenzoyl)(methyl)amino)-N,2-dimethyl-N'-(tetrahydro-2H-pyran-2-yloxy)malonamide is known.

The compound of general formula [5] can be produced similarly to Production Method 2 from a compound of general formula [8] and a compound of general formula [7].

[Production Method B]

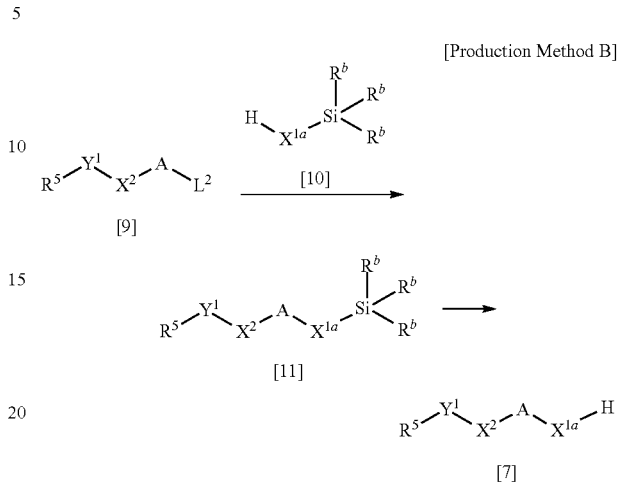

(B-1)

wherein three $R^b$ moieties are the same or different and each represent a $C_{1-6}$ alkyl group or an aromatic hydrocarbon group; $L^2$ represents a bromine atom or an iodine atom; and $R^5$, $X^{1a}$, $X^2$, $Y^1$ and A are as defined above.

As compounds of general formula [9], for example, 1-(4-iodophenyl)ethane-1,2-diol and 1-(4-bromophenyl)-2-methoxyethanol are known.

As compounds of general formula [10], for example, trimethylsilylacetylene and triisopropylsilylacetylene are known.

The compound of general formula [11] can be produced similarly to Production Method 2 from a compound of general formula [9] and a compound of general formula [10].

The compound of general formula [11] may be used in next reaction without being isolated.

(B-2)

The compound of general formula [7] can be produced by deprotecting a compound of general formula [11]. This reaction can be carried out by, for example, a method described in Protective Groups in Organic Synthesis, 4th edition, p. 927-933, 2007, John Wiley & Sons, Inc.

[Production Method C]

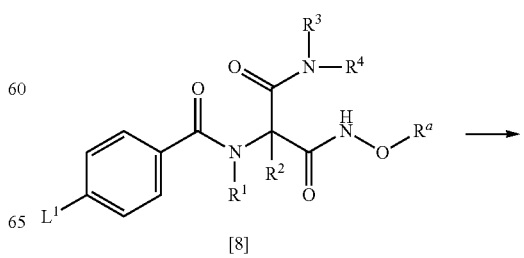

-continued

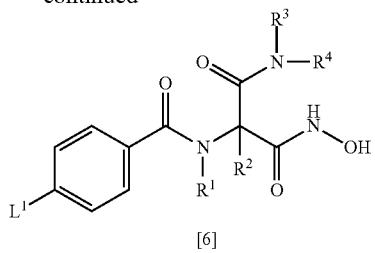

[6]

wherein $R^2$, $R^3$, $R^4$, $R^a$ and $L^1$ are as defined above.

The compound of general formula [6] can be produced by deprotecting the compound of general formula [8] similarly to Production Method 1.

The compounds used in the production methods mentioned above may have isomers (e.g., optical isomers, geometric isomers and tautomers). In this case, these isomers may be used. Alternatively, the compounds used in the production methods mentioned above may be any of solvates, hydrates and crystals in various forms. In this case, these solvates, hydrates and crystals in various forms may be used.

The compounds used in the production methods mentioned above may have a protectable substituent such as an amino group, a hydroxyl group or a carboxyl group, for example. In this case, these groups may be protected in advance with usual protecting groups, and after reaction, these protecting groups may be eliminated by methods known per se in the art.

For use as a medicine, the compound of general formula [1] of the present invention may be appropriately mixed with pharmaceutical aids usually used in formulation, such as an excipient, a carrier and a diluent. The resulting preparation can be administered orally or parenterally in a form such as tablets, capsules, powders, syrups, granules, pills, suspensions, emulsions, solutions, dusts, suppositories, eye drops, nasal drops, eardrops, patches, ointments or injections according to a routine method. The administration method, the dose and the number of doses of the preparation can be appropriately selected according to the age, body weight and symptoms of a patient. Usually, the compound of the present invention can be administered to an adult once to several times a day at a daily dose of 0.01 to 1000 mg/kg through an oral or parenteral (e.g., injection, drip infusion and administration to a rectal site) route.

Next, the usefulness of a typical compound of the present invention will be described with reference to the following Test Examples.

Test Example 1

Test to Evaluate *Pseudomonas aeruginosa* LpxC Enzyme Inhibitory Activity

The *Pseudomonas aeruginosa* LpxC enzyme activity was measured by reacting LpxC with its substrate UDP-3-O—(R-3-hydroxydecanoyl)-N-acetylglucosamine and measuring the amount of the reaction product by the quantification of an amino group present in the product. This measurement was carried out according to a method described in, for example, International Publication No. WO 11/132712 pamphlet or a method similar thereto.

Specifically, to the *Pseudomonas aeruginosa* LpxC enzyme (which was obtained by preparing chromosomal DNA from *Pseudomonas aeruginosa*, obtaining the *Pseudomonas aeruginosa* LpxC gene by PCR (polymerase chain reaction) using LpxC-specific primers, and incorporating this gene into a vector, followed by gene expression using *Escherichia coli*), 20 μmol/L UDP-3-O—(R-3-hydroxydecanoyl)-N-acetylglucosamine (Wako Pure Chemical Industries, Ltd.) was added, and the mixture was incubated at 25° C. for 1 hour. This reaction was carried out in a 40 mmol/L HEPES buffer solution (pH 8.0) containing 0.02% Brij 35 and 80 μmol/L dithiothreitol. The reaction was terminated by the addition of 20% acetic acid (final concentration: 0.95%) to the reaction solution. Then, fluorescamine (final concentration: 1.6 mg/mL) dissolved in anhydrous dioxane was added thereto. The amount of the reaction product was detected at an excitation wavelength/fluorescence wavelength=390 nm/495 nm. Each test compound was allowed to coexist at various concentrations in the reaction to obtain an inhibition curve. From the inhibition curve, the concentration at which the test compound inhibited 50% of the amount of the reaction product ($IC_{50}$ value) was determined and used as an index for *Pseudomonas aeruginosa* LpxC enzyme inhibitory activity.

As a result, the test compounds of Examples 1, 3, 16, 17, 19, 20, 23, 24, 25, 33, 35, 36, 39 and 40 had an $IC_{50}$ value of less than 50 nM.

Test Example 2

Test to Evaluate Antibacterial Activity

The minimum inhibitory concentration (MIC) was measured according to the CLSI (Clinical and Laboratory Standards Institute) standard method using a broth microdilution method given below.

The bacteria used were a *Pseudomonas aeruginosa* ATCC27853 strain, an *Escherichia coli* ATCC25922 strain and a *Klebsiella pneumoniae* ATCC13883 strain. Test bacterial cells of each strain cultured overnight in a Mueller-Hinton agar medium were scraped off and suspended at the McFarland 0.5 standard, and this suspension was diluted 10-fold to prepare an inoculum solution. The inoculum solution (0.005 mL) was inoculated to a cation-adjusted Mueller-Hinton medium containing each test compound and cultured at 35° C. for 16 to 20 hours. The minimum drug concentration at which bacterial growth was not visible to the naked eye was defined as MIC. The results are shown in Tables 1 to 3.

TABLE 1

| Test compound (Example No.) | *Pseudomonas aeruginosa* ATCC27853 strain MIC (μg/mL) |
|---|---|
| 1 | 1 |
| 2 | 1 |
| 3 | 1 |
| 7 | 1 |
| 8 | 1 |
| 10 | 1 |
| 12 | 1 |
| 13 | 1 |
| 15 | 1 |
| 16 | 1 |
| 17 | 1 |
| 18 | 1 |
| 19 | 1 |
| 20 | 1 |
| 22 | 1 |
| 23 | 1 |
| 24 | 1 |

TABLE 1-continued

| Test compound (Example No.) | Pseudomonas aeruginosa ATCC27853 strain MIC (µg/mL) |
|---|---|
| 25 | 0.5 |
| 26 | 1 |
| 27 | 1 |
| 32 | 1 |
| 33 | 1 |
| 34 | 1 |
| 35 | 1 |
| 36 | 0.5 |
| 37 | 1 |
| 39 | 1 |
| 40 | 1 |

TABLE 2

| Test compound (Example No.) | Escherichia coli ATCC25922 strain MIC (µg/mL) |
|---|---|
| 1 | 0.25 |
| 4 | 0.25 |
| 7 | 0.25 |
| 8 | 0.25 |
| 9 | 0.5 |
| 10 | 0.25 |
| 11 | 0.0625 |
| 12 | 0.0625 |
| 13 | 0.25 |
| 16 | 0.25 |
| 21 | 0.5 |
| 23 | 0.25 |
| 24 | 0.5 |
| 25 | 0.5 |
| 28 | 0.5 |
| 29 | 0.125 |
| 31 | 0.5 |
| 32 | 0.5 |
| 33 | 0.5 |
| 34 | 0.5 |
| 36 | 0.25 |
| 37 | 0.125 |
| 38 | 0.25 |
| 39 | 0.5 |
| 40 | 0.5 |

TABLE 3

| Test compound (Example No.) | Klebsiella pneumoniae ATCC13883 strain MIC (µg/mL) |
|---|---|
| 1 | 1 |
| 4 | 0.5 |
| 7 | 0.5 |
| 8 | 1 |
| 10 | 0.5 |
| 11 | 0.5 |
| 12 | 0.125 |
| 13 | 1 |
| 16 | 1 |
| 23 | 1 |
| 29 | 0.5 |
| 31 | 1 |
| 35 | 1 |
| 36 | 1 |
| 37 | 0.5 |
| 39 | 1 |
| 40 | 1 |

Test Example 3

Test on Defense Against Mouse General Infection Using *Pseudomonas aeruginosa*

The mice used were male ICR SPF mice (4 weeks old: 5 individuals per group). To prepare a bacterial inoculum solution, a *Pseudomonas aeruginosa* clinical isolate (S-3232 strain) cultured overnight at 37° C. on a Mueller-Hinton agar plate was cultured for 4 hours in a cation-adjusted Mueller-Hinton medium and then diluted 10-fold with a 10% mucin/phosphate buffer solution to prepare the inoculum solution. Infection was induced by the intraperitoneal inoculation of 0.5 mL of the inoculum solution (approximately $10^4$ CFU/mouse) to each mouse. Each test compound was dissolved in a 10% hydroxypropylated β-cyclodextrin/2.5% mannitol aqueous solution and subcutaneously administered a single dose of 12.5 mg/kg at 1 hour after the infection. Three days after the infection, the number of survivors was recorded.

As a result, all of the mice died in the control group without the administration of the test compound, whereas 80% or more of the mice were confirmed to survive 3 days after the bacterial inoculation in the group given the test compound of Example 3, 6, 17, 19, 20, 24, 25, 32, 33, 35 or 39, demonstrating in vivo anti *Pseudomonas aeruginosa* activity. Also, 80% or more of the mice were confirmed to survive 3 days after the bacterial inoculation in the group given, for example, 6.25 mg/kg of the test compound of Example 19 or 20, demonstrating in vivo excellent anti-*Pseudomonas aeruginosa* activity.

Test Example 4

Test on Defense Against Mouse Systemic Infection Using Multidrug-Resistant *Pseudomonas aeruginosa*

The mice used were male ICR SPF mice (4 weeks old: 5 individuals per group). To prepare a bacterial inoculum solution, a multidrug-resistant *Pseudomonas aeruginosa* clinical isolate (S-2838 strain) cultured overnight at 37° C. on a Mueller-Hinton agar plate was cultured for 5 hours in a cation-adjusted Mueller-Hinton medium and then diluted 10-fold with a 10% mucin/phosphate buffer solution to prepare the inoculum solution. Infection was induced by the intraperitoneal inoculation of 0.5 mL of the inoculum solution (approximately $10^6$ CFU/mouse) to each mouse. Each test compound was dissolved in a 10% hydroxypropylated β-cyclodextrin/2.5% mannitol aqueous solution and intravenously administered to the tail a single dose of 50 mg/kg at 1 hour after the infection. Three days after the infection, the number of survivors was recorded.

As a result, all of the mice died in the control group without the administration of the test compound, whereas 100% of the mice were confirmed to survive 3 days after the bacterial inoculation in the group given the test compound of Example 19, 20, 23 or 39, demonstrating in vivo anti-multidrug-resistant *Pseudomonas aeruginosa* activity. Also, 60% or more of the mice were confirmed to survive 3 days after the bacterial inoculation in the group given, for example, 25 mg/kg of the test compound of Example 20, demonstrating in vivo excellent anti-multidrug-resistant *Pseudomonas aeruginosa* activity.

Test Example 5

Test on Mouse Model with Urinary Tract Infection by Multidrug-Resistant *Pseudomonas aeruginosa*

The mice used were female ICR SPF mice (5 weeks old: 5 individuals per group). To prepare a bacterial inoculum solution, a *Pseudomonas aeruginosa* clinical isolate (S-2838 strain) was suspended in sterile saline. Infection was induced by the inoculation of 0.2 mL of the inoculum solution (approximately $10^3$ CFU/mouse) through the urethra of each mouse. Each test compound was dissolved in a 10% hydroxypropylated β-cyclodextrin/2.5% mannitol aqueous solution and intravenously administered to the tail at a dose of 25 mg/kg once 2 hours after the infection. The numbers of bacterial colonies of the next day of the infection in the kidneys were recorded, and an average thereof was calculated.

As a result, the group given the test compound of Example 19, 20, 23, 24 or 39 was confirmed to have a decrease of 2 log CFU/kidney or more in the numbers of bacterial colonies in the kidneys, as compared with the control group without the administration of the test compound, demonstrating anti-*Pseudomonas aeruginosa* activity in the urinary tract infection models. Also, the group given, for example, 12.5 mg/kg of the test compound of Examples 20 was confirmed to have a decrease of 2 log CFU/kidney or more in the numbers of bacterial colonies in the kidneys, as compared with the control group without the administration of the test compound, demonstrating excellent anti-*Pseudomonas aeruginosa* activity in the urinary tract infection models.

Test Example 6

Test on Mouse Model with Pulmonary Infection by Multidrug-Resistant *Pseudomonas aeruginosa*

The mice used were male ICR SPF mice (4.5 weeks old at the time of infection: 5 individuals per group). In order to achieve a transient compromised state, cyclophosphamide was intraperitoneally administered at a dose of 200 mg/kg to each mouse 4 days before injection. To prepare a bacterial inoculum solution, a *Pseudomonas aeruginosa* clinical isolate (S-2838 strain) was suspended in sterile saline. Infection was induced by the inoculation of 0.05 mL of the inoculum solution (approximately $10^5$ CFU/mouse) to each mouse intranasally. Each test compound was dissolved in a 10% hydroxypropylated β-cyclodextrin/2.5% mannitol aqueous solution and intravenously administered to the tail at a dose of 50 mg/kg twice 2 and 8 hours after the infection. The numbers of bacterial colonies of the next day of the infection in the lungs were recorded, and an average thereof was calculated.

As a result, the group given the test compound of Example 19, 20, 23, 24, 39 or 40 was confirmed to have a decrease of 2 log CFU/lung or more in the numbers of bacterial colonies in the lungs, as compared with the control group without the administration of the test compound, demonstrating anti-*Pseudomonas aeruginosa* activity in the pulmonary infection models. Also, the group given, for example, 25 mg/kg of the test compound of Examples 20 was confirmed to have a decrease of 2 log CFU/lung or more in the numbers of bacterial colonies in the lungs, as compared with the control group without the administration of the test compound, demonstrating excellent anti-*Pseudomonas aeruginosa* activity in the pulmonary infection models.

Test Example 7

Test on Inhibition of Vero Cell Growth

Each test compound was dissolved in dimethyl sulfoxide, adjusted to each concentration using E'MEM, and then dispensed at 0.1 mL/well to 96-well microplates. The Vero cell suspension was prepared at $3 \times 10^4$ cells/mL using E'MEM supplemented with 20% FBS, inoculated thereto at 0.1 mL/well, and cultured at 37° C. for 3 days under 5% $CO_2$. At the completion of the culture, PBS supplemented with 1 mg/mL 2,3-bis-(2-methoxy-4-nitro-5-sulfophenyl)-5-((phenylamino)carbonyl)-2H-tetrazolium inner salt monosodium salt (XTT) and 25 μM phenazine methosulfate (PMS) was prepared and added thereto at 50 μL/well. Approximately 2 hours later, the absorbance at 450 nm was measured using a microplate reader.

The absorbance ratio between a test compound-non-supplemented control and each well was calculated to calculate the concentration at which the compound inhibited 50% of cell growth ($CC_{50}$; μg/mL).

As a result, the test compounds of Examples 1, 2, 3, 4, 5, 6, 7, 8, 9, 10, 13, 17, 19, 20, 22, 23, 24, 25, 28, 29, 31, 33, 34, 35 and 36 all had $CC_{50}$ of 100 μg/mL or more.

Test Example 8

Evaluation of hERG Inhibitory Activity

HEK 293 cells (human embryo kidney 293 cells, Cytomyx LLC) transfected with hERG gene (human ether-a-go-go related gene) were used. The culture solution used was a MEM medium containing 10% fetal bovine serum and 1% nonessential amino acid and further supplemented with Geneticin at a concentration of 400 μg/mL. The cells were cultured in a carbonic acid gas incubator (37.0° C., 5% $CO_2$).

The hERG current was measured by a whole cell clamp method. A glass cover with the cells for measurement attached thereto was placed in a dish and perfused at a rate of 2 mL/min with a perfusate (composition: 137 mmol/L NaCl, 4 mmol/L KCl, 10 mmol/L HEPES, 1.8 mmol/L $CaCl_2$, 1 mmol/L $MgCl_2$, 10 mmol/L glucose, pH 7.4). The inside temperature of the perfusion chamber was kept at 25° C. The cells were contacted with a glass electrode (2.0 to 8.0 MΩ) charged with an internal solution (composition: 130 mmol/L KCl, 1 mmol/L $MgCl_2$, 5 mmol/L EGTA, 10 mmol/L HEPES, 5 mmol/L MgATP, pH 7.2) to break the patch membranes, followed by the measurement of the hERG current using a patch clamp amplifier (EPC-7 Plus, HEKA) via patch clamp software pClamp 10 (Molecular Devices Corporation). The pulse protocol involved a holding potential of −80 mV, a depolarizing pulse of +20 mV for 1.5 seconds and a repolarizing pulse of −50 mV for 1.5 seconds. After confirmation that a stable current waveform was obtained, each test compound was applied thereto.

Before the application and 10 minutes after the application, the peak value of tail current in the hERG current waveform was analyzed to calculate the ratio of the value 10 minutes after the application to the value before the application (relative value, %).

As a result, the test compounds of Examples 20 and 23 did not exhibit hERG inhibitory activity up to 300 μmol/L.

Test Example 9

In Vitro Micronucleus Test for Examining Presence or Absence of Genotoxicity

In order to examine the inducibility of the chromosomal aberrations by each test compound in cultured cells, the in vitro micronucleus test was carried out. This test was carried out by a short-time treatment method (in the presence and absence of a metabolic activation) and a 30-hour treatment method using Chinese hamster lung fibroblasts (CHL/IU cells). The concentration of the test compound was set to 1.00 mmol/L as the maximum dose with reference to the "Guidance on Genotoxicity Testing and Data Interpretation for Pharmaceuticals Intended for Human Use". Specimens were observed as to doses of 0.25, 0.50 and 1.00 mmol/L.

The cells were inoculated at $15 \times 10^4$ cells to a 60-mm dish (IWAKI) and precultured at 37° C. for 24 hours under 5% $CO_2$ using a MEM medium (Sigma-Aldrich Co., Ltd.) containing 10% newborn calf serum (Sigma-Aldrich Co., Ltd.) and 50 U/mL-50 µg/mL Penicillin-Streptomycin (Sigma-Aldrich Co., Ltd.). After the completion of the preculture, a vehicle (DMSO) or each test compound was added thereto. In the short-time treatment method, 6 hours after the culture, the cells were washed with PBS(−) (Sigma-Aldrich Co., Ltd.), and then, the medium was replaced with a fresh medium, followed by further culture for 24 hours. In the 30-hour treatment method, after the addition of the test compound, the cells were cultured for 30 hours. After the completion of the culture, the cells were dissociated using a 0.05% trypsin-EDTA solution (Sigma-Aldrich Co., Ltd.). After centrifugation, the supernatant was removed, and 3 mL of a 0.075 mol/L aqueous potassium chloride solution was added to the cells. After hypotonic treatment at room temperature for 5 minutes, the cells were fixed with an ice-cold fixing solution (methanol:acetic acid=19:1) to prepare a glass slide specimen (giemsa-stained (Merck)). Two thousand cells per dose were observed to measure the number of cells having the micronucleus. When the frequency of appearance of the micronucleus in the test compound group was significantly increased as compared with the vehicle control group, the test compound was confirmed to be positive. When this frequency of appearance was equivalent to that of the vehicle control, the test compound was confirmed to be negative.

As a result, the test compound of Example 20 was negative at a dose of 1 mmol/L or lower in both of the treatment methods.

Test Example 10

Measurement of Binding Ratio to Plasma Protein

Each test compound was added to human serum to prepare a 1 µg/mL spiked serum, which was then left standing at room temperature for 1 hour or longer. A filtrate (20 µL) was collected by a centrifugal ultrafiltration method (molecular weight cutoff: 10,000, 1500×g, 25° C., 10 min), then human serum and an internal standard solution (furosemide-acetonitrile solution) were added thereto. To the compound-spiked serum, PBS and an internal standard solution were added. Each mixture was stirred and then centrifuged, and the concentration in the supernatant was determined by LC-MS/MS.

The ratio of protein binding was determined according to the following calculation expression:

Ratio of protein binding (%)=(1−(Concentration of the filtrate)/(Concentration of the compound-spiked serum))×100

As a result, the test compounds of Examples 3, 5, 20, 23, 24, 25, 33 and 35 all had a ratio of protein binding of 80% or less.

Test Example 11

Inhibitory Effect on Liver Drug-Metabolizing Enzyme in Human

Pooled human liver microsomes were used. Substrates and their final concentrations as well as the positive controls and their final concentrations were as described in Tables 4 and 5. The reaction was carried out in a phosphate buffer solution (100 mmol/L, pH 7.4), and the final concentrations of the reaction system were set to 0.5 mg/mL human liver microsome protein, 1.55 mmol/L oxidized form of nicotinamide adenine dinucleotide phosphate (NADP+), 3.3 mmol/L glucose-6-phosphate, 3.3 mmol/L magnesium chloride and 0.4 Units/mL glucose-6-phosphate dehydrogenase (G6PDH). The final concentration of each compound in the reaction solution was set to 100 µM. Each of these reaction solutions was incubated at 37° C. for 30 minutes. Then, the substrates were added thereto and reacted at 37° C. for 10 minutes. The reaction was terminated by the addition of a 1.5-fold volume of an internal standard solution (acetonitrile solution containing 0.25 mmol/L dextrorphan and 2% formic acid). Then, the solution was centrifuged, and the concentration of metabolites in the supernatant was determined by LC-MS/MS.

The ratio of inhibitory activity by addition of the inhibitor was determined according to the following calculation expression:

Ratio of inhibitory activity (%)=(1−(Concentration of CYP metabolites in the presence of the test compound)/(Concentration of CYP metabolites in the absence of the test compound))×100

As a result, the test compounds of Examples 3, 9, 13, 17, 20, 23 and 24 all had a ratio of inhibitory activity of 30% or less.

TABLE 4

| Molecular species | Substrate name | Final concentration of addition (µmol/L) |
| --- | --- | --- |
| CYP1A2 | Phenacetin | 10 |
| CYP2C8 | Amodiaquine | 0.2 |
| CYP2C9 | Tolbutamide | 100 |
| CYP2C19 | (S)-Mephenytoin | 40 |
| CYP2D6 | (±)-Bufuralol | 4 |
| CYP3A4 | Midazolam | 1 |
| GYP3A4 | Testosterone | 5 |

TABLE 5

| Molecular species | Positive control | Final concentration of addition (µmol/L) |
| --- | --- | --- |
| CYP1A2 | Furafyline | 10 |
| CYP2C8 | Quercetin | 10 |
| CYP2C9 | Tienilic acid | 1 |
| CYP2C19 | Ticlopidine | 1 |
| CYP2D6 | Paroxetine | 2 |
| CYP3A4 | Verapamil | 10 |

Next, the present invention will be described with reference to Reference Examples and Examples. However, the present invention is not intended to be limited by them.

The silica gel column chromatography is flash column chromatography, and its carrier is B.W. silica gel BW-300 from Fuji Silysia Chemical Ltd., unless otherwise specified. The carrier for basic silica gel column chromatography is silica gel DNH from Fuji Silysia Chemical Ltd., unless otherwise specified.

The mixing ratios for an eluent are indicated by volume ratio.

PLC plate silica gel $60F_{254}$ manufactured by Merck Japan Ltd. was used for preparative silica gel thin-layer chromatography. Celpure manufactured by Advanced Minerals Corp. was used.

Each abbreviation in each Reference Example or Example is as defined below.
ESI: Electrospray Ionization
Et: Ethyl
IPE: Diisopropyl ether
Me: Methyl
THP: Tetrahydro-2H-pyran-2-yl
TBS: t-Butyldimethylsilyl
s: Singlet
brs: Broad singlet
d: Doublet
dd: Double doublet
dt: Double triplet
m: Multiplet
t: Triplet For NMR spectra, for example, the description [1.81], 1.82 (3H, s) means that peaks derived from each diastereomer in a diastereomeric mixture are observed as singlets at 1.81 and 1.82 and the total number of protons is 3H.

Reference Example 1

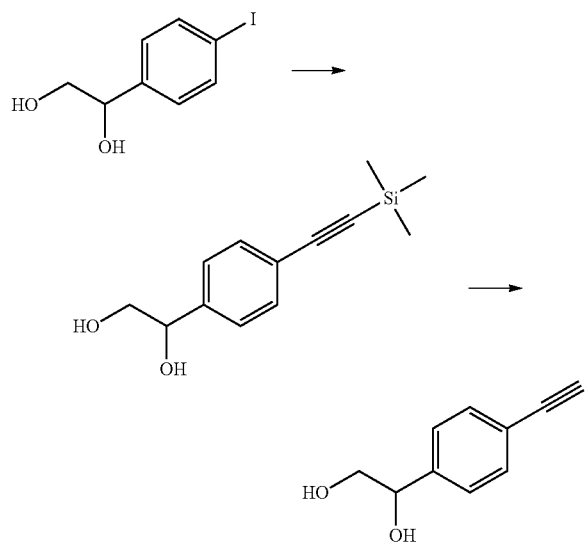

To a mixture of 1.00 g of 1-(4-iodophenyl)ethane-1,2-diol, 10 mL of tetrahydrofuran, 132 mg of bis-triphenylphosphinepalladium(II) dichloride, 72 mg of copper(I) iodide, and 1.5 mL of trimethylsilylacetylene, 2.6 mL of triethylamine was added under a nitrogen atmosphere and under ice cooling, and the resulting mixture was stirred at room temperature for 1 hour and 30 minutes. Ethyl acetate and a saturated aqueous solution of ammonium chloride were added to the reaction mixture, and the resulting mixture was neutralized with 1 mol/L hydrochloric acid. The organic layer was separated, washed with a saturated aqueous solution of sodium chloride, and then dried over anhydrous sodium sulfate. The solvent was distilled off under reduced pressure, 15 mL of methanol and 104 mg of potassium carbonate were added to the residue, and the resulting mixture was stirred at room temperature for 1 hour and 30 minutes. Water was added to the reaction mixture, the resulting mixture was neutralized with 1 mol/L hydrochloric acid, ethyl acetate and Celpure were added, and then the insoluble material was filtered off. The organic layer of the filtrate was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=70:30] to obtain a light brown solid. IPE was added thereto, and the solid was collected by filtration to obtain 369 mg of 1-(4-ethynylphenyl)ethane-1,2-diol as a light brown solid. $^1$H-NMR (400 MHz, CDCl$_3$) δ: 2.01 (1H, dd, J=7.1, 4.9 Hz), 2.54 (1H, d, J=3.4 Hz), 3.08 (1H, s), 3.59-3.69 (1H, m), 3.73-3.83 (1H, m), 4.80-4.89 (1H, m), 7.34 (2H, d, J=8.0 Hz), 7.49 (2H, d, J=8.0 Hz)

Reference Example 2

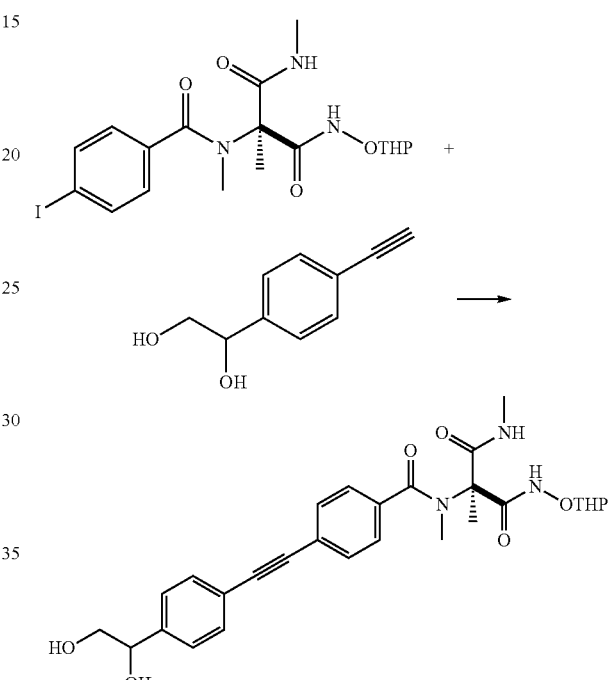

To a mixture of 146 mg of 1-(4-ethynylphenyl)ethane-1,2-diol, 150 mg of (2S)-2-((4-iodobenzoyl)(methyl)amino)-N,2-dimethyl-N'-(tetrahydro-2H-pyran-2-yloxy)malonamide, 21 mg of bis-triphenylphosphinepalladium(II) dichloride, 11 mg of copper(I) iodide, and 1.5 mL of tetrahydrofuran, 0.25 mL of triethylamine was added under a nitrogen atmosphere and under ice cooling, and the resulting mixture was stirred at the same temperature for 2 hours. A saturated aqueous solution of ammonium chloride and ethyl acetate were added to the reaction mixture, the pH was adjusted to 6.4 with 1 mol/L hydrochloric acid, and the insoluble material was filtered off. The organic layer of the filtrate was separated, and the aqueous layer was extracted with ethyl acetate. The organic layer was combined with the extract and dried over anhydrous sodium sulfate. The solvent was distilled off under reduced pressure, and the obtained residue was purified by silica gel column chromatography [eluent; acetone:chloroform=50:50→60:40] to obtain 143 mg of (2S)-2-((4-((4-(1,2-dihydroxyethyl)phenyl)ethynyl)benzoyl)(methyl)amino)-N,2-dimethyl-N'-(tetrahydro-2H-pyran-2-yloxy)malonamide as a light brown foamy solid.

$^1$H-NMR (400 MHz, CDCl$_3$) δ: 1.45-1.70 (3H, m), 1.71-1.93 (3H, m), [1.81], 1.82 (3H, s), 2.11-2.21 (1H, m), 2.66-2.76 (1H, m), [2.85], 2.86 (3H, d, J=4.3 Hz), [3.17], 3.20 (3H, s), 3.54-3.70 (2H, m), 3.74-3.83 (1H, m), [3.83-3.92], 3.98-4.08 (1H, m), 4.79-4.89 (1H, m), 4.92-5.04 (1H, m), 7.36 (2H, d, J=8.3 Hz), 7.45-7.59 (6H, m), [6.94-7.05], 7.60-7.67 (1H, m), [10.10], 10.51 (1H, s)

Reference Example 3

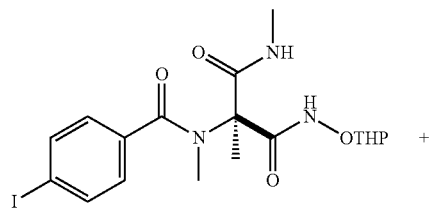

(methyl)amino)-N,2-dimethyl-N'-(tetrahydro-2H-pyran-2-yloxy)malonamide was obtained as a yellow oil.

$^1$H-NMR (400 MHz, CDCl$_3$) δ: 1.51-1.66 (3H, m), 1.71 (1H, d, J=6.4 Hz), 1.75-1.91 (3H, m), [1.81], 1.82 (3H, s), 2.82-2.90 (3H, m), [3.17], 3.20 (3H, s), 3.52-3.70 (3H, m), 3.75-3.83 (2H, m), 3.83-4.06 (1H, m), 4.59 (2H, s), 4.94-5.03 (1H, m), 7.34 (2H, d, J=8.0 Hz), 7.48-7.55 (4H, m), 7.58 (2H, d, J=8.3 Hz), [7.00-7.09], 7.61-7.71 (1H, m), [10.16], 10.56 (1H, s)

Reference Example 4

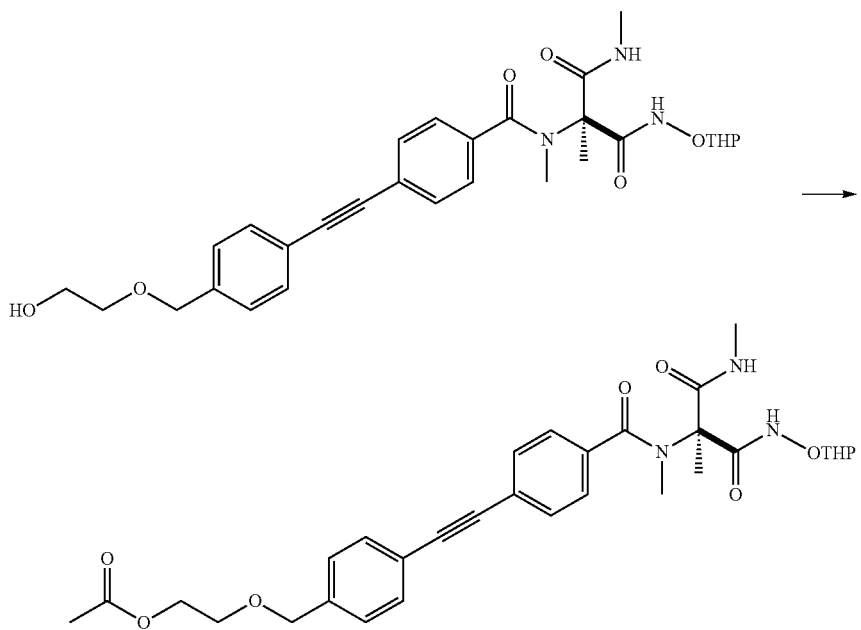

-continued

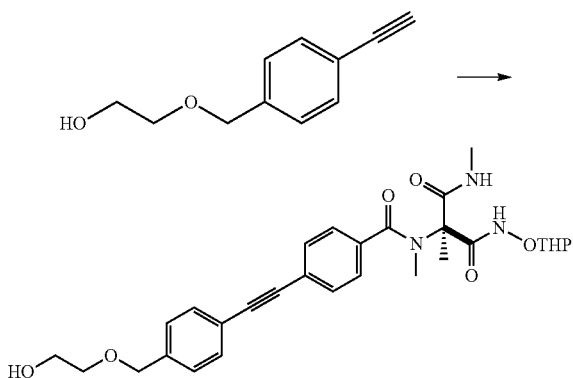

In the same manner as in Reference Example 2, from 144 mg of 2-((4-ethynylbenzyl)oxy)ethanol and 100 mg of (2S)-2-((4-iodobenzoyl)(methyl)amino)-N,2-dimethyl-N'-(tetrahydro-2H-pyran-2-yloxy)malonamide, 123 mg of (2S)-2-((4-((4-((2-hydroxyethoxy)methyl)phenyl)ethynyl)benzoyl)

To 157 mg of (2S)-2-((4-((4-((2-hydroxyethoxy)methyl)phenyl)ethynyl)benzoyl)(methyl)amino)-N,2-dimethyl-N'-(tetrahydro-2H-pyran-2-yloxy)malonamide, 1.5 mL of pyridine and 82 μL of acetic anhydride were added, and the resulting mixture was stirred at room temperature for 2 hours. At the same temperature, 27 μL of acetic anhydride was added to the reaction mixture, and the resulting mixture was stirred for 1 hour and 30 minutes. To the reaction mixture, 1.0 mL of methanol, ethyl acetate, and water were successively added. The organic layer was separated, washed successively with 1 mol/L hydrochloric acid, a saturated aqueous solution of sodium hydrogen carbonate, and a saturated aqueous solution of sodium chloride, and then dried over anhydrous sodium sulfate. The solvent was distilled off under reduced pressure to obtain 144 mg of 2-((4-((4-((methyl((1S)-1-methyl-2-(methylamino)-2-oxo-1-(((tetrahydro-2H-pyran-2-yloxy)amino)carbonyl)ethyl)amino)carbonyl)phenyl)ethynyl)benzyl)oxy)ethyl acetate as a yellow foamy solid.

$^1$H-NMR (400 MHz, CDCl$_3$) δ: 1.47-1.63 (3H, m), 1.75-1.90 (3H, m), [1.82], 1.83 (3H, s), 2.10 (3H, s), [2.86], 2.87

(3H, d, J=4.3 Hz), [3.17], 3.20 (3H, s), 3.62-3.67 (1H, m), 3.67-3.73 (2H, m), 3.92-4.08 (1H, m), 4.24-4.30 (2H, m), 4.59 (2H, s), 4.94-5.03 (1H, m), 7.34 (2H, d, J=8.3 Hz), 7.48-7.56 (4H, m), 7.58 (2H, d, J=8.0 Hz) [6.96-7.03], 7.61-7.69 (1H, m), [10.08], 10.49 (1H, s)

Reference Example 5

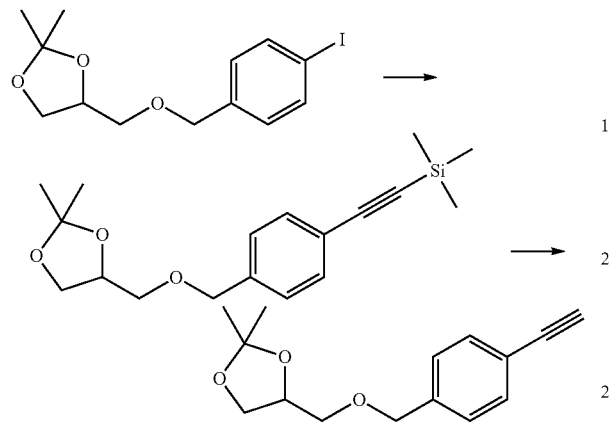

In the same manner as in Reference Example 1, from 550 mg of 4-(((4-iodobenzyl)oxy)methyl)-2,2-dimethyl-1,3-dioxolane, 352 mg of 4-(((4-ethynylbenzyl)oxy)methyl)-2,2-dimethyl-1,3-dioxolane was obtained as a yellow oil.

$^{1}$H-NMR (400 MHz, CDCl$_3$) δ: 1.37 (3H, s), 1.42 (3H, s), 3.07 (1H, s), 3.48 (1H, dd, J=9.8, 5.4 Hz), 3.55 (1H, dd, J=9.6, 5.8 Hz), 3.74 (1H, dd, J=8.3, 6.4 Hz), 4.06 (1H, dd, J=8.3, 6.6 Hz), 4.25-4.36 (1H, m), 4.55 (1H, d, J=12.5 Hz), 4.59 (1H, d, J=12.5 Hz), 7.29 (2H, d, J=8.1 Hz), 7.47 (2H, d, J=8.1 Hz)

Reference Example 6

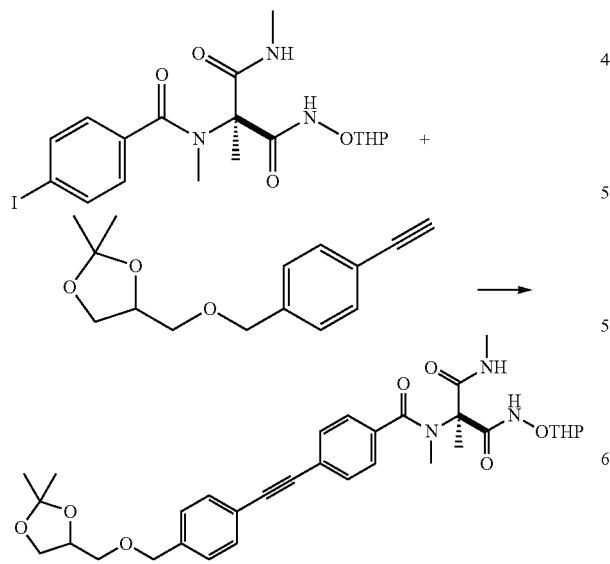

In the same manner as in Reference Example 2, from 350 mg of 4-(((4-ethynylbenzyl)oxy)methyl)-2,2-dimethyl-1,3-dioxolane and 154 mg of (2S)-2-((4-iodobenzoyl)(methyl) amino)-N,2-dimethyl-N'-(tetrahydro-2H-pyran-2-yloxy) malonamide, 236 mg of (2S)-2-((4-((4-(((2,2-dimethyl-1,3-dioxolan-4-yl)methoxy)methyl)phenyl)ethynyl)benzoyl) (methyl)amino)-N,2-dimethyl-N'-(tetrahydro-2H-pyran-2-yloxy)malonamide was obtained as a brown oil.

$^{1}$H-NMR (400 MHz, CDCl$_3$) δ: 1.38 (3H, s), 1.43 (3H, s), 1.48-1.68 (3H, m), 1.70-1.92 (3H, m), [1.82], 1.83 (3H, s), [2.85], 2.87 (3H, d, J=4.3 Hz), [3.17], 3.20 (3H, s), 3.50 (1H, dd, J=9.8, 5.4 Hz), 3.57 (1H, dd, J=9.8, 5.8 Hz), [3.54-3.61], 3.63-3.69 (1H, m), 3.76 (1H, dd, J=8.3, 6.6 Hz), [3.84-3.92], 3.98-4.06 (1H, m), 3.98-4.15 (1H, m), 4.28-4.37 (1H, m), 4.57 (1H, d, J=12.4 Hz), 4.62 (1H, d, J=12.2 Hz), 4.93-5.05 (1H, m), 7.34 (2H, d, J=8.0 Hz), 7.48-7.54 (4H, m), 7.58 (2H, d, J=8.0 Hz), [6.96-7.04], 7.61-7.71 (1H, m), [10.08], 10.50 (1H, s)

Reference Example 7

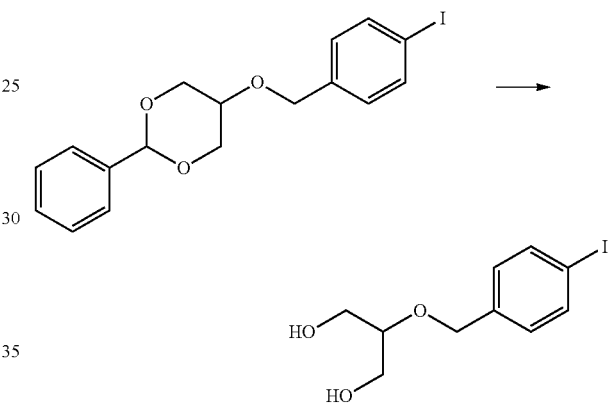

To a mixture of 1.71 g of 5-((4-iodobenzyl)oxy)-2-phenyl-1,3-dioxane, 1.7 mL of methanol, and 15.3 mL of dichloromethane, 163 mg of p-toluenesulfonic acid monohydrate was added under ice cooling, and the resulting mixture was stirred at room temperature for 3 hours. To the reaction mixture, 13.6 mL of methanol was added, the resulting mixture was stirred for 2 hours, then 1.1 mL of triethylamine was added, and the solvent was distilled off under reduced pressure. The obtained residue was purified by silica gel column chromatography [eluent; ethyl acetate: hexane=70:30→90:10], IPE was added, and the solid material was collected by filtration to obtain 895 mg of 2-((4-iodobenzyl)oxy)propane-1,3-diol as a white solid.

$^{1}$H-NMR (400 MHz, CDCl$_3$) δ: 1.91-1.97 (2H, m), 3.56-3.64 (1H, m), 3.69-3.88 (4H, m), 4.61 (2H, s), 7.11 (2H, d, J=7.8 Hz), 7.66-7.74 (2H, m)

Reference Example 8

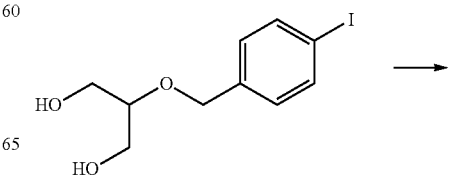

-continued

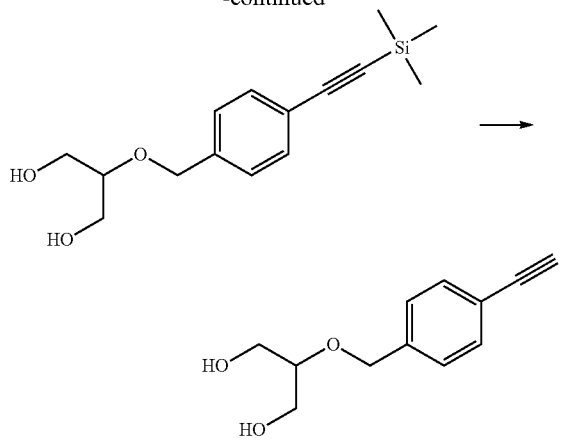

In the same manner as in Reference Example 1, from 1.01 g of 2-((4-iodobenzyl)oxy)propane-1,3-diol, 243 mg of 2-((4-ethynylbenzyl)oxy)propane-1,3-diol was obtained as a yellow solid.

$^1$H-NMR (400 MHz, CDCl$_3$) δ: 1.93-1.96 (2H, m), 3.08 (1H, s), 3.58-3.63 (1H, m), 3.72-3.85 (4H, m), 4.67 (2H, s), 7.32 (2H, d, J=7.8 Hz), 7.49 (2H, d, J=8.1 Hz)

Reference Example 9

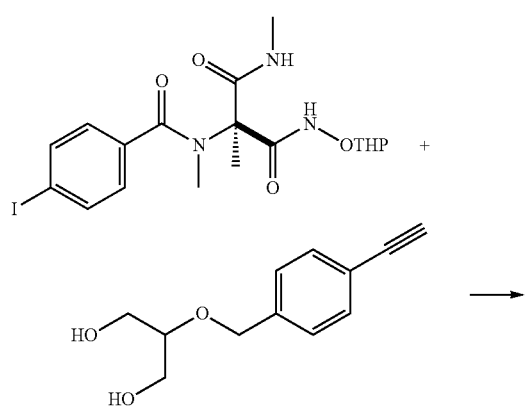

In the same manner as in Reference Example 2, from 150 mg of (2S)-2-((4-iodobenzoyl)(methyl)amino)-N,2-dimethyl-N'-(tetrahydro-2H-pyran-2-yloxy)malonamide and 185 mg of 2-((4-ethynylbenzyl)oxy)propane-1,3-diol, 205 mg of (2S)-2-((4-((4-((2-hydroxy-1-(hydroxymethyl)ethoxy)methyl)phenyl)ethynyl)benzoyl)(methyl)amino)-N,2-dimethyl-N'-(tetrahydro-2H-pyran-2-yloxy)malonamide was obtained as a yellow solid.

$^1$H-NMR (400 MHz, CDCl$_3$) δ: 1.52-1.63 (3H, m), 1.75-1.87 (3H, m), [1.81], 1.83 (3H, s), 1.93-2.00 (2H, m), 2.84-2.88 (3H, m), [3.17], 3.20 (3H, s), 3.59-3.66 (2H, m), 3.74-3.88 (5H, m), 4.69 (2H, s), [4.96], 5.00 (1H, d, J=2.9 Hz), 7.36 (2H, d, J=8.3 Hz), 7.48-7.61 (6H, m), [7.00], 7.63 (1H, s), [10.10], 10.51 (1H, s)

Reference Example 10

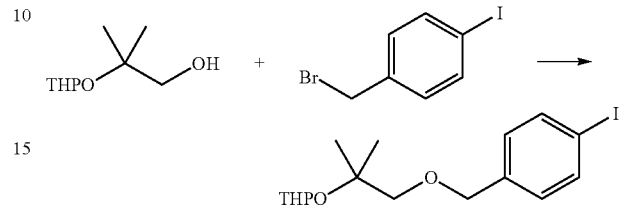

To a stirred 10 mL of N,N-dimethylformamide, 424 mg of a 60% suspension of sodium hydride in mineral oil was added under ice cooling, and then a solution of 1.50 g of 2-methyl-2-(tetrahydro-2H-pyran-2-yloxy)propan-1-ol in 10 mL of N,N-dimethylformamide was added at the same temperature. The resulting mixture was stirred at room temperature for 30 minutes, and then 2.10 g of 4-iodobenzyl bromide was added to the reaction mixture under ice cooling. The resulting mixture was stirred at room temperature for 1 hour and 30 minutes, allowed to stand at room temperature for 15 hours, and then stirred for 45 minutes. The reaction mixture was cooled under ice cooling, water and ethyl acetate were added, the resulting mixture was neutralized with 1 mol/L hydrochloric acid, and the insoluble material was filtered off. The organic layer of the filtrate was separated, and the solvent was distilled off under reduced pressure. The obtained residue was purified by silica gel column chromatography [eluent; ethyl acetate:hexane=10:90] to obtain 1.11 g of 2-(2-((4-iodobenzyl)oxy)-1,1-dimethylethoxy)tetrahydro-2H-pyran as a colorless oil.

$^1$H-NMR (400 MHz, CDCl$_3$) δ: 1.26 (6H, s), 1.49-1.51 (4H, m), 1.62-1.68 (1H, m), 1.80-1.88 (1H, m), 3.34 (1H, d, J=9.5 Hz), 3.39 (1H, d, J=9.5 Hz), 3.41-3.45 (1H, m), 3.91-3.96 (1H, m), 4.50 (2H, s), 4.80-4.83 (1H, m), 7.09 (2H, d, J=8.5 Hz), 7.67 (2H, dd, J=6.6, 1.7 Hz)

Reference Example 11

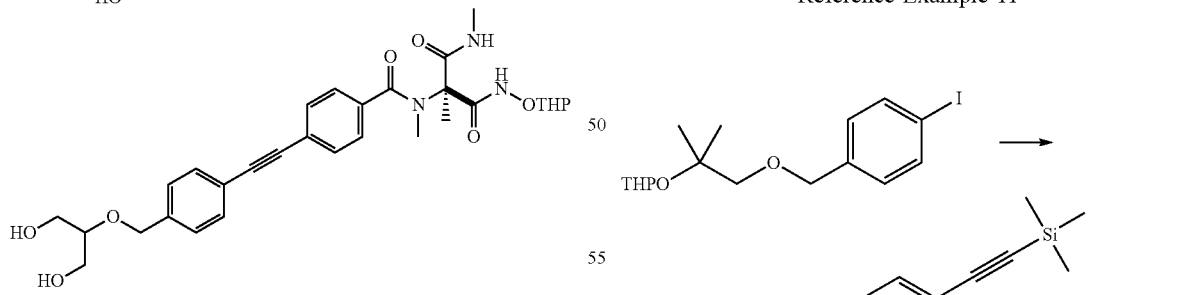

In the same manner as in Reference Example 1, from 1.11 g of 2-(2-((4-iodobenzyl)oxy)-1,1-dimethylethoxy)tetrahydro-2H-pyran, 612 mg of 2-(2-((4-ethynylbenzyl)oxy)-1,1-dimethylethoxy)tetrahydro-2H-pyran was obtained as a colorless oil.

¹H-NMR (400 MHz, CDCl₃) δ: 1.27 (6H, s), 1.46-1.54 (4H, m), 1.63-1.68 (1H, m), 1.80-1.88 (1H, m), 3.06 (1H, s), 3.34-3.45 (3H, m), 3.92-3.97 (1H, m), 4.56 (2H, s), 4.81-4.83 (1H, m), 7.29 (2H, d, J=7.8 Hz), 7.47 (2H, d, J=8.0 Hz)

Reference Example 12

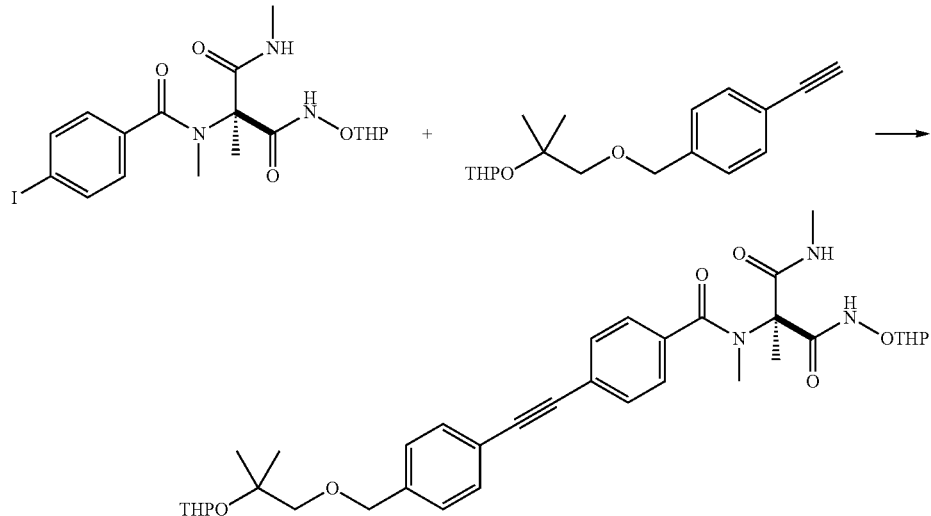

In the same manner as in Reference Example 2, from 346 mg of 2-(2-((4-ethynylbenzyl)oxy)-1,1-dimethylethoxy)tetrahydro-2H-pyran and 200 mg of (2S)-2-((4-iodobenzoyl)(methyl)amino)-N,2-dimethyl-N'-(tetrahydro-2H-pyran-2-yloxy)malonamide, 264 mg of (2S)—N,2-dimethyl-2-(methyl(4-((4-((2-methyl-2-(tetrahydro-2H-pyran-2-yloxy)propoxy)methyl)phenyl)ethynyl)benzoyl)amino)-N'-(tetrahydro-2H-pyran-2-yloxy)malonamide was obtained as a yellow oil.

¹H-NMR (400 MHz, CDCl₃) δ: 1.28 (6H, s), 1.44-1.92 (12H, m), [1.82], 1.88 (3H, s), [2.85], 2.86 (3H, d, J=4.4 Hz), [3.17], 3.20 (3H, s), 3.38-3.49 (3H, m), [3.52-3.60], 3.63-3.71 (1H, m), 3.83-4.06 (2H, m), 4.58 (2H, s), 4.81-4.87 (1H, m), [4.94-4.98], 4.98-5.02 (1H, m), 7.34 (2H, d, J=8.0 Hz), 7.48-7.56 (4H, m), 7.58 (2H, d, J=8.0 Hz), [6.94-7.04], 7.62-7.66 (1H, m), [10.10], 10.51 (1H, s)

Reference Example 13

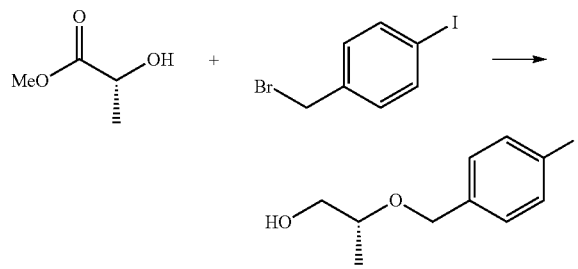

To a mixture of 742 mg of 4-iodobenzyl bromide and 8.0 mL of N,N-dimethylformamide, 240 mg of a 60% suspension of sodium hydride in mineral oil was added under a nitrogen atmosphere and under ice cooling, and the resulting mixture was stirred at the same temperature for 1 hour. To the reaction mixture, 520 mg of (R)-(+)-methyl lactate and 240 mg of a 60% suspension of sodium hydride in mineral oil were added, and the resulting mixture was stirred at the same temperature for 2 hours. Water and ethyl acetate were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=15:85] to obtain a 518 mg of a colorless oil.

To 518 mg of the obtained colorless oil, 5.0 mL of dichloromethane was added, then 6.5 mL of a 1 mol/L solution of diisobutylaluminum hydride in toluene was added to the reaction mixture under a nitrogen atmosphere at −78° C., and then the resulting mixture was stirred at the same temperature for 20 minutes. To the reaction mixture, 1 mL of an aqueous solution of Rochelle salt was added, then diethyl ether and an aqueous solution of Rochelle salt were added, and the resulting mixture was stirred at room temperature for 2 hours. The organic layer was separated, washed with a saturated aqueous solution of sodium chloride, and then dried over anhydrous magnesium sulfate. The solvent was distilled off under reduced pressure to obtain a colorless oil.

To the obtained colorless oil, 5.0 mL of ethanol was added, then 92 mg of sodium borohydride was added under a nitrogen atmosphere and under ice cooling, and then the resulting mixture was stirred at the same temperature for 45 minutes. A saturated aqueous solution of ammonium chloride and ethyl acetate were added to the reaction mixture. The organic layer was separated, washed with a saturated aqueous solution of sodium chloride, and then dried over anhydrous sodium sulfate. The solvent was distilled off under reduced pressure to obtain 456 mg of (2R)-2-((4-iodobenzyl)oxy)propan-1-ol as a colorless oil.

¹H-NMR (400 MHz, CDCl₃) δ: 1.17 (3H, d, J=6.1 Hz), 1.94-2.02 (1H, m), 3.47-3.57 (1H, m), 3.57-3.78 (2H, m), 4.44 (1H, d, J=12.0 Hz), 4.59 (1H, d, J=12.0 Hz), 7.10 (2H, d, J=7.8 Hz), 7.68 (2H, d, J=8.1 Hz)

Reference Example 14

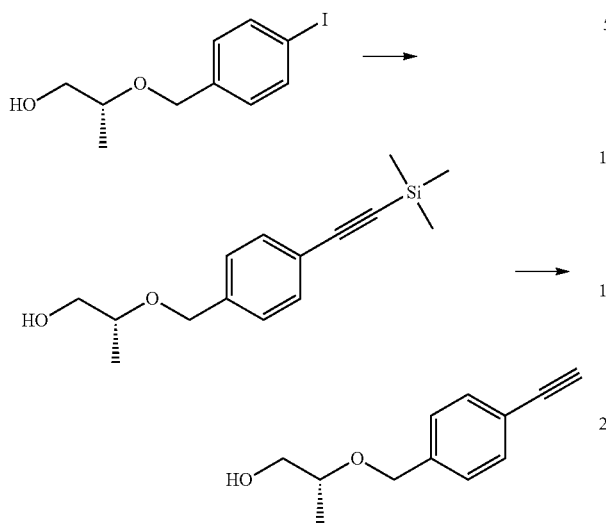

In the same manner as in Reference Example 1, from 456 mg of (2R)-2-((4-iodobenzyl)oxy)propan-1-ol, 230 mg of (2R)-2-((4-ethynylbenzyl)oxy)propan-1-ol was obtained as a brown oil.

$^1$H-NMR (400 MHz, CDCl$_3$) δ: 1.18 (3H, d, J=6.3 Hz), 1.94-2.03 (1H, m), 3.07 (1H, s), 3.49-3.58 (1H, m), 3.58-3.74 (2H, m), 4.50 (1H, d, J=12.0 Hz), 4.65 (1H, d, J=12.0 Hz), 7.31 (2H, d, J=8.1 Hz), 7.48 (2H, d, J=8.3 Hz)

Reference Example 15

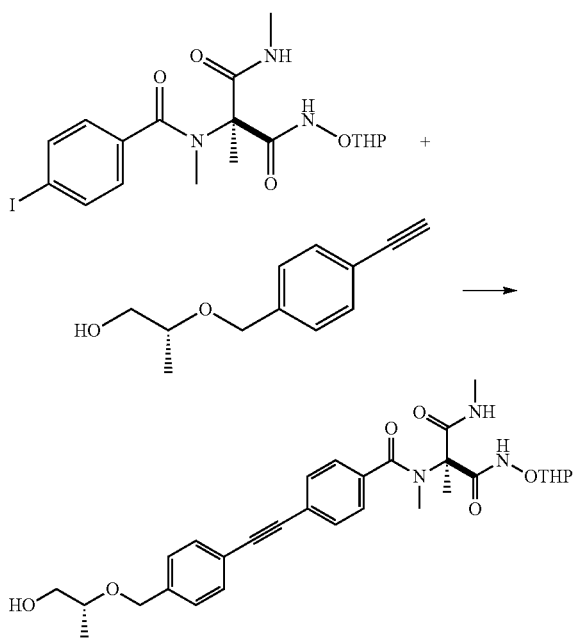

In the same manner as in Reference Example 2, from 199 mg of (2R)-2-((4-ethynylbenzyl)oxy)propan-1-ol and 200 mg of (2S)-2-((4-iodobenzoyl)(methyl)amino)-N,2-dimethyl-N'-(tetrahydro-2H-pyran-2-yloxy)malonamide, 137 mg of (2S)-2-((4-((4-(((1R)-2-hydroxy-1-methyl ethoxy)methyl)phenyl)ethynyl)benzoyl)(methyl)amino)-N, 2-dimethyl-N'-(tetrahydro-2H-pyran-2-yloxy)malonamide was obtained as a brown foamy solid.

$^1$H-NMR (400 MHz, CDCl$_3$) δ: 1.20 (3H, d, J=6.4 Hz), 1.50-1.67 (3H, m), 1.76-1.91 (3H, m), [1.82], 1.83 (3H, s), 1.96-2.03 (1H, m), 2.83-2.90 (3H, m), [3.17], 3.20 (3H, s), 3.49-3.76 (4H, m), 3.84-4.08 (1H, m), 4.52 (1H, d, J=11.7 Hz), 4.68 (1H, d, J=12.0 Hz), 4.93-5.03 (1H, m), 7.35 (2H, d, J=8.0 Hz), 7.49-7.56 (4H, m), 7.58 (2H, d, J=8.0 Hz), [6.97-7.02], 7.61-7.67 (1H, m), [10.09], 10.51 (1H, s)

Reference Example 16

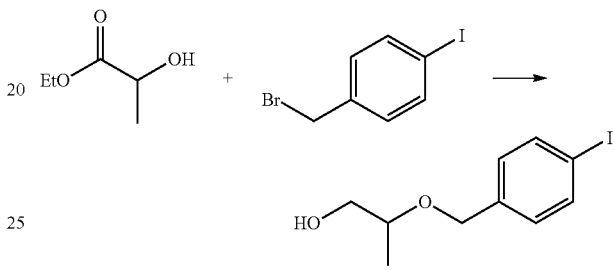

In the same manner as in Reference Example 13, from 266 mg of (S)-(−)-ethyl lactate, 404 mg of (2S)-2-((4-iodobenzyl)oxy)propan-1-ol was obtained as a colorless oil.

$^1$H-NMR (400 MHz, CDCl$_3$) δ: 1.17 (3H, d, J=6.1 Hz), 1.95 (1H, s), 3.45-3.56 (1H, m), 3.59-3.72 (2H, m), 4.44 (1H, d, J=12.0 Hz), 4.59 (1H, d, J=11.7 Hz), 7.10 (2H, d, J=7.8 Hz), 7.68 (2H, d, J=8.3 Hz)

Reference Example 17

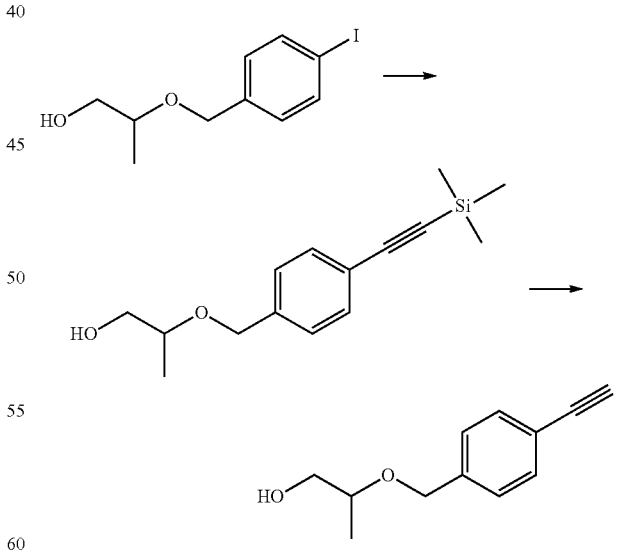

In the same manner as in Reference Example 1, from 404 mg of (2S)-2-((4-iodobenzyl)oxy)propan-1-ol, 172 mg of (2S)-2-((4-ethynylbenzyl)oxy)propan-1-ol was obtained as a brown oil.

$^1$H-NMR (400 MHz, CDCl$_3$) δ: 1.18 (3H, d, J=6.1 Hz), 1.95 (1H, s), 3.07 (1H, s), 3.48-3.58 (1H, m), 3.58-3.74 (2H, m), 4.50 (1H, d, J=12.0 Hz), 4.65 (1H, d, J=12.2 Hz), 7.31 (2H, d, J=8.1 Hz), 7.48 (2H, d, J=8.0 Hz)

Reference Example 18

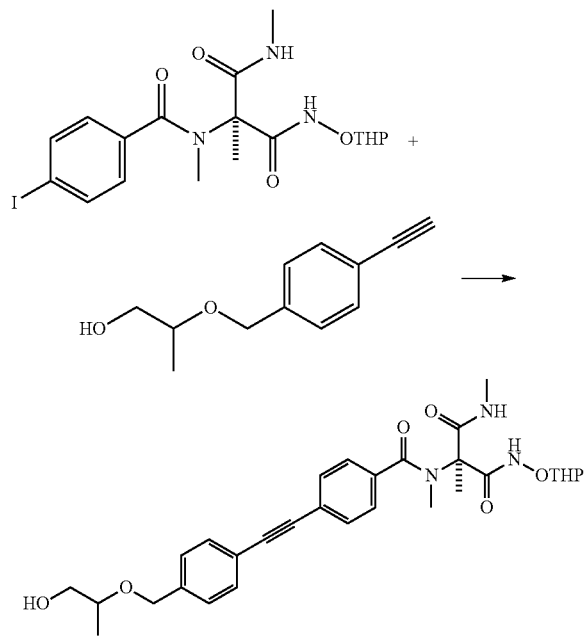

In the same manner as in Reference Example 2, from 172 mg of (2S)-2-((4-ethynylbenzyl)oxy)propan-1-ol and 110 mg of (2S)-2-((4-iodobenzoyl)(methyl)amino)-N,2-dimethyl-N'-(tetrahydro-2H-pyran-2-yloxy)malonamide, 151 mg of (2S)-2-((4-((4-(((1S)-2-hydroxy-1-methylethoxy)methyl)phenyl)ethynyl)benzoyl)(methyl)amino)-N,2-dimethyl-N'-(tetrahydro-2H-pyran-2-yloxy)malonamide was obtained as a brown foamy solid.

$^1$H-NMR (400 MHz, CDCl$_3$) δ: 1.20 (3H, d, J=6.4 Hz), 1.43-1.70 (3H, m), 1.71-1.95 (3H, in), [1.81], 1.83 (3H, s), 1.95-2.02 (1H, m), 2.80-2.93 (3H, m), [3.17], 3.20 (3H, s), 3.48-3.76 (4H, m), 3.82-4.07 (1H, m), 4.52 (1H, d, J=12.0 Hz), 4.67 (1H, d, J=12.2 Hz), 4.93-5.04 (1H, m), 7.35 (2H, d, J=7.8 Hz), 7.47-7.56 (4H, m), 7.58 (2H, d, J=8.3 Hz), [6.96-7.04], 7.62-7.68 (1H, m), [10.07], 10.49 (1H, s)

Reference Example 19

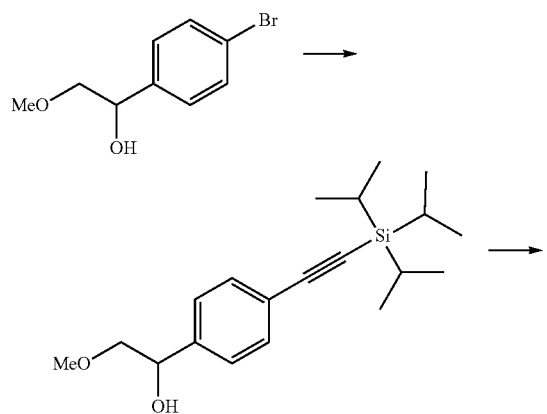

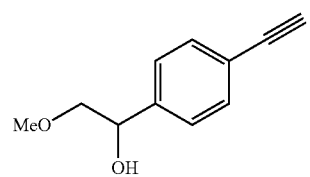

To a mixture of 200 mg of 1-(4-bromophenyl)-2-methoxyethanol, 61 mg of bis-triphenylphosphinepalladium (II) dichloride, and 33 mg of copper(I) iodide, 2.0 mL of n-butyl acetate, 0.97 mL of triisopropylsilylacetylene and 1.2 mL of triethylamine were added under a nitrogen atmosphere, and the resulting mixture was stirred under reflux for 1 hour. The reaction mixture was cooled, ethyl acetate and water were added, and the pH was adjusted to 5.1 with 6 mol/L hydrochloric acid, and then the insoluble material was filtered off. The organic layer of the filtrate was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=15:85] to obtain 143 mg of a brown oil.

To 143 mg of the obtained brown oil, 1.5 mL of tetrahydrofuran was added, then 0.65 mL of a 1 mol/L solution of tetra-n-butylammonium fluoride in tetrahydrofuran was added under ice cooling, and the resulting mixture was stirred at the same temperature for 30 minutes and then at room temperature for 1 hour. A saturated aqueous solution of ammonium chloride and water were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=35:65] to obtain 69 mg of 1-(4-ethynylphenyl)-2-methoxyethanol as a yellow oil.

$^1$H-NMR (400 MHz, CDCl$_3$) δ: 2.74-2.79 (1H, m), 3.07 (1H, s), 3.37-3.46 (1H, m), 3.43 (3H, s), 3.52-3.56 (1H, m), 4.86-4.94 (1H, m), 7.35 (2H, d, J=8.5 Hz), 7.48 (2H, d, J=8.1 Hz)

Reference Example 20

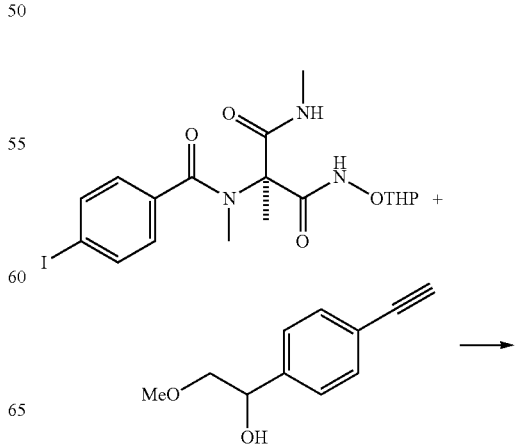

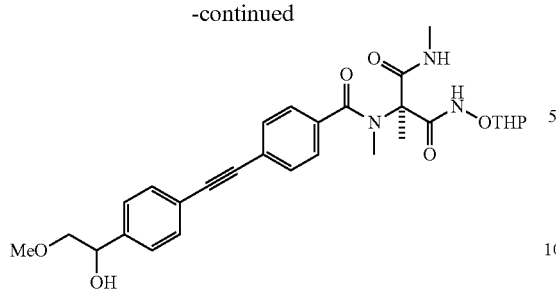

In the same manner as in Reference Example 2, from 69 mg of 1-(4-ethynylphenyl)-2-methoxyethanol and 100 mg of (2S)-2-((4-iodobenzoyl)(methyl)amino)-N,2-dimethyl-N'-(tetrahydro-2H-pyran-2-yloxy)malonamide, 114 mg of (2S)-2-((4-((4-(1-hydroxy-2-methoxyethyl)phenyl)ethynyl)benzoyl)(methyl)amino)-N,2-dimethyl-N'-(tetrahydro-2H-pyran-2-yloxy)malonamide was obtained as a yellow foamy solid.

$^1$H-NMR (400 MHz, CDCl$_3$) δ: 1.75-1.91 (3H, m), 1.51-1.70 (3H, m), [1.81], 1.82 (3H, s), 2.86 (3H, d, J=4.4 Hz), [3.17], 3.20 (3H, s), 3.33 (3H, s), 3.54-3.72 (3H, m), 3.95-4.07 (1H, m), 4.33 (1H, dd, J=7.7, 4.3 Hz), 4.94-5.03 (1H, m), 7.31 (2H, d, J=8.3 Hz), 7.49-7.61 (6H, m), [6.98-7.05], 7.61-7.68 (1H, m), [10.11], 10.52 (1H, s)

Reference Example 21

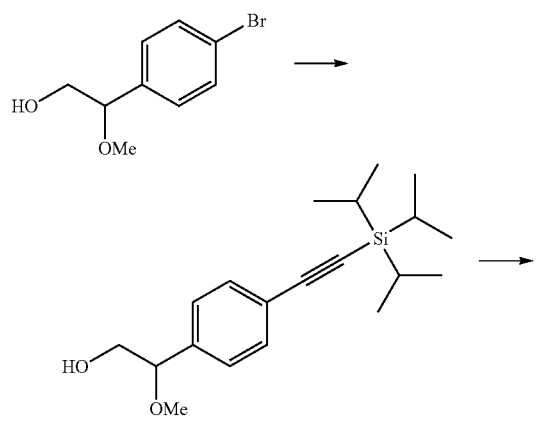

In the same manner as in Reference Example 19, from 170 mg of 2-(4-bromophenyl)-2-methoxyethanol, 80 mg of 2-(4-ethynylphenyl)-2-methoxyethanol was obtained as a colorless oil.

$^1$H-NMR (400 MHz, CDCl$_3$) δ: 3.08 (1H, s), 3.31 (3H, s), 3.56-3.68 (2H, m), 4.29-4.32 (1H, m), 7.27 (2H, d, J=8.3 Hz), 7.50 (2H, d, J=8.3 Hz)

Reference Example 22

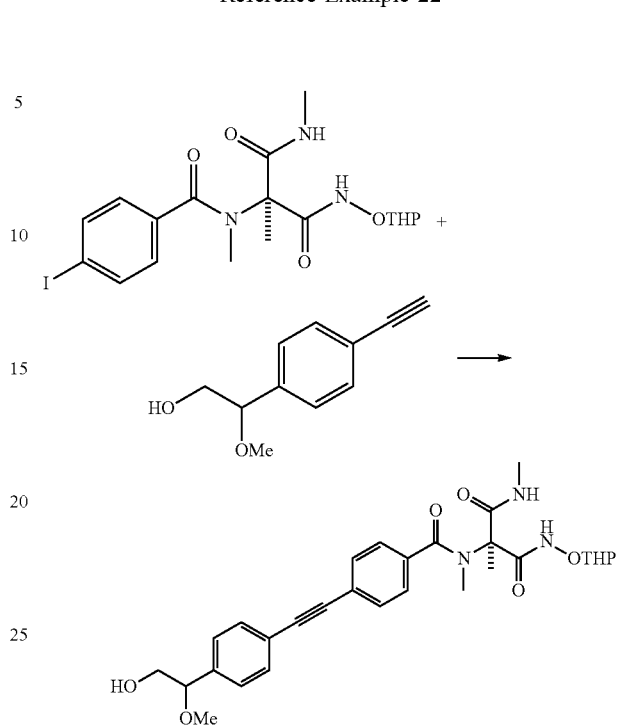

In the same manner as in Reference Example 2, from 72 mg of 2-(4-ethynylphenyl)-2-methoxyethanol and 100 mg of (2S)-2-((4-iodobenzoyl)(methyl)amino)-N,2-dimethyl-N'-(tetrahydro-2H-pyran-2-yloxy)malonamide, 73 mg of (2S)-2-((4-((4-(2-hydroxy-1-methoxyethyl)phenyl)ethynyl)benzoyl)(methyl)amino)-N,2-dimethyl-N'-(tetrahydro-2H-pyran-2-yloxy)malonamide was obtained as a yellow foamy solid.

$^1$H-NMR (400 MHz, CDCl$_3$) δ: 1.44-1.70 (3H, m), 1.74-1.93 (3H, m), [1.82], 1.83 (3H, s), 2.78 (1H, d, J=2.4 Hz), 2.83-2.90 (3H, m), [3.17], 3.20 (3H, s), 3.38-3.49 (1H, m), 3.45 (3H, s), 3.54-3.72 (1H, m), 3.56 (1H, dd, J=9.8, 3.2 Hz), 3.84-4.08 (1H, m), 4.89-4.95 (1H, m), 4.95-5.04 (1H, m), 7.39 (2H, d, J=8.0 Hz), 7.48-7.56 (4H, m), 7.58 (2H, d, J=8.5 Hz), [6.97-7.04], 7.61-7.68 (1H, m), [10.08], 10.49 (1H, s)

Reference Example 23

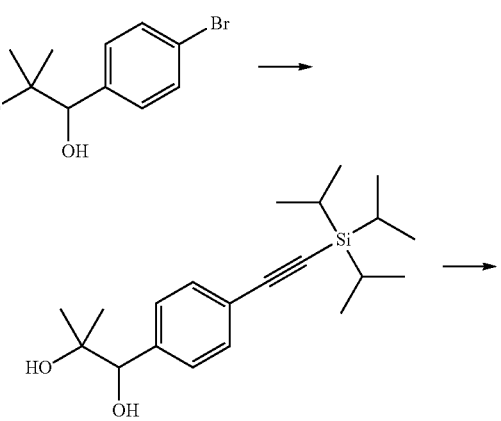

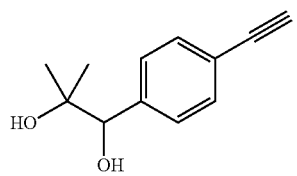

In the same manner as in Reference Example 19, from 223 mg of 1-(4-bromophenyl)-2-methylpropane-1,2-diol, 87 mg of 1-(4-ethynylphenyl)-2-methylpropane-1,2-diol was obtained as a colorless oil.

$^1$H-NMR (400 MHz, CDCl$_3$) δ: 1.08 (3H, s), 1.24 (3H, s), 2.61-2.66 (1H, m), 3.08 (1H, s), 4.53 (1H, d, J=3.2 Hz), 7.35 (2H, d, J=8.5 Hz), 7.47 (2H, d, J=8.3 Hz)

Reference Example 24

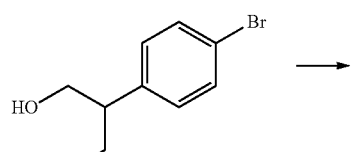

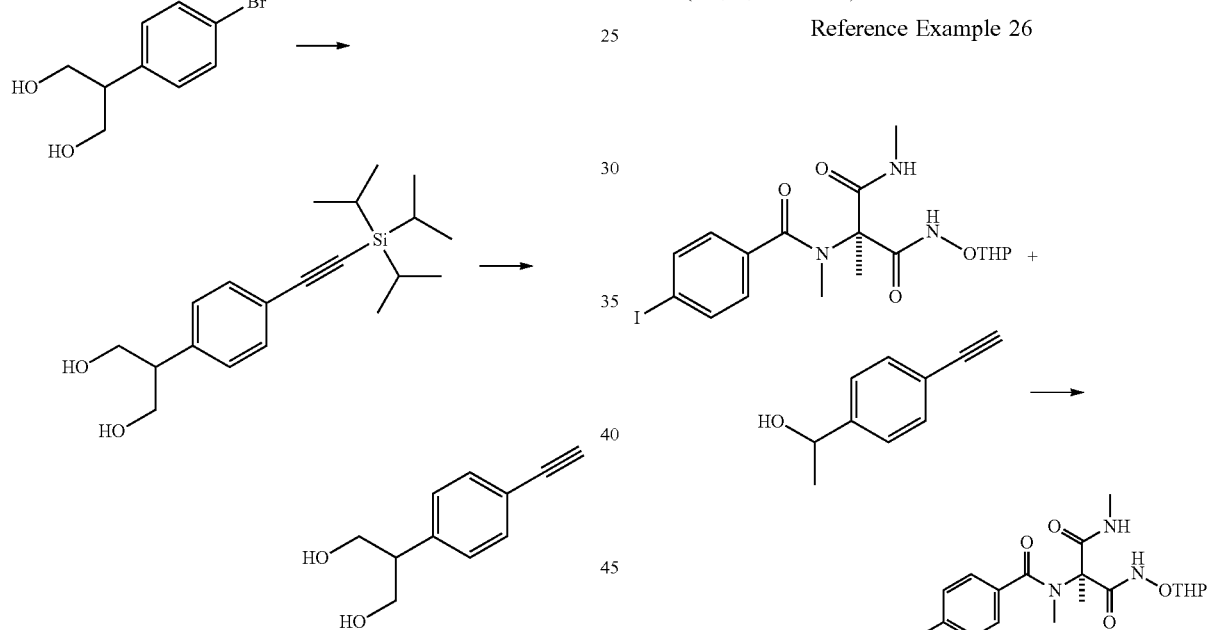

In the same manner as in Reference Example 19, from 570 mg of 2-(4-bromophenyl)propane-1,3-diol, 360 mg of 2-(4-ethynylphenyl)propane-1,3-diol was obtained as a pale yellow solid.

$^1$H-NMR (400 MHz, CDCl$_3$) δ: 1.95-2.01 (1H, m), 3.07 (1H, s), 3.06-3.16 (1H, m), 3.90-4.05 (4H, m), 7.21 (2H, d, J=8.3 Hz), 7.47 (2H, d, J=8.0 Hz)

Reference Example 25

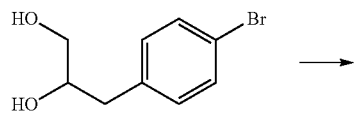

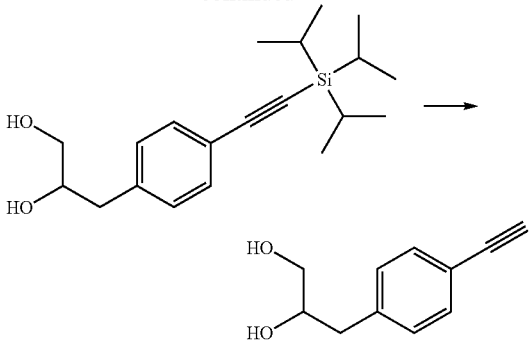

In the same manner as in Reference Example 19, from 554 mg of 3-(4-bromophenyl)propane-1,2-diol, 289 mg of 3-(4-ethynylphenyl)propane-1,2-diol was obtained as a yellow oil.

$^1$H-NMR (400 MHz, CDCl$_3$) δ: 2.55 (2H, s), 2.70-2.80 (2H, m), 3.07 (1H, s), 3.45-3.49 (1H, m), 3.64 (1H, dd, J=11.2, 2.9 Hz), 3.87-3.91 (1H, m), 7.18 (2H, d, J=8.1 Hz), 7.44 (2H, d, J=8.3 Hz)

Reference Example 26

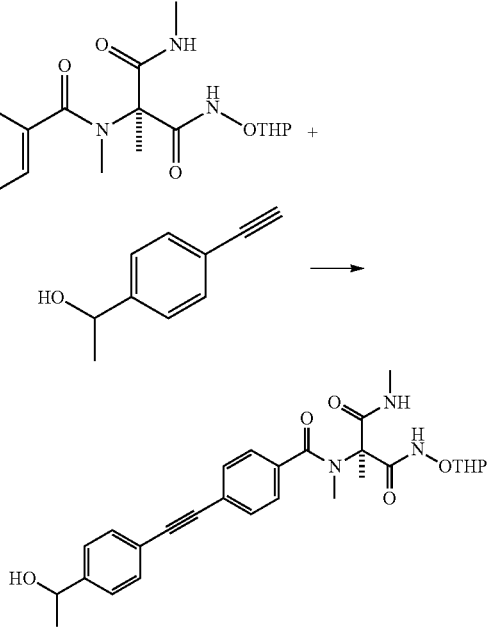

In the same manner as in Reference Example 2, from 877 mg of 1-(4-ethynylphenyl)ethanol and 1.47 g of (2S)-2-((4-iodobenzoyl)(methyl)amino)-N,2-dimethyl-N'-(tetrahydro-2H-pyran-2-yloxy)malonamide, 1.42 g of (2S)-2-((4-((4-(1-hydroxyethyl)phenyl)ethynyl)benzoyl)(methyl)amino)-N,2-dimethyl-N'-(tetrahydro-2H-pyran-2-yloxy)malonamide was obtained as a pale yellow solid.

$^1$H-NMR (400 MHz, CDCl$_3$) δ: 1.51 (3H, d, J=6.6 Hz), 1.55-1.69 (3H, m), 1.74-1.92 (4H, m), [1.81], 1.82 (3H, s), [2.85], 2.86 (3H, d, J=4.3 Hz), [3.17], 3.20 (3H, s), [3.54-3.61], 3.61-3.70 (1H, m), [3.84-3.91], 3.98-4.07 (1H, m), 4.89-5.03 (2H, m), 7.38 (2H, d, J=8.0 Hz), 7.47-7.55 (4H, m), 7.58 (2H, d, J=8.3 Hz), [6.97-7.04], 7.61-7.68 (1H, m), [10.10], 10.51 (1H, s)

Reference Example 27

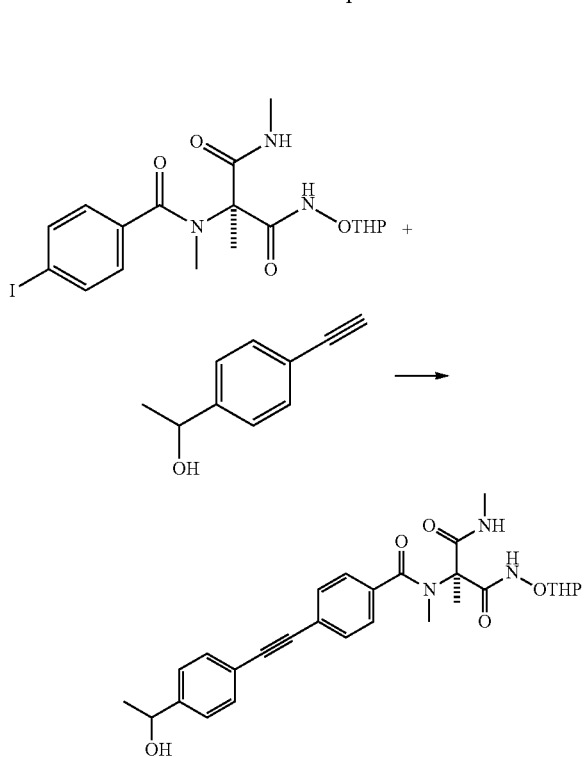

In the same manner as in Reference Example 2, from 90 mg of (1S)-1-(4-ethynylphenyl)ethanol and 250 mg of (2S)-2-((4-iodobenzoyl)(methyl)amino)-N,2-dimethyl-N'-(tetrahydro-2H-pyran-2-yloxy) malonamide, 210 mg of (2S)-2-((4-((4-((1S)-1-hydroxyethyl)phenyl)ethynyl)benzoyl)(methyl)amino)-N,2-dimethyl-N'-(tetrahydro-2H-pyran-2-yloxy)malonamide was obtained as a pale yellow foamy solid.

$^1$H-NMR (400 MHz, CDCl$_3$) δ: 1.47-1.71 (3H, m), 1.51 (3H, d, J=6.6 Hz), 1.74-1.93 (4H, m), [1.81], 1.82 (3H, s), 2.82-2.91 (3H, m), [3.17], 3.20 (3H, s), 3.51-3.72 (1H, m), 3.82-4.07 (1H, m), 4.89-5.03 (2H, m), 7.39 (2H, d, J=8.3 Hz), 7.37-7.55 (4H, m), 7.58 (2H, d, J=8.3 Hz), [6.97-7.03], 7.61-7.68 (1H, m), [10.09], 10.50 (1H, s)

Reference Example 28

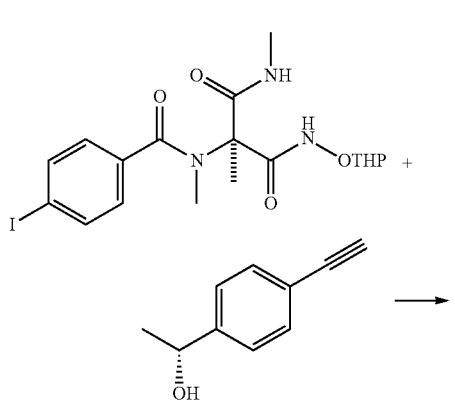

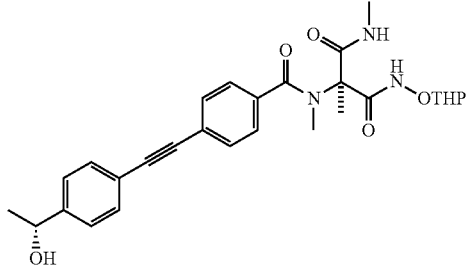

In the same manner as in Reference Example 2, from 136 mg of (1R)-1-(4-ethynylphenyl)ethanol and 228 mg of (2S)-2-((4-iodobenzoyl)(methyl)amino)-N,2-dimethyl-N'-(tetrahydro-2H-pyran-2-yloxy)malonamide, 220 mg of (2S)-2-((4-((4-((1R)-1-hydroxyethyl)phenyl)ethynyl)benzoyl)(methyl)amino)-N,2-dimethyl-N'-(tetrahydro-2H-pyran-2-yloxy)malonamide was obtained as a pale yellow solid.

$^1$H-NMR (400 MHz, CDCl$_3$) δ: 1.50 (3H, d, J=6.4 Hz), 1.53-1.69 (3H, m), 1.69-1.90 (3H, m), [1.81], 1.82 (3H, s), 1.93 (1H, d, J=3.2 Hz), 2.82-2.89 (3H, m), [3.17], 3.20 (3H, s), 3.53-3.71 (1H, m), 3.92-4.07 (1H, m), 4.86-5.04 (2H, m), 7.38 (2H, d, J=8.3 Hz), 7.47-7.55 (4H, m), 7.58 (2H, d, J=8.1 Hz), [6.95-7.05], 7.60-7.68 (1H, m), [10.11], 10.52 (1H, s)

Reference Example 29

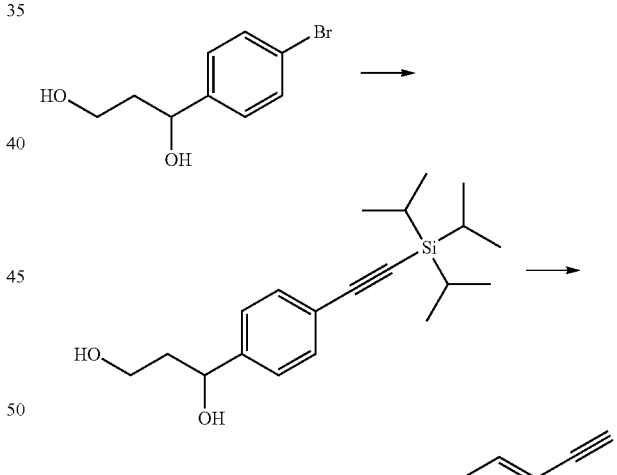

In the same manner as in Reference Example 19, from 1.40 g of 1-(4-bromophenyl)propane-1,3-diol, 628 mg of 1-(4-ethynylphenyl)propane-1,3-diol was obtained as a yellow oil.

$^1$H-NMR (400 MHz, CDCl$_3$) δ: 1.89-2.02 (2H, m), 2.48 (1H, s), 3.07 (1H, s), 3.20 (1H, s), 3.84-3.86 (2H, m), 4.95-4.98 (1H, m), 7.32 (2H, d, J=8.0 Hz), 7.48 (2H, d, J=8.1 Hz)

Reference Example 30

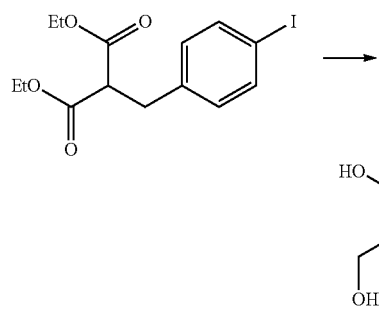

To a mixture of 2.5 g of diethyl (4-iodobenzyl)malonate and 25 mL of dichloromethane, 40 mL of a 1 mol/L solution of diisobutylaluminum hydride in toluene was added under a nitrogen atmosphere at −76° C., and the resulting mixture was stirred at the same temperature for 1 hour. Diethyl ether and an aqueous solution of Rochelle salt were successively added to the reaction mixture, and the resulting mixture was stirred at room temperature for 1 hour and then was allowed to stand overnight. The organic layer was separated, and the aqueous layer was extracted with ethyl acetate three times. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=70:30→80:20] to obtain 304 mg of 2-(4-iodobenzyl)propane-1,3-diol as a white solid.

$^1$H-NMR (400 MHz, CDCl$_3$) δ: 1.93-2.08 (3H, m), 2.60 (2H, d, J=7.6 Hz), 3.63-3.72 (2H, m), 3.77-3.85 (2H, m), 6.96 (2H, d, J=8.0 Hz), 7.61 (2H, d, J=8.0 Hz)

Reference Example 31

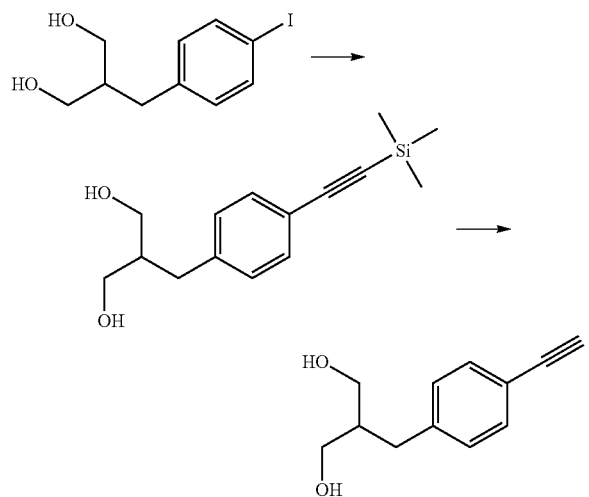

In the same manner as in Reference Example 1, from 290 mg of 2-(4-iodobenzyl)propane-1,3-diol, 185 mg of 2-(4-ethynylbenzyl)propane-1,3-diol was obtained as a light brown solid.

$^1$H-NMR (400 MHz, CDCl$_3$) δ: 1.97-2.15 (3H, m), 2.65 (2H, d, J=7.6 Hz), 3.05 (1H, s), 3.60-3.75 (2H, m), 3.75-3.91 (2H, m), 7.16 (2H, d, J=8.0 Hz), 7.42 (2H, d, J=8.3 Hz)

Reference Example 32

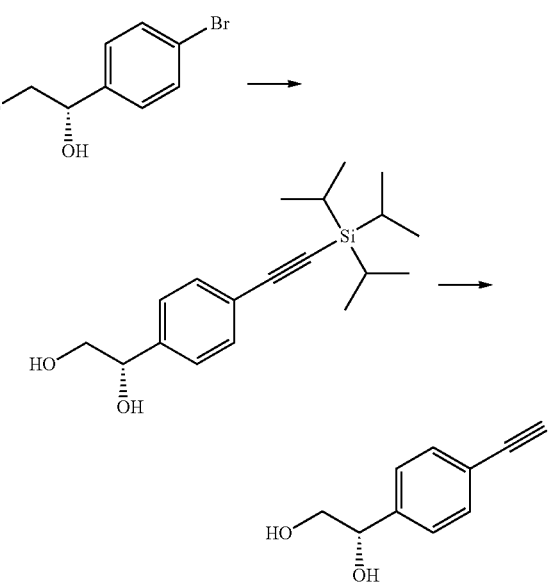

To a mixture of 1.08 g of (1S)-1-(4-bromophenyl)ethane-1,2-diol, 350 mg of bis-triphenylphosphinepalladium(II) dichloride, 190 mg of copper(I) iodide, and 10 mL of n-butyl acetate, 7.8 mL of triisopropylsilylacetylene and 7.0 mL of triethylamine were added under a nitrogen atmosphere, and the resulting mixture was stirred under reflux for 1 hour. The reaction mixture was cooled, a saturated aqueous solution of ammonium chloride was added, the pH was adjusted to 6.2 with 6 mol/L hydrochloric acid, then Celpure and ethyl acetate were added, and then the insoluble material was filtered off. The organic layer of the filtrate was separated, washed with a saturated aqueous solution of sodium chloride, and then dried over anhydrous magnesium sulfate. The solvent was distilled off under reduced pressure, and the obtained residue was subjected to silica gel column chromatography [eluent; ethyl acetate:hexane=40:60→45:55] to obtain 1.32 g of a yellow oil.

To a mixture of 1.32 g of the obtained yellow oil and 13 mL of tetrahydrofuran, 6.2 mL of a 1 mol/L solution of tetra-n-butylammonium fluoride in tetrahydrofuran was added under ice cooling, and the resulting mixture was stirred at the same temperature for 30 minutes and then at room temperature for 45 minutes. A saturated aqueous solution of ammonium chloride was added to the reaction mixture, the pH was adjusted to 2.0 with 1 mol/L hydrochloric acid, and then ethyl acetate was added. The organic layer was separated, and the aqueous layer was extracted with ethyl acetate twice. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=50:50→70:30] to obtain 513 mg of a light brown solid. Hexane was added thereto, and the solid material was collected by filtration to obtain 466 mg of (1S)-1-(4-ethynylphenyl)ethane-1,2-diol as a light brown solid.

$^1$H-NMR (400 MHz, CDCl$_3$) δ: 1.97-2.07 (1H, m), 2.56 (1H, d, J=3.4 Hz), 3.08 (1H, s), 3.56-3.70 (1H, m), 3.71-3.82 (1H, m), 4.79-4.88 (1H, m), 7.34 (2H, d, J=8.3 Hz), 7.49 (2H, d, J=8.3 Hz)

Reference Example 33

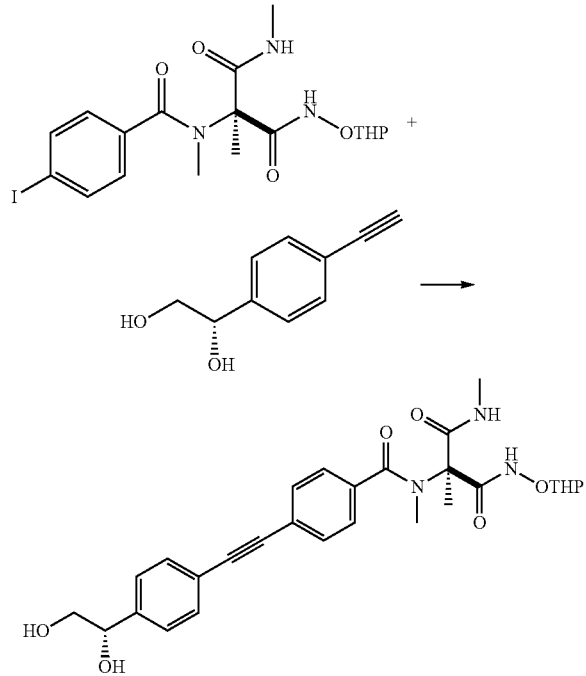

To a mixture of 587 mg of (2S)-2-((4-iodobenzoyl)(methyl)amino)-N,2-dimethyl-N'-(tetrahydro-2H-pyran-2-yloxy)malonamide, 253 mg of (1S)-1-(4-ethynylphenyl)ethane-1,2-diol, 84 mg of bis-triphenylphosphinepalladium(II) dichloride, 46 mg of copper(I) iodide, and 6.0 mL of tetrahydrofuran, 0.59 mL of triethylamine was added under a nitrogen atmosphere and under ice cooling, and the resulting mixture was stirred at the same temperature for 2 hours. A saturated aqueous solution of ammonium chloride and ethyl acetate were added to the reaction mixture, and the pH was adjusted to 6.4 with 1 mol/L hydrochloric acid. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=40:60] to obtain 767 mg of (2S)-2-((4-((4-((1S)-1,2-dihydroxyethyl)phenyl)ethynyl)benzoyl)(methyl)amino)-N,2-dimethyl-N'-(tetrahydro-2H-pyran-2-yloxy)malonamide as a pale yellow foamy solid.

$^1$H-NMR (400 MHz, CDCl$_3$) δ: 1.50-1.68 (3H, m), 1.71-1.92 (3H, m), [1.82], 1.83 (3H, s), 2.08-2.14 (1H, m), 2.63-2.68 (1H, m), [2.86], 2.87 (3H, d, J=4.1 Hz), [3.17], 3.20 (3H, s), 3.53-3.83 (3H, m), 3.83-4.07 (1H, m), 4.83-4.89 (1H, m), 4.93-5.03 (1H, m), 7.37 (2H, d, J=8.0 Hz), 7.48-7.61 (6H, m), [6.97-7.04], 7.61-7.67 (1H, m), [10.10], 10.51 (1H, s)

Reference Example 34

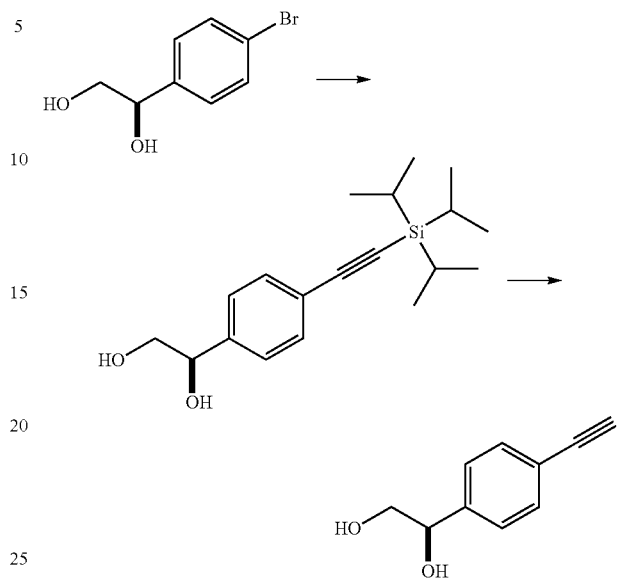

In the same manner as in Reference Example 32, from 1.09 g of (1R)-1-(4-bromophenyl)ethane-1,2-diol, 558 mg of (1R)-1-(4-ethynylphenyl)ethane-1,2-diol was obtained as a white solid.

$^1$H-NMR (400 MHz, CDCl$_3$) δ: 2.00 (1H, dd, J=7.1, 4.9 Hz), 2.54 (1H, d, J=3.4 Hz), 3.08 (1H, s), 3.60-3.68 (1H, m), 3.73-3.81 (1H, m), 4.80-4.88 (1H, m), 7.34 (2H, d, J=8.1 Hz), 7.49 (2H, d, J=8.0 Hz)

Reference Example 35

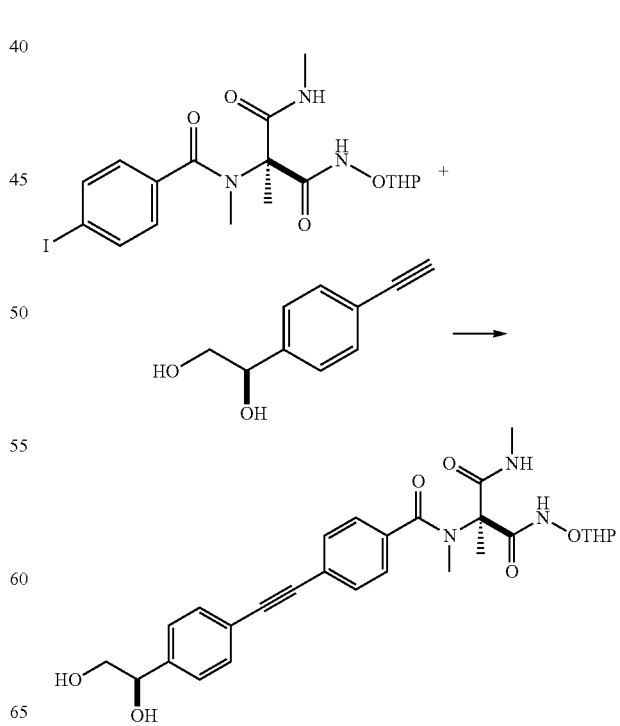

In the same manner as in Reference Example 33, from 587 mg of (2S)-2-((4-iodobenzoyl)(methyl)amino)-N,2-dimethyl-N'-(tetrahydro-2H-pyran-2-yloxy)malonamide and 291 mg of (1R)-1-(4-ethynylphenyl)ethane-1,2-diol, 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide was obtained as a light brown foamy solid.

$^1$H-NMR (400 MHz, CDCl$_3$) δ: 1.53-1.69 (3H, m), 1.76-1.92 (3H, m), [1.81], 1.82 (3H, s), 2.27-2.37 (1H, m), 2.83-2.91 (4H, m), [3.17], 3.19 (3H, s), 3.53-3.83 (3H, m), [3.83-3.92], 3.98-4.08 (1H, m), 4.81-4.88 (1H, m), 4.94-5.04 (1H, m), 7.35 (2H, d, J=8.1 Hz), 7.45-7.59 (6H, m), [6.96-7.06], 7.59-7.68 (1H, m), [10.14], 10.56 (1H, s)

Reference Example 36

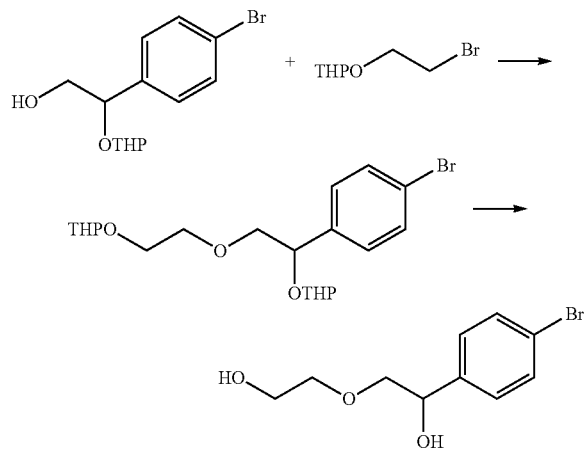

To a mixture of 750 mg of 2-(4-bromophenyl)-2-(tetrahydro-2H-pyran-2-yloxy)ethanol, 7.0 mL of N,N-dimethylformamide, and 724 mg of 2-(2-bromoethoxy)tetrahydro-2H-pyran, 277 mg of a 60% suspension of sodium hydride in mineral oil was added under a nitrogen atmosphere and under ice cooling, and the resulting mixture was stirred at the same temperature for 5 hours. A saturated aqueous solution of ammonium chloride and ethyl acetate were added to the reaction mixture. The organic layer was separated, washed with water and a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=30:70] to obtain 940 mg of a colorless oil.

To 940 mg of the obtained colorless oil, 1 mL of methanol, 9 mL of dichloromethane, and 85 mg of p-toluenesulfonic acid monohydrate were added, and the resulting mixture was stirred at room temperature for 30 minutes. Water was added to the reaction mixture, and the resulting mixture was neutralized with a saturated aqueous solution of sodium hydrogen carbonate. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=60:40] to obtain 422 mg of 1-(4-bromophenyl)-2-(2-hydroxyethoxy)ethanol as a white solid.

$^1$H-NMR (400 MHz, CDCl$_3$) δ: 2.11-2.19 (1H, m), 3.02 (1H, s), 3.47-3.52 (1H, m), 3.61-3.73 (3H, m), 3.76-3.82 (2H, m), 4.89 (1H, d, J=8.3 Hz), 7.27 (2H, d, J=8.6 Hz), 7.49 (2H, d, J=8.3 Hz)

Reference Example 37

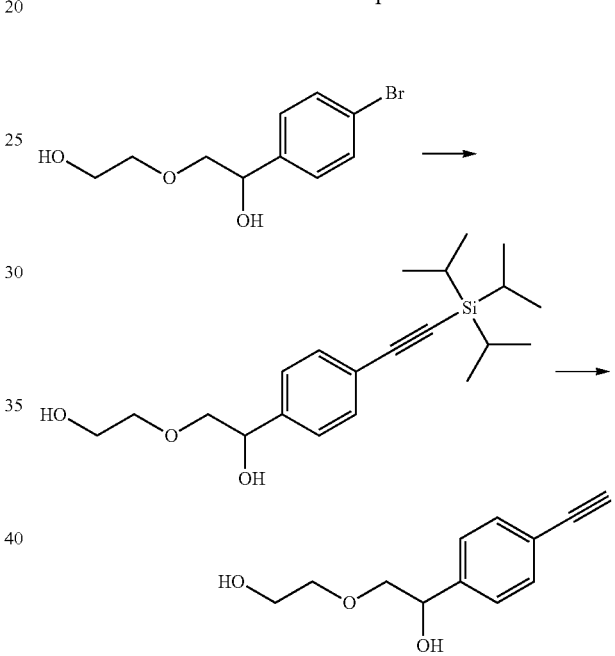

In the same manner as in Reference Example 19, from 422 mg of 1-(4-bromophenyl)-2-(2-hydroxyethoxy)ethanol, 210 mg of 1-(4-ethynylphenyl)-2-(2-hydroxyethoxy)ethanol was obtained as a yellow oil.

$^1$H-NMR (400 MHz, CDCl$_3$) δ: 2.51 (1H, brs), 3.07 (1H, s), 3.32 (1H, brs), 3.48-3.53 (1H, m), 3.60-3.72 (3H, m), 3.76-3.82 (2H, m), 4.93 (1H, dd, J=8.8, 3.0 Hz), 7.35 (2H, d, J=8.3 Hz), 7.48 (2H, d, J=8.3 Hz)

Reference Example 38

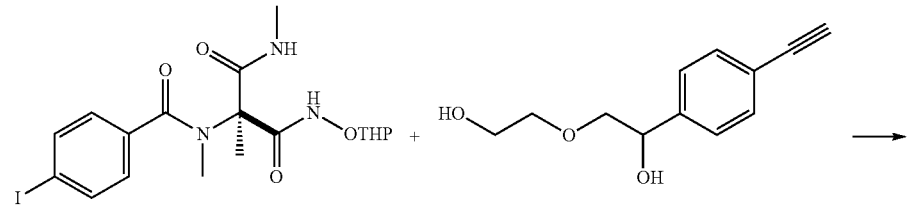

-continued

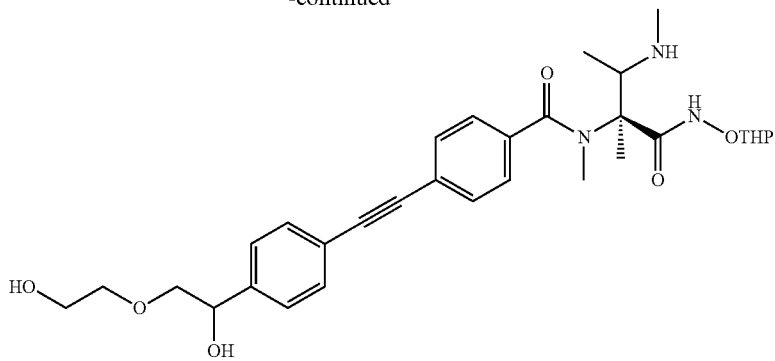

In the same manner as in Reference Example 2, from 210 mg of 1-(4-ethynylphenyl)-2-(2-hydroxyethoxy)ethanol and 300 mg of (2S)-2-((4-iodobenzoyl)(methyl)amino)-N,2-dimethyl-N'-(tetrahydro-2H-pyran-2-yloxy)malonamide, 340 mg of (2S)-2-((4-((4-(1-hydroxy-2-(2-hydroxyethoxy)ethyl)phenyl)ethynyl)benzoyl)(methyl)amino)-N,2-dimethyl-N'-(tetrahydro-2H-pyran-2-yloxy)malonamide was obtained as a yellow foamy solid.

$^1$H-NMR (400 MHz, CDCl$_3$) δ: 1.53-1.69 (3H, m), 1.75-1.93 (3H, m), [1.81], 1.82 (3H, s), 2.82-2.91 (3H, m), 3.06 (1H, s), [3.17], 3.20 (3H, m), 3.45-3.62 (1H, m), 3.72-3.75 (4H, m), 3.80 (2H, s), 3.84-4.07 (1H, m), 4.92-5.03 (2H, m), 7, 39 (2H, d, J=8.1 Hz), 7.49-7.55 (2H, m), 7.50 (2H, d, J=8.1 Hz), 7.57 (2H, d, J=8.0 Hz), [6.98-7.05], 7.62-7.69 (1H, m), [10.11], 10.52 (1H, s)

Reference Example 39

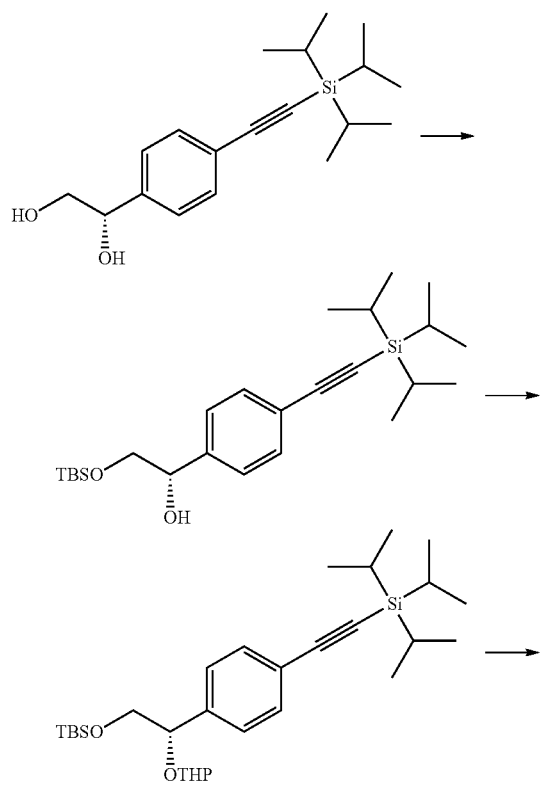

-continued

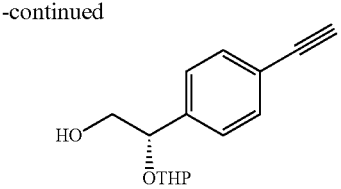

To a mixture of 2.79 g of (1S)-1-(4-(((triisopropylsilyl)ethynyl)phenyl)ethane-1,2-diol, 28 mL of dichloromethane, 2.7 mL of triethylamine, and 213 mg of N,N-dimethylaminopyridine obtained in the same manner as in Reference Example 19, 1.45 g of tert-butyldimethylsilyl chloride was added under a nitrogen atmosphere and under ice cooling, and the resulting mixture was stirred at room temperature for 2 hours, and then was allowed to stand at the same temperature overnight. A saturated aqueous solution of ammonium chloride and ethyl acetate were added to the reaction mixture, and the pH was adjusted to 4.0 with 6 mol/L hydrochloric acid. The organic layer was separated, washed with a saturated aqueous solution of sodium chloride, and then dried over anhydrous magnesium sulfate. The solvent was distilled off under reduced pressure to obtain 3.70 g of a brown oil.

To 3.70 g of the obtained brown oil, 28 mL of dichloromethane and 439 mg of pyridinium p-toluenesulfonate were added, 2.4 mL of 3,4-dihydro-2H-pyran was added under ice cooling, and then the resulting mixture was stirred at room temperature for 5 hours. To the reaction mixture, 3.0 mL of triethylamine was added, and the solvent was distilled off under reduced pressure. Water and ethyl acetate were added to the obtained residue. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; diethyl ether:hexane=10:90] to obtain 3.65 g of a yellow oil.

To 3.65 g of the obtained yellow oil, 18 mL of tetrahydrofuran was added, then 17 mL of a 1 mol/L solution of tetra-n-butylammonium fluoride in tetrahydrofuran was added under ice cooling, and the resulting mixture was stirred at room temperature for 1 hour. A saturated aqueous solution of ammonium chloride and ethyl acetate were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=30:70→40:60] to obtain 1.78 g of (2S)-2-(4-ethynylphenyl)-2-(tetrahydro-2H-pyran-2-yloxy)ethanol as a white solid.

¹H-NMR (400 MHz, CDCl₃) δ: 1.40-1.93 (6H, m), 2.11-2.20 (1H, m), [3.06], 3.07 (1H, s), 3.51-3.61 (1H, m), 3.62-3.76 (2H, m), [3.25-3.34], 3.92-4.07 (1H, m), [4.48-4.53], 4.79-4.86 (1H, m), [4.70-4.75], 4.87-4.93 (1H, m), [7.29], 7.35 (2H, d, J=8.3 Hz), 7.45 (2H, d, J=8.0 Hz)

Reference Example 40

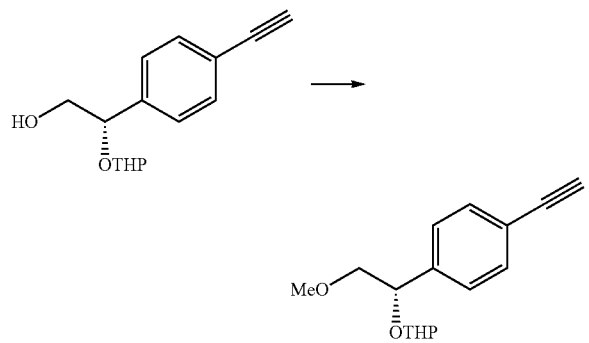

To a mixture of 800 mg of (2S)-2-(4-ethynylphenyl)-2-(tetrahydro-2H-pyran-2-yloxy)ethanol, 4.0 mL of dimethyl sulfoxide, and 0.4 mL of methyl iodide, 545 mg of potassium hydroxide was added under a nitrogen atmosphere and under ice cooling, and the resulting mixture was stirred at room temperature for 1 hour and 30 minutes. Toluene and a saturated aqueous solution of ammonium chloride were added to the reaction mixture, and the pH was adjusted to 6.1 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=10:90] to obtain 836 mg of 2-((1S)-1-(4-ethynylphenyl)-2-methoxyethoxy)tetrahydro-2H-pyran as a colorless oil.

¹H-NMR (400 MHz, CDCl₃) δ: 1.40-1.94 (6H, m), [3.05], 3.07 (1H, s), [3.36], 3.39 (3H, s), 3.45-3.56 (2H, m), [3.56-3.62], 3.62-3.69 (1H, m), [3.28-3.35], 3.97-4.06 (1H, m), [4.80-4.85], 4.91-4.97 (1H, m), [4.41-4.46], 4.97-5.01 (1H, m), [7.30], 7.37 (2H, d, J=8.4 Hz), 7.44-7.51 (2H, m)

Reference Example 41

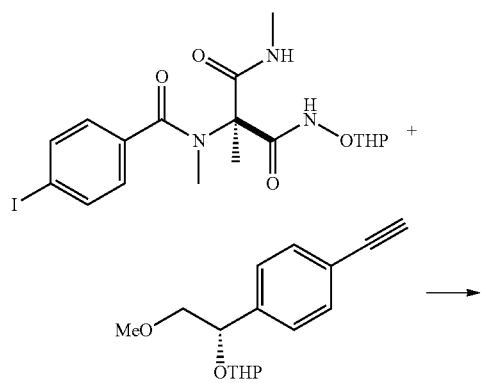

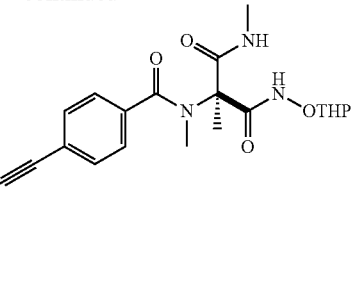

To a mixture of 478 mg of 2-((1S)-1-(4-ethynylphenyl)-2-methoxyethoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(II) dichloride, and 23 mg of copper(I) iodide, 0.51 mL of triethylamine was added under a nitrogen atmosphere and under ice cooling, and the resulting mixture was stirred at the same temperature for 2 hours and 30 minutes. A saturated aqueous solution of ammonium chloride and ethyl acetate were added to the reaction mixture, and the pH was adjusted to 6.0 with 6 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; acetone:chloroform=10:90] to obtain 485 mg of (2S)-2-((4-((4-((1S)-2-methoxy-1-(tetrahydro-2H-pyran-2-yl oxy)ethyl)phenyl)ethynyl)benzoyl)(methyl)amino)-N,2-dimethyl-N'-(tetrahydro-2H-pyran-2-yloxy)malonamide as a brown foamy solid.

¹H-NMR (400 MHz, CDCl₃) δ: 1.42-1.94 (12H, m), [1.81], 1.82 (3H, s), [2.85], 2.86 (3H, d, J=4.4 Hz), [3.17], 3.20 (3H, s), [3.37], 3.40 (3H, s), 3.47-3.72 (4H, m), [3.29-3.36], 3.83-3.91 (1H, m), 3.97-4.07 (1H, m), [4.43-4.48], 4.93-4.98 (1H, m), [4.84], 4.95 (1H, dd, J=7.3, 4.2 Hz), 4.98-5.03 (1H, m), [7.34], 7.41 (2H, d, J=8.3 Hz), 7.44-7.61 (6H, m), [6.96-7.04], 7.62-7.72 (1H, m), [10.01], 10.53 (1H, s)

Reference Example 42

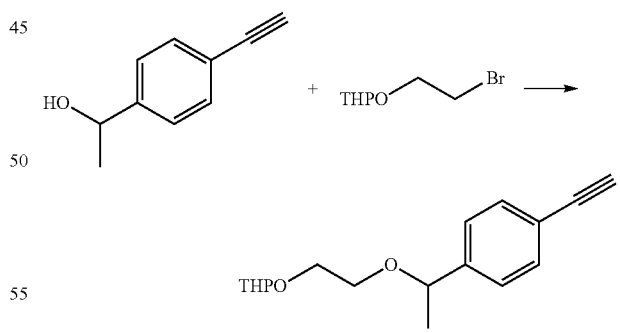

In the same manner as in Reference Example 40, from 730 mg of 1-(4-ethynylphenyl)ethanol and 1.1 mL of 2-(2-bromoethoxy)tetrahydro-2H-pyran, 826 mg of 2-(2-(1-(4-ethynylphenyl)ethoxy)ethoxy)tetrahydro-2H-pyran was obtained as a yellow oil.

¹H-NMR (400 MHz, CDCl₃) δ: 1.43 (3H, d, J=6.6 Hz), 1.48-1.64 (4H, m), 1.68-1.76 (1H, m), 1.79-1.91 (1H, m), 3.06 (1H, s), 3.47-3.51 (3H, m), 3.55-3.62 (1H, m), 3.80-3.89 (2H, m), 4.45-4.50 (1H, m), 4.60-4.65 (1H, m), 7.30 (2H, dd, J=8.3, 3.2 Hz), 7.46-7.48 (2H, m)

Reference Example 43

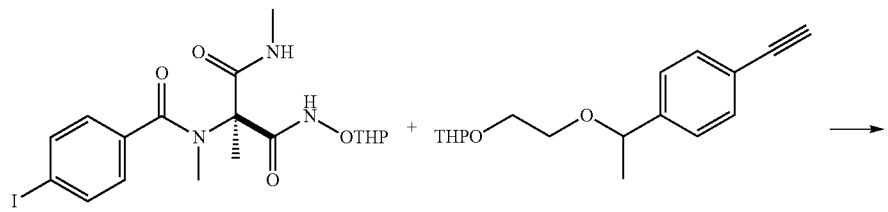

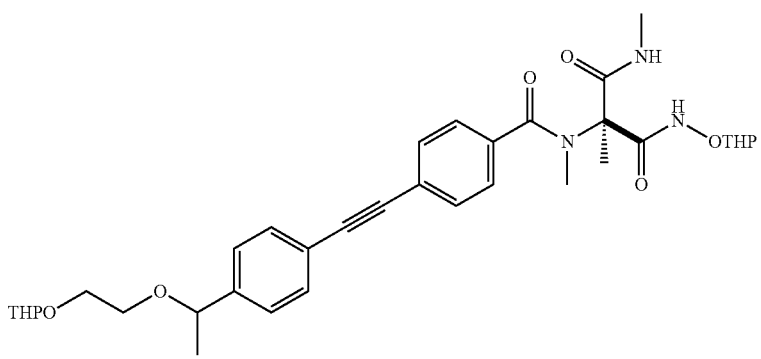

In the same manner as in Reference Example 2, from 219 mg of 2-(2-(1-(4-ethynylphenyl)ethoxy)ethoxy)tetrahydro-2H-pyran and 200 mg of (2S)-2-((4-iodobenzoyl)(methyl)amino)-N,2-dimethyl-N'-(tetrahydro-2H-pyran-2-yloxy)malonamide, 323 mg of (2S)—N,2-dimethyl-2-(methyl(4-((4-(1-(2-(tetrahydro-2H-pyran-2-yloxy)ethoxy)ethyl)phenyl)ethynyl)benzoyl)amino)-N'-(tetrahydro-2H-pyran-2-yloxy)malonamide was obtained as a brown oil.

$^1$H-NMR (400 MHz, CDCl$_3$) δ: 1.45 (3H, d, J=6.4 Hz), 1.56-1.62 (8H, m), 1.80-1.86 (4H, m), [1.81], 1.83 (3H, s), [2.85], 2.87 (3H, d, J=3.9 Hz), [3.18], 3.20 (3H, s), 3.50-3.53 (3H, m), 3.57-3.64 (2H, m), 3.81-3.87 (3H, m), 4.47-4.52 (1H, m), 4.61-4.66 (1H, m), 4.95-5.01 (1H, m), 7.34 (2H, dd, J=8.3, 2.9 Hz), 7.52 (4H, dd, J=7.8, 3.2 Hz), 7.58 (2H, d, J=8.5 Hz), [7.00], 7.64 (1H, s), [10.10], 10.51 (1H, s)

Reference Example 44

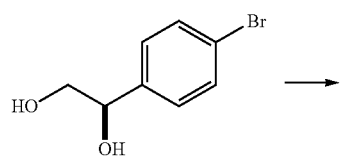

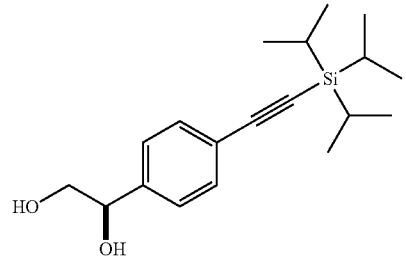

To a mixture of 410 mg of (1R)-1-(4-bromophenyl)ethane-1,2-diol, 6 mg of tri-tert-butylphosphonium tetrafluoroborate, 4 mg of copper(I) iodide, 3 mg of palladium(II) sodium chloride trihydrate, and 2.1 mL of tetramethylethylenediamine, 0.5 mL of triisopropylsilylacetylene was added under a nitrogen atmosphere, and the resulting mixture was stirred at 85° C. for 1 hour and 50 minutes. The reaction mixture was cooled, water and ethyl acetate was added, and the resulting mixture was neutralized with 6 mol/L hydrochloric acid. The organic layer was separated, washed with a saturated aqueous solution of sodium chloride, then anhydrous magnesium sulfate and silica gel DNH were added, and the insoluble material was filtered off. The solvent was distilled off under reduced pressure to obtain 701 mg of (1R)-1-(4-((triisopropylsilyl)ethynyl)phenyl)ethane-1,2-diol as a yellow oil.

$^1$H-NMR (400 MHz, CDCl$_3$) δ: 1.13 (21H, s), 2.53-2.60 (1H, m), 3.59-3.67 (1H, m), 3.71-3.80 (1H, m), 4.80-4.87 (1H, m), 7.31 (2H, d, J=8.0 Hz), 7.48 (2H, d, J=8.0 Hz)

Reference Example 45

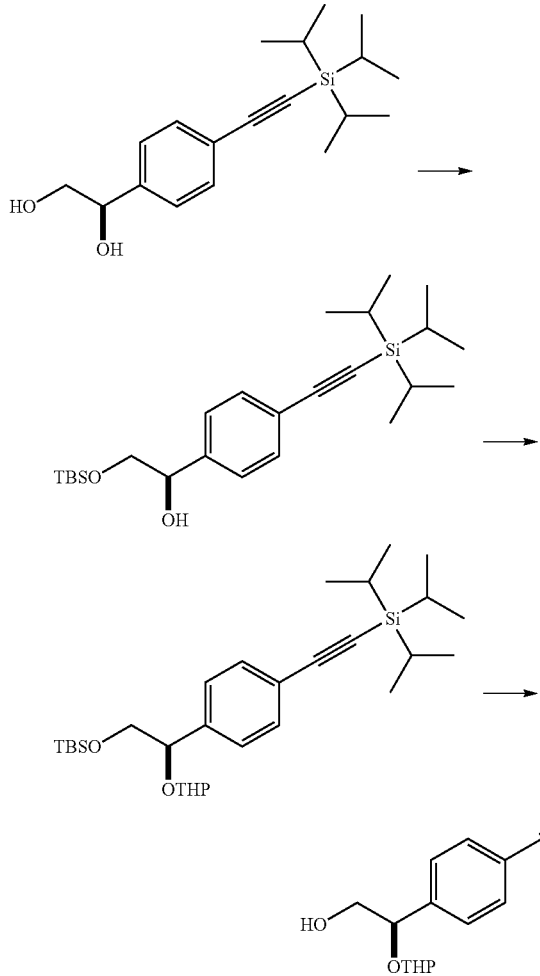

In the same manner as in Reference Example 39, from 9.35 g of (1R)-1-(4-((triisopropylsilyl)ethynyl)phenyl)ethane-1,2-diol, 8.97 g of (2R)-2-(4-ethynylphenyl)-2-(tetrahydro-2H-pyran-2-yloxy)ethanol was obtained as a pale yellow solid.

$^1$H-NMR (400 MHz, CDCl$_3$) δ: 1.41-1.93 (6H, m), [2.13], 3.02 (1H, brs), [3.06], 3.07 (1H, s), 3.50-3.61 (1H, m), 3.62-3.78 (2H, m), [3.26-3.35], 3.97-4.06 (1H, m), [4.48-4.56], 4.79-4.86 (1H, m), [4.69-4.76], 4.86-4.93 (1H, m), [7.29], 7.35 (2H, d, J=8.3 Hz), 7.48 (2H, d, J=8.0 Hz)

Reference Example 46

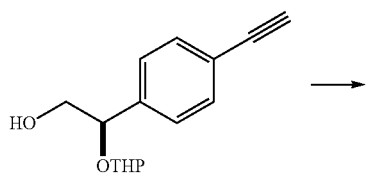

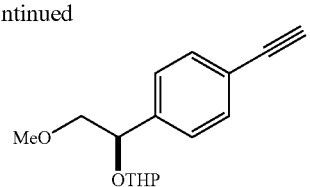

In the same manner as in Reference Example 40, from 900 mg of (2R)-2-(4-ethynylphenyl)-2-(tetrahydro-2H-pyran-2-yloxy)ethanol, 859 mg of 2-((1R)-1-(4-ethynylphenyl)-2-methoxyethoxy)tetrahydro-2H-pyran was obtained as a white solid.

$^1$H-NMR (400 MHz, CDCl$_3$) δ: 1.39-1.95 (6H, m), [3.05], 3.07 (1H, s), [3.36], 3.38 (3H, s), 3.44-3.71 (3H, m), [3.26-3.35], 3.97-4.07 (1H, m), [4.79-4.86], 4.90-4.96 (1H, m), [4.41-4.46], 4.97-5.01 (1H, m), [7.30], 7.37 (2H, d, J=8.3 Hz), [7.46], 7.47 (2H, d, J=8.3 Hz)

Reference Example 47

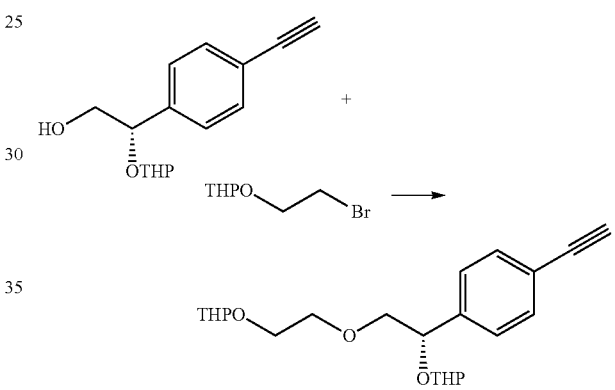

To a mixture of 800 mg of (2S)-2-(4-ethynylphenyl)-2-(tetrahydro-2H-pyran-2-yloxy)ethanol, 4.0 mL of dimethyl sulfoxide, and 0.98 mL of 2-(2-bromoethoxy)tetrahydro-2H-pyran, 545 mg of potassium hydroxide was added under water cooling, and the resulting mixture was stirred at room temperature for 2 hours. To the reaction mixture, 0.49 mL of 2-(2-bromoethoxy)tetrahydro-2H-pyran and 272 mg of potassium hydroxide were added, and the resulting mixture was stirred at room temperature for 2 hours. Toluene and a saturated aqueous solution of ammonium chloride were added to the reaction mixture, and the pH was adjusted to 6.0 with 6 mol/L hydrochloric acid. The organic layer was separated, and the aqueous layer was extracted with ethyl acetate. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=20:80→25:75] to obtain 1.15 g of 2-((1S)-1-(4-ethynylphenyl)-2-(2-(tetrahydro-2H-pyran-2-yloxy)ethoxy)ethoxy)tetrahydro-2H-pyran as a colorless oil.

$^1$H-NMR (400 MHz, CDCl$_3$) δ: 1.40-1.95 (12H, m), [3.05], 3.06 (1H, m), 3.26-4.08 (10H, m), 4.56-4.69 (1H, m), [4.81-4.89], 4.89-4.98 (1H, m), [4.43-4.52], 4.98-5.06 (1H, m), [7.30], 7.37 (2H, d, J=8.3 Hz), 7.46 (2H, d, J=8.3 Hz)

Reference Example 48

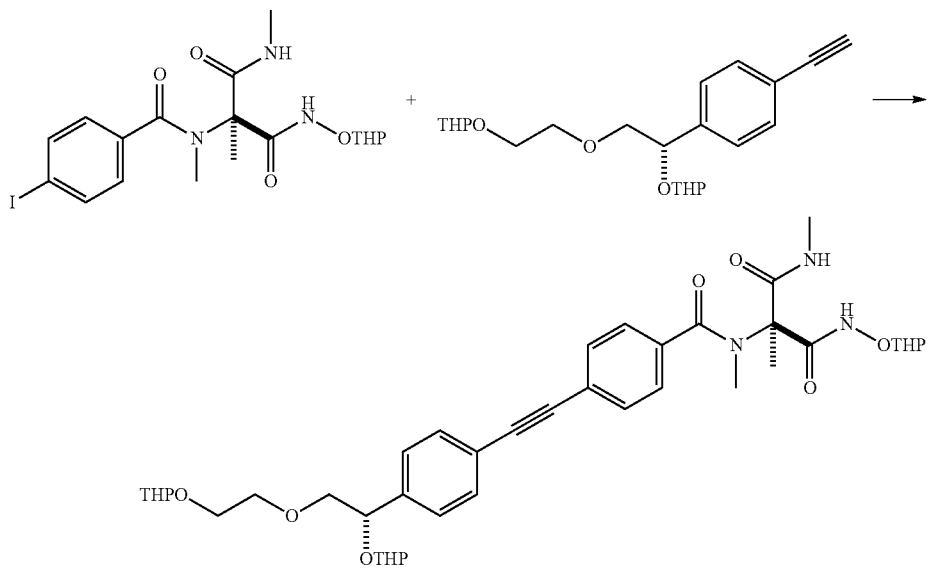

To a mixture of 685 mg of 2-((1S)-1-(4-ethynylphenyl)-2-(2-(tetrahydro-2H-pyran-2-yloxy)ethoxy)ethoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(II) dichloride, and 23 mg of copper(I) iodide, 0.51 mL of triethylamine was added under a nitrogen atmosphere and under ice cooling, and the resulting mixture was stirred at the same temperature for 2 hours and 30 minutes. A saturated aqueous solution of ammonium chloride and ethyl acetate were added to the reaction mixture, and the pH was adjusted to 6.2 with 6 mol/L hydrochloric acid. The organic layer was separated, and the aqueous layer was extracted with ethyl acetate. The organic layer was combined with the extract, washed with a saturated aqueous solution of sodium chloride, and then dried over anhydrous magnesium sulfate. The solvent was distilled off under reduced pressure, and the obtained residue was purified by silica gel column chromatography [eluent; acetone:chloroform=20:80] to obtain 422 mg of (2S)—N,2-dimethyl-2-(methyl(4-((4-((1S)-1-(tetrahydro-2H-pyran-2-yl oxy)-2-(2-(tetrahydro-2H-pyran-2-yloxy)ethoxy)ethyl)phenyl)ethynyl)benzoyl)amino)-N'-(tetrahydro-2H-pyran-2-yloxy)malonamide as a yellow foamy solid.

$^1$H-NMR (400 MHz, CDCl$_3$) δ: 1.40-1.97 (18H, m), [1.81], 1.82 (3H, s), [2.85], 2.86 (3H, d, J=4.3 Hz), [3.17], 3.20 (3H, s), 3.43-3.90 (10H, m), [3.28-3.37], 3.79-3.90 (1H, m), 3.97-4.08 (1H, m), 4.58-4.64 (1H, m), [4.83-4.89], 4.92-4.98 (1H, m), [4.49], 4.96 (1H, s), 4.98-5.06 (1H, m), [7.34], 7.41 (2H, d, J=8.2 Hz), 7.47-7.54 (4H, m), 7.57 (2H, d, J=8.0 Hz), [6.95-7.05], 7.60-7.69 (1H, m), [10.08], 10.49 (1H, s)

Reference Example 49

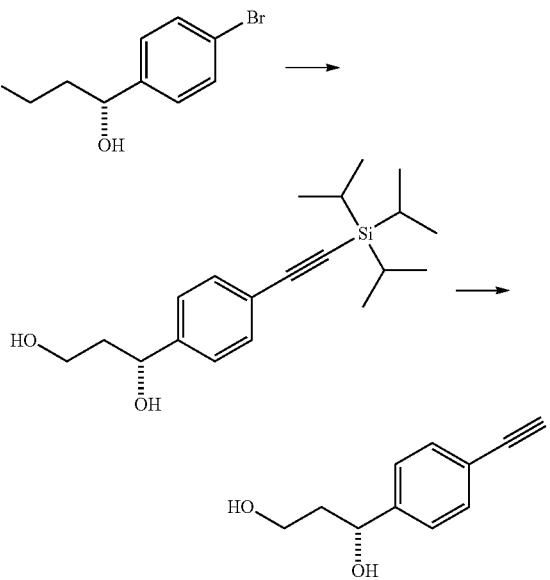

To 915 mg of (1R)-1-(4-bromophenyl)propane-1,3-diol, 9.0 mL of n-butyl acetate, 277 mg of bis-triphenylphosphinepalladium(II) dichloride, 150 mg of copper(I) iodide, 4.4 mL of triisopropylsilylacetylene, and 5.5 mL of triethylamine were added, and the resulting mixture was stirred under reflux for 1 hour. To the reaction mixture, 277 mg of bis-triphenylphosphinepalladium(II) dichloride, 150 mg of copper(I) iodide, 4.4 mL of triisopropylsilylacetylene, and 5.5 mL of triethylamine were added, and the resulting mixture was stirred under reflux for 3 hours and 45 minutes. The reaction mixture was cooled, a saturated aqueous solution of ammonium chloride and ethyl acetate were added, the resulting mixture was neutralized with concentrated hydrochloric acid, then Celpure was added, and the insoluble material was filtered off. The organic layer of the filtrate was separated, and then dried over anhydrous magnesium sulfate. The solvent was distilled off under reduced pressure, and the obtained residue was purified by silica gel column chromatography [eluent; ethyl acetate:hexane=50:50] to obtain 455 mg of a brown oil.

To a mixture of 455 mg of the obtained brown oil and 4.5 mL of tetrahydrofuran, 1.6 mL of a 1 mol/L solution of tetra-n-butylammonium fluoride in tetrahydrofuran was added at room temperature, and the resulting mixture was stirred at the same temperature for 50 minutes. Water and ethyl acetate were added to the reaction mixture, and the pH was adjusted to 4.8 with 1 mol/L hydrochloric acid. The organic layer was separated, and the aqueous layer was extracted with ethyl acetate. The organic layer was combined with the extract, and then dried over anhydrous magnesium sulfate. The solvent was distilled off under reduced pressure, and the obtained residue was purified by silica gel column chromatography [eluent; methanol:chloroform=5:95] to obtain 215 mg of (1R)-1-(4-ethynylphenyl)propane-1,3-diol as a brown oil.

$^1$H-NMR (400 MHz, CDCl$_3$) δ: 1.93-2.00 (2H, m), 3.07 (1H, s), 3.86-3.88 (2H, m), 4.93 (1H, dd, J=8.3, 3.9 Hz), 7.33 (2H, d, J=8.3 Hz), 7.49 (2H, d, J=8.3 Hz)

Reference Example 50

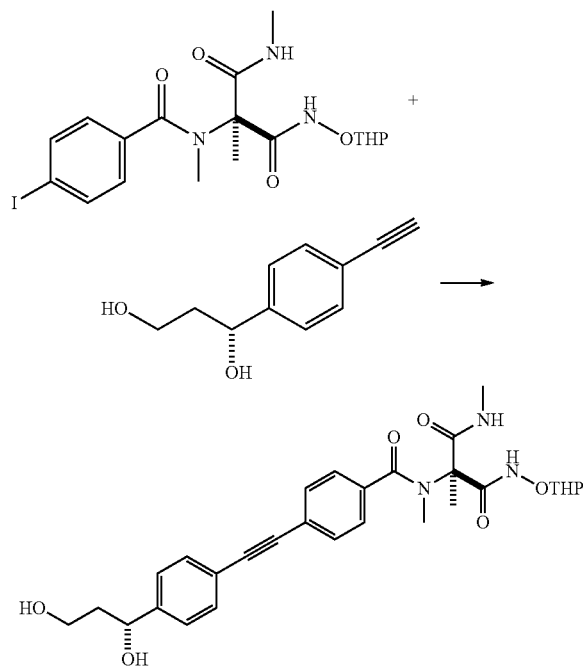

To a mixture of 155 mg of (1R)-1-(4-ethynylphenyl)propane-1,3-diol, 2.0 mL of tetrahydrofuran, 200 mg of (2S)-2-((4-iodobenzoyl)(methyl)amino)-N,2-dimethyl-N'-(tetrahydro-2H-pyran-2-yloxy)malonamide, 28 mg of bis-triphenylphosphinepalladium(II) dichloride and 15 mg of copper(I) iodide, 0.4 mL of triethylamine was added under ice cooling, and the resulting mixture was stirred at the same temperature for 2 hours and 20 minutes. A saturated aqueous solution of ammonium chloride and ethyl acetate were added to the reaction mixture, and the pH was adjusted to 6.8 with concentrated hydrochloric acid. The organic layer was separated, and then dried over anhydrous magnesium sulfate. The solvent was distilled off under reduced pressure, and the obtained residue was purified by silica gel column chromatography [eluent; acetone:chloroform=40:60→45:55] to obtain 254 mg of (2S)-2-((4-((4-((1R)-1,3-dihydroxypropyl)phenyl)ethynyl)benzoyl)(methyl)amino)-N,2-dimethyl-N'-(tetrahydro-2H-pyran-2-yloxy)malonamide as a brown solid.

$^1$H-NMR (400 MHz, CDCl$_3$) δ: 1.53-1.66 (4H, m), 1.76-1.89 (3H, m), [1.81], 1.82 (3H, s), 1.93-2.02 (1H, m), [2.85-2.86], 2.86-2.87 (3H, m), [3.17], 3.20 (3H, s), [3.53-3.60], 3.63-3.68 (1H, m), 3.89 (2H, s), [3.84-3.93], 3.97-4.07 (1H, m), 4.95-5.03 (2H, m), 7.36 (2H, d, J=8.3 Hz), 7.47-7.57 (6H, m), [6.98-7.04], 7.62-7.66 (1H, m), [10.13], 10.53 (1H, s)

Reference Example 51

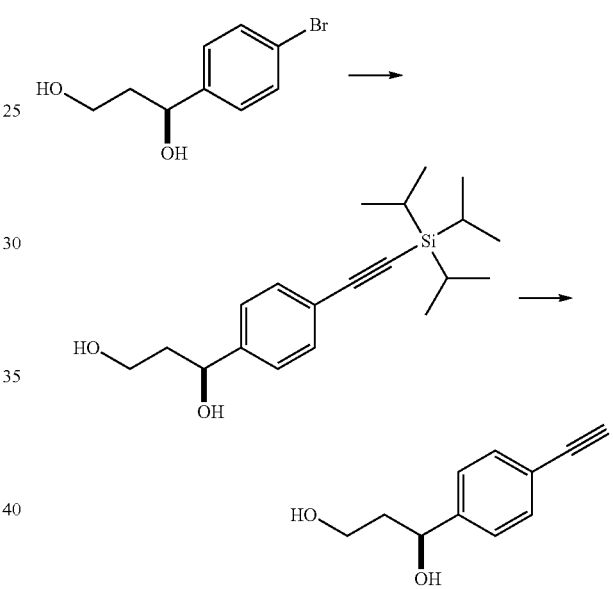

To 1.03 g of (1S)-1-(4-bromophenyl)propane-1,3-diol, 13 mg of tri-tert-butylphosphonium tetrafluoroborate, 8 mg of copper(I) iodide, 8 mg of palladium(II) sodium chloride trihydrate, 5.0 mL of tetramethylethylenediamine, and 1.1 mL of triisopropylsilylacetylene were added, and the resulting mixture was stirred at 85° C. for 1 hour and 30 minutes. To the reaction mixture, 13 mg of tri-tert-butylphosphonium tetrafluoroborate, 8 mg of copper(I) iodide, 8 mg of palladium(II) sodium chloride trihydrate, and 0.25 mL of triisopropylsilylacetylene were added, and the resulting mixture was stirred at the same temperature for 3 hours. The reaction mixture was cooled, ethyl acetate and a saturated aqueous solution of ammonium chloride were added, and the resulting mixture was neutralized with concentrated hydrochloric acid. The organic layer was separated, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; ethyl acetate:hexane=40:60] to obtain 789 mg of a yellow oil.

To 789 mg of the obtained yellow oil, 7.8 mL of tetrahydrofuran and 2.8 mL of a 1 mol/L solution of tetra-n- butylammonium fluoride in tetrahydrofuran were added, and the resulting mixture was stirred at room temperature for 1 hour. Water and ethyl acetate were added to the reaction mixture, and the pH was adjusted to 4.2 with 1 mol/L hydrochloric acid. The organic layer was separated, and then dried over anhydrous sodium sulfate. The solvent was distilled off under reduced pressure, and the obtained residue was purified by silica gel column chromatography [eluent; methanol:ethyl acetate=5:95] to obtain 370 mg of (1S)-1-(4-ethynylphenyl)propane-1,3-diol as a brown solid.

$^1$H-NMR (400 MHz, CDCl$_3$) δ: 1.90-2.00 (2H, m), 2.46 (1H, s), 3.07 (1H, s), 3.18 (1H, s), 3.84-3.86 (2H, m), 4.94-4.97 (1H, m), 7.32 (2H, d, J=8.1 Hz), 7.48 (2H, d, J=8.3 Hz)

Reference Example 52

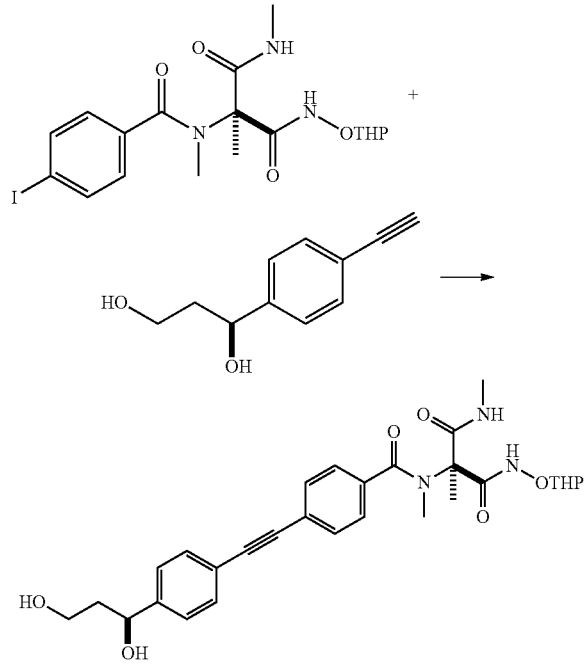

To a mixture of 232 mg of (1S)-1-(4-ethynylphenyl)propane-1,3-diol, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 42 mg of bis-triphenylphosphinepalladium(II) dichloride, and 22 mg of copper(I) iodide, 0.67 mL of triethylamine was added under ice cooling, and the resulting mixture was stirred at the same temperature for 30 minutes. A saturated aqueous solution of ammonium chloride and ethyl acetate were added to the reaction mixture, and the pH was adjusted to 6.5 with concentrated hydrochloric acid. The organic layer was separated, and then dried over anhydrous sodium sulfate. The solvent was distilled off under reduced pressure, and the obtained residue was purified by silica gel column chromatography [eluent; acetone:chloroform=40:60→45:55] to obtain 377 mg of (2S)-2-((4-((4-((1S)-1,3-dihydroxypropyl)phenyl)ethynyl)benzoyl)(methyl)amino)-N,2-dimethyl-N'-(tetrahydro-2H-pyran-2-yloxy)malonamide as a brown solid.

$^1$H-NMR (400 MHz, CDCl$_3$) δ: 1.53-1.64 (3H, m), 1.75-1.89 (3H, m), [1.81], 1.82 (3H, s), 1.92-2.05 (2H, m), 2.28 (1H, s), 2.82-2.89 (3H, m), 3.05 (1H, s), [3.17], 3.20 (3H, s), [3.52-3.60], 3.63-3.70 (1H, m), 3.84-3.94 (2H, m), [3.84-3.94], 3.97-4.09 (1H, m), 4.95-5.04 (2H, m), 7.36 (2H, d, J=8.1 Hz), 7.46-7.61 (6H, m), [7.02], 7.63 (1H, s), [10.12], 10.53 (1H, s)

Reference Example 53

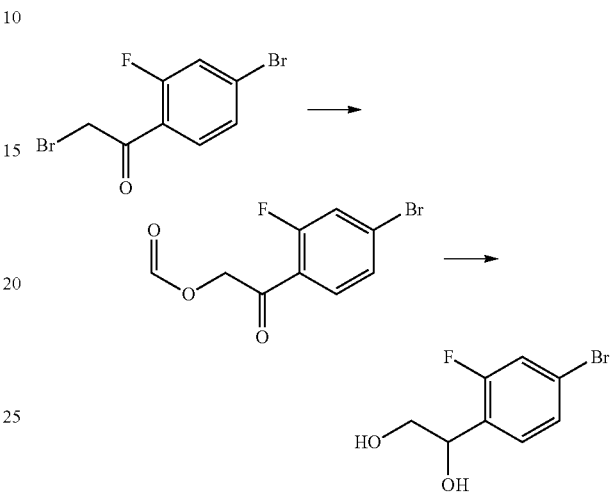

To 3.03 g of 2-bromo-1-(4-bromo-2-fluorophenyl)ethanone, 30 mL of N,N-dimethylformamide and 2.04 g of sodium formate were added, and the resulting mixture was stirred at 45° C. for 1 hour. The reaction mixture was cooled, and water was added. The solid material was collected by filtration, washed with water, and then dried to obtain a 2.16 g of yellow solid.

To a mixture of the obtained yellow solid and 20 mL of methanol, 1.25 g of sodium borohydride was added in 5 portions for 35 minutes under a nitrogen atmosphere and under ice cooling, and the resulting mixture was stirred at room temperature for 1 hour. A saturated aqueous solution of ammonium chloride and ethyl acetate were successively added to the reaction mixture under ice cooling. The organic layer was separated, washed with water and a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=35:65] to obtain 1.56 g of 1-(4-bromo-2-fluorophenyl)ethane-1,2-diol as a yellow oil.

$^1$H-NMR (400 MHz, CDCl$_3$) δ: 1.98-2.05 (1H, m), 2.55-2.71 (1H, m), 3.55-3.70 (1H, m), 3.78-3.93 (1H, m), 5.04-5.17 (1H, m), 7.20-7.25 (1H, m), 7.31-7.34 (1H, m), 7.41-7.42 (1H, m)

Reference Example 54

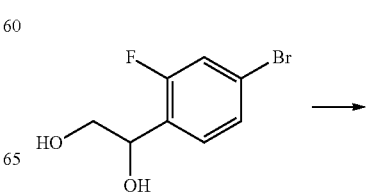

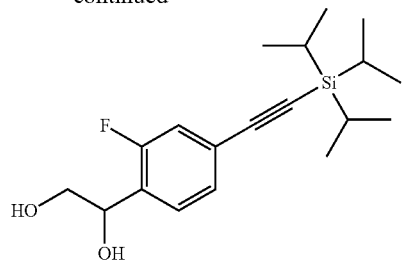

To 1.56 g of 1-(4-bromo-2-fluorophenyl)ethane-1,2-diol, 19 mg of tri-tert-butylphosphonium tetrafluoroborate, 13 mg of copper(I) iodide, 12 mg of palladium(II) sodium chloride trihydrate, 7.5 mL of tetramethylethylenediamine, and 1.78 mL of triisopropylsilylacetylene were added, and the resulting mixture was stirred at 85° C. for 1 hour and 50 minutes. The reaction mixture was cooled, 19 mg of tri-tert-butylphosphonium tetrafluoroborate, 13 mg of copper(I) iodide, 12 mg of palladium(II) sodium chloride trihydrate, and 1.78 mL of triisopropylsilylacetylene were added, and the resulting mixture was stirred at 90° C. for 1 hour. The reaction mixture was cooled, and ethyl acetate and water were added. The organic layer was separated, washed successively with water and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=35:65] to obtain 1.90 g of 1-(2-fluoro-4-((triisopropylsilyl)ethynyl)phenyl)ethane-1,2-diol as a yellow oil.

$^1$H-NMR (400 MHz, CDCl$_3$) δ: 1.11-1.12 (21H, m), 2.60-2.63 (1H, m), 3.59-3.64 (1H, m), 3.82-3.85 (1H, m), 5.12-5.14 (1H, m), 7.14 (1H, dd, J=10.8, 1.2 Hz), 7.28 (1H, dd, J=8.0, 1.5 Hz), 7.46 (1H, dd, J=7.8, 7.8 Hz)

Reference Example 55

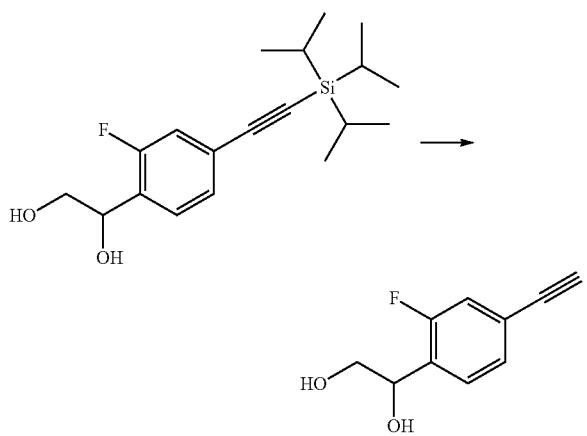

To 337 mg of 1-(2-fluoro-4-((triisopropylsilyl)ethynyl)phenyl)ethane-1,2-diol, 3.0 mL of tetrahydrofuran and 1.5 mL of a 1 mol/L solution of tetra-n-butylammonium fluoride in tetrahydrofuran were added, and the resulting mixture was stirred at room temperature for 1 hour and 30 minutes. A saturated aqueous solution of ammonium chloride and ethyl acetate were added to the reaction mixture. The organic layer was separated, washed successively with water and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=70:30] to obtain 98 mg of 1-(4-ethynyl-2-fluorophenyl)ethane-1,2-diol as a yellow oil.

$^1$H-NMR (400 MHz, CDCl$_3$) δ: 2.02 (1H, brs), 2.62 (1H, brs), 3.11 (1H, s), 3.63 (1H, dd, J=11.0, 7.8 Hz), 3.84-3.88 (1H, m), 5.12-5.15 (1H, m), 7.16 (1H, dd, J=10.7, 1.5 Hz), 7.31 (1H, dd, J=8.1, 1.5 Hz), 7.50 (1H, dd, J=7.8, 7.8 Hz)

Reference Example 56

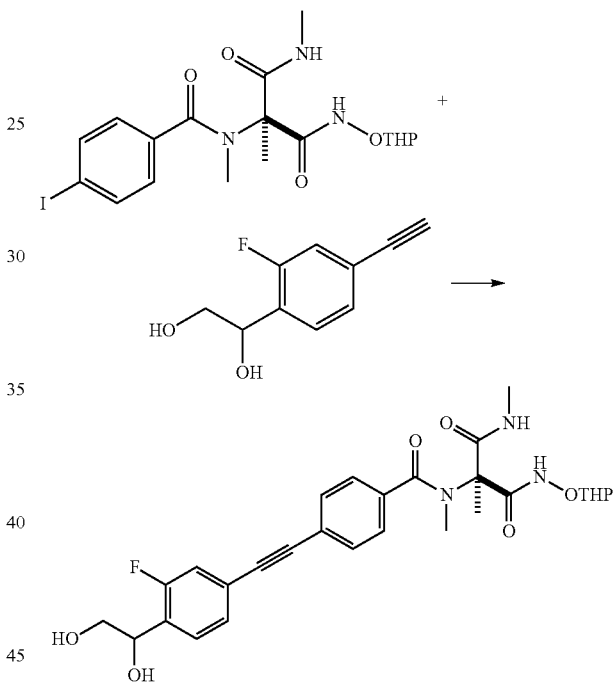

In the same manner as in Reference Example 2, from 98 mg of 1-(4-ethynyl-2-fluorophenyl)ethane-1,2-diol and 180 mg of (2S)-2-((4-iodobenzoyl)(methyl)amino)-N,2-dimethyl-N'-(tetrahydro-2H-pyran-2-yloxy)malonamide, 198 mg of (2S)-2-((4-((4-(1,2-dihydroxyethyl)-3-fluorophenyl)ethynyl)benzoyl)(methyl)amino)-N,2-dimethyl-N'-(tetrahydro-2H-pyran-2-yloxy)malonamide was obtained as a yellow oil.

$^1$H-NMR (400 MHz, CDCl$_3$) δ: 1.47-1.68 (3H, m), 1.75-1.91 (3H, m), [1.81], 1.83 (3H, s), 2.11 (1H, s), 2.73-2.79 (1H, m), 2.83-2.90 (3H, m), [3.17], 3.19 (3H, s), 3.54-4.06 (4H, m), 4.94-5.02 (1H, m), 5.12-5.18 (1H, m), 7.16-7.23 (1H, m), 7.34 (1H, d, J=7.8 Hz), 7.47-7.54 (3H, m), 7.57 (2H, d, J=8.5 Hz), [6.95-7.00], 7.60-7.66 (1H, m), [10.09], 10.51 (1H, s)

Reference Example 57

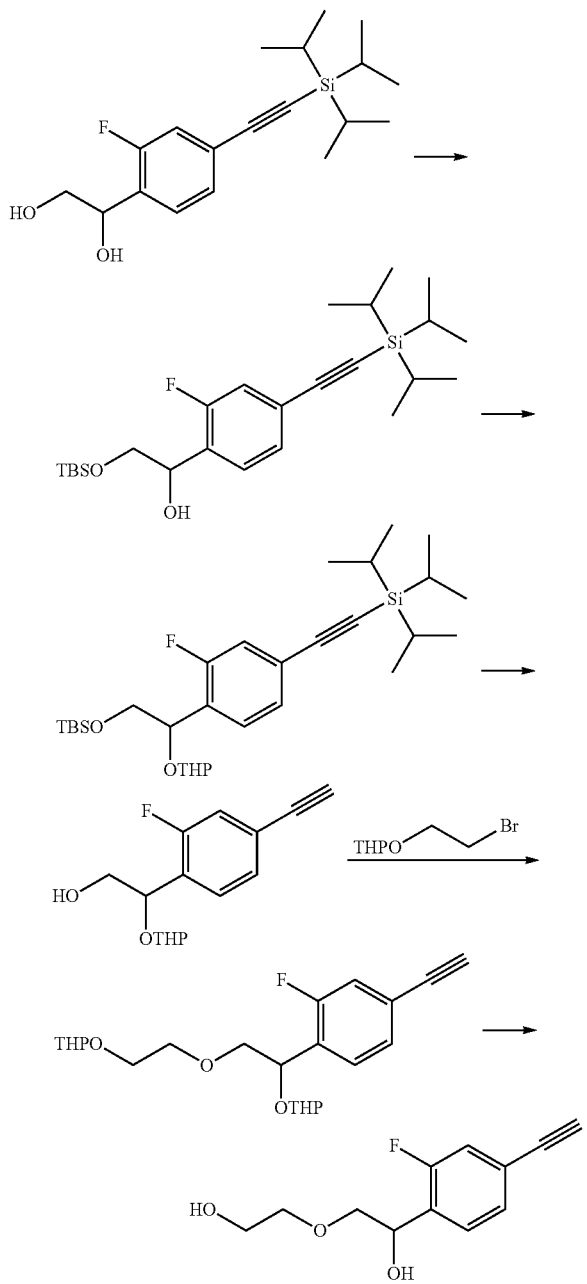

To a mixture of 1.90 g of 1-(2-fluoro-4-((triisopropylsilyl)ethynyl)phenyl)ethane-1,2-diol and 20 mL of dichloromethane, 847 mg of tert-butyldimethylsilyl chloride and 2.0 mL of triethylamine were successively added under a nitrogen atmosphere and under ice cooling, and the resulting mixture was stirred at room temperature for 8 hours and 30 minutes. To the reaction mixture, 206 mg of N,N-dimethylaminopyridine was added, and the resulting mixture was allowed to stand overnight. To the reaction mixture, 98 mg of tert-butyldimethylsilyl chloride was added, and the resulting mixture was stirred at room temperature for 1 hour and 45 minutes. Water was added to the reaction mixture, and the pH was adjusted to 7.9 with 6 mol/L hydrochloric acid. The organic layer was separated, washed successively with water and a saturated aqueous solution of sodium chloride, and then dried over anhydrous sodium sulfate. The solvent was distilled off under reduced pressure to obtain 2.69 g of a yellow oil.

To the obtained yellow oil, 20 mL of dichloromethane, 1.03 mL of 3,4-dihydro-2H-pyran, and 282 mg of pyridinium p-toluenesulfonate were added, and the resulting mixture was stirred at room temperature for 1 hour and 30 minutes. To the reaction mixture, 53 mg of p-toluenesulfonic acid monohydrate was added, and the resulting mixture was stirred for 1 hour. To the reaction mixture, 53 mg of p-toluenesulfonic acid monohydrate was added, and the resulting mixture was stirred for 50 minutes. Water was added to the reaction mixture. The organic layer was separated, washed successively with 1 mol/L hydrochloric acid, a saturated aqueous solution of sodium hydrogen carbonate, and a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=2:98→4:96]. To the obtained crudely purified product, 20 mL of dichloromethane, 1.03 mL of 3,4-dihydro-2H-pyran, and 282 mg of pyridinium p-toluenesulfonate were added, and the resulting mixture was stirred at room temperature for 1 hour and 30 minutes. Water was added to the reaction mixture, and the resulting mixture was neutralized with a saturated aqueous solution of sodium hydrogen carbonate. The organic layer was separated, washed successively with a saturated aqueous solution of sodium hydrogen carbonate and a saturated aqueous solution of sodium chloride, and then dried over anhydrous sodium sulfate. The solvent was distilled off under reduced pressure to obtain 2.55 g of a colorless oil.

To a mixture of 2.55 g of the obtained colorless oil and 25 mL of tetrahydrofuran, 11 mL of a 1 mol/L solution of tetra-n-butylammonium fluoride in tetrahydrofuran was added under ice cooling, and the resulting mixture was stirred at room temperature for 1 hour and 45 minutes. A saturated aqueous solution of ammonium chloride and ethyl acetate were added to the reaction mixture. The organic layer was separated, washed successively with water and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=20:80] to obtain 1.10 g of a colorless oil.

To a mixture of 317 mg of the obtained colorless oil, 3.0 mL of dimethyl sulfoxide, and 0.22 mL of 2-(2-bromoethoxy)tetrahydro-2H-pyran, 337 mg of potassium hydroxide was added under a nitrogen atmosphere, and the resulting mixture was stirred at room temperature for 1 hour. To the reaction mixture, 0.22 mL of 2-(2-bromoethoxy)tetrahydro-2H-pyran was added, and the resulting mixture was stirred at room temperature for 1 hour and 30 minutes. To the reaction mixture, 0.11 mL of 2-(2-bromoethoxy)tetrahydro-2H-pyran was added, and the resulting mixture was stirred at room temperature for 2 hours. To the reaction mixture, 0.11 mL of 2-(2-bromoethoxy)tetrahydro-2H-pyran was added, and the resulting mixture was allowed to stand at room temperature overnight. Ethyl acetate and water were added to the reaction mixture. The organic layer was separated, washed successively with 1 mol/L hydrochloric acid and a saturated aqueous solution of sodium chloride, and then dried over anhydrous sodium sulfate. The solvent was distilled off under reduced pressure to obtain a yellow oil.

To the obtained yellow oil, 0.3 mL of methanol, 3.0 mL of dichloromethane, and 46 mg of p-toluenesulfonic acid monohydrate were successively added, and the resulting mixture was stirred at room temperature for 1 hour and 30 minutes. Water and ethyl acetate were added to the reaction mixture, and the resulting mixture was neutralized with a saturated aqueous solution of sodium hydrogen carbonate. The organic layer was separated, washed successively with water and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=55:45] to obtain 169 mg of 1-(4-ethynyl-2-fluorophenyl)-2-(2-hydroxyethoxy)ethanol as a colorless oil.

$^1$H-NMR (400 MHz, CDCl$_3$) δ: 3.11 (1H, s), 3.47-3.51 (1H, m), 3.57-3.62 (1H, m), 3.66-3.77 (4H, m), 4.41 (1H, brs), 5.23 (1H, dd, J=8.5, 2.4 Hz), 7.12-7.15 (1H, m), 7.27-7.29 (1H, m), 7.49-7.53 (1H, m)

Reference Example 58

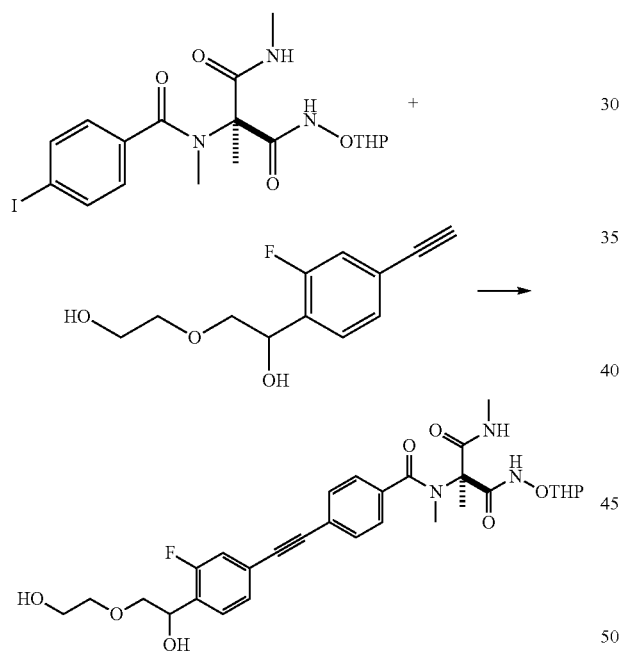

In the same manner as in Reference Example 2, from 169 mg of 1-(4-ethynyl-2-fluorophenyl)-2-(2-hydroxyethoxy)ethanol and 200 mg of (2S)-2-((4-iodobenzoyl)(methyl)amino)-N,2-dimethyl-N'-(tetrahydro-2H-pyran-2-yloxy)malonamide, 232 mg of (2S)-2-((4-((3-fluoro-4-(1-hydroxy-2-(2-hydroxyethoxy)ethyl)phenyl)ethynyl)benzoyl)(methyl)amino)-N,2-dimethyl-N'-(tetrahydro-2H-pyran-2-yloxy)malonamide was obtained as a yellow foamy solid.

$^1$H-NMR (400 MHz, CDCl$_3$) δ: 1.46-1.72 (3H, m), 1.76-1.94 (3H, m), [1.82], 1.83 (3H, s), 2.98-3.05 (1H, m), 2.82-2.91 (3H, m), [3.17], 3.20 (3H, s), 3.47-3.83 (8H, m), 3.83-4.08 (1H, m), 4.94-5.04 (1H, m), 5.22-5.29 (1H, m), 7.17-7.24 (1H, m), 7.35 (2H, d, J=7.6 Hz), 7.48-7.60 (4H, m), [6.95-7.05], 7.61-7.67 (1H, m), [10.08], 10.49 (1H, s)

Reference Example 59

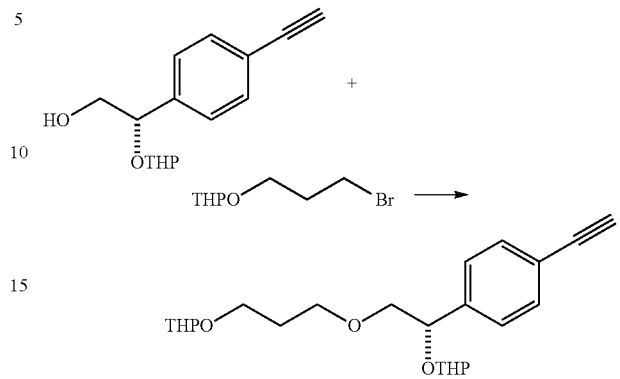

To 411 mg of (2S)-2-(4-ethynylphenyl)-2-(tetrahydro-2H-pyran-2-yloxy)ethanol, 4.0 mL of dimethyl sulfoxide, 745 mg of 2-(3-bromopropoxy)tetrahydro-2H-pyran, and 469 mg of potassium hydroxide were added, and the resulting mixture was stirred at room temperature for 3 hours. Ethyl acetate and water were added to the reaction mixture. The organic layer was separated, washed successively with water, 1 mol/L hydrochloric acid, and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=15:85] to obtain 532 mg of 2-(3-((2S)-2-(4-ethynylphenyl)-2-(tetrahydro-2H-pyran-2-yloxy)ethoxy)propoxy)tetrahydro-2H-pyran as a colorless oil.

$^1$H-NMR (400 MHz, CDCl$_3$) δ: 1.40-1.95 (14H, m), [3.05], 3.06 (1H, s), 3.29-4.06 (10H, m), [4.45-4.48], 4.50-4.57 (1H, m), [4.80-4.85], 4.88-4.94 (1H, m), [4.50-4.57], 4.98-5.03 (1H, m), [7.29], 7.36 (2H, d, J=8.2 Hz), 7.46 (2H, d, J=8.3 Hz)

Reference Example 60

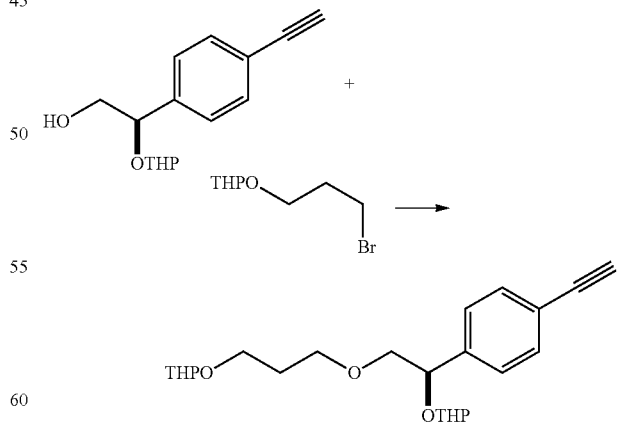

To a mixture of 900 mg of (2R)-2-(4-ethynylphenyl)-2-(tetrahydro-2H-pyran-2-yloxy)ethanol, 4.5 mL of dimethyl sulfoxide, and 1.54 mL of 2-(3-bromopropoxy)tetrahydro-2H-pyran, 768 mg of potassium hydroxide was added under ice cooling, and the resulting mixture was stirred at room temperature for 2 hours and 30 minutes. To the reaction mixture, 0.15 mL of 2-(3-bromopropoxy)tetrahydro-2H-pyran and 77 mg of potassium hydroxide were added, and the resulting mixture was stirred at room temperature for 1 hour and 30 minutes. Toluene and water were added to the reaction mixture, and the pH was adjusted to 6.6 with 6 mol/L hydrochloric acid. The organic layer was separated, and the aqueous layer was extracted with ethyl acetate. The organic layer was combined with the extract, washed successively with water and a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=20:80] to obtain 1.42 g of 2-(3-((2R)-2-(4-ethynylphenyl)-2-(tetrahydro-2H-pyran-2-yloxy)ethoxy)propoxy)tetrahydro-2H-pyran as a colorless oil.

$^{1}$H-NMR (400 MHz, CDCl$_{3}$) δ: 1.39-1.94 (14H, m), [3.05], 3.06 (1H, s), 3.28-4.08 (10H, m), [4.45-4.49], 4.58-4.62 (1H, m), [4.82-4.88], 4.91-4.97 (1H, m), [4.58-4.62], 4.99-5.05 (1H, m), [7.30], 7.37 (2H, d, J=8.2 Hz), 7.46 (2H, d, J=8.0 Hz)

Reference Example 61

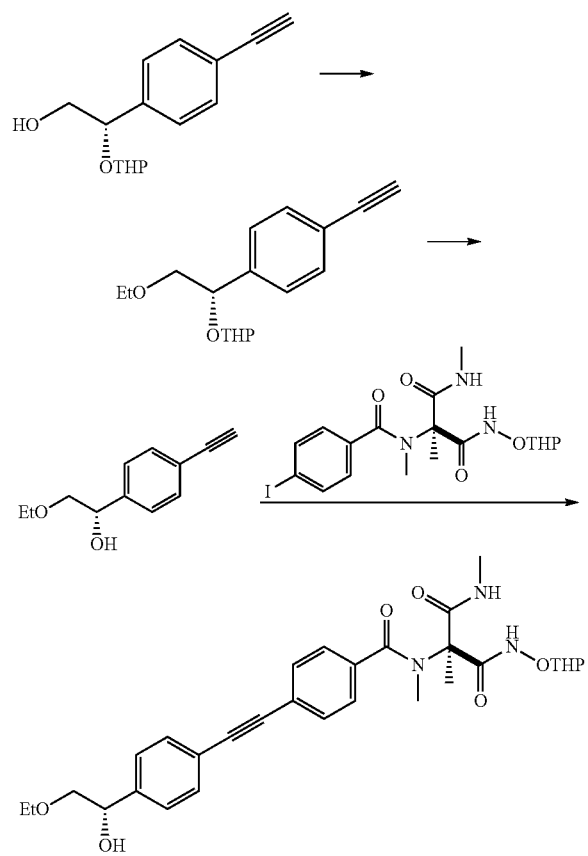

To 300 mg of (2S)-2-(4-ethynylphenyl)-2-(tetrahydro-2H-pyran-2-yloxy)ethanol, 3.0 mL of dimethyl sulfoxide, 0.2 mL of ethyl iodide, and 205 mg of potassium hydroxide were successively added, and the resulting mixture was stirred at room temperature for 2 hours and 30 minutes. Ethyl acetate and water were added to the reaction mixture. The organic layer was separated, washed successively with 1 mol/L hydrochloric acid and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=10:90] to obtain 259 mg of a white solid.

To 259 mg of the obtained white solid, 0.2 mL of methanol, 2.0 mL of dichloromethane, and 36 mg of p-toluenesulfonic acid monohydrate were added, and the resulting mixture was stirred at room temperature for 40 minutes. Water and ethyl acetate were added to the reaction mixture, and the resulting mixture was neutralized with a saturated aqueous solution of sodium hydrogen carbonate. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; ethyl acetate:hexane=15:85] to obtain 194 mg of a colorless oil.

To a mixture of 194 mg of the obtained colorless oil, 200 mg of (2S)-2-((4-iodobenzoyl)(methyl)amino)-N,2-dimethyl-N'-(tetrahydro-2H-pyran-2-yloxy)malonamide, 2.0 mL of tetrahydrofuran, 29 mg of bis-triphenylphosphinepalladium(II) dichloride, and 16 mg of copper(I) iodide, 0.22 mL of triethylamine was added under nitrogen purge and under ice cooling, and the resulting mixture was stirred at the same temperature for 40 minutes. Water and ethyl acetate were added to the reaction mixture, and the pH was adjusted to 2 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=15:85] to obtain 259 mg of (2S)-2-((4-((4-((1S)-2-ethoxy-1-hydroxyethyl)phenyl)ethynyl)benzoyl)(methyl)amino)-N,2-dimethyl-N'-(tetrahydro-2H-pyran-2-yloxy)malonamide as a brown foamy solid.

$^{1}$H-NMR (400 MHz, CDCl$_{3}$) δ: 1.21-1.30 (3H, m), 1.51-1.70 (3H, m), 1.74-1.92 (3H, m), [1.82], 1.83 (3H, s), 2.82-2.91 (4H, m), [3.17], 3.20 (3H, s), 3.38-3.46 (1H, m), 3.52-3.70 (4H, m), 3.83-4.08 (1H, m), 4.88-4.95 (1H, m), 4.95-5.03 (1H, m), 7.39 (2H, d, J=8.1 Hz), 7.50 (2H, d, J=8.3 Hz), 7.52 (2H, dd, J=7.8, 2.7 Hz), 7.58 (2H, d, J=8.3 Hz), [6.96-7.03], 7.61-7.67 (1H, m), [10.08], 10.50 (1H, s)

Reference Example 62

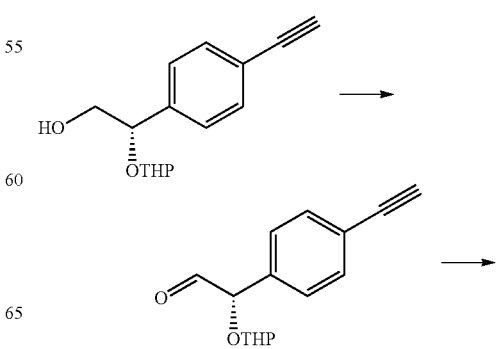

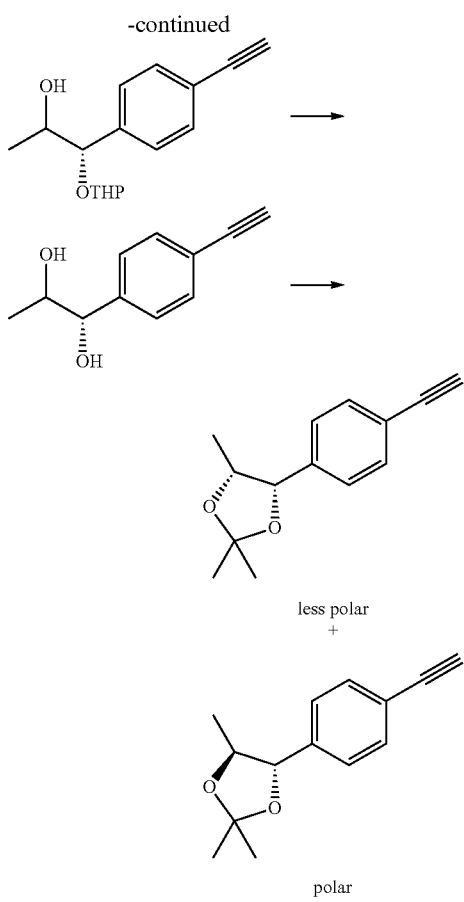

less polar

+ polar

To a mixture of 616 mg of (2S)-2-(4-ethynylphenyl)-2-(tetrahydro-2H-pyran-2-yloxy)ethanol, 6.5 mL of dichloromethane, 0.41 mg of 1-methyl-2-azaadamantan-N-oxyl, 29 mg of potassium bromide, 39 mg of tetra-n-butylammonium bromide, and 3.3 mL of an aqueous solution of sodium carbonate, 4.0 mL of an aqueous solution of sodium hypochlorite and 5.5 mL of an aqueous solution of sodium carbonate were added under ice cooling, and the resulting mixture was stirred at the same temperature for 1 hour and 30 minutes. To the reaction mixture, 1 mg of 1-methyl-2-azaadamantan-N-oxyl was added, the resulting mixture was stirred for 30 minutes, then 2.0 mL of an aqueous solution of sodium hypochlorite and 2.8 mL of an aqueous solution of sodium carbonate were added, and the resulting mixture was stirred for 1 hour. To the reaction mixture, 2.0 mL of an aqueous solution of sodium hypochlorite and 2.8 mL of an aqueous solution of sodium carbonate were added, the resulting mixture was stirred for 30 minutes, and then a saturated aqueous solution of sodium thiosulfate and ethyl acetate were added. The organic layer was separated, washed with a saturated aqueous solution of sodium chloride, and then dried over anhydrous sodium sulfate. The solvent was distilled off under reduced pressure to obtain 476 mg of a yellow oil.

To a mixture of 476 mg of the obtained yellow oil and 5.0 mL of tetrahydrofuran, 3.3 mL of a 1 mol/L solution of methylmagnesium bromide in diethyl ether was added under a nitrogen atmosphere at −65° C., and the resulting mixture was stirred for 30 minutes. To the reaction mixture, 1.6 mL of a 1 mol/L solution of methylmagnesium bromide in diethyl ether was added, and the resulting mixture was stirred for 1 hour. Diethyl ether and a saturated aqueous solution of ammonium chloride were added to the reaction mixture, and the resulting mixture was neutralized with 6 mol/L hydrochloric acid. The organic layer was separated, washed successively with 1 mol/L hydrochloric acid and a saturated aqueous solution of sodium chloride, and then dried over anhydrous sodium sulfate. The solvent was distilled off under reduced pressure to obtain a yellow oil.

To the obtained yellow oil, 0.5 mL of methanol, 5.0 mL of dichloromethane, and 95 mg of p-toluenesulfonic acid monohydrate were successively added, and the resulting mixture was stirred at room temperature for 3 hours. Diethyl ether and water were added to the reaction mixture, and the resulting mixture was neutralized with a saturated aqueous solution of sodium hydrogen carbonate. The organic layer was separated, washed with a saturated aqueous solution of sodium chloride, and then dried over anhydrous sodium sulfate. The solvent was distilled off under reduced pressure to obtain 460 mg of a yellow oil.

To 460 mg of the obtained yellow oil, 5.0 mL of dichloromethane, 0.9 mL of dimethoxypropane, and 95 mg of p-toluenesulfonic acid monohydrate were added, and the resulting mixture was stirred at room temperature for 15 minutes. Ethyl acetate and water were added to the reaction mixture, and the resulting mixture was neutralized with a saturated aqueous solution of sodium hydrogen carbonate. The organic layer was separated, washed successively with water and a saturated aqueous solution of sodium chloride, and then dried over anhydrous sodium sulfate. The solvent was distilled off under reduced pressure, and the obtained residue was purified by silica gel column chromatography [eluent; diethyl ether:hexane=0:100→4:96] to obtain 179 mg of (4S,5R)-4-(4-ethynylphenyl)-2,2,5-trimethyl-1,3-dioxolane as a yellow oil and 279 mg of (4S,5S)-4-(4-ethynylphenyl)-2,2,5-trimethyl-1,3-dioxolane as a yellow oil.

(4S,5R)-4-(4-ethynylphenyl)-2,2,5-trimethyl-1,3-dioxolane $^1$H-NMR (400 MHz, CDCl$_3$) δ: 1.29 (3H, d, J=6.1 Hz), 1.52 (3H, s), 1.55 (3H, s), 3.08 (1H, s), 3.79-3.85 (1H, m), 4.46 (1H, d, J=8.3 Hz), 7.34 (2H, d, J=7.3 Hz), 7.49 (2H, d, J=8.0 Hz)

(4S,5S)-4-(4-ethynylphenyl)-2,2,5-trimethyl-1,3-dioxolane $^1$H-NMR (400 MHz, CDCl$_3$) δ: 0.79 (3H, d, J=6.6 Hz), 1.46 (3H, s), 1.63 (3H, s), 3.07 (1H, s), 4.53-4.60 (1H, m), 5.18 (1H, d, J=6.8 Hz), 7.25 (2H, d, J=8.5 Hz), 7.46-7.49 (2H, m)

Reference Example 63

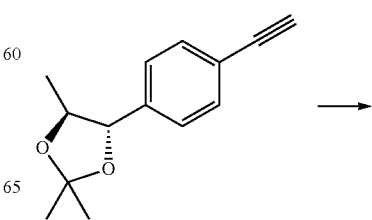

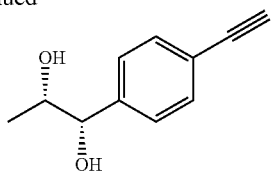

To a mixture of 297 mg of (4S,5S)-4-(4-ethynylphenyl)-2,2,5-trimethyl-1,3-dioxolane, 0.3 mL of methanol, and 3.0 mL of dichloromethane, 78 mg of p-toluenesulfonic acid monohydrate was added under ice cooling, and the resulting mixture was stirred at room temperature for 3 hours and 30 minutes. Ethyl acetate and water were added to the reaction mixture, and the resulting mixture was neutralized with a saturated aqueous solution of sodium hydrogen carbonate. The organic layer was separated, washed successively with a saturated aqueous solution of sodium hydrogen carbonate and a saturated aqueous solution of sodium chloride, and then the organic layer was dried over anhydrous sodium sulfate. The solvent was distilled off under reduced pressure, and the obtained residue was purified by silica gel column chromatography [eluent; ethyl acetate:hexane=65:35] to obtain 181 mg of (1S,2S)-1-(4-ethynylphenyl)propane-1,2-diol as a colorless oil.

$^1$H-NMR (400 MHz, CDCl$_3$) δ: 1.06 (3H, d, J=6.6 Hz), 1.84 (1H, d, J=1.8 Hz), 2.35-2.40 (1H, m), 3.08 (1H, s), 4.01-4.05 (1H, m), 4.71-4.73 (1H, m), 7.33 (2H, d, J=8.1 Hz), 7.49 (2H, d, J=8.3 Hz)

Reference Example 64

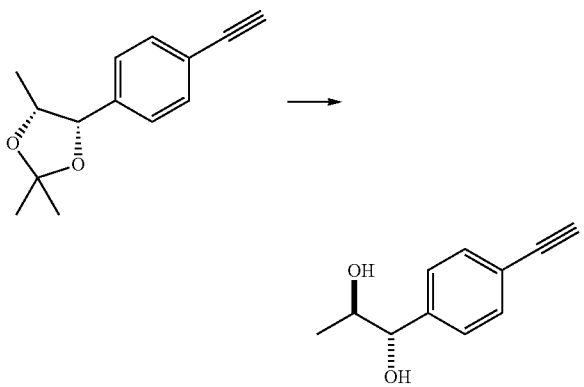

To 179 mg of (4S,5R)-4-(4-ethynylphenyl)-2,2,5-trimethyl-1,3-dioxolane, 2.0 mL of methanol and 46 mg of p-toluenesulfonic acid monohydrate were added, and the resulting mixture was stirred at room temperature for 6 hours. Ethyl acetate and water were added to the reaction mixture, and the resulting mixture was neutralized with a saturated aqueous solution of sodium hydrogen carbonate. The organic layer was separated, washed successively with a saturated aqueous solution of sodium hydrogen carbonate and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=65:35] to obtain 122 mg of (1S,2R)-1-(4-ethynylphenyl)propane-1,2-diol as a colorless oil.

$^1$H-NMR (400 MHz, CDCl$_3$) δ: 1.08 (3H, d, J=6.1 Hz), 2.33 (1H, d, J=3.6 Hz), 2.61 (1H, d, J=3.4 Hz), 3.08 (1H, s), 3.82-3.86 (1H, m), 4.39-4.41 (1H, m), 7.32 (2H, d, J=8.0 Hz), 7.49 (2H, d, J=8.3 Hz)

Reference Example 65

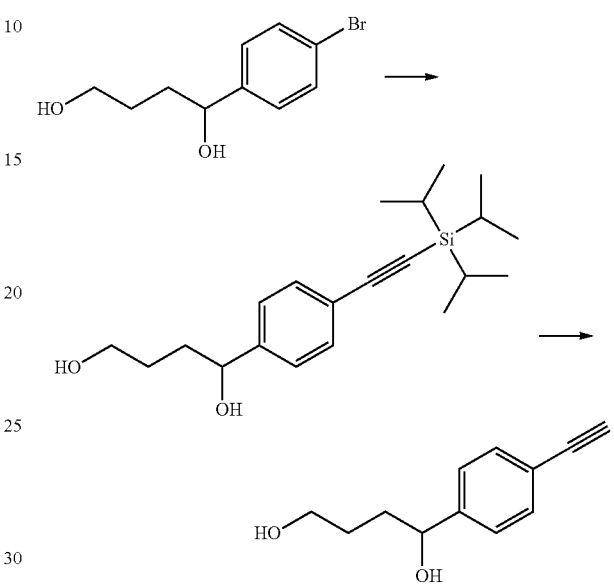

To 757 mg of 1-(4-bromophenyl)butane-1,4-diol, 9 mg of tri-tert-butylphosphonium tetrafluoroborate, 6 mg of copper (I) iodide, 5 mg of palladium(II) sodium chloride trihydrate, 3.7 mL of tetramethylethylenediamine, and 0.81 mL of triisopropylsilylacetylene were added, and the resulting mixture was stirred at 87° C. for 3 hours and 30 minutes. To the reaction mixture, 4 mg of tri-tert-butylphosphonium tetrafluoroborate, 3 mg of copper(I) iodide, 3 mg of palladium(II) sodium chloride trihydrate, and 0.17 mL of triisopropylsilylacetylene were added, and the resulting mixture was stirred at 85° C. for 2 hours and 15 minutes. The reaction mixture was cooled, ethyl acetate and a saturated aqueous solution of ammonium chloride were added, and the resulting mixture was neutralized with concentrated hydrochloric acid. The organic layer was separated, and then dried over anhydrous sodium sulfate. The solvent was distilled off under reduced pressure, and the obtained residue was purified by silica gel column chromatography [eluent; ethyl acetate:hexane=35:65→40:60] to obtain 715 mg of a yellow oil.

To 715 mg of the obtained yellow oil, 7.1 mL of tetrahydrofuran and 2.4 mL of a 1 mol/L solution of tetra-n-butylammonium fluoride in tetrahydrofuran were added, and the resulting mixture was stirred at room temperature for 30 minutes. Water and ethyl acetate were added to the reaction mixture, and the pH was adjusted to 4.1 with 6 mol/L hydrochloric acid. The organic layer was separated, and the aqueous layer was extracted with ethyl acetate. The organic layer was combined with the extract, and then dried over anhydrous magnesium sulfate. The solvent was distilled off under reduced pressure, and the obtained residue was purified by silica gel column chromatography [eluent; ethyl acetate:hexane=60:40→100:0] to obtain 327 mg of 1-(4-ethynylphenyl)butane-1,4-diol as a yellow solid.

¹H-NMR (400 MHz, CDCl₃) δ: 1.62-1.75 (2H, m), 1.83-1.88 (2H, m), 3.06 (1H, s), 3.66-3.75 (2H, m), 4.74-4.77 (1H, m), 7.32 (2H, d, J=8.1 Hz), 7.48 (2H, d, J=8.3 Hz)

Reference Example 66

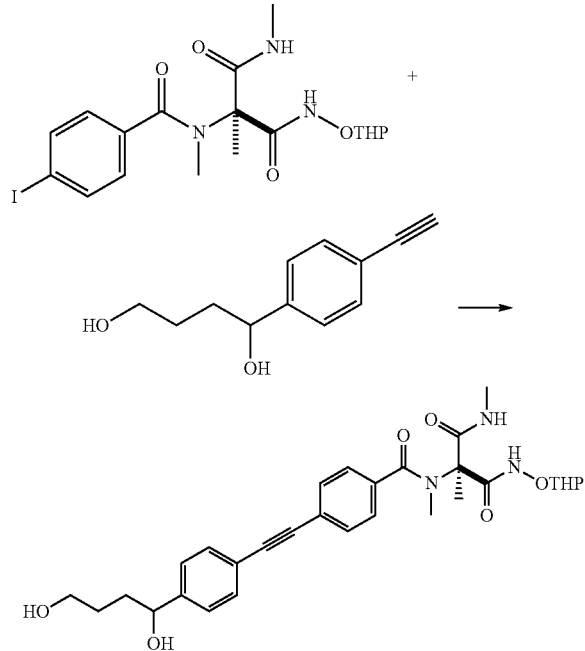

To a mixture of 251 mg of 1-(4-ethynylphenyl)butane-1,4-diol, 300 mg of (2S)-2-((4-iodobenzoyl)(methyl)amino)-N,2-dimethyl-N'-(tetrahydro-2H-pyran-2-yloxy)malonamide, 42 mg of bis-triphenylphosphinepalladium(II) dichloride, 22 mg of copper(I) iodide, and 3.0 mL of tetrahydrofuran, 0.67 mL of triethylamine was added under ice cooling, and the resulting mixture was stirred at the same temperature for 1 hour. A saturated aqueous solution of ammonium chloride and ethyl acetate were added to the reaction mixture, and the pH was adjusted to 6.1 with concentrated hydrochloric acid. The organic layer was separated, and then dried over anhydrous sodium sulfate. The solvent was distilled off under reduced pressure, and the obtained residue was purified by silica gel column chromatography [eluent; acetone:chloroform=40:60→45:55] to obtain 394 mg of (2S)-2-((4-((4-(1,4-dihydroxybutyl)phenyl)ethynyl)benzoyl)(methyl)amino)-N, 2-dimethyl-N'-(tetrahydro-2H-pyran-2-yloxy)malonamide as a brown solid.

¹H-NMR (400 MHz, CDCl₃) δ: 1.45-1.61 (3H, m), 1.62-1.75 (2H, m), 1.78-1.92 (5H, m), [1.81], 1.82 (3H, s), [2.85], 2.86 (3H, d, J=3.8 Hz), [3.17], 3.20 (3H, s), [3.52-3.61], 3.63-3.72 (1H, m), 3.67-3.78 (2H, m), [3.83-3.93], 3.97-4.07 (1H, m), 4.73-4.83 (1H, m), [4.94-4.98], 4.98-5.04 (1H, m), 7.36 (2H, d, J=8.0 Hz), 7.47-7.61 (6H, m), [6.97-7.03], 7.61-7.65 (1H, m), [10.10], 10.51 (1H, s)

Reference Example 67

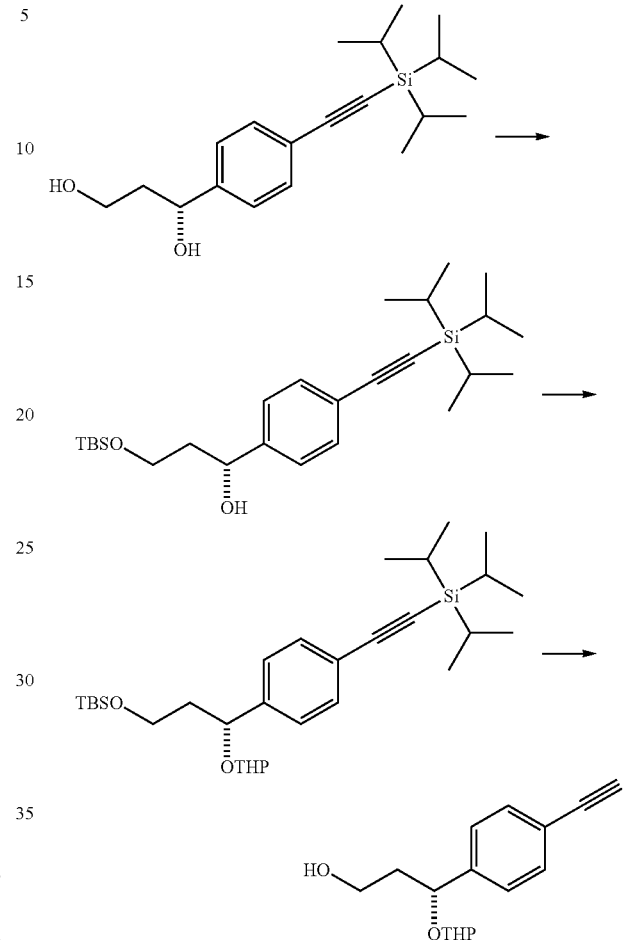

In the same manner as in Reference Example 39, from 871 mg of (1R)-1-(4-((triisopropylsilyl)ethynyl)phenyl)propane-1,3-diol, 519 mg of (3R)-3-(4-ethynylphenyl)-3-(tetrahydro-2H-pyran-2-yloxy)propan-1-ol was obtained as a colorless oil.

¹H-NMR (400 MHz, CDCl₃) δ: 1.46-1.60 (4H, m), 1.66-1.73 (1H, m), 1.77-1.85 (1H, m), 1.90-2.00 (2H, m), 2.88 (1H, s), [3.06], 3.07 (1H, s), 3.48-3.57 (1H, m), 3.74-3.77 (1H, m), [3.62-3.70], 3.85-3.89 (1H, m), [3.26-3.31], 3.94-3.99 (1H, m), [4.36-4.38], 4.94-4.98 (1H, m), 4.82-4.87 (1H, m), [7.28], 7.34 (2H, d, J=8.6 Hz), 7.47 (2H, dd, J=8.3, 2.0 Hz)

Reference Example 68

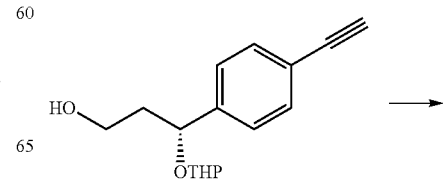

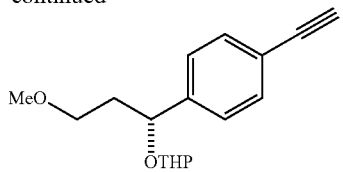

In the same manner as in Reference Example 40, from 519 mg of (3R)-3-(4-ethynylphenyl)-3-(tetrahydro-2H-pyran-2-yloxy)propan-1-ol, 322 mg of 2-(((1R)-1-(4-ethynylphenyl)-3-methoxypropyl)oxy)tetrahydro-2H-pyran was obtained as a colorless oil.

$^1$H-NMR (400 MHz, CDCl$_3$) δ: 1.38-1.94 (7H, m), 1.99-2.14 (1H, m), [3.05], 3.06 (1H, s), 3.22-3.57 (6H, m), 3.86-3.96 (1H, m), [4.38-4.40], 4.79-4.80 (1H, m), [4.71-4.74], 4.83-4.87 (1H, m), 7.25-7.37 (2H, m), 7.44-7.50 (2H, m)

Reference Example 69

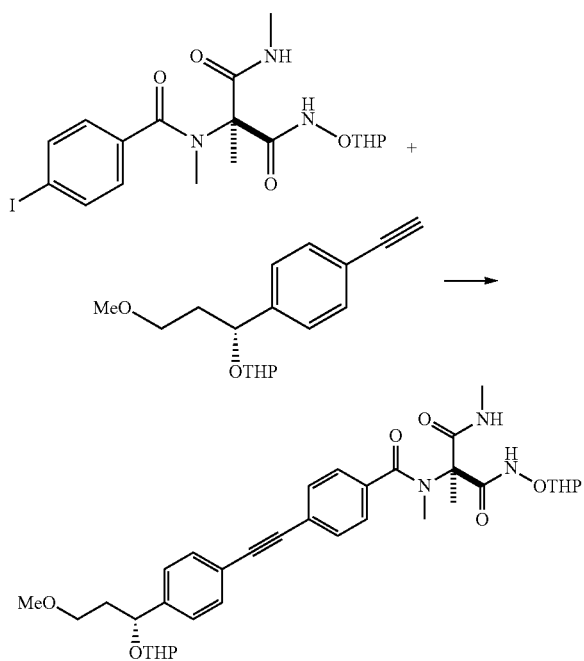

To a mixture of 322 mg of 2-(((1R)-1-(4-ethynylphenyl)-3-methoxypropyl)oxy)tetrahydro-2H-pyran, 2.6 mL of tetrahydrofuran, 260 mg of (2S)-2-((4-iodobenzoyl)(methyl)amino)-N,2-dimethyl-N'-(tetrahydro-2H-pyran-2-yloxy)malonamide, 37 mg of bis-triphenylphosphinepalladium(II) dichloride, and 20 mg of copper(I) iodide, 0.59 mL of triethylamine was added under ice cooling, and the resulting mixture was stirred at the same temperature for 30 minutes. A saturated aqueous solution of ammonium chloride and ethyl acetate were added to the reaction mixture, and the pH was adjusted to 6.8 with concentrated hydrochloric acid. The organic layer was separated, and then dried over anhydrous sodium sulfate. The solvent was distilled off under reduced pressure, and the obtained residue was purified by silica gel column chromatography [eluent; acetone:chloroform=10:90] to obtain 453 mg of (2S)-2-((4-((4-((1R)-3-methoxy-1-(tetrahydro-2H-pyran-2-yloxy)propyl)phenyl)ethynyl)benzoyl)(methyl)amino)-N,2-dimethyl-N'-(tetrahydro-2H-pyran-2-yloxy)malonamide as a brown solid.

$^1$H-NMR (400 MHz, CDCl$_3$) δ: 1.39-1.75 (9H, m), 1.75-1.96 (4H, m), [1.81], 1.82 (3H, s), 2.02-2.19 (1H, m), 2.83-2.90 (3H, m), [3.17], 3.20 (3H, s), 3.23-3.41 (1H, m), [3.31], 3.33 (3H, s), 3.43-3.61 (3H, m), [3.63-3.71], 3.83-3.96 (1H, m), [3.83-3.96], 3.96-4.07 (1H, m), [4.40-4.44], 4.80-4.83 (1H, m), [4.72-4.79], 4.85-4.91 (1H, m), [4.95-4.98], 4.98-5.03 (1H, m), [7.31], 7.38 (2H, d, J=8.3 Hz), 7.48-7.54 (4H, m), 7.57 (2H, d, J=8.3 Hz), [6.96-7.03], 7.61-7.66 (1H, m), [10.08], 10.49 (1H, s)

Reference Example 70

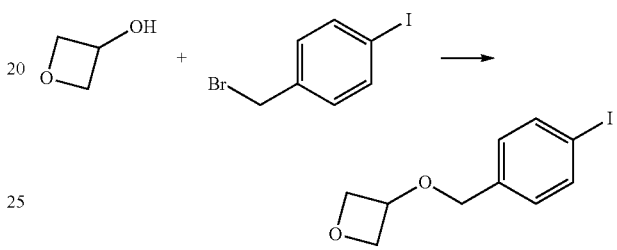

To a mixture of 111 mg of oxetan-3-ol, 5 mL of N,N-dimethylformamide, and 445 mg of 4-iodobenzyl bromide, 120 mg of a 60% suspension of sodium hydride in mineral oil was added under a nitrogen atmosphere and under ice cooling, and the resulting mixture was stirred at the same temperature for 1 hour. Water and ethyl acetate were added to the reaction mixture, and the resulting mixture was neutralized with 6 mol/L hydrochloric acid. The organic layer was separated, washed with water and a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=20:80] to obtain 400 mg of 3-((4-iodobenzyl)oxy)oxetane as a white solid.

$^1$H-NMR (400 MHz, CDCl$_3$) δ: 4.39 (2H, s), 4.59-4.66 (3H, m), 4.69-4.77 (2H, m), 7.08 (2H, d, J=8.0 Hz), 7.69 (2H, d, J=8.3 Hz)

Reference Example 71

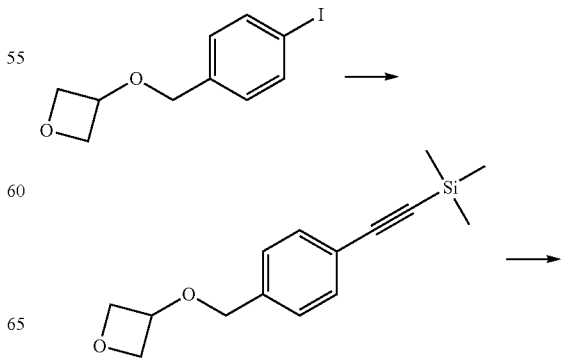

-continued

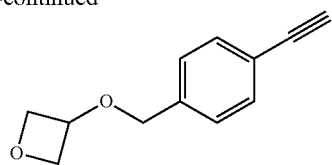

In the same manner as in Reference Example 1, from 400 mg of 3-((4-iodobenzyl)oxy)oxetane, 199 mg of 3-((4-ethynylbenzyl)oxy)oxetane was obtained as a yellow oil.

$^1$H-NMR (400 MHz, CDCl$_3$) δ: 3.08 (1H, s), 4.45 (2H, s), 4.60-4.69 (3H, m), 4.69-4.77 (2H, m), 7.29 (2H, d, J=8.0 Hz), 7.48 (2H, d, J=8.1 Hz)

Reference Example 72

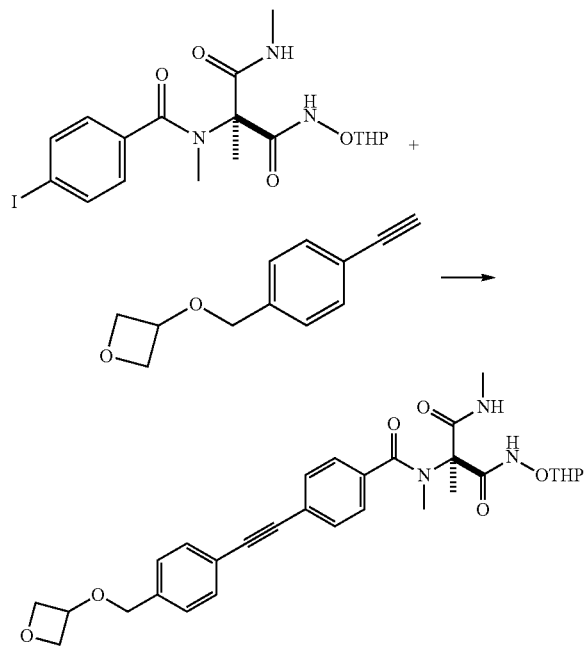

In the same manner as in Reference Example 2, from 199 mg of 3-((4-ethynylbenzyl)oxy)oxetane and 120 mg of (2S)-2-((4-iodobenzoyl)(methyl)amino)-N,2-dimethyl-N'-(tetrahydro-2H-pyran-2-yloxy)malonamide, 140 mg of (2S)—N,2-dimethyl-2-(methyl(4-((4-((oxetan-3-yl oxy) methyl)phenyl)ethynyl)benzoyl)amino)-N'-(tetrahydro-2H-pyran-2-yloxy)malonamide was obtained as a brown foamy solid.

$^1$H-NMR (400 MHz, CDCl$_3$) δ: 1.51-1.72 (3H, m), 1.82-1.94 (3H, m), [1.82], 1.83 (3H, s), 2.82-2.91 (3H, m), [3.17], 3.20 (3H, s), 3.51-3.71 (1H, m), 3.82-4.08 (1H, m), 4.47 (2H, s), 4.61-4.71 (3H, m), 4.71-4.81 (2H, m), 4.91-5.06 (1H, m), 7.34 (2H, d, J=8.0 Hz), 7.49-7.56 (4H, m), 7.58 (2H, d, J=8.3 Hz), [6.96-7.03], 7.61-7.69 (1H, m), [10.08], 10.50 (1H, s)

Reference Example 73

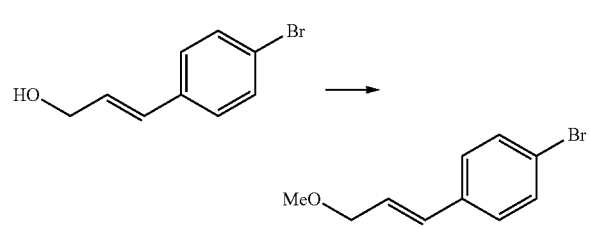

To a mixture of 6.02 g of (2E)-3-(4-bromophenyl)-2-propen-1-ol, 27 mL of dimethyl sulfoxide, and 3.1 mL of methyl iodide, 4.14 g of potassium hydroxide was added under ice cooling, and the resulting mixture was stirred at room temperature for 2 hours and 30 minutes. To the reaction mixture, 1.04 g of potassium hydroxide and 0.8 mL of methyl iodide were added, and the resulting mixture was stirred at room temperature for 45 minutes. Water was added to the reaction mixture, the pH was adjusted to 6.5 with 6 mol/L hydrochloric acid, and then ethyl acetate and water were added. The organic layer was separated, washed with a saturated aqueous solution of sodium chloride, and then dried over anhydrous magnesium sulfate. The solvent was distilled off under reduced pressure to obtain 5.47 g of 1-bromo-4-((1E)-3-methoxy-1-propen-1-yl)benzene as a white solid.

$^1$H-NMR (400 MHz, CDCl$_3$) δ: 3.39 (3H, s), 4.04-4.13 (2H, m), 6.27 (1H, dt, J=15.8, 5.8 Hz), 6.55 (1H, d, J=16.1 Hz), 7.24 (2H, d, J=8.6 Hz), 7.43 (2H, d, J=8.6 Hz)

Reference Example 74

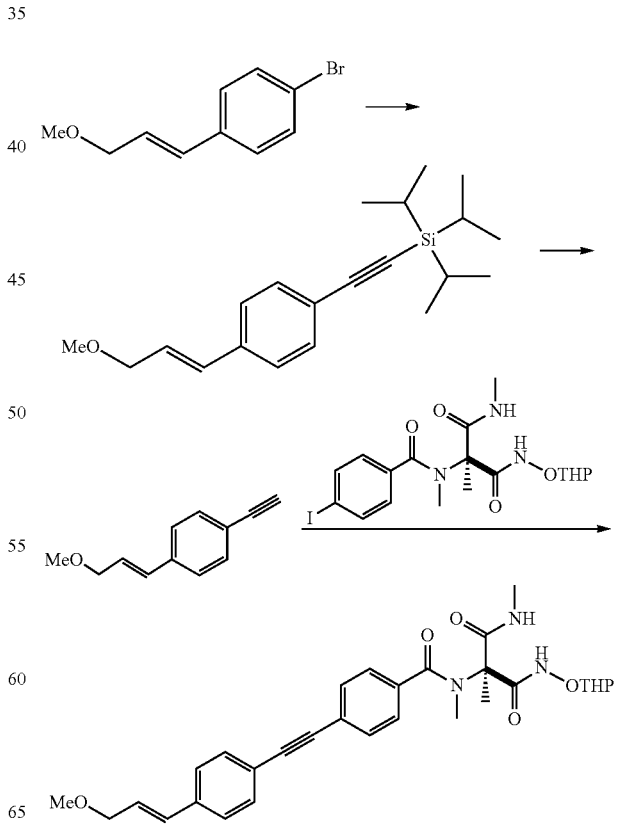

To a mixture of 567 mg of 1-bromo-4-((1E)-3-methoxy-1-propen-1-yl)benzene, 175 mg of bis-triphenylphosphinepalladium(II) dichloride, 95 mg of copper(I) iodide, 6.0 mL of n-butyl acetate, and 1.96 mL of triisopropylsilylacetylene, 2.4 mL of triethylamine was added under a nitrogen atmosphere, and the resulting mixture was stirred under reflux for 1 hour and 30 minutes. To the reaction mixture, 87 mg of bis-triphenylphosphinepalladium(II) dichloride, 48 mg of copper(I) iodide, 1.7 mL of triisopropylsilylacetylene, and 1.0 mL of triethylamine were added, and the resulting mixture was stirred under reflux for 1 hour and 30 minutes. Ethyl acetate and a saturated aqueous solution of ammonium chloride were added to the reaction mixture, the pH was adjusted to 6.6 with 1 mol/L hydrochloric acid, then Celpure was added, and the insoluble material was filtered off. The organic layer of the filtrate was separated, washed with a saturated aqueous solution of sodium chloride, and then dried over anhydrous magnesium sulfate. The solvent was distilled off under reduced pressure, and the obtained residue was purified by silica gel column chromatography [eluent; diethyl ether:hexane=4:96→6:94] to obtain 837 mg of a yellow oil.

To a mixture of the obtained yellow oil, 4.0 mL of tetrahydrofuran, and 0.23 mL of acetic acid, 3.8 mL of a 1 mol/L solution of tetra-n-butylammonium fluoride in tetrahydrofuran was added under ice cooling, and the resulting mixture was stirred at room temperature for 1 hour and 30 minutes. To the reaction mixture, 2.0 mL of a 1 mol/L solution of tetra-n-butylammonium fluoride in tetrahydrofuran was added, and the resulting mixture was stirred at room temperature for 1 hour. A saturated aqueous solution of ammonium chloride and diethyl ether were added to the reaction mixture, and the pH was adjusted to 2 with 1 mol/L hydrochloric acid. The organic layer was separated, washed with a saturated aqueous solution of sodium chloride, and then dried over anhydrous magnesium sulfate. The solvent was distilled off under reduced pressure to obtain 430 mg of a yellow oil.

To a mixture of 430 mg of the obtained yellow oil, 1.5 mL of tetrahydrofuran, 152 mg of (2S)-2-((4-iodobenzoyl)(methyl)amino)-N,2-dimethyl-N'-(tetrahydro-2H-pyran-2-yloxy)malonamide, 22 mg of bis-triphenylphosphinepalladium(II) dichloride, and 12 mg of copper(I) iodide, 0.43 mL of triethylamine was added under a nitrogen atmosphere and under ice cooling, and the resulting mixture was stirred at the same temperature for 1 hour. A saturated aqueous solution of ammonium chloride and ethyl acetate were added to the reaction mixture, and the pH was adjusted to 6.4 with 1 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=10:90→20:80] to obtain 230 mg of (2S)-2-((4-((1E)-3-methoxy-1-propen-1-yl)phenyl)ethynyl)benzoyl)(methyl)amino)-N,2-dimethyl-N'-(tetrahydro-2H-pyran-2-yloxy)malonamide as a brown foamy solid.

$^1$H-NMR (400 MHz, CDCl$_3$) δ: 1.49-1.68 (3H, m), 1.74-1.90 (3H, m), [1.81], 1.82 (3H, s), [2.85], 2.86 (3H, d, J=4.0 Hz), [3.17], 3.20 (3H, s), 3.41 (3H, s), [3.53-3.60], 3.63-3.72 (1H, m), [3.84-3.92], 3.98-4.06 (1H, m), 4.09-4.14 (2H, m), 4.94-5.02 (1H, m), 6.29-6.39 (1H, m), 6.61 (1H, d, J=15.8 Hz), 7.38 (2H, d, J=8.3 Hz), 7.44-7.54 (4H, m), 7.57 (2H, d, J=7.8 Hz), [6.97-7.03], 7.62-7.71 (1H, m), [10.08], 10.50 (1H, s)

Reference Example 75

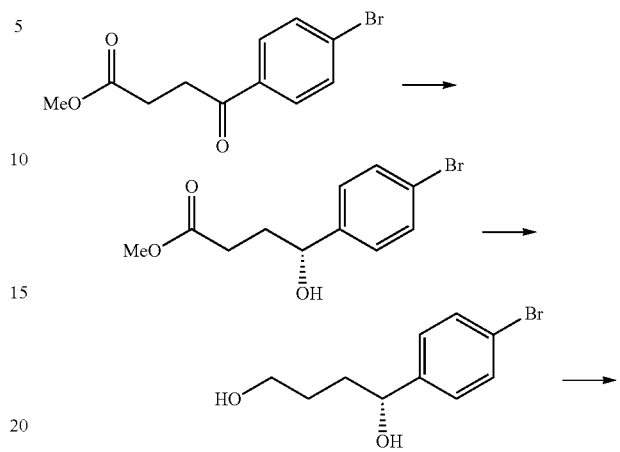

To 6.0 mL of tetrahydrofuran, 92 mg of (S)-(−)-2-methyl-CBS-oxazaborolidine was added, then a solution of 0.9 g of methyl 4-(4-bromophenyl)-4-oxobutanoate in 3.5 mL of tetrahydrofuran and 3.5 mL of a 0.95 mol/L solution of borane-tetrahydrofuran complex in tetrahydrofuran were added dropwise for 1 hour under ice cooling, and the resulting mixture was stirred at room temperature for 3 hours. To the reaction mixture, 8.0 mL of a 1 mol/L aqueous solution of potassium carbonate was added, and then diethyl ether was added. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=50:50] to obtain 580 mg of a colorless oil.

To 571 mg of the obtained colorless oil, 5.7 mL of ethanol was added, and the resulting mixture was stirred under ice cooling. Then, 160 mg of sodium borohydride was added at the same temperature, and then the resulting mixture was stirred at room temperature for 2 hours and 30 minutes. The reaction mixture was poured into 20 mL of iced water, and the resulting mixture was neutralized with 3 mol/L hydrochloric acid. Ethyl acetate was added to the reaction mixture to separate the organic layer. The organic layer was dried over anhydrous sodium sulfate, then the solvent was distilled off under reduced pressure, and then the obtained residue was purified by silica gel column chromatography [eluent; ethyl acetate:hexane=50:50 20→75:25] to obtain 515 mg of (1R)-1-(4-bromophenyl)butane-1,4-diol as a colorless oil.

$^1$H-NMR (400 MHz, CDCl$_3$) δ: 1.57-1.74 (2H, m), 1.78-1.87 (2H, m), 3.60-3.76 (2H, m), 4.66-4.73 (1H, m), 7.20-7.26 (2H, m), 7.43-7.49 (2H, m)

Reference Example 76

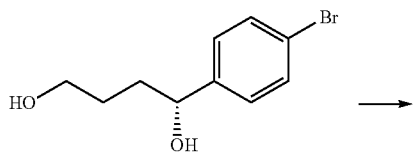

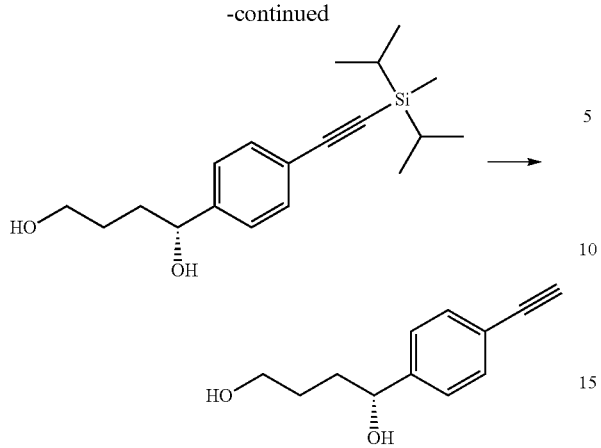

To 365 mg of (1R)-1-(4-bromophenyl)butane-1,4-diol, 4.3 mg of tri-tert-butylphosphonium tetrafluoroborate, 2.8 mg of copper(I) iodide, 5.2 mg of palladium(II) sodium chloride trihydrate, 1.8 mL of tetramethylethylenediamine, and 0.50 mL of triisopropylsilylacetylene were added, and the resulting mixture was stirred at 110° C. for 1 hour. The reaction mixture was cooled, ethyl acetate and a saturated aqueous solution of ammonium chloride were added, the resulting mixture was neutralized with 3 mol/L hydrochloric acid, and then the organic layer was separated. The organic layer was washed with a saturated aqueous solution of sodium chloride, dried over anhydrous sodium sulfate, and then the solvent was distilled off under reduced pressure. To the obtained residue, 3.5 mL of tetrahydrofuran and 1.6 mL of a 1 mol/L solution of tetra-n-butylammonium fluoride in tetrahydrofuran were added, and the resulting mixture was stirred at room temperature for 30 minutes. Then 0.2 mL of a 1 mol/L solution of tetra-n-butylammonium fluoride in tetrahydrofuran was added to the reaction mixture, and the resulting mixture was stirred at room temperature for 40 minutes. Water and ethyl acetate were added to the reaction mixture, the pH was adjusted to 4.5 with 3 mol/L hydrochloric acid, and then the organic layer was separated. The organic layer was washed with a saturated aqueous solution of sodium chloride, and then dried over anhydrous sodium sulfate. The solvent was distilled off under reduced pressure, and the obtained residue was purified by silica gel column chromatography [eluent; ethyl acetate:hexane=67:33→100: 0] to obtain 282 mg of (1R)-1-(4-ethynylphenyl)butane-1, 4-diol as a white solid.

$^1$H-NMR (400 MHz, CDCl$_3$) δ: 1.59-1.77 (2H, m), 1.80-1.90 (2H, m), 3.06 (1H, s), 3.63-3.78 (2H, m), 4.75 (1H, dd, J=7.1, 5.6 Hz), 7.29-7.35 (2H, m), 7.44-7.51 (2H, m)

Reference Example 77

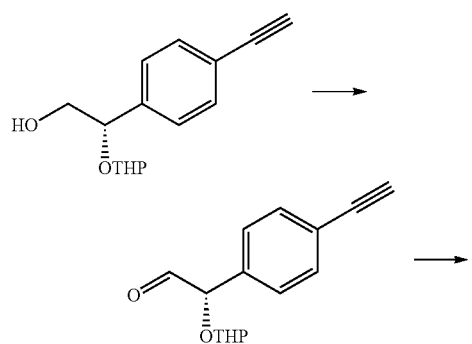

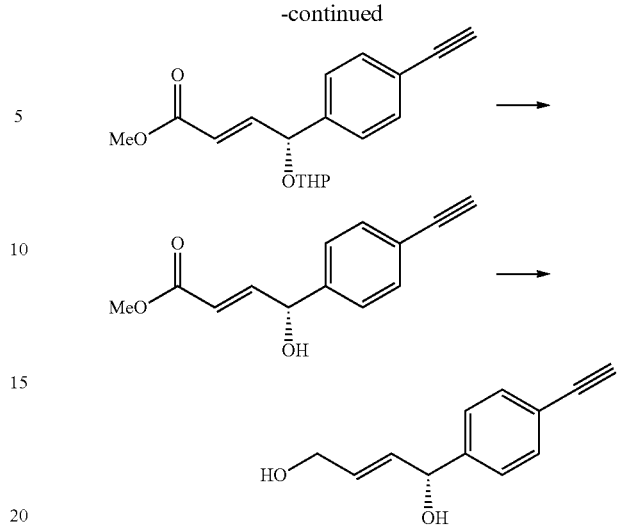

To 800 mg of (2S)-2-(4-ethynylphenyl)-2-(tetrahydro-2H-pyran-2-yloxy)ethanol, 8.0 mL of dichloromethane, 628 mg of sodium hydrogen carbonate, and 1.79 g of Dess-Martin periodinane were added, and the resulting mixture was stirred at room temperature for 1 hour. An aqueous solution of sodium hydrogen carbonate and diethyl ether were added to the reaction mixture. Then an aqueous solution of a sodium thiosulfate was added to the reaction mixture, and the insoluble material was filtered off. The organic layer was separated, dried over anhydrous magnesium sulfate, and then the solvent was distilled off under reduced pressure. To the obtained residue, 10 mL of dichloromethane and 2.17 g of ethyl (triphenylphosphoranylidene) acetate were added, and the resulting mixture was stirred at room temperature for 2 hours. Ethyl acetate and water were added to the reaction mixture to separate the organic layer. The organic layer was dried over anhydrous magnesium sulfate, and then the solvent was distilled off under reduced pressure. The obtained residue was purified by silica gel column chromatography [eluent; ethyl acetate:hexane=14: 86→20:80] to obtain 801 mg of a pale yellow oil.

To 611 mg of the obtained pale yellow oil, 6.1 mL of methanol and 77 mg of p-toluenesulfonic acid monohydrate were added, and the resulting mixture was stirred at room temperature for 1 hour. Ethyl acetate was added to the reaction mixture, and the resulting mixture was neutralized with a saturated aqueous solution of sodium hydrogen carbonate. The organic layer was separated, and then dried over anhydrous magnesium sulfate. The solvent was distilled off under reduced pressure, and the obtained residue was purified by silica gel column chromatography [eluent; ethyl acetate:hexane=67:33→80:20] to obtain 450 mg of a colorless oil.

To 450 mg of the obtained yellow oil, 13.0 mL of dichloromethane was added, and the resulting mixture was cooled to −60° C. under a nitrogen atmosphere. Then, 6.5 mL of a 1 mol/L solution of diisobutylaluminum hydride in hexane was added dropwise at the same temperature, and the resulting mixture was stirred at the same temperature for 1 hour. To the reaction mixture, 0.41 mL of a 1 mol/L solution of diisobutylaluminum hydride in hexane was added dropwise at the same temperature, and the resulting mixture was stirred at the same temperature for 30 minutes. The reaction mixture was diluted with diethyl ether, a saturated aqueous solution of Rochelle salt was added, and the resulting mixture was stirred at room temperature for 40 minutes, and then allowed to stand overnight. The organic layer was separated, dried over anhydrous magnesium sulfate, and then the solvent was distilled off under reduced pressure. The obtained residue was purified by silica gel column chromatography [eluent; acetone:chloroform=9:91→17:83] to obtain 290 mg of (1R,2E)-1-(4-ethynylphenyl)but-2-ene-1,4-diol as a pale yellow oil.

$^1$H-NMR (400 MHz, CDCl$_3$) δ: 1.42 (1H, t, J=5.8 Hz), 2.02 (1H, t, J=3.7 Hz), 3.07 (1H, s), 4.15-4.22 (2H, m), 5.22-5.27 (1H, m), 5.90-5.95 (2H, m), 7.30-7.37 (2H, m), 7.45-7.52 (2H, m)

Reference Example 78

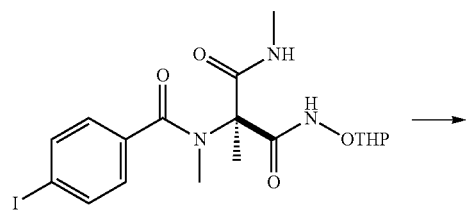

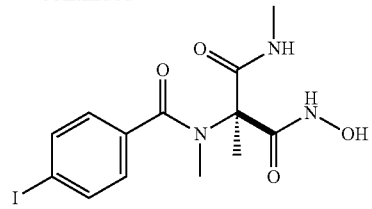

In the same manner as in Example 16, from 700 mg of (2S)-2-((4-iodobenzoyl)(methyl)amino)-N,2-dimethyl-N'-(tetrahydro-2H-pyran-2-yloxy)malonamide, 420 mg of (2S)—N-hydroxy-2-((4-iodobenzoyl)(methyl)amino)-N',2-dimethyl-malonamide was obtained as a yellow solid.

$^1$H-NMR (400 MHz, CDCl$_3$) δ: 1.79 (3H, s), 2.83 (3H, d, J=4.9 Hz), 3.15 (3H, s), 6.84 (1H, s), 7.24 (2H, d, J=8.3 Hz), 7.78 (2H, d, J=8.6 Hz), 10.52 (1H, s)

Example 1

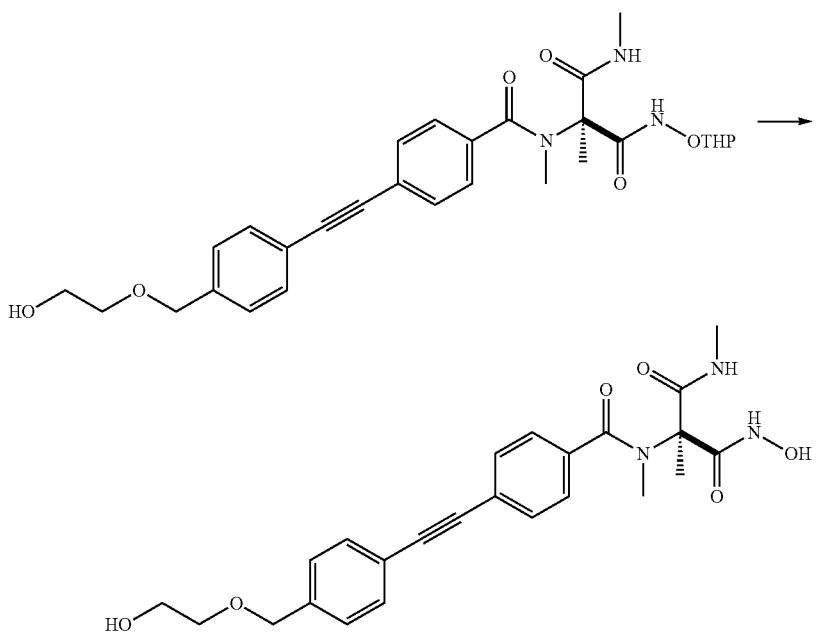

To 123 mg of (2S)-2-((4-((4-((2-hydroxyethoxy)methyl)phenyl)ethynyl)benzoyl)(methyl)amino)-N,2-dimethyl-N'-(tetrahydro-2H-pyran-2-yloxy)malonamide, 1.2 mL of 1,4-dioxane and 0.60 mL of a 1 mol/L aqueous solution of sulfuric acid were added, and the resulting mixture was stirred at room temperature for 1 hour and 30 minutes. Ethyl acetate and water were added to the reaction mixture. The organic layer was separated, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=6:94] to obtain 57 mg of a yellow solid. Ethyl acetate and IPE were added thereto, and the solid material was collected by filtration to obtain 47 mg of (2S)—N- hydroxy-2-((4-((4-((2-hydroxyethoxy)methyl)phenyl)ethynyl)benzoyl)(methyl)amino)-N',2-dimethyl-malonamide as a yellow solid.

$^1$H-NMR (400 MHz, CD$_3$OD) δ: 1.77 (3H, s), 2.79 (3H, s), 3.17 (3H, s), 3.57-3.59 (2H, m), 3.70-3.72 (2H, m), 4.58 (2H, s), 7.40 (2H, d, J=8.0 Hz), 7.51-7.62 (6H, m); MS (ESI): 476 [M+Na]$^+$, 453 [M-H]$^-$

Example 2

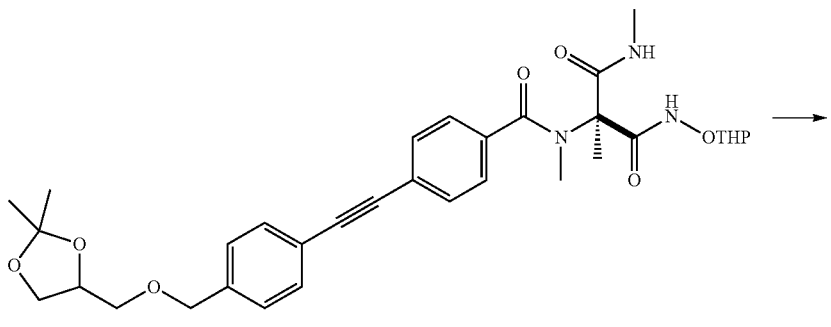

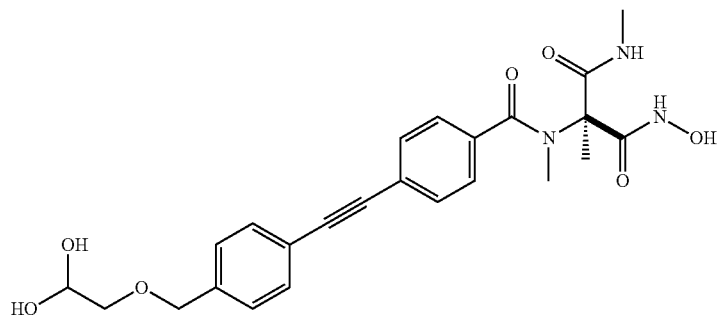

To 194 mg of (2S)-2-((4-((4-(((2,2-dimethyl-1,3-dioxolan-4-yl)methoxy)methyl)phenyl)ethynyl)benzoyl)(methyl)amino)-N,2-dimethyl-N'-(tetrahydro-2H-pyran-2-yloxy)malonamide, 0.97 mL of 1,4-dioxane and 0.94 mL of a 1 mol/L aqueous solution of sulfuric acid were added, and the resulting mixture was stirred at room temperature for 1 hour and 30 minutes. To the reaction mixture, 0.32 mL of a 1 mol/L aqueous solution of sulfuric acid was added, and the resulting mixture was stirred at room temperature for 1 hour and 30 minutes. Ethyl acetate and water were added to the reaction mixture. The organic layer was separated, sodium chloride was added to the aqueous layer, and the aqueous layer was extracted with ethyl acetate twice. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=8:92→10:90] to obtain 91 mg of a yellow solid. Ethyl acetate and IPE were added thereto, and the solid material was collected by filtration to obtain 71 mg of (2S)-2-((4-((4-((2,3-dihydroxypropoxy)methyl)phenyl)ethynyl)benzoyl)(methyl)amino)-N-hydroxy-N',2-dimethylmalonamide as a pale yellow solid.

$^1$H-NMR (600 MHz, CD$_3$OD) δ: 1.77 (3H, s), 2.79 (3H, s), 3.17 (3H, s), 3.48-3.63 (4H, m), 3.77-3.83 (1H, m), 4.58 (2H, s), 7.39 (2H, d, J=8.4 Hz), 7.52 (2H, d, J=8.2 Hz), 7.56 (2H, d, J=8.5 Hz), 7.61 (2H, d, J=8.4 Hz); MS (ESI): 506 [M+Na]$^+$, 482 [M-H]$^-$

Example 3

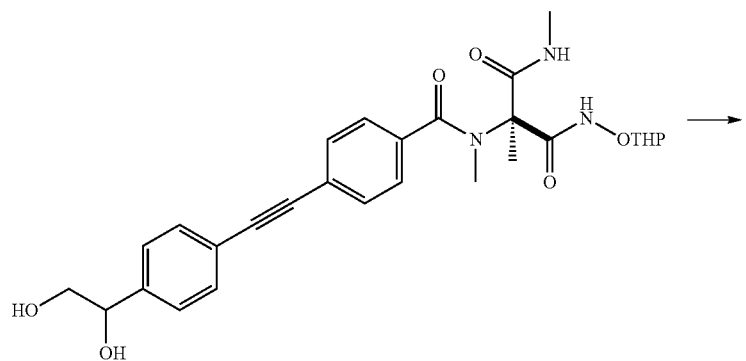

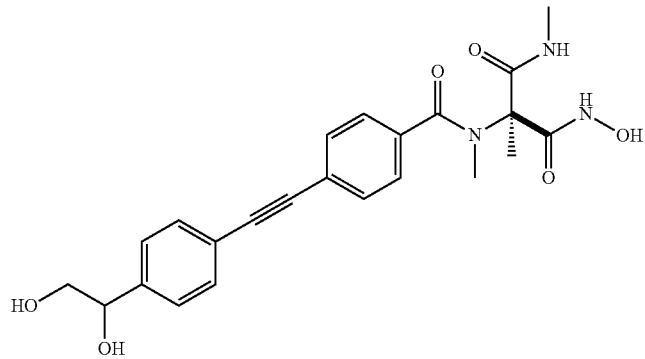

To 140 mg of (2S)-2-((4-((4-(1,2-dihydroxyethyl)phenyl)ethynyl)benzoyl)(methyl)amino)-N,2-dimethyl-N'-(tetrahydro-2H-pyran-2-yloxy)malonamide, 0.7 mL of 1,4-dioxane and 0.8 mL of a 1 mol/L aqueous solution of sulfuric acid were added, and the resulting mixture was stirred at room temperature for 2 hours. Ethyl acetate, water, and sodium chloride were added to the reaction mixture, and the solid material was collected by filtration. The organic layer of the filtrate was separated, and the aqueous layer was extracted with ethyl acetate three times. The solid material, the organic layer, and the extract were combined together, and then the solvent was distilled off under reduced pressure. The obtained residue was purified by silica gel column chromatography [eluent; methanol:chloroform=10:90→15:85] to obtain 113 mg of a yellow solid. Ethyl acetate and IPE were added thereto, and the solid material was collected by filtration to obtain 75 mg of (2S)-2-((4-((4-(1,2-dihydroxyethyl)phenyl)ethynyl)benzoyl)(methyl)amino)-N-hydroxy-N',2-dimethyl-malonamide as a yellow solid.

$^1$H-NMR (400 MHz, CD$_3$OD) δ: 1.77 (3H, s), 2.79 (3H, s), 3.17 (3H, s), 3.56-3.67 (2H, m), 4.67-4.73 (1H, m), 7.41 (2H, d, J=8.1 Hz), 7.51 (2H, d, J=8.3 Hz), 7.53-7.63 (4H, m); MS (ESI): 462 [M+Na]$^+$, 438 [M-H]$^-$

Example 4 hour. Water was added to the reaction mixture, and the solid material was collected by filtration. The organic layer of the filtrate was separated, washed with a saturated aqueous solution of sodium chloride, and then dried over anhydrous sodium sulfate. The solvent was distilled off under reduced pressure, and the obtained residue was combined with the solid material collected by filtration and purified by silica gel column chromatography [eluent; methanol:chloroform=6:94] to obtain 90 mg of a yellow solid. Ethyl acetate and IPE were added thereto, and the solid material was collected by filtration to obtain 76 mg of 2-((4-((4-((((1S)-2-(hydroxyamino)-1-methyl-1-((methylamino)carbonyl)-2-oxoethyl)(methyl)amino)carbonyl)phenyl)ethynyl)benzyl)oxy)ethyl acetate as a pale yellow solid.

$^1$H-NMR (400 MHz, CD$_3$OD) δ: 1.68 (3H, s), 1.96 (3H, s), 2.70 (3H, s), 3.08 (3H, s), 3.60-3.64 (2H, m), 4.13-4.17

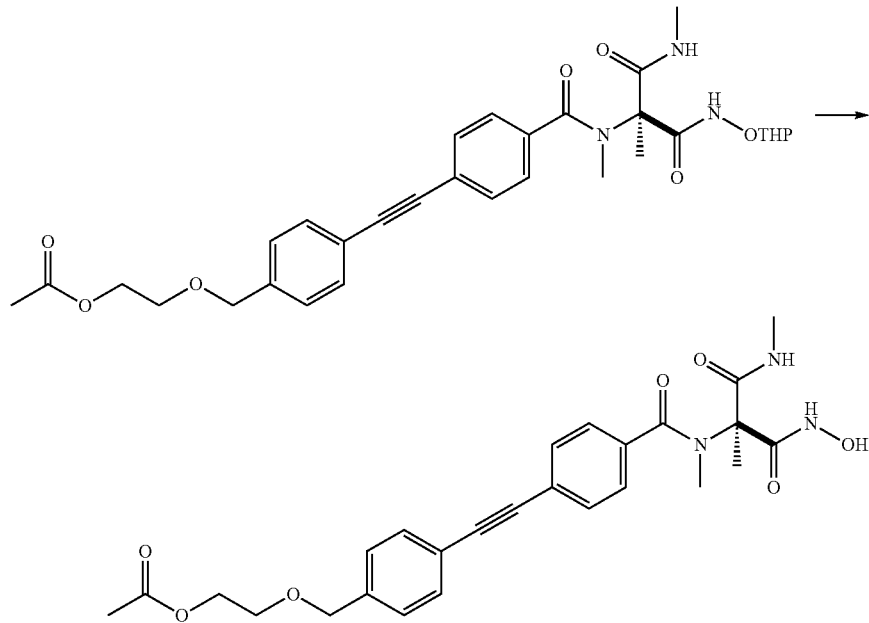

To 144 mg of 2-((4-((4-((methyl((1S)-1-methyl-2-(methylamino)-2-oxo-1-(((tetrahydro-2H-pyran-2-yloxy)amino)carbonyl)ethyl)amino)carbonyl)phenyl)ethynyl)benzyl)oxy)ethyl acetate, 1.5 mL of 1,4-dioxane and 0.75 mL of a 1 mol/L aqueous solution of sulfuric acid were added, and the resulting mixture was stirred at room temperature for 1

(2H, m), 4.47-4.51 (2H, m), 7.29 (2H, d, J=8.5 Hz), 7.45-7.54 (6H, m); MS (ESI): 518 [M+Na]$^+$, 494 [M-H]$^-$

Example 5

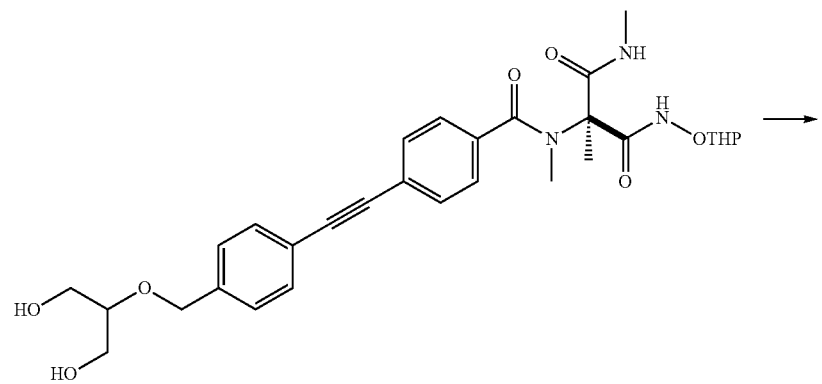

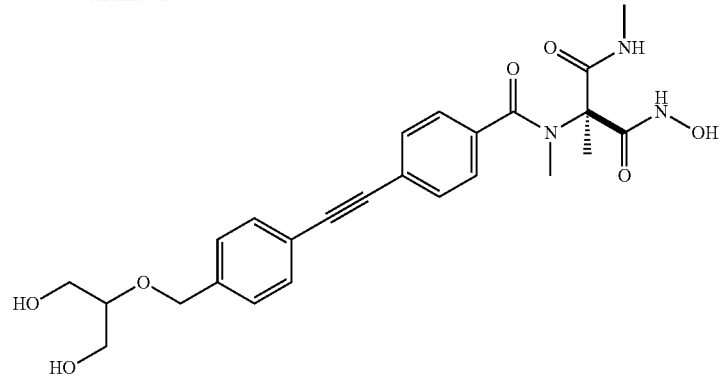

To 205 mg of (2S)-2-((4-((4-((2-hydroxy-1-(hydroxymethyl)ethoxy)methyl)phenyl)ethynyl)benzoyl)(methyl)amino)-N,2-dimethyl-N'-(tetrahydro-2H-pyran-2-yloxy)malonamide, 1.0 mL of 1,4-dioxane and 1.0 mL of a 1 mol/L aqueous solution of sulfuric acid were added, and the resulting mixture was stirred at room temperature for 3 hours. To the reaction mixture, 0.36 mL of a 1 mol/L aqueous solution of sulfuric acid was added, and the resulting mixture was stirred at room temperature for 1 hour. Ethyl acetate and water were added to the reaction mixture. The organic layer was separated, sodium chloride was added to the aqueous layer, and the aqueous layer was extracted with ethyl acetate twice. The organic layer was combined with the extract, and then dried over anhydrous sodium sulfate. The solvent was distilled off under reduced pressure, the obtained residue was purified by silica gel column chromatography [eluent; methanol:chloroform=5:95], 2-propanol and IPE were added, and the solid material was collected by filtration to obtain 51 mg of (2S)—N-hydroxy-2-((4-((4-((2-hydroxy-1-(hydroxymethyl)ethoxy)methyl)phenyl)ethynyl)benzoyl)(methyl)amino)-N',2-dimethylmalonamide as a yellow solid.

$^1$H-NMR (400 MHz, CD$_3$OD) δ: 1.77 (3H, s), 2.79 (3H, s), 3.17 (3H, s), 3.61-3.72 (5H, m), 4.71 (2H, s), 7.44 (2H, d, J=8.6 Hz), 7.51 (2H, d, J=8.1 Hz), 7.56 (2H, d, J=8.6 Hz), 7.61 (2H, d, J=8.6 Hz); MS (ESI): 506 [M+Na]$^+$, 482 [M-H]$^-$

Example 6

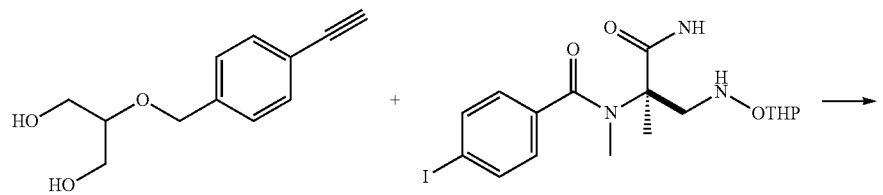

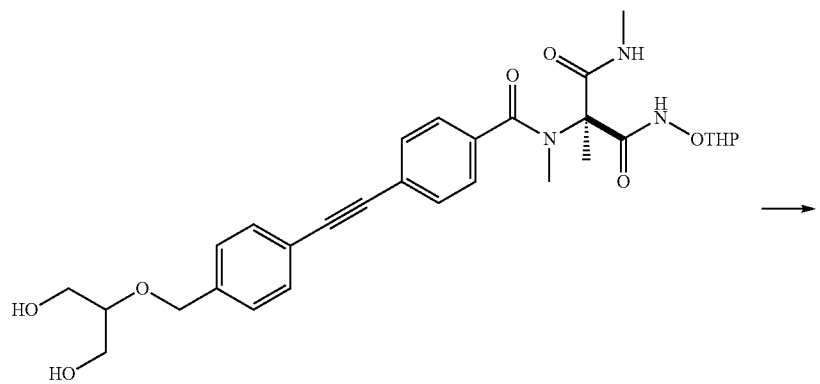

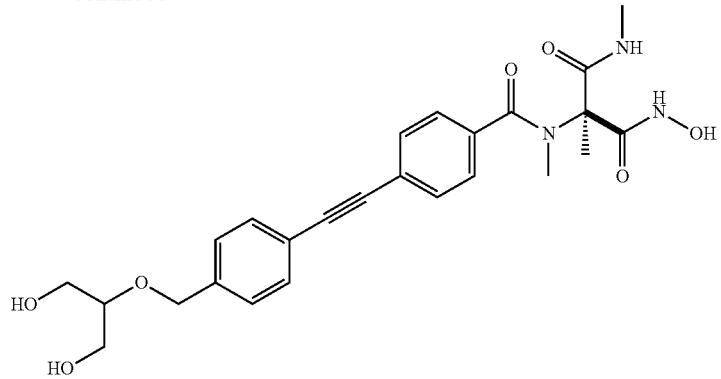

To a mixture of 158 mg of 2-(4-ethynylphenyl)propane-1,3-diol, 150 mg of (2S)-2-((4-iodobenzoyl)(methyl)amino)-N,2-dimethyl-N'-(tetrahydro-2H-pyran-2-yloxy)malonamide, 1.5 mL of tetrahydrofuran, 21 mg of bis-triphenylphosphinepalladium(II) dichloride, and 11 mg of copper(I) iodide, 0.25 mL of triethylamine was added under a nitrogen atmosphere and under ice cooling, and the resulting mixture was stirred at the same temperature for 1 hour. A saturated aqueous solution of ammonium chloride and ethyl acetate were added to the reaction mixture, and the pH was adjusted to 6 with 1 mol/L hydrochloric acid. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=50:50] to obtain 206 mg of a pale yellow oil.

1.0 mL of 1,4-dioxane and 1.2 mL of a 1 mol/L aqueous solution of sulfuric acid were added to 206 mg of the obtained pale yellow oil, and the resulting mixture was stirred at room temperature for 1 hour and 30 minutes. To the reaction mixture, 0.40 mL of a 1 mol/L aqueous solution of sulfuric acid was added, and the resulting mixture was stirred at room temperature for 3 hours. Ethyl acetate and water were added to the reaction mixture. The organic layer was separated, sodium chloride was added to the aqueous layer, and the aqueous layer was extracted with ethyl acetate twice. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=10:90→15:85] to obtain 61 mg of a yellow oil. Thereto, 2-Propanol and IPE were added, and the solid material was collected by filtration to obtain 45 mg of (2S)—N-hydroxy-2-((4-((4-(2-hydroxy-1-(hydroxymethyl)ethyl)phenyl)ethynyl)benzoyl)(methyl)amino)-N',2-dimethyl-malonamide as a yellow solid.

$^1$H-NMR (400 MHz, CD$_3$OD) δ: 1.77 (3H, s), 2.79 (3H, s), 2.93-3.03 (1H, m), 3.17 (3H, s), 3.74-3.82 (2H, m), 3.82-3.90 (2H, m), 7.30 (2H, d, J=8.0 Hz), 7.49 (2H, d, J=8.3 Hz), 7.53-7.63 (4H, m); MS (ESI): 476 [M+Na]$^+$, 452 [M-H]$^-$

Example 7

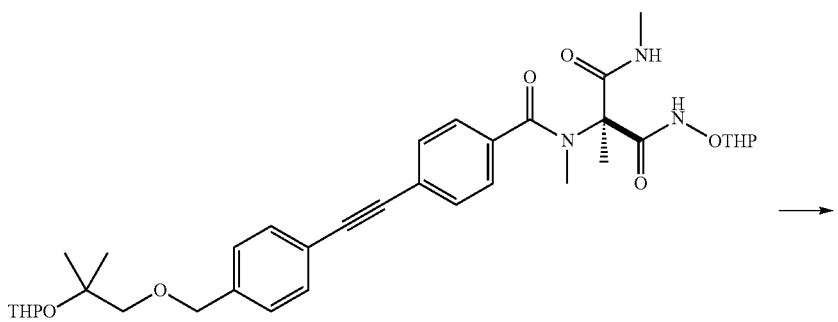

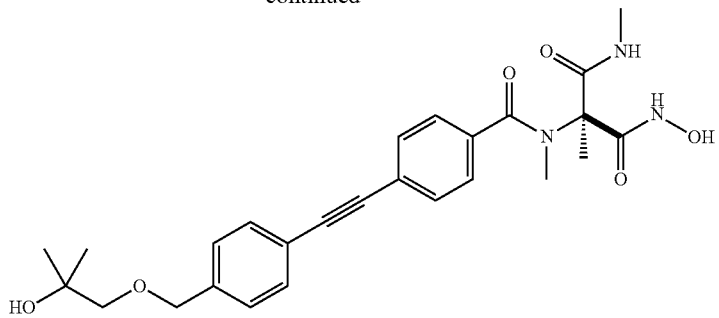

To 264 mg of (2S)—N,2-dimethyl-2-(methyl(4-((4-((2-methyl-2-(tetrahydro-2H-pyran-2-yloxy)propoxy)methyl)phenyl)ethynyl)benzoyl)amino)-N'-(tetrahydro-2H-pyran-2-yloxy)malonamide, 1.3 mL of 1,4-dioxane and 1.8 mL of a 1 mol/L aqueous solution of sulfuric acid were added, and the resulting mixture was stirred at room temperature for 1 hour. Ethyl acetate and water were added to the reaction mixture. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=50:50→70:30] to obtain 103 mg of a yellow solid. Ethyl acetate and IPE were added thereto, and the solid material was collected by filtration to obtain 74 mg of (2S)—N-hydroxy-2-((4-((4-((2-hydroxy-2-methylpropoxy)methyl)phenyl)ethynyl)benzoyl)(methyl)amino)-N',2-dimethyl-malonamide as a yellow solid.

$^1$H-NMR (400 MHz, CD$_3$OD) δ: 1.21 (6H, s), 1.77 (3H, s), 2.79 (3H, s), 3.17 (3H, s), 4.56-4.62 (2H, m), 7.39 (2H, d, J=8.6 Hz), 7.52 (2H, d, J=8.5 Hz), 7.56 (2H, d, J=8.6 Hz), 7.61 (2H, d, J=8.6 Hz); MS (ESI): 504 [M+Na]$^+$, 480 [M-H]$^-$

Example 8

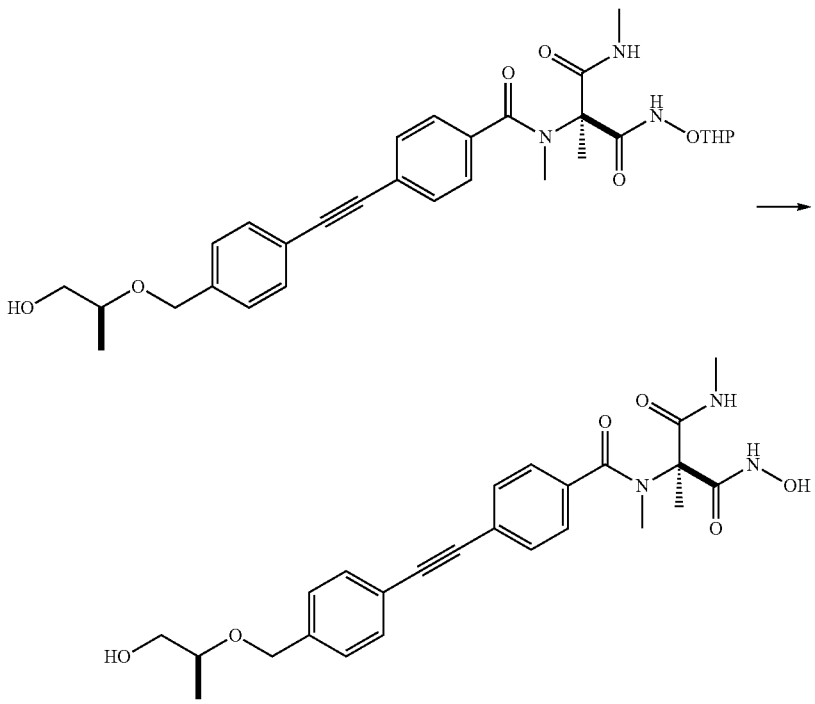

To 151 mg of (2S)-2-((4-((4-(((1S)-2-hydroxy-1-methylethoxy)methyl)phenyl)ethynyl)benzoyl)(methyl)amino)-N,2-dimethyl-N'-(tetrahydro-2H-pyran-2-yloxy)malonamide, 1.5 mL of 1,4-dioxane and 0.78 mL of a 1 mol/L aqueous solution of sulfuric acid were added, and the resulting mixture was stirred at room temperature for 1 hour. Ethyl acetate, water, and sodium chloride were added to the reaction mixture, and the solid material was collected by filtration. The organic layer of the filtrate was separated, and then dried over anhydrous sodium sulfate. The solvent was distilled off under reduced pressure, ethyl acetate was added to the obtained residue and the solid material collected by filtration, and the solid material was collected by filtration to obtain 57 mg of (2S)—N-hydroxy-2-((4-((4-(((1S)-2-hydroxy-1-methyl ethoxy)methyl)phenyl)ethynyl)benzoyl)(methyl)amino)-N',2-dimethylmalonamide as a white solid.

$^1$H-NMR (400 MHz, CD$_3$OD) δ: 1.17 (3H, d, J=6.1 Hz), 1.77 (3H, s), 2.79 (3H, s), 3.17 (3H, s), 3.52-3.57 (2H, m), 3.58-3.66 (1H, m), 4.57-4.67 (2H, m), 7.41 (2H, d, J=8.3 Hz), 7.53-7.64 (6H, m); MS (ESI): 490 [M+Na]$^+$, 466 [M-H]$^-$

Example 9

To 73 mg of (2S)-2-((4-((4-(2-hydroxy-1-methoxyethyl)phenyl)ethynyl)benzoyl)(methyl)amino)-N,2-dimethyl-N'-(tetrahydro-2H-pyran-2-yloxy)malonamide, 1.0 mL of 1,4-dioxane and 0.52 mL of a 1 mol/L aqueous solution of sulfuric acid were added, and the resulting mixture was stirred at room temperature for 50 minutes. Ethyl acetate and water were added to the reaction mixture. The organic layer was separated, and the aqueous layer was extracted with ethyl acetate twice. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=8:92] to obtain 60 mg of a yellow oil. IPE was added thereto, and the solid material was collected by filtration to obtain 34 mg of (2S)—N-hydroxy-2-((4-((4-(2-hydroxy-1-methoxyethyl)phenyl)ethynyl)benzoyl)(methyl)amino)-N',2-dimethyl-malonamide as a yellow solid.

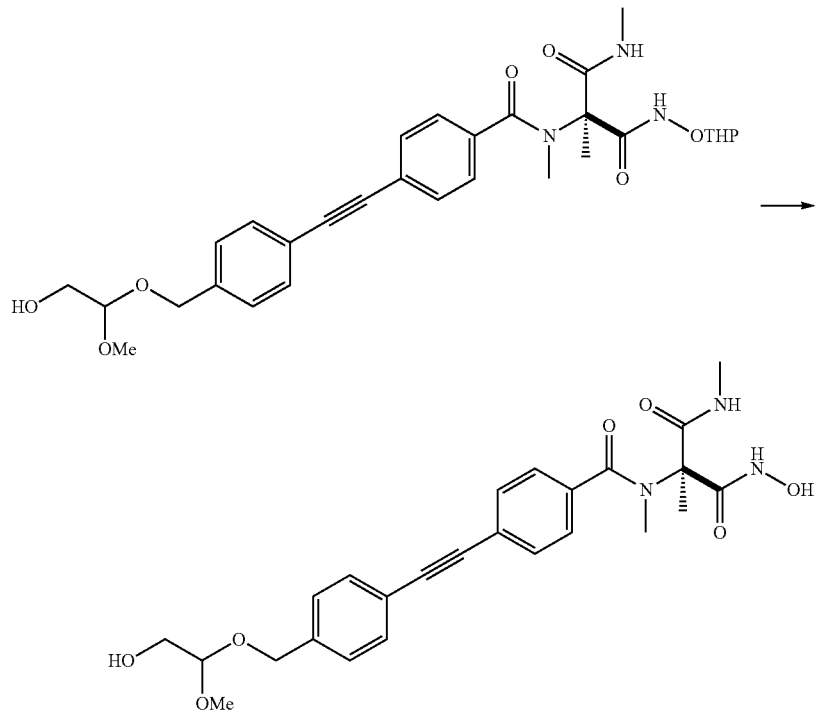

$^1$H-NMR (400 MHz, CD$_3$OD) δ: 1.77 (3H, s), 2.79 (3H, s), 3.17 (3H, s), 3.53-3.68 (2H, m), 4.26-4.33 (1H, m), 7.36 (2H, d, J=8.0 Hz), 7.52-7.63 (6H, m); MS (ESI): 476 [M+Na]$^+$, 452 [M-H]$^-$

Example 10

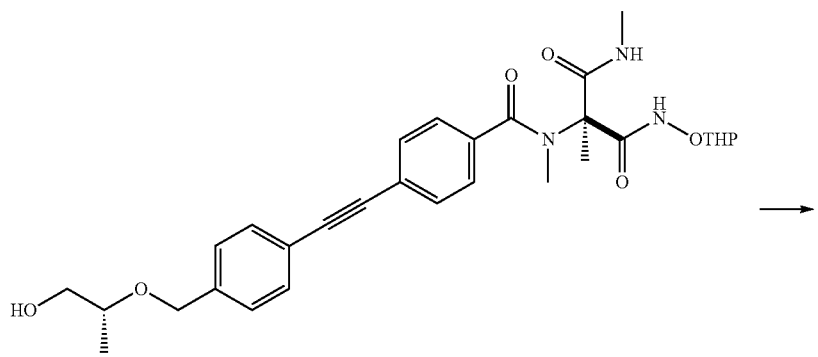

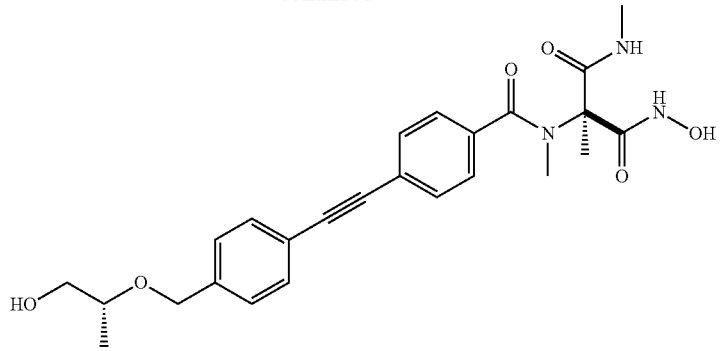

To 138 mg of (2S)-2-((4-((4-(((1R)-2-hydroxy-1-methylethoxy)methyl)phenyl)ethynyl)benzoyl)(methyl)amino)-N,2-dimethyl-N'-(tetrahydro-2H-pyran-2-yloxy)malonamide, 1.5 mL of 1,4-dioxane and 0.75 mL of a 1 mol/L aqueous solution of sulfuric acid were added, and the resulting mixture was stirred at room temperature for 1 hour and 30 minutes. Ethyl acetate and water were added to the reaction mixture. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=4:96→6:94] to obtain 70 mg of a yellow solid. Ethyl acetate and IPE were added thereto, and the solid material was collected by filtration to obtain 58 mg of (2S)—N-hydroxy-2-((4-((4-(((1R)-2-hydroxy-1-methylethoxy)methyl)phenyl)ethynyl)benzoyl)(methyl)amino)-N',2-dimethyl-malonamide as a yellow solid.

$^1$H-NMR (400 MHz, CD$_3$OD) δ: 1.17 (3H, d, J=6.1 Hz), 1.77 (3H, s), 2.79 (3H, s), 3.17 (3H, s), 3.52-3.58 (2H, m), 3.58-3.66 (1H, m), 4.57-4.65 (2H, m), 7.41 (2H, d, J=8.5 Hz), 7.53-7.64 (6H, m); MS (ESI): 490 [M+Na]$^+$, 466 [M-H]$^-$

Example 11

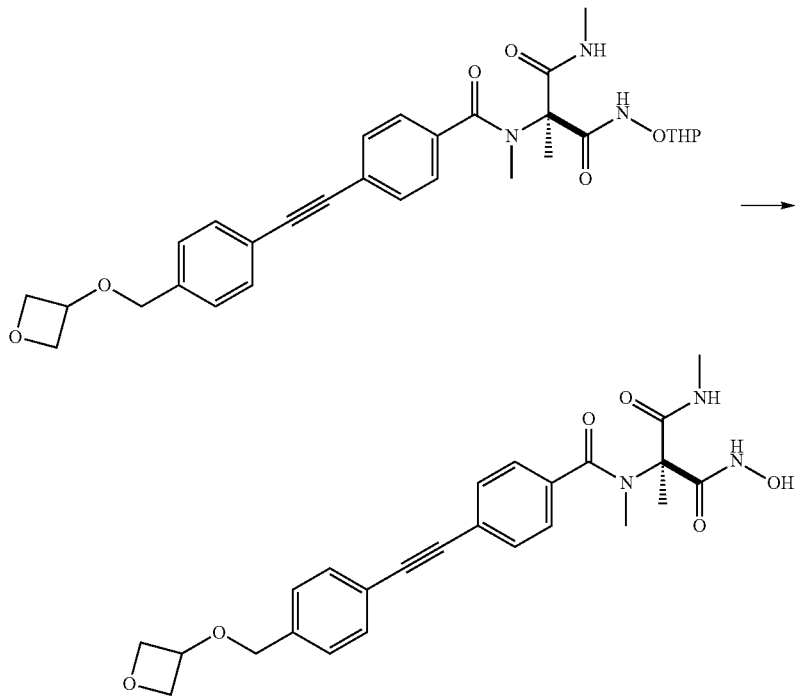

To 140 mg of (2S)—N,2-dimethyl-2-(methyl(4-((4-((oxetan-3-yloxy)methyl)phenyl)ethynyl)benzoyl)amino)-N'-(tetrahydro-2H-pyran-2-yl oxy)malonamide, 1.5 mL of 1,4-dioxane and 0.75 mL of a 1 mol/L aqueous solution of sulfuric acid were added, and the resulting mixture was stirred at room temperature for 2 hours. Ethyl acetate and water were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=2:98→4:96] to obtain 80 mg of a yellow solid. Ethyl acetate and IPE were added thereto, and the solid material was collected by filtration to obtain 73 mg of (2S)—N-hydroxy-N',2-dimethyl-2-(methyl(4-((4-((oxetan-3-yloxy)methyl)phenyl)ethynyl)benzoyl)amino)malonamide as a pale yellow solid.

¹H-NMR (400 MHz, CD₃OD) δ: 1.77 (3H, s), 2.79 (3H, s), 3.17 (3H, s), 4.50 (2H, s), 4.55-4.61 (2H, m), 4.65-4.72 (1H, m), 4.74-4.78 (2H, m), 7.39 (2H, d, J=8.6 Hz), 7.53-7.65 (6H, m); MS (ESI): 464 [M-H]⁻

Example 12

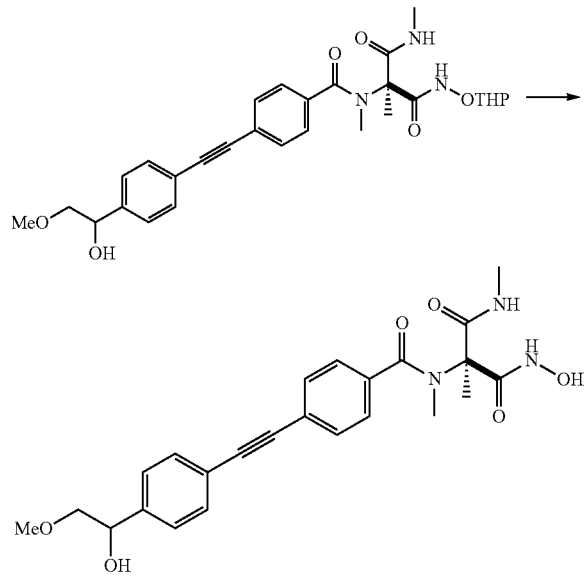

To 230 mg of (2S)-2-((4-((4-((1E)-3-methoxy-1-propen-1-yl)phenyl)ethynyl)benzoyl)(methyl)amino)-N,2-dimethyl-N'-(tetrahydro-2H-pyran-2-yloxy)malonamide, 1.1 mL of 1,4-dioxane and 1.5 mL of a 1 mol/L aqueous solution of sulfuric acid were added, and the resulting mixture was stirred at room temperature for 1 hour. Water was added to the reaction mixture, and the solid material was collected by filtration. Ethanol was added to the obtained solid material, and then the solvent was distilled off under reduced pressure. Ethyl acetate and IPE were added to the obtained residue, and the solid material was collected by filtration to obtain 117 mg of (2S)—N-hydroxy-2-((4-((4-((1E)-3-methoxy-1-propen-1-yl)phenyl)ethynyl)benzoyl)(methyl)amino)-N',2-dimethyl-malonamide as a light brown solid.

¹H-NMR (400 MHz, CD₃OD) δ: 1.77 (3H, s), 2.79 (3H, s), 3.17 (3H, s), 3.47 (3H, s), 4.08-4.13 (2H, m), 6.34-6.43 (1H, m), 6.65 (1H, d, J=15.9 Hz), 7.42-7.52 (4H, m), 7.53-7.63 (4H, m); MS (ESI): 472 [M+Na]⁺, 448 [M-H]⁻

Example 13

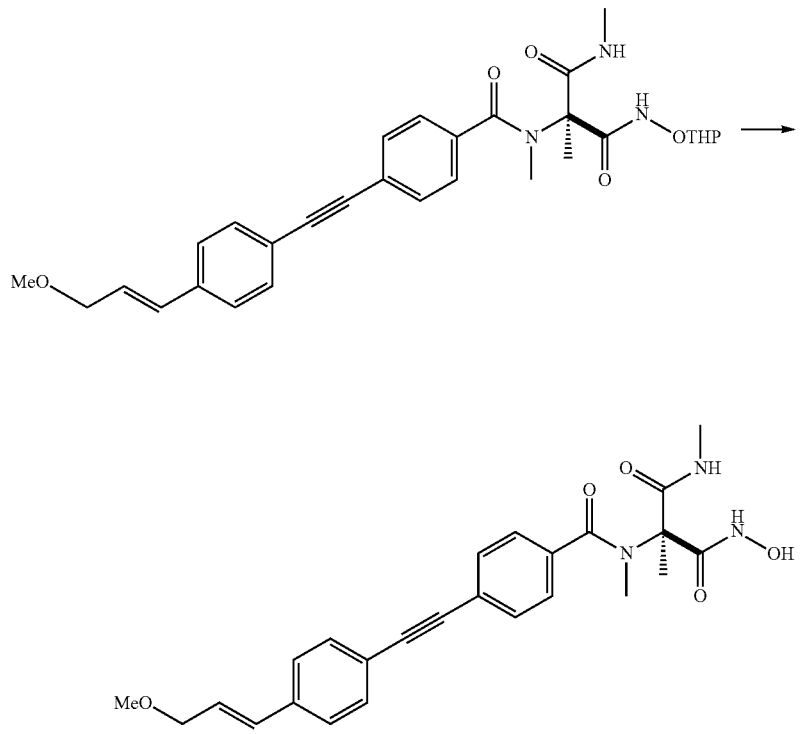

To 114 mg of (2S)-2-((4-((4-(1-hydroxy-2-methoxyethyl) phenyl)ethynyl)benzoyl)(methyl)amino)-N,2-dimethyl-N'-(tetrahydro-2H-pyran-2-yloxy)malonamide, 1.5 mL of methanol and 8 mg of p-toluenesulfonic acid monohydrate were added, and the resulting mixture was stirred at room temperature for 30 minutes. Water was added to the reaction mixture, the resulting mixture was neutralized with a saturated aqueous solution of sodium hydrogen carbonate, and then ethyl acetate was added. The organic layer was separated, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=6:94] to obtain 93 mg of a yellow oil. Ethyl acetate and IPE were added thereto, and the solid material was collected by filtration to obtain 63 mg of (2S)—N-hydroxy-2-((4-((4-(1-hydroxy-2-methoxyethyl)phenyl)ethynyl)benzoyl)(methyl)amino)-N', 2-dimethyl-malonamide as a yellow solid.

$^{1}$H-NMR (400 MHz, CD$_{3}$OD) δ: 1.77 (3H, s), 2.79 (3H, s), 3.17 (3H, s), 3.37 (3H, s), 3.47-3.52 (2H, m), 4.59 (1H, s), 7.41 (2H, d, J=8.3 Hz), 7.54-7.63 (6H, m); MS (ESI): 476 [M+Na]$^{+}$, 452 [M-H]$^{-}$

Example 14

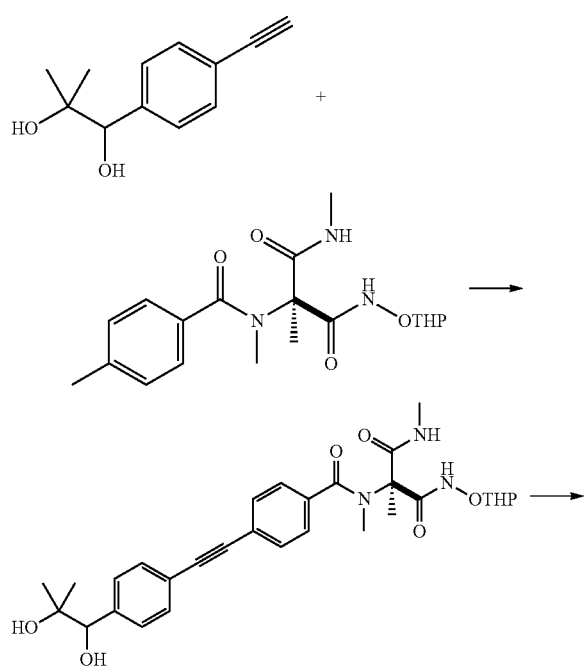

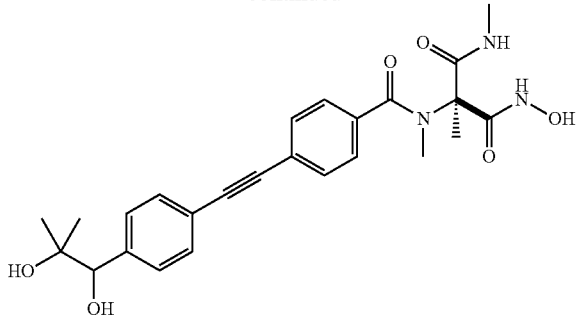

To a mixture of 110 mg of (2S)-2-((4-iodobenzoyl)(methyl)amino)-N,2-dimethyl-N'-(tetrahydro-2H-pyran-2-yloxy)malonamide, 87 mg of 1-(4-ethynylphenyl)-2-methylpropane-1,2-diol, 15 mg of bis-triphenylphosphinepalladium(II) dichloride, 8 mg of copper (I) iodide, and 1.5 mL of tetrahydrofuran, 0.31 mL of triethylamine was added under ice cooling, and the resulting mixture was stirred at the same temperature for 2 hours. Water and ethyl acetate were added to the reaction mixture, and the pH was adjusted to 2 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=30:70] to obtain 104 mg of a yellow solid.

To 104 mg of the obtained yellow solid, 1.0 mL of methanol and 7 mg of p-toluenesulfonic acid monohydrate were added, and the resulting mixture was stirred at room temperature for 1 hour and 15 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=6:94] to obtain a yellow oil. Ethyl acetate and IPE were added thereto, and the solid material was collected by filtration to obtain 45 mg of (2S)-2-((4-((4-(1,2-dihydroxy-2-methylpropyl)phenyl)ethynyl)benzoyl)(methyl)amino)-N-hydroxy-N',2-dimethylmalonamide as a yellow solid.

$^{1}$H-NMR (400 MHz, CD$_{3}$OD) δ: 1.13 (3H, s), 1.14 (3H, s), 1.77 (3H, s), 2.79 (3H, s), 3.17 (3H, s), 4.46 (1H, s), 7.40-7.52 (4H, m), 7.52-7.64 (4H, m); MS (ESI): 490 [M+Na]$^{+}$, 466 [M-H]$^{-}$

Example 15

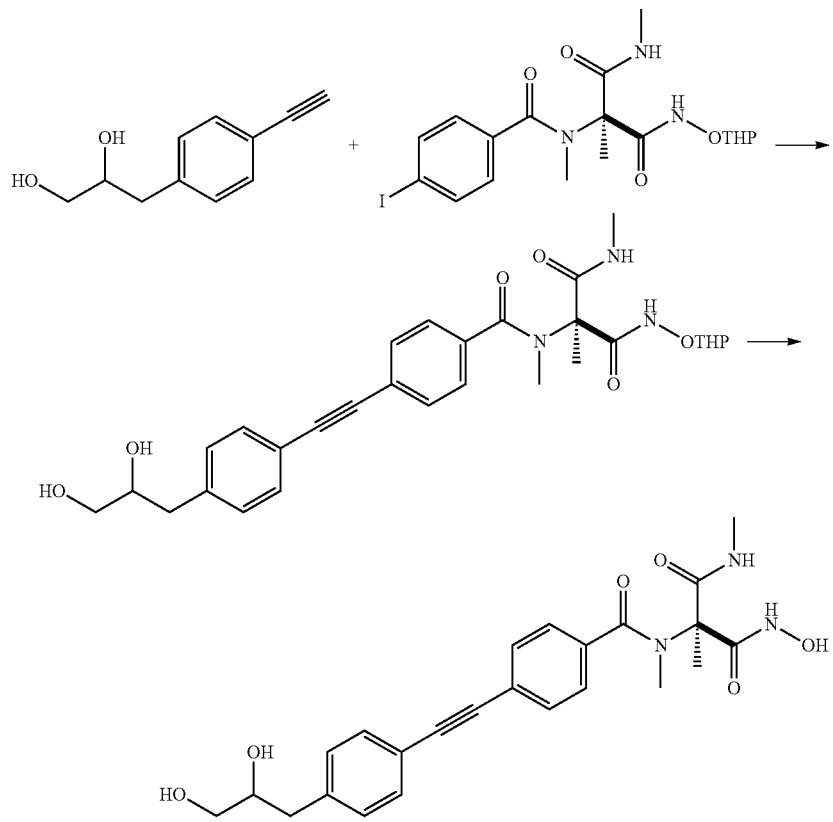

To a mixture of 155 mg of 3-(4-ethynylphenyl)propane-1,2-diol, 2.0 mL of tetrahydrofuran, 200 mg of (2S)-2-((4-iodobenzoyl)(methyl)amino)-N,2-dimethyl-N'-(tetrahydro-2H-pyran-2-yloxy)malonamide, 28 mg of bis-triphenylphosphinepalladium(II) dichloride, and 15 mg of copper(I) iodide, 0.4 mL of triethylamine was added under ice cooling, and the resulting mixture was stirred at the same temperature for 20 minutes. A saturated aqueous solution of ammonium chloride and ethyl acetate were added to the reaction mixture, and the pH was adjusted to 6.4 with 1 mol/L hydrochloric acid. The organic layer was separated, and then dried over anhydrous sodium sulfate. The solvent was distilled off under reduced pressure, and the obtained residue was purified by silica gel column chromatography [eluent; methanol:ethyl acetate=2:98→5:95] to obtain 292 mg of a brown solid.

To 292 mg of the obtained brown solid, 2.9 mL of methanol and 21 mg of p-toluenesulfonic acid monohydrate were added, and the resulting mixture was stirred at room temperature for 30 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, the obtained residue was purified by silica gel column chromatography [eluent; methanol:chloroform=10:90], ethyl acetate and IPE were added, and the solid material was collected by filtration to obtain 59 mg of (2S)-2-((4-((4-(2,3-dihydroxypropyl)phenyl)ethynyl)benzoyl)(methyl)amino)-N-hydroxy-N',2-dimethylmalonamide as a yellow solid.

$^1$H-NMR (400 MHz, CD$_3$OD) δ: 1.77 (3H, s), 2.65-2.73 (1H, m), 2.79 (3H, s), 2.84-2.92 (1H, m), 3.17 (3H, s), 3.43-3.54 (2H, m), 3.77-3.85 (1H, m), 7.29 (2H, d, J=8.6 Hz), 7.46 (2H, d, J=8.6 Hz), 7.53-7.63 (4H, m); MS (ESI): 476 [M+Na]$^+$, 452 [M-H]$^-$

Example 16

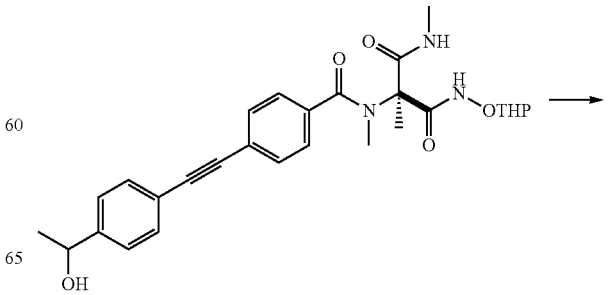

-continued

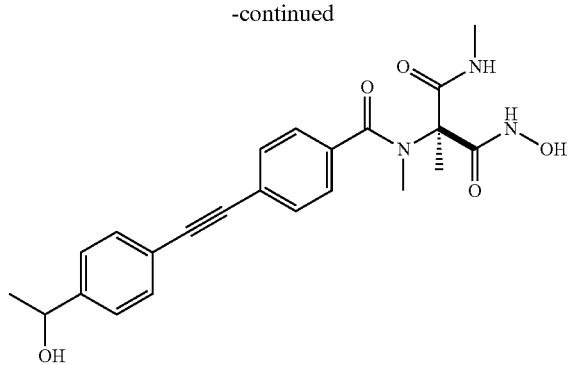

To a mixture of 507 mg of (2S)-2-((4-((4-(1-hydroxyethyl)phenyl)ethynyl)benzoyl)(methyl)amino)-N, 2-dimethyl-N'-(tetrahydro-2H-pyran-2-yloxy)malonamide and 5.0 mL of methanol, 38 mg of p-toluenesulfonic acid monohydrate was added under ice cooling, and the resulting mixture was stirred at the same temperature for 2 hours and 30 minutes. Water was added to the reaction mixture, the resulting mixture was neutralized with a saturated aqueous solution of sodium hydrogen carbonate, and the solid material was collected by filtration. Ethyl acetate and IPE were added to the obtained solid material, and the solid material was collected by filtration to obtain 301 mg of (2S)—N-hydroxy-2-((4-((4-(1-hydroxyethyl)phenyl)ethynyl)benzoyl)(methyl)amino)-N',2-dimethyl-malonamide as a light brown solid.

$^1$H-NMR (400 MHz, CD$_3$OD) δ: 1.43 (3H, d, J=6.6 Hz), 1.77 (3H, s), 2.79 (3H, s), 3.17 (3H, s), 7.40 (2H, d, J=8.0 Hz), 7.50 (2H, d, J=8.3 Hz), 7.54-7.61 (4H, m); MS (ESI): 446 [M+Na]$^+$, 422 [M-H]$^-$

Example 17

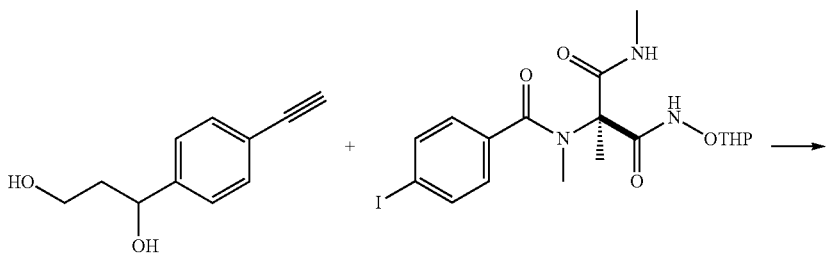

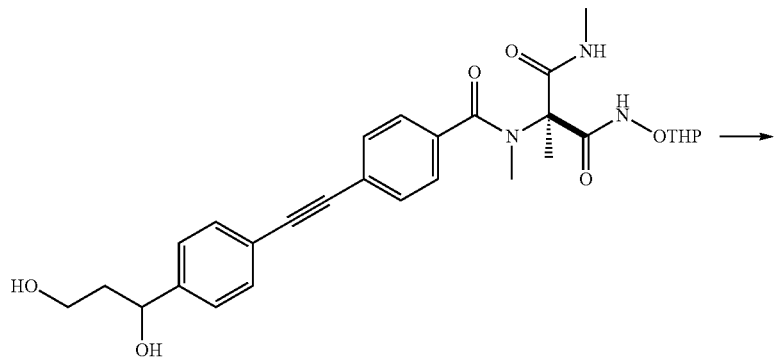

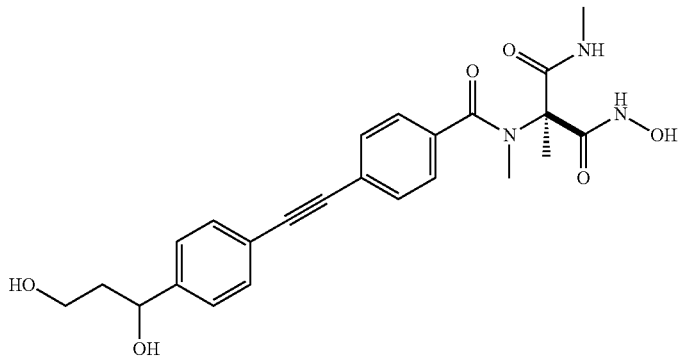

To a mixture of 155 mg of 1-(4-ethynylphenyl)propane-1,3-diol, 2.0 mL of tetrahydrofuran, 200 mg of (2S)-2-((4-iodobenzoyl)(methyl)amino)-N,2-dimethyl-N'-(tetrahydro-2H-pyran-2-yloxy)malonamide, 28 mg of bis-triphenylphosphinepalladium(II) dichloride, and 15 mg of copper(I) iodide, 0.4 mL of triethylamine was added under ice cooling, and the resulting mixture was stirred at the same temperature for 15 minutes. A saturated aqueous solution of ammonium chloride and ethyl acetate were added to the reaction mixture, and the pH was adjusted to 6.4 with 1 mol/L hydrochloric acid. The organic layer was separated, and then dried over anhydrous sodium sulfate. The solvent was distilled off under reduced pressure, and the obtained residue was purified by silica gel column chromatography [eluent; methanol:ethyl acetate=2:98→6:94] to obtain 265 mg of a brown oil.

To 265 mg of the obtained brown oil, 2.6 mL of methanol and 19 mg of p-toluenesulfonic acid monohydrate were added, and the resulting mixture was stirred at room temperature for 45 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, the obtained residue was purified by silica gel column chromatography [eluent; methanol:ethyl acetate=6:94→10:90], ethyl acetate and IPE were added, and the solid material was collected by filtration to obtain 87 mg of (2S)-2-((4-((4-(1,3-dihydroxypropyl)phenyl)ethynyl)benzoyl)(methyl)amino)-N-hydroxy-N',2-dimethylmalonamide as a yellow solid.

$^1$H-NMR (400 MHz, CD$_3$OD) δ: 1.68 (3H, s), 1.73-1.90 (2H, m), 2.70 (3H, s), 3.08 (3H, s), 3.48-3.57 (1H, m), 3.57-3.67 (1H, m), 7.30 (2H, d, J=8.1 Hz), 7.40-7.45 (2H, m), 7.45-7.54 (4H, m); MS (ESI): 476 [M+Na]$^+$, 452 [M-H]$^-$

Example 18

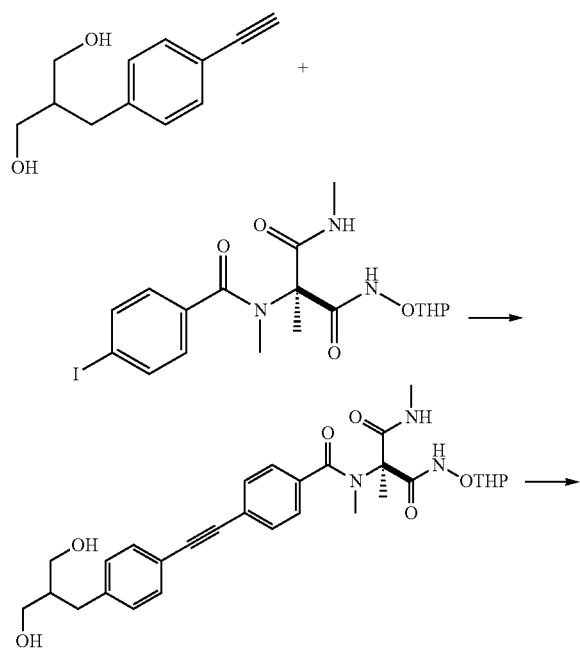

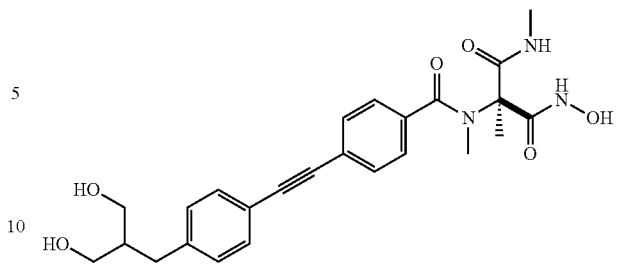

To a mixture of 180 mg of 2-(4-ethynylbenzyl)propane-1,3-diol, 185 mg of ((2S)-2-((4-iodobenzoyl)(methyl)amino)-N,2-dimethyl-N'-(tetrahydro-2H-pyran-2-yloxy)malonamide, 27 mg of bis-triphenylphosphinepalladium(II) dichloride, 14 mg of copper(I) iodide, and 1.8 mL of tetrahydrofuran, 0.26 mL of triethylamine was added under a nitrogen atmosphere and under ice cooling, and the resulting mixture was stirred at the same temperature for 1 hour. A saturated aqueous solution of ammonium chloride and ethyl acetate were added to the reaction mixture, and the pH was adjusted to 6.1 with 1 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=50:50] to obtain 230 mg of a brown oil.

To a mixture of 230 mg of the obtained brown oil and 2.3 mL of methanol, 16 mg of p-toluenesulfonic acid monohydrate was added under ice cooling, the resulting mixture was stirred at the same temperature for 30 minutes, and then at room temperature for 1 hour. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; methanol:chloroform=10:90→15:85] to obtain a yellow solid. Ethyl acetate and IPE were added thereto, and the solid material was collected by filtration to obtain 135 mg of (2S)—N-hydroxy-2-((4-((4-(3-hydroxy-2-(hydroxymethyl)propyl)phenyl)ethynyl)benzoyl)(methyl)amino)-N',2-dimethyl-malonamide as a pale yellow solid.

$^1$H-NMR (400 MHz, CD$_3$OD) δ: 1.77 (3H, s), 1.87-1.96 (1H, m), 2.68 (2H, d, J=7.3 Hz), 2.79 (3H, s), 3.17 (3H, s), 3.55 (4H, d, J=5.6 Hz), 7.26 (2H, d, J=8.3 Hz), 7.45 (2H, d, J=8.3 Hz), 7.53-7.63 (4H, m); MS (ESI): 490 [M+Na]$^+$, 466 [M-H]$^-$

Example 19

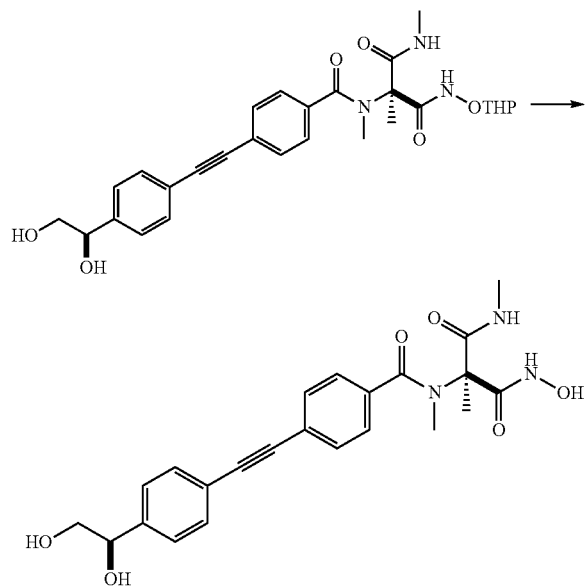

To a mixture of 797 mg of (2S)-2-((4-((4-((1R)-1,2-dihydroxyethyl)phenyl)ethynyl)benzoyl)(methyl)amino)-N,2-dimethyl-N'-(tetrahydro-2H-pyran-2-yloxy)malonamide and 6.3 mL of methanol, 46 mg of p-toluenesulfonic acid monohydrate was added under ice cooling, and the resulting mixture was stirred at the same temperature for 30 minutes and then at room temperature for 45 minutes. Water and ethyl acetate were added to the reaction mixture, and the resulting mixture was neutralized with a saturated aqueous solution of sodium hydrogen carbonate. The organic layer was separated, and the aqueous layer was extracted with ethyl acetate twice. Sodium chloride was added to the aqueous layer, and the solid material was collected by filtration. Sodium chloride and ethyl acetate were added to the filtrate, and the solid material was collected by filtration. The organic layer of the filtrate was separated, the organic layer, the extract, and the solid material thus obtained were combined together, and then the solvent was distilled off under reduced pressure. The obtained residue was purified by silica gel column chromatography [eluent; methanol:chloroform=10:90→15:85] to obtain 556 mg of a yellow foamy solid. Ethyl acetate and IPE were added thereto, and the solid material was collected by filtration to obtain 458 mg of (2S)-2-((4-((4-((1R)-1,2-dihydroxyethyl)phenyl)ethynyl)benzoyl)(methyl)amino)-N-hydroxy-N',2-dimethyl-malonamide as a yellow solid.

$^1$H-NMR (400 MHz, CD$_3$OD) δ: 1.78 (3H, s), 2.80 (3H, s), 3.17 (3H, s), 3.57-3.67 (2H, m), 4.68-4.74 (1H, m), 7.42 (2H, d, J=8.3 Hz), 7.52 (2H, d, J=8.3 Hz), 7.56 (2H, d, J=8.6 Hz), 7.61 (2H, d, J=8.6 Hz); MS (ESI): 462 [M+Na]$^+$, 438 [M-H]$^-$

Example 20

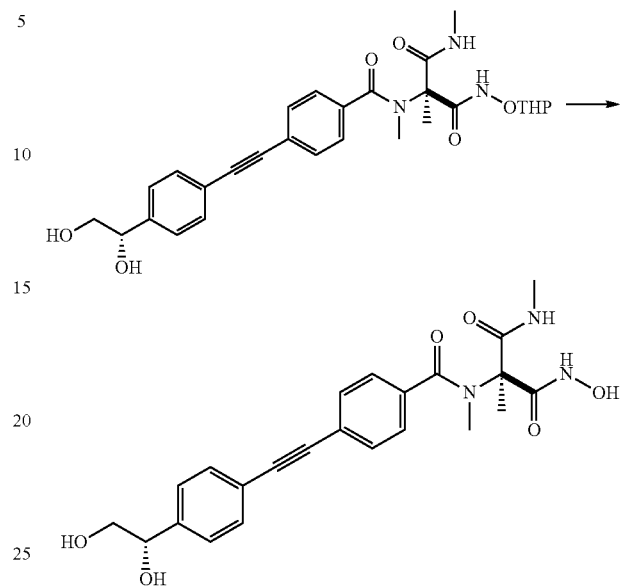

To a mixture of 767 mg of (2S)-2-((4-((4-((1S)-1,2-dihydroxyethyl)phenyl)ethynyl)benzoyl)(methyl)amino)-N,2-dimethyl-N'-(tetrahydro-2H-pyran-2-yloxy)malonamide and 6.0 mL of methanol, 46 mg of p-toluenesulfonic acid monohydrate was added under ice cooling, and the resulting mixture was stirred at the same temperature for 40 minutes and then at room temperature for 1 hour. Water and ethyl acetate were added to the reaction mixture, and the resulting mixture was neutralized with a saturated aqueous solution of sodium hydrogen carbonate. The organic layer was separated, ethyl acetate and sodium chloride were added to the aqueous layer, and the solid material was collected by filtration. The organic layer of the filtrate was separated, ethyl acetate and sodium chloride were added to the aqueous layer, and the solid material was collected by filtration. The organic layer of the filtrate was separated, the organic layer and the solid material thus obtained were combined together, and then the solvent was distilled off under reduced pressure. The obtained residue was purified by silica gel column chromatography [eluent; methanol:chloroform=10:90→15:85] to obtain 585 mg of a yellow foamy solid. Ethyl acetate and IPE were added thereto, and the solid material was collected by filtration to obtain 463 mg of (2S)-2-((4-((4-((1S)-1,2-dihydroxyethyl)phenyl)ethynyl)benzoyl)(methyl)amino)-N-hydroxy-N',2-dimethyl-malonamide as a yellow solid.

$^1$H-NMR (400 MHz, CD$_3$OD) δ: 1.77 (3H, s), 2.79 (3H, s), 3.17 (3H, s), 3.55-3.68 (2H, m), 4.67-4.74 (1H, m), 7.41 (2H, d, J=8.3 Hz), 7.51 (2H, d, J=8.3 Hz), 7.55 (2H, d, J=8.5 Hz), 7.68 (2H, d, J=8.5 Hz); MS (ESI): 462 [M+Na]$^+$, 438 [M-H]$^-$

Example 21

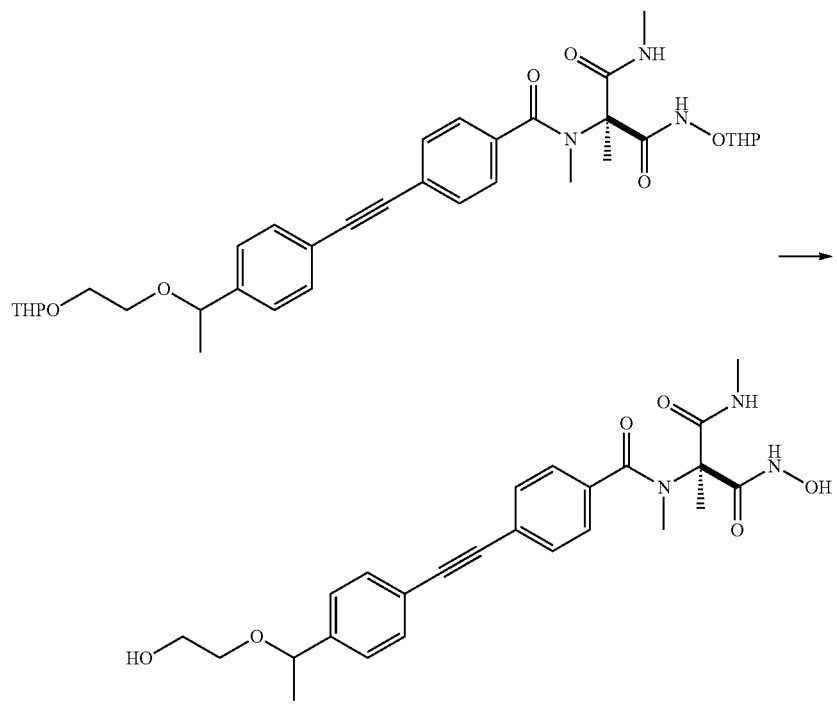

To 323 mg of (2S)—N,2-dimethyl-2-(methyl(4-((4-(1-(2-(tetrahydro-2H-pyran-2-yloxy)ethoxy)ethyl)phenyl)ethynyl)benzoyl)amino)-N'-(tetrahydro-2H-pyran-2-yloxy)malonamide, 3.2 mL of methanol and 19 mg of p-toluenesulfonic acid monohydrate were added, and the resulting mixture was stirred at room temperature for 1 hour. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, the obtained residue was purified by silica gel column chromatography [eluent; acetone:chloroform=50:50→90:10], ethyl acetate and IPE were added, and the solid material was collected by filtration to obtain 157 mg of (2S)—N-hydroxy-2-((4-((4-(1-(2-hydroxyethoxy)ethyl)phenyl)ethynyl)benzoyl)(methyl)amino)-N',2-dimethyl-malonamide as a white solid.

$^1$H-NMR (400 MHz, CD$_3$OD) δ: 1.42 (3H, d, J=6.3 Hz), 1.77 (3H, s), 2.79 (3H, s), 3.17 (3H, s), 3.37-3.44 (2H, m), 3.62-3.78 (2H, m), 4.47-4.55 (1H, m), 7.38 (2H, d, J=8.0 Hz), 7.49-7.66 (6H, m); MS (ESI): 490 [M+Na]$^+$, 466 [M-H]$^-$

Example 22

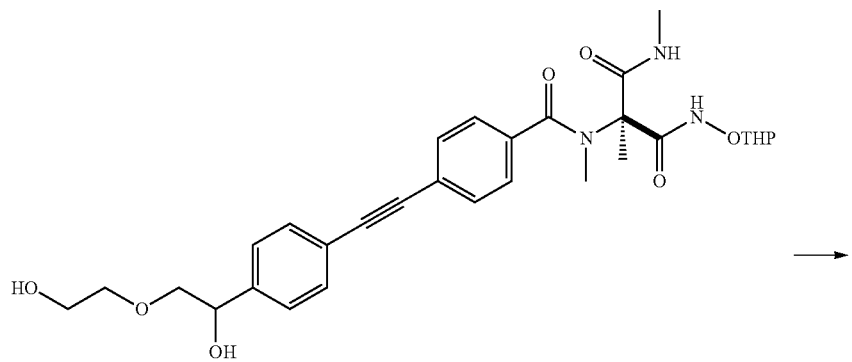

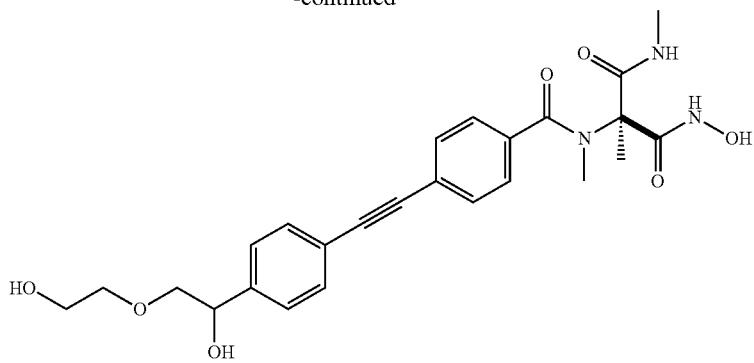

To 340 mg of (2S)-2-((4-((4-(1-hydroxy-2-(2-hydroxyethoxy)ethyl)phenyl)ethynyl)benzoyl)(methyl)amino)-N,2-dimethyl-N'-(tetrahydro-2H-pyran-2-yloxy)malonamide, 3.0 mL of methanol and 22 mg of p-toluenesulfonic acid monohydrate were added, and the resulting mixture was stirred at room temperature for 20 minutes. Water and ethyl acetate were added to the reaction mixture, the resulting mixture was neutralized with a saturated aqueous solution of sodium hydrogen carbonate, and then sodium chloride was added. The organic layer was separated, and the aqueous layer was extracted with ethyl acetate five times. The organic layer was combined with the extract, washed with a saturated aqueous solution of sodium chloride, and then dried over anhydrous sodium sulfate. The solvent was distilled off under reduced pressure, the obtained residue was purified by silica gel column chromatography [eluent; methanol:chloroform=8:92], IPE was added, and the solid material was collected by filtration to obtain 141 mg of (2S)—N-hydroxy-2-((4-((4-(1-hydroxy-2-(2-hydroxyethoxy)ethyl)phenyl)ethynyl)benzoyl)(methyl)amino)-N',2-dimethyl-malonamide as a yellow solid.

$^1$H-NMR (400 MHz, CD$_3$OD) δ: 1.77 (3H, s), 2.79 (3H, s), 3.17 (3H, s), 3.51-3.74 (6H, m), 7.43 (2H, d, J=8.0 Hz), 7.48-7.63 (6H, m); MS (ESI): 506 [M+Na]$^+$, 482 [M-H]$^-$

Example 23

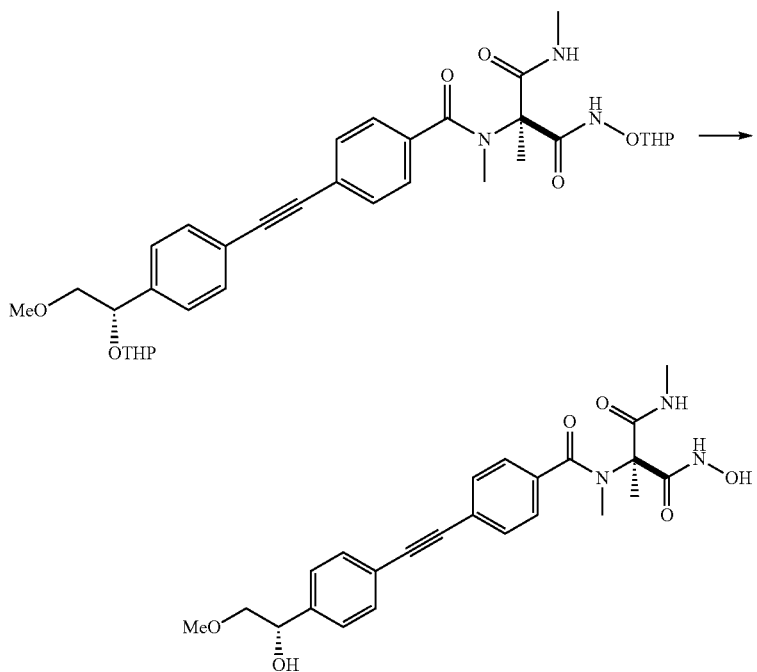

To a mixture of 485 mg of (2S)-2-((4-((4-((1S)-2-methoxy-1-(tetrahydro-2H-pyran-2-yloxy)ethyl)phenyl)ethynyl)benzoyl)(methyl)amino)-N,2-dimethyl-N'-(tetrahydro-2H-pyran-2-yloxy)malonamide and 4.8 mL of methanol, 23 mg of p-toluenesulfonic acid monohydrate was added under ice cooling, and the resulting mixture was stirred at the same temperature for 10 minutes and then at room temperature for 1 hour. Water and ethyl acetate were added to the reaction mixture, and the resulting mixture was neutralized with a saturated aqueous solution of sodium hydrogen carbonate. The organic layer was separated, and the obtained aqueous layer was extracted with ethyl acetate. Sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; methanol:chloroform=4:96→6:94] to obtain 288 mg of a brown solid. Ethyl acetate and IPE were added thereto, and the solid material was collected by filtration to obtain 240 mg of (2S)—N-hydroxy-2-((4-((4-((1S)-1-hydroxy-2-methoxyethyl)phenyl)ethynyl)benzoyl)(methyl)amino)-N',2-dimethyl-malonamide as a brown solid.

¹H-NMR (400 MHz, CD₃OD) δ: 1.77 (3H, s), 2.79 (3H, s), 3.17 (3H, s), 3.37 (3H, s), 3.50 (2H, d, J=5.9 Hz), 7.41 (2H, d, J=8.3 Hz), 7.47-7.65 (6H, m); MS (ESI): 476 [M+Na]⁺, 452 [M-H]⁻

Example 24 acetate were added to the reaction mixture, and the resulting mixture was neutralized with a saturated aqueous solution of sodium hydrogen carbonate. The organic layer was separated, the aqueous layer was extracted with ethyl acetate, then sodium chloride was added to the aqueous layer, and then the aqueous layer was extracted with a mixture of ethyl acetate and tetrahydrofuran (ethyl acetate:tetrahydrofuran=4:1) twice. The organic layer was combined with the extract, and then dried over anhydrous sodium sulfate. The solvent was distilled off under reduced pressure, and the obtained residue was purified by silica gel column chromatography [eluent; methanol:chloroform=15:85] to obtain 291 mg of a yellow foamy solid. Ethyl acetate and IPE were added thereto, and the solid material was collected by filtration to obtain 247 mg of (2S)—N-hydroxy-2-((4-((4-

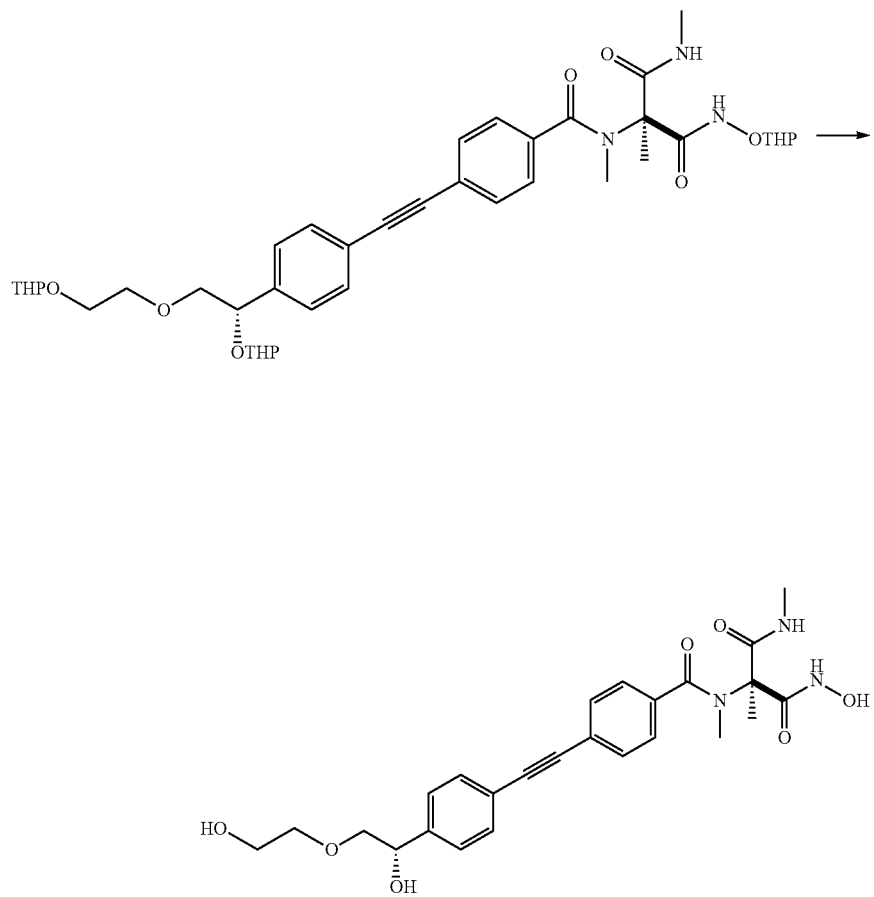

To a mixture of 422 mg of (2S)—N,2-dimethyl-2-(methyl (4-((4-((1S)-1-(tetrahydro-2H-pyran-2-yl oxy)-2-(2-(tetrahydro-2H-pyran-2-yloxy)ethoxy)ethyl)phenyl)ethynyl)benzoyl)amino)-N'-(tetrahydro-2H-pyran-2-yloxy)malonamide and 4.2 mL of methanol, 23 mg of p-toluenesulfonic acid monohydrate was added under ice cooling, and the resulting mixture was stirred at the same temperature for 10 minutes, and then at room temperature for 1 hour. Water and ethyl ((1S)-1-hydroxy-2-(2-hydroxyethoxy)ethyl)phenyl)ethynyl) benzoyl)(methyl)amino)-N',2-dimethyl-malonamide as a pale yellow solid.

¹H-NMR (400 MHz, CD₃OD) δ: 1.77 (3H, s), 2.79 (3H, s), 3.17 (3H, s), 3.49-3.73 (6H, m), 7.43 (2H, d, J=8.3 Hz), 7.48-7.64 (6H, m); MS (ESI): 506 [M+Na]⁺, 482 [M-H]⁻

Example 25

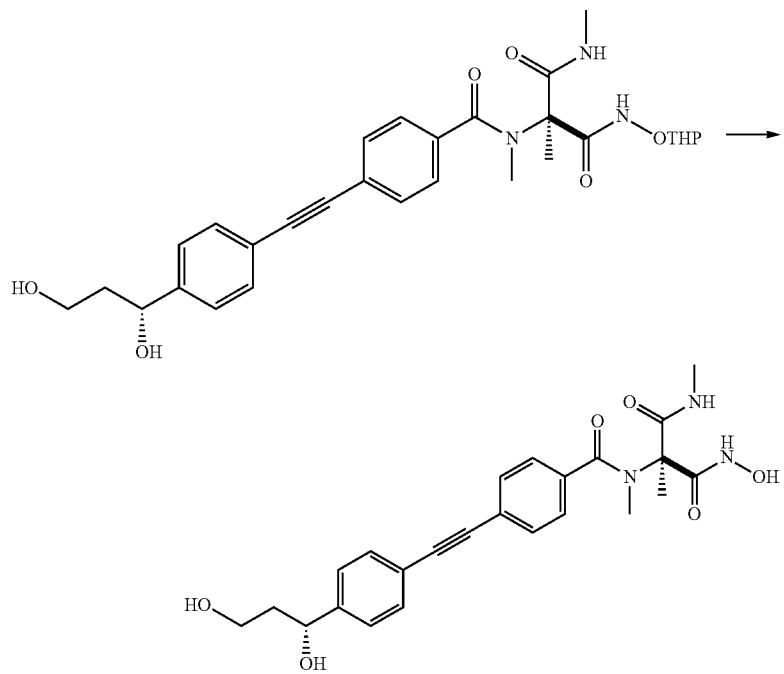

To 254 mg of (2S)-2-((4-((4-(((1R)-1,3-dihydroxypropyl)phenyl)ethynyl)benzoyl)(methyl)amino)-N,2-dimethyl-N'-(tetrahydro-2H-pyran-2-yloxy)malonamide, 2.5 mL of methanol and 17 mg of p-toluenesulfonic acid monohydrate were added, and the resulting mixture was stirred at room temperature for 45 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; acetone:chloroform=60:40→90:10] to obtain 111 mg of a yellow oil. Ethyl acetate and IPE were added thereto, and the solid material was collected by filtration to obtain 81 mg of (2S)-2-((4-((4-(((1R)-1,3-dihydroxypropyl)phenyl)ethynyl)benzoyl)(methyl)amino)-N-hydroxy-N',2-dimethyl-malonamide as a yellow solid.

$^{1}$H-NMR (400 MHz, CD$_{3}$OD) δ: 1.77 (3H, s), 1.83-1.99 (2H, m), 2.79 (3H, s), 3.17 (3H, s), 3.56-3.67 (1H, m), 3.67-3.76 (1H, m), 7.39 (2H, d, J=8.1 Hz), 7.49-7.65 (6H, m); MS (ESI): 476 [M+Na]$^{+}$, 452 [M-H]$^{-}$

Example 26

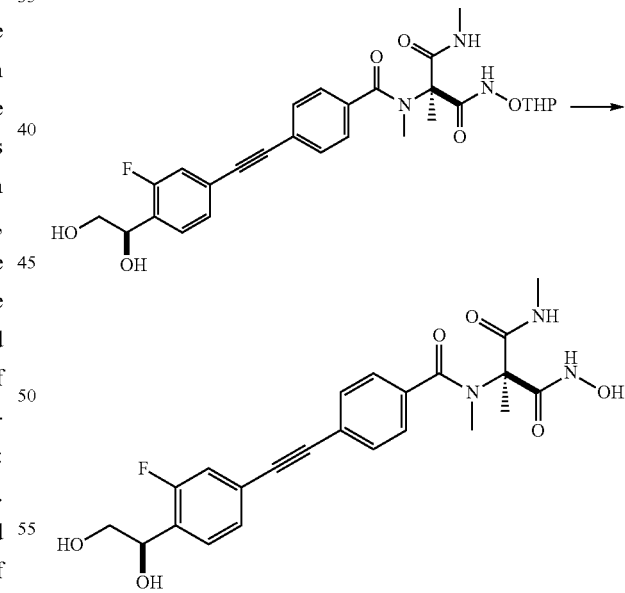

To 198 mg of (2S)-2-((4-((4-(1,2-dihydroxyethyl)-3-fluorophenyl)ethynyl)benzoyl)(methyl)amino)-N,2-dimethyl-N'-(tetrahydro-2H-pyran-2-yloxy)malonamide, 2.0 mL of methanol and 14 mg of p-toluenesulfonic acid monohydrate were added, and the resulting mixture was stirred at room temperature for 20 minutes. Water and ethyl acetate were added to the reaction mixture, the resulting mixture was neutralized with a saturated aqueous solution of sodium hydrogen carbonate, and then sodium chloride was added.

The organic layer was separated, and the aqueous layer was extracted with ethyl acetate three times. The organic layer was combined with the extract, and then dried over anhydrous sodium sulfate. The solvent was distilled off under reduced pressure, and the obtained residue was purified by silica gel column chromatography [eluent; methanol:chloroform=10:90] to obtain a yellow solid. Ethyl acetate and IPE were added thereto, and the solid material was collected by filtration to obtain 72 mg of (2S)-2-((4-((4-(1,2-dihydroxyethyl)-3-fluorophenyl)ethynyl)benzoyl)(methyl)amino)-N-hydroxy-N',2-dimethyl-malonamide as a yellow solid.

$^1$H-NMR (400 MHz, CD$_3$OD) δ: 1.77 (3H, s), 2.79 (3H, s), 3.16 (3H, s), 3.60 (1H, dd, J=11.5, 7.1 Hz), 3.66-3.75 (1H, m), 4.98-5.07 (1H, m), 7.25 (1H, dd, J=10.7, 1.5 Hz), 7.34-7.41 (1H, m), 7.51-7.68 (5H, m); MS (ESI): 480 [M+Na]$^+$, 456 [M-H]$^-$

Example 27 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; methanol:chloroform=8:92]. The obtained product was further purified by preparative silica gel thin-layer chromatography [mobile solvent system; methanol:chloroform=1:10, Rf=0.1-0.2, eluent; methanol:chloroform=20:80] to obtain a yellow oil. IPE was added thereto, and the solid material was collected by filtration to obtain 91 mg of (2S)-2-((4-((3-fluoro-4-(1-hydroxy-2-(2-hydroxyethoxy)ethyl)phenyl)ethynyl)ben-

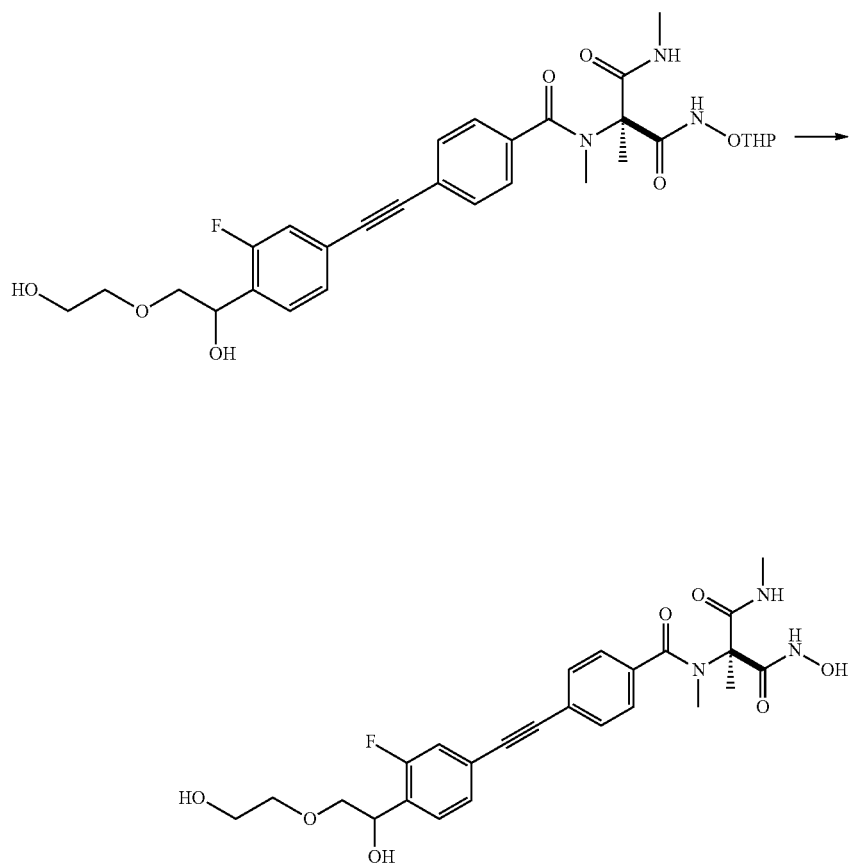

To 232 mg of (2S)-2-((4-((3-fluoro-4-(1-hydroxy-2-(2-hydroxyethoxy)ethyl)phenyl)ethynyl)benzoyl)(methyl)amino)-N,2-dimethyl-N'-(tetrahydro-2H-pyran-2-yloxy)malonamide, 2.3 mL of methanol and 15 mg of p-toluenesulfonic acid monohydrate were added, and the resulting mixture was stirred at room temperature for 25 zoyl)(methyl)amino)-N-hydroxy-N',2-dimethylmalonamide as a pale yellow solid.

$^1$H-NMR (400 MHz, CD$_3$OD) δ: 1.77 (3H, s), 2.79 (3H, s), 3.16 (3H, s), 3.52-3.75 (6H, m), 5.12-5.22 (1H, m), 7.21-7.32 (1H, m), 7.32-7.43 (1H, m), 7.53-7.67 (5H, m); MS (ESI): 524 [M+Na]$^+$, 500 [M-H]$^-$

Example 28

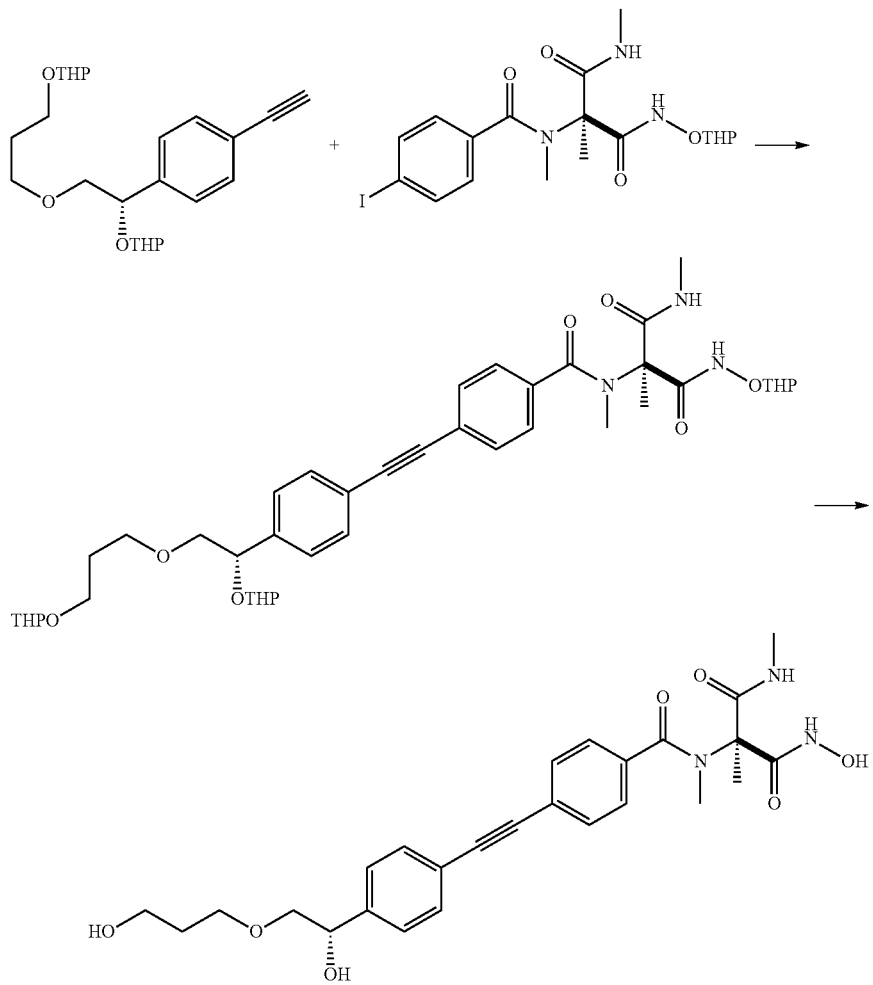

To a mixture of 532 mg of 2-(3-((2S)-2-(4-ethynylphenyl)-2-(tetrahydro-2H-pyran-2-yloxy)ethoxy)propoxy)tetrahydro-2H-pyran, 250 mg of (2S)-2-((4-iodobenzoyl)(methyl)amino)-N,2-dimethyl-N'-(tetrahydro-2H-pyran-2-yloxy)malonamide, 36 mg of bis-triphenylphosphinepalladium(II) dichloride, and 19 mg of copper(I) iodide, 3.0 mL of tetrahydrofuran was added under a nitrogen atmosphere, then 0.36 mL of triethylamine was added thereto under ice cooling, and then the resulting mixture was stirred at the same temperature for 1 hour. Water and ethyl acetate were added to the reaction mixture, and the pH was adjusted to 1 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=15:85] to obtain 409 mg of a brown foamy solid.

To 400 mg of the obtained brown solid, 3.0 mL of methanol and 15 mg of p-toluenesulfonic acid monohydrate were added, and the resulting mixture was stirred at room temperature for 30 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=55:45] to obtain a yellow solid. Ethyl acetate and IPE were added thereto, and the solid material was collected by filtration to obtain 133 mg of (2S)—N-hydroxy-2-((4-((4-((1S)-1-hydroxy-2-(3-hydroxypropoxy)ethyl)phenyl)ethynyl)benzoyl)(methyl)amino)-N',2-dimethyl-malonamide as a yellow solid.

$^1$H-NMR (400 MHz, CD$_3$OD) δ: 1.73-1.83 (5H, m), 2.79 (3H, s), 3.17 (3H, s), 3.52-3.66 (6H, m), 7.42 (2H, d, J=8.0 Hz), 7.49-7.65 (6H, m); MS (ESI): 520 [M+Na]$^+$, 496 [M-H]$^-$

Example 29

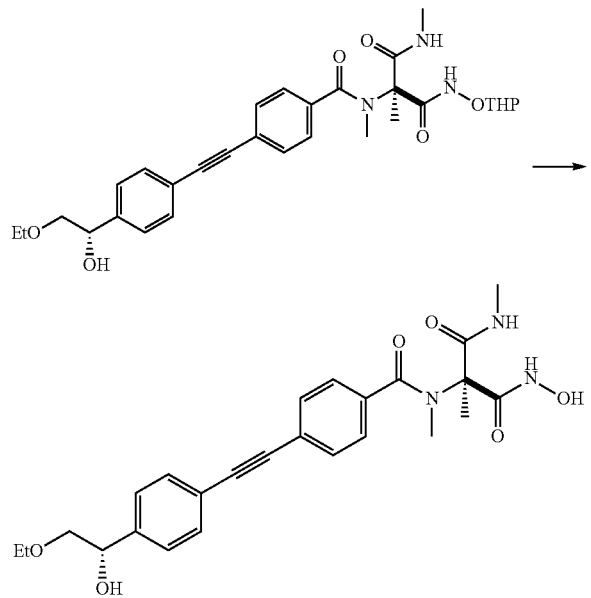

To 259 mg of (2S)-2-((4-((4-((1S)-2-ethoxy-1-hydroxy-ethyl)phenyl)ethynyl)benzoyl)(methyl)amino)-N,2-dimethyl-N'-(tetrahydro-2H-pyran-2-yloxy)malonamide, 2.0 mL of methanol and 15 mg of p-toluenesulfonic acid monohydrate were added, and the resulting mixture was stirred at room temperature for 30 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=35:65] to obtain a yellow solid. Ethyl acetate and IPE were added thereto, and the solid material was collected by filtration to obtain 134 mg of (2S)-2-((4-((4-((1S)-2-ethoxy-1-hydroxyethyl)phenyl)ethynyl)benzoyl)(methyl)amino)-N-hydroxy-N',2-dimethyl-malonamide as a pale yellow solid.

$^1$H-NMR (400 MHz, CD$_3$OD) δ: 1.18 (3H, t, J=7.1 Hz), 1.77 (3H, s), 2.79 (3H, s), 3.17 (3H, s), 3.49-3.59 (4H, m), 7.42 (2H, d, J=8.3 Hz), 7.48-7.64 (6H, m); MS (ESI): 490 [M+Na]$^+$, 466 [M-H]$^-$

Example 30

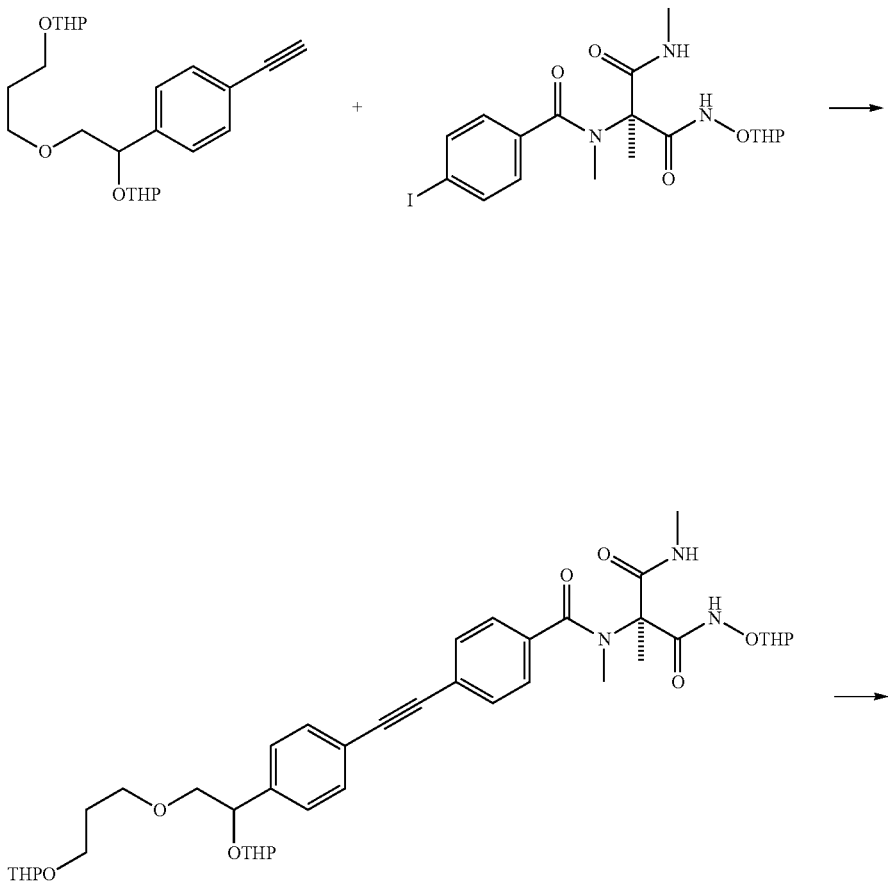

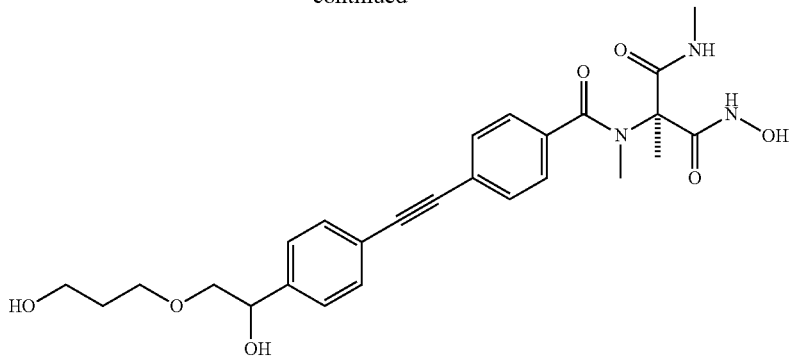

To a mixture of 710 mg of 2-(3-((2R)-2-(4-ethynylphenyl)-2-(tetrahydro-2H-pyran-2-yloxy)ethoxy)propoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(II) dichloride, and 23 mg of copper(I) iodide, 0.51 mL of triethylamine was added under a nitrogen atmosphere and under ice cooling, and the resulting mixture was stirred at the same temperature for 1 hour. A saturated aqueous solution of ammonium chloride and ethyl acetate were added to the reaction mixture, and the pH was adjusted to 6.4 with 1 mol/L hydrochloric acid. The organic layer was separated, washed with a saturated aqueous solution of sodium chloride, and then dried over anhydrous magnesium sulfate. The solvent was distilled off under reduced pressure, and the obtained residue was purified by silica gel column chromatography [eluent; acetone:chloroform=15:85] to obtain 485 mg of a brown solid.

4.8 mL of methanol and 24 mg of p-toluenesulfonic acid monohydrate were added to 480 mg of the obtained brown solid, and the resulting mixture was stirred at room temperature for 1 hour. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate twice. The organic layer was combined with the extract, and then dried over anhydrous sodium sulfate. The solvent was distilled off under reduced pressure, and the obtained residue was purified by silica gel column chromatography [eluent; methanol:chloroform=15:85] to obtain 271 mg of a yellow solid. Ethyl acetate and IPE were added thereto, and the solid material was collected by filtration to obtain 181 mg of (2S)—N-hydroxy-2-((4-((4-((1R)-1-hydroxy-2-(3-hydroxypropoxy)ethyl)phenyl)ethynyl)benzoyl)(methyl)amino)-N',2-dimethyl-malonamide as a yellow solid.

$^1$H-NMR (400 MHz, CD$_3$OD) δ: 1.77-1.79 (5H, m), 2.79 (3H, s), 3.17 (3H, s), 3.50-3.66 (6H, m), 7.42 (2H, d, J=8.1 Hz), 7.51 (2H, d, J=8.3 Hz), 7.53-7.64 (4H, m); MS (ESI): 520 [M+Na]$^+$, 496 [M-H]$^-$

Example 31

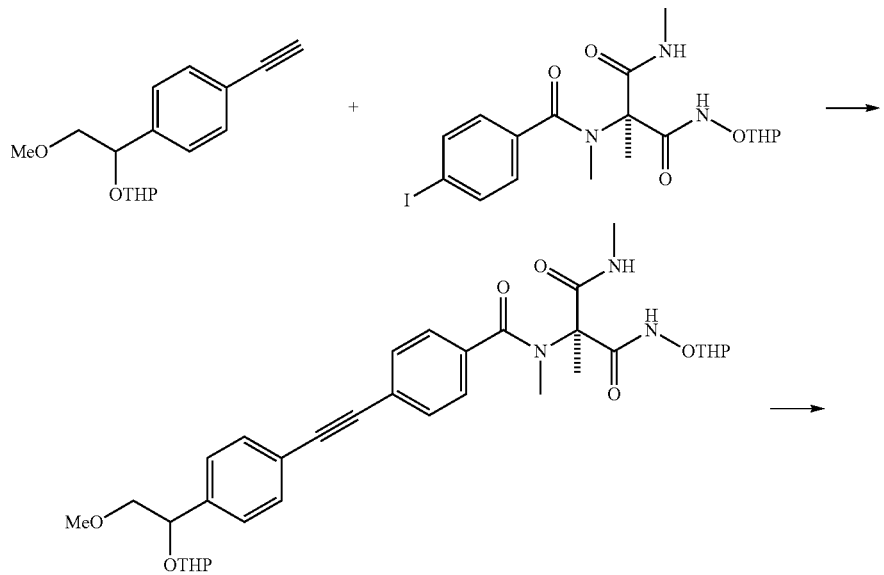

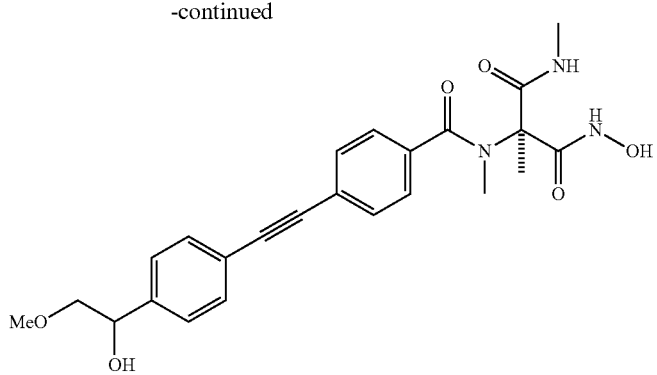

To a mixture of 478 mg of 2-((1R)-1-(4-ethynylphenyl)-2-methoxyethoxy)tetrahydro-2H-pyran, 3.0 mL of tetrahydrofuran, 300 mg of (2S)-2-((4-iodobenzoyl)(methyl)amino)-N,2-dimethyl-N'-(tetrahydro-2H-pyran-2-yloxy)malonamide, 43 mg of bis-triphenylphosphinepalladium(II) dichloride, and 23 mg of copper(I) iodide, 0.51 mL of triethylamine was added under a nitrogen atmosphere and under ice cooling, and the resulting mixture was stirred at the same temperature for 3 hours. A saturated aqueous solution of ammonium chloride and ethyl acetate were added to the reaction mixture, and the pH was adjusted to 6.1 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=10:90→15:85] to obtain 423 mg of a brown solid.

4.0 mL of methanol and 25 mg of p-toluenesulfonic acid monohydrate were added to 423 mg of the obtained brown solid, and the resulting mixture was stirred at room temperature for 1 hour. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; methanol:chloroform=6:94] to obtain 288 mg of a brown solid. Ethyl acetate and IPE were added thereto, and the solid material was collected by filtration to obtain 231 mg of (2S)—N-hydroxy-2-((4-((4-((1R)-1-hydroxy-2-methoxyethyl)phenyl)ethynyl)benzoyl)(methyl)amino)-N',2-dimethyl-malonamide as a light brown solid.

$^1$H-NMR (400 MHz, CD$_3$OD) δ: 1.77 (3H, s), 2.79 (3H, s), 3.17 (3H, s), 3.38 (3H, s), 3.50 (2H, d, J=5.9 Hz), 7.41 (2H, d, J=8.3 Hz), 7.47-7.64 (6H, m); MS (ESI): 476 [M+Na]$^+$, 452 [M-H]$^-$

Example 32

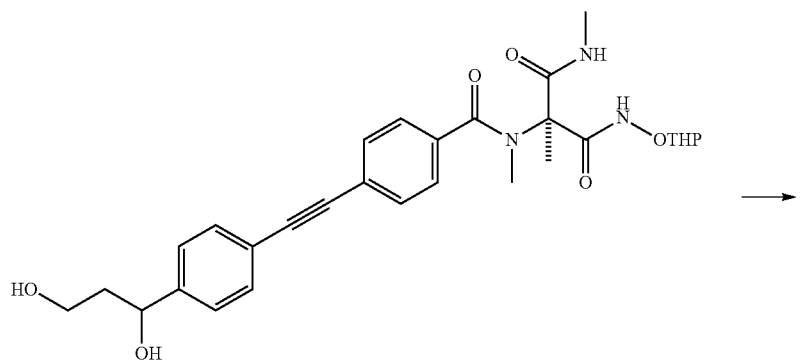

-continued

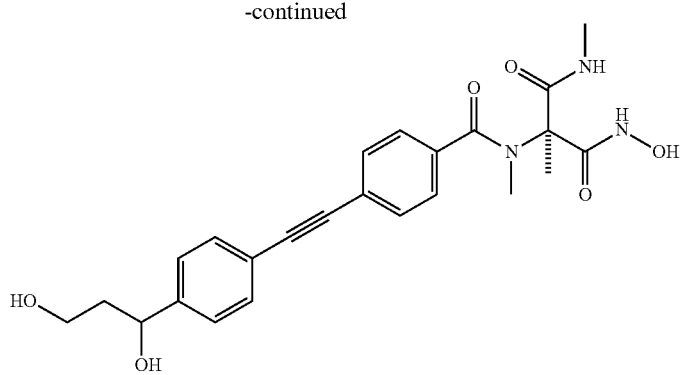

To 377 mg of (2S)-2-((4-((4-((1S)-1,3-dihydroxypropyl)phenyl)ethynyl)benzoyl)(methyl)amino)-N,2-dimethyl-N'-(tetrahydro-2H-pyran-2-yloxy)malonamide, 3.7 mL of methanol and 26 mg of p-toluenesulfonic acid monohydrate were added, and the resulting mixture was stirred at room temperature for 5 hours. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; methanol:chloroform=10:90] to obtain 136 mg of a yellow solid. Ethyl acetate and IPE were added thereto, and the solid material was collected by filtration to obtain 133 mg of (2S)-2-((4-((4-((1S)-1,3-dihydroxypropyl)phenyl)ethynyl)benzoyl)(methyl)amino)-N-hydroxy-N',2-dimethyl-malonamide as a yellow solid.

$^1$H-NMR (400 MHz, CD$_3$OD) δ: 1.77 (3H, s), 1.82-2.03 (2H, m), 2.79 (3H, s), 3.17 (3H, s), 3.57-3.67 (1H, m), 3.67-3.77 (1H, m), 7.39 (2H, d, J=8.3 Hz), 7.48-7.66 (6H, m); MS (ESI): 476 [M+Na]$^+$, 452 [M-H]$^-$

Example 33

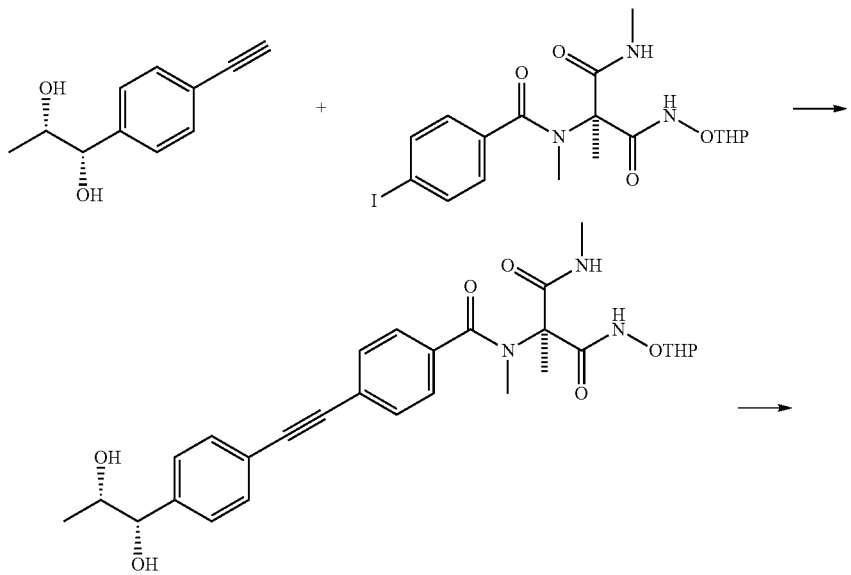

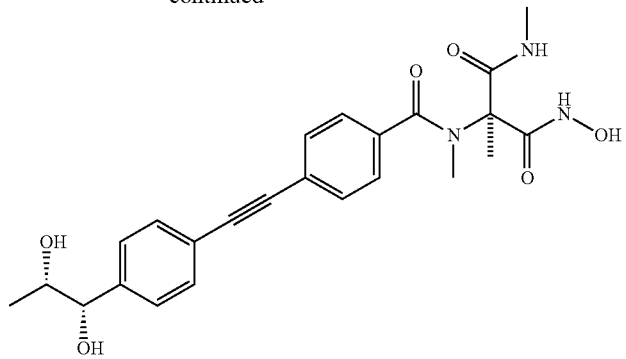

To a mixture of 181 mg of (1S,2S)-1-(4-ethynylphenyl)propane-1,2-diol, 200 mg of (2S)-2-((4-iodobenzoyl)(methyl)amino)-N,2-dimethyl-N'-(tetrahydro-2H-pyran-2-yloxy)malonamide, 29 mg of bis-triphenylphosphinepalladium(II) dichloride, and 16 mg of copper(I) iodide, 2.0 mL of tetrahydrofuran was added under a nitrogen atmosphere, 0.29 mL of triethylamine was added under ice cooling, and then the resulting mixture was stirred at the same temperature for 30 minutes. Water and ethyl acetate were added to the reaction mixture, and the pH was adjusted to 6.5 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=30:70] to obtain 217 mg of a yellow solid.

To 217 mg of the obtained yellow solid, 2.0 mL of methanol and 15 mg of p-toluenesulfonic acid monohydrate were added, and the resulting mixture was stirred at room temperature for 30 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=55:45] to obtain a yellow oil. Ethyl acetate and IPE were added thereto, and the solid material was collected by filtration to obtain 98 mg of (2S)-2-((4-((4-((1S,2S)-1,2-dihydroxypropyl)phenyl)ethynyl)benzoyl)(methyl)amino)-N-hydroxy-N',2-dimethylmalonamide as a yellow solid.

$^1$H-NMR (400 MHz, CD$_3$OD) δ: 1.13 (3H, d, J=5.3 Hz), 1.77 (3H, s), 2.79 (3H, s), 3.17 (3H, s), 3.82-3.91 (1H, m), 4.51 (1H, d, J=5.1 Hz), 7.40 (2H, d, J=7.8 Hz), 7.48-7.65 (6H, m); MS (ESI): 476 [M+Na]$^+$, 452 [M-H]$^-$

Example 34

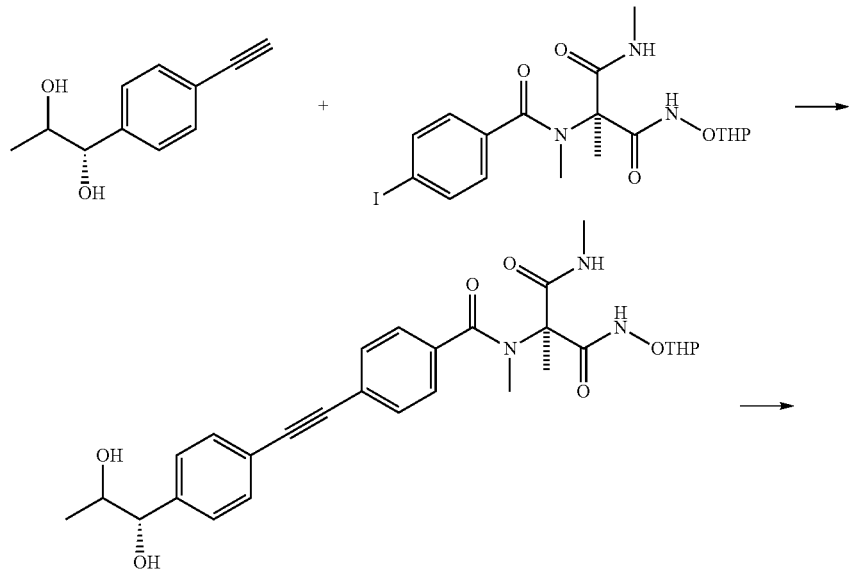

-continued

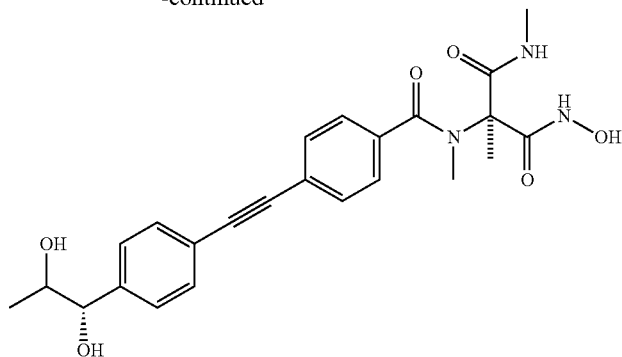

To a mixture of 122 mg of (1S,2R)-1-(4-ethynylphenyl)propane-1,2-diol, 170 mg of (2S)-2-((4-iodobenzoyl)(methyl)amino)-N,2-dimethyl-N'-(tetrahydro-2H-pyran-2-yloxy)malonamide, 24 mg of bis-triphenylphosphinepalladium(II) dichloride, and 13 mg of copper(I) iodide, 2.0 mL of tetrahydrofuran was added under a nitrogen atmosphere, 0.24 mL of triethylamine was added under ice cooling, and then the resulting mixture was stirred at the same temperature for 2 hours and 30 minutes. Water and ethyl acetate were added to the reaction mixture, and the pH was adjusted to 5.5 with 6 mol/L hydrochloric acid. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=30:70] to obtain 133 mg of a yellow solid.

To 133 mg of the obtained yellow solid, 2.0 mL of methanol and 6 mg of p-toluenesulfonic acid monohydrate were added, and the resulting mixture was stirred at room temperature for 40 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate three times. The organic layer was combined with the extract, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=50:50] to obtain a yellow solid. Ethyl acetate and IPE were added thereto, and the solid material was collected by filtration to obtain 50 mg of (2S)-2-((4-((4-((1S,2R)-1,2-dihydroxypropyl)phenyl)ethynyl)benzoyl)(methyl)amino)-N-hydroxy-N',2-dimethyl-malonamide as a pale yellow solid.

$^1$H-NMR (400 MHz, CD$_3$OD) δ: 0.99 (3H, d, J=6.4 Hz), 1.77 (3H, s), 2.79 (3H, s), 3.17 (3H, s), 3.78-3.86 (1H, m), 4.40 (1H, d, J=6.6 Hz), 7.39 (2H, d, J=8.3 Hz), 7.53-7.63 (6H, m); MS (ESI): 476 [M+Na]$^+$, 452[M-H]$^-$

Example 35

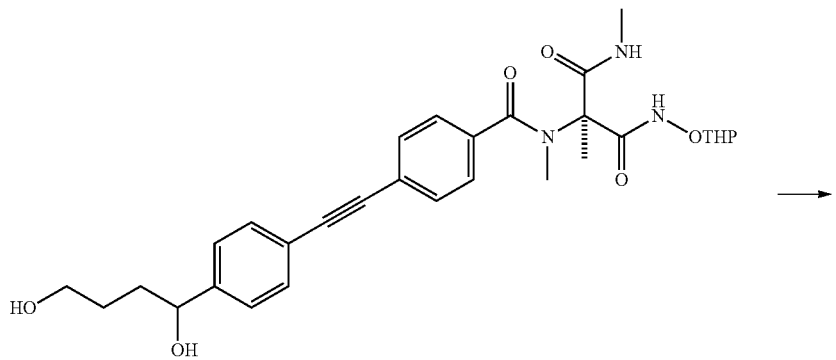

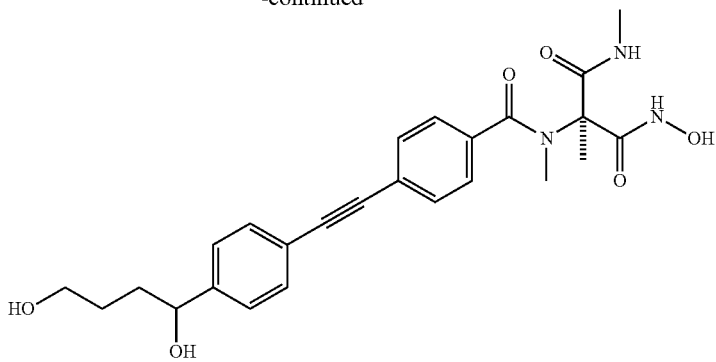

To 394 mg of (2S)-2-((4-((4-(1,4-dihydroxybutyl)phenyl)ethynyl)benzoyl)(methyl)amino)-N,2-dimethyl-N'-(tetrahydro-2H-pyran-2-yloxy)malonamide, 3.9 mL of methanol and 27 mg of p-toluenesulfonic acid monohydrate were added, and the resulting mixture was stirred at room temperature for 2 hours and 30 minutes. Water and ethyl acetate were added to the reaction mixture, and the resulting mixture was neutralized with a saturated aqueous solution of sodium hydrogen carbonate. The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; methanol:chloroform=0:100→10:90] to obtain 238 mg of a yellow solid. Ethyl acetate and IPE were added thereto, and the solid material was collected by filtration to obtain 161 mg of (2S)-2-((4-((4-(1,4-dihydroxybutyl)phenyl)ethynyl)benzoyl)(methyl)amino)-N-hydroxy-N',2-dimethyl-malonamide as a yellow solid.

$^1$H-NMR (400 MHz, CD$_3$OD) δ: 1.46-1.58 (1H, m), 1.58-1.69 (1H, m), 1.73-1.82 (5H, m), 2.79 (3H, s), 3.17 (3H, s), 3.52-3.59 (2H, m), 4.63-4.69 (1H, m), 7.38 (2H, d, J=8.0 Hz), 7.50 (2H, d, J=8.3 Hz), 7.53-7.63 (4H, m); MS (ESI): 490 [M+Na]$^+$, 466 [M-H]$^-$

Example 36

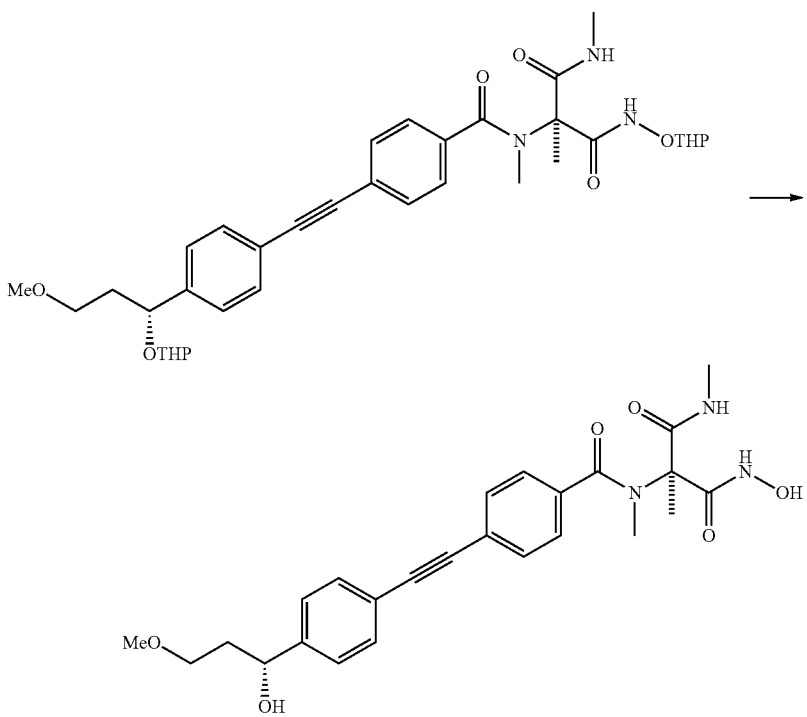

To 453 mg of (2S)-2-((4-((4-((1R)-3-methoxy-1-(tetrahydro-2H-pyran-2-yloxy)propyl)phenyl)ethynyl)benzoyl)(methyl)amino)-N,2-dimethyl-N'-(tetrahydro-2H-pyran-2-yloxy)malonamide, 4.5 mL of methanol and 27 mg of p-toluenesulfonic acid monohydrate were added, and the resulting mixture was stirred at room temperature for 2 hours. Water and ethyl acetate were added to the reaction mixture, and the resulting mixture was neutralized with a saturated aqueous solution of sodium hydrogen carbonate.

The organic layer was separated, sodium chloride was added to the aqueous layer, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; methanol:chloroform=3:97→6:94] to obtain 174 mg of a yellow solid. Ethyl acetate and IPE were added thereto, and the solid material was collected by filtration to obtain 172 mg of (2S)—N-hydroxy-2-((4-((4-((1R)-1-hydroxy-3-methoxypropyl)phenyl)ethynyl)benzoyl)(methyl)amino)-N',2-dimethylmalonamide as a yellow solid.

$^1$H-NMR (400 MHz, CD$_3$OD) δ: 1.77 (3H, s), 1.89-1.99 (2H, m), 2.79 (3H, s), 3.17 (3H, s), 3.33 (3H, s), 3.35-3.42 (1H, m), 3.49-3.58 (1H, m), 4.76-4.83 (1H, m), 7.38 (2H, d, J=8.0 Hz), 7.54-7.63 (6H, m); MS (ESI): 490 [M+Na]$^+$, 466 [M-H]$^-$

Example 37

$^1$H-NMR (400 MHz, CD$_3$OD) δ: 1.43 (3H, d, J=6.6 Hz), 1.77 (3H, s), 2.79 (3H, s), 3.17 (3H, s), 7.39 (2H, d, J=8.1 Hz), 7.50 (2H, d, J=8.3 Hz), 7.53-7.63 (4H, m); MS (ESI): 446 [M+Na]$^+$, 422 [M-H]$^-$

Example 38

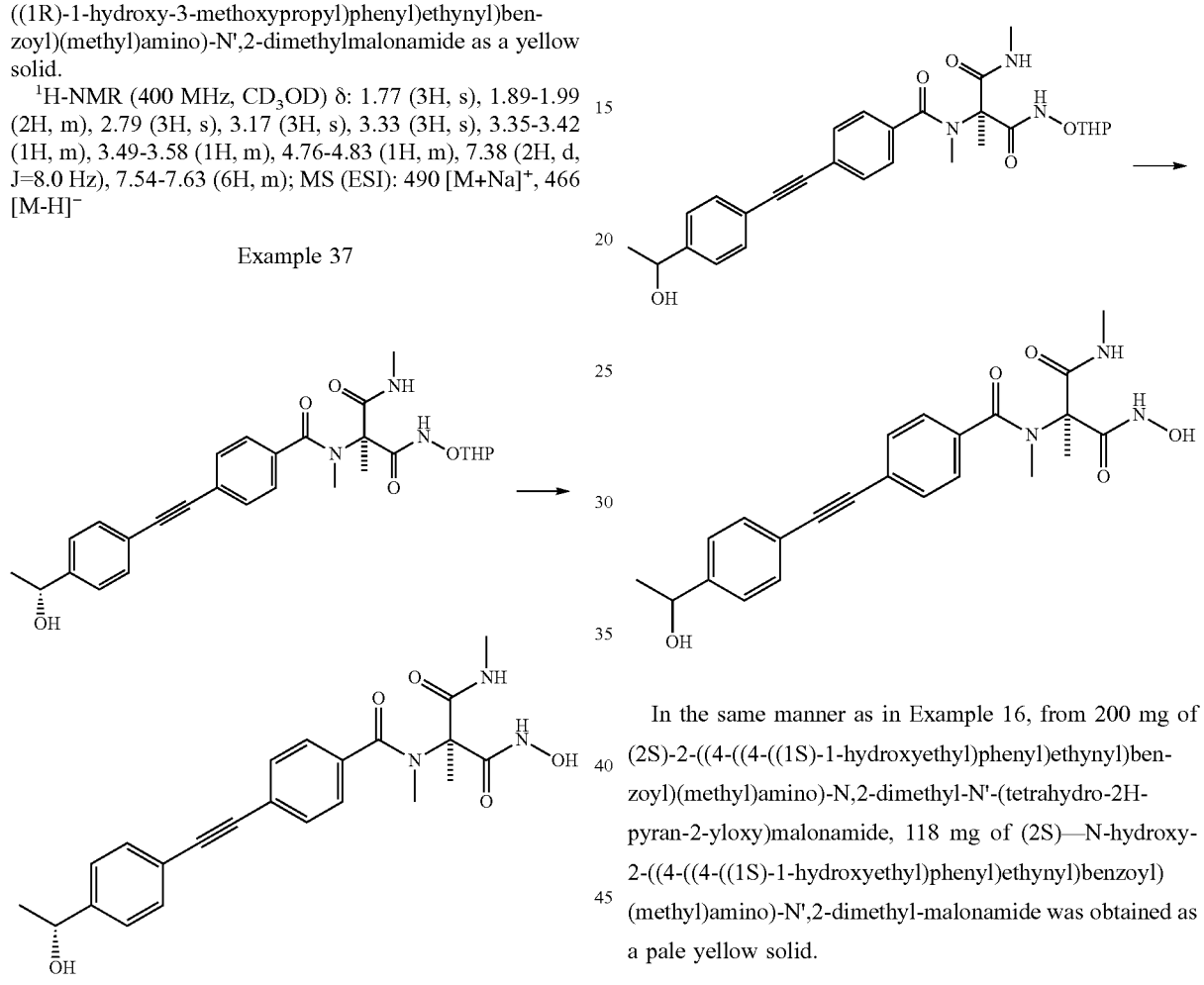

In the same manner as in Example 16, from 220 mg of (2S)-2-((4-((4-((1R)-1-hydroxyethyl)phenyl)ethynyl)benzoyl)(methyl)amino)-N,2-dimethyl-N'-(tetrahydro-2H-pyran-2-yloxy)malonamide, 139 mg of (2S)—N-hydroxy-2-((4-((4-((1R)-1-hydroxyethyl)phenyl)ethynyl)benzoyl)(methyl)amino)-N',2-dimethyl-malonamide was obtained as a pale yellow solid.

In the same manner as in Example 16, from 200 mg of (2S)-2-((4-((4-((1S)-1-hydroxyethyl)phenyl)ethynyl)benzoyl)(methyl)amino)-N,2-dimethyl-N'-(tetrahydro-2H-pyran-2-yloxy)malonamide, 118 mg of (2S)—N-hydroxy-2-((4-((4-((1S)-1-hydroxyethyl)phenyl)ethynyl)benzoyl)(methyl)amino)-N',2-dimethyl-malonamide was obtained as a pale yellow solid.

$^1$H-NMR (400 MHz, CD$_3$OD) δ: 1.43 (3H, d, J=6.3 Hz), 1.77 (3H, s), 2.79 (3H, s), 3.17 (3H, s), 7.39 (2H, d, J=8.1 Hz), 7.50 (2H, d, J=8.3 Hz), 7.53-7.63 (4H, m); MS (ESI): 446 [M+Na]$^+$, 422 [M-H]$^-$

Example 39

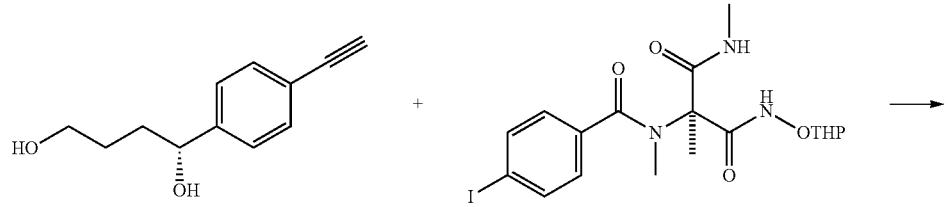

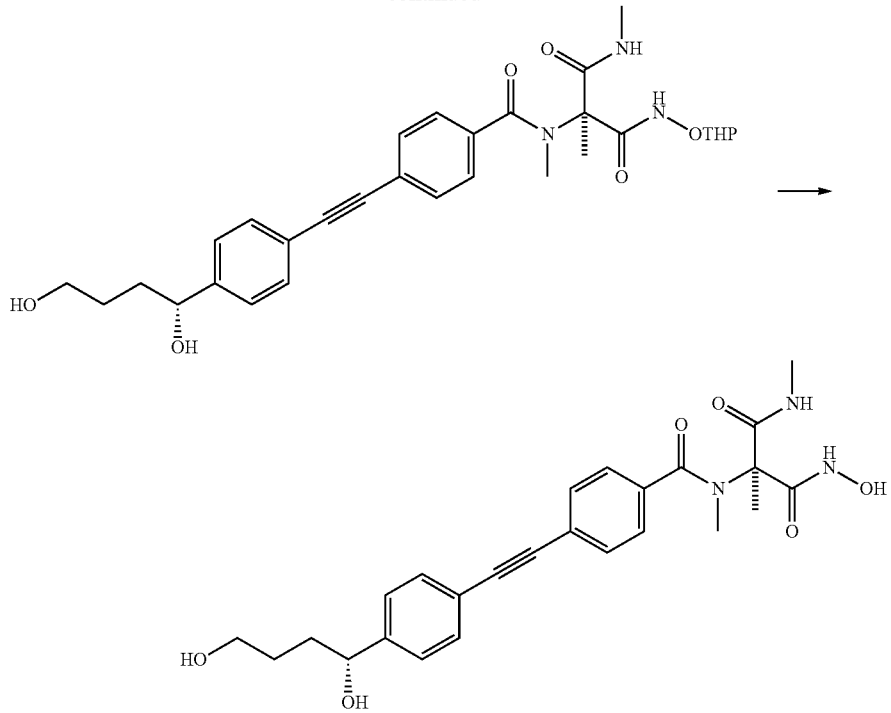

To 267 mg of (1R)-1-(4-ethynylphenyl)butane-1,4-diol, 312 mg of (2S)-2-((4-iodobenzoyl)(methyl)amino)-N,2-dimethyl-N'-(tetrahydro-2H-pyran-2-yloxy)malonamide, 45 mg of bis(triphenylphosphine)palladium(II) dichloride, 24 mg of copper(I) iodide, and 3.1 mL of tetrahydrofuran were successively added. To the reaction mixture, 0.71 mL of triethylamine was added under ice cooling, and the resulting mixture was stirred for 2 hours. A saturated aqueous solution of ammonium chloride and ethyl acetate were added to the reaction mixture. The organic layer was separated, washed with a saturated aqueous solution of sodium chloride, and then dried over anhydrous sodium sulfate. The solvent was distilled off under reduced pressure, and the obtained residue was purified by silica gel column chromatography [eluent; acetone:chloroform=25:75→60:40] to obtain 386 mg of a red oil.

To 383 mg of the obtained red oil, 3.8 mL of methanol and 26 mg of p-toluenesulfonic acid monohydrate were added, and the resulting mixture was stirred at room temperature for 1 hour and 30 minutes. Water and ethyl acetate were added to the reaction mixture to separate the organic layer. Sodium chloride was added to the aqueous layer, and the aqueous layer was extracted with ethyl acetate. The organic layer was combined with the extract, and then dried over anhydrous sodium sulfate. The solvent was distilled off under reduced pressure, and the obtained residue was purified by silica gel column chromatography [eluent; methanol:chloroform=9:91→14:86] to obtain a yellow oil. Ethyl acetate and IPE were added to the obtained yellow oil, and the solid material was collected by filtration to obtain 200 mg of (2S)-2-((4-((4-((1R)-1,4-dihydroxybutyl)phenyl)ethynyl)benzoyl)(methyl)amino)-N-hydroxy-N',2-dimethyl-malonamide as a pale yellow solid.

$^1$H-NMR (400 MHz, CD$_3$OD) δ: 1.55-1.70 (2H, m), 1.70-1.84 (2H, m), 1.76 (3H, s), 2.79 (3H, s), 3.16 (3H, s), 3.56 (2H, t, J=6.5 Hz), 4.66 (1H, t, J=6.6 Hz), 7.38 (2H, d, J=8.1 Hz), 7.51 (2H, d, J=8.3 Hz), 7.55 (2H, d, J=8.3 Hz), 7.60 (2H, d, J=8.1 Hz); MS (ESI): 490 [M+Na]$^+$, 466 [M-H]$^-$

Example 40

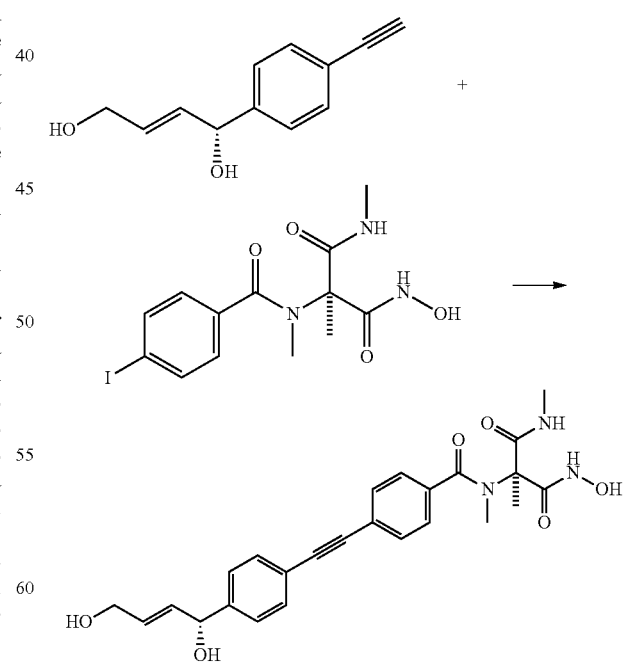

To 267 mg of (1R,2E)-1-(4-ethynylphenyl)but-2-ene-1,4-diol, 274 mg of (2S)—N-hydroxy-2-((4-iodobenzoyl)(methyl)amino)-N',2-dimethyl-malonamide, 48 mg of bis (triphenylphosphine)palladium(II) dichloride, 26 mg of copper(I) iodide, and 6.0 mL of tetrahydrofuran were successively added, then 0.47 mL of triethylamine was added, and the resulting mixture was stirred at room temperature for 1 hour. A saturated aqueous solution of ammonium chloride and ethyl acetate were added to the reaction mixture to separate the organic layer. The organic layer was dried over anhydrous magnesium sulfate, and then the solvent was distilled off under reduced pressure. The obtained residue was purified by silica gel column chromatography [eluent; acetone:chloroform=40:60→67:33] to obtain a pale yellow solid. Ethyl acetate and hexane were added to the obtained pale yellow solid, and the solid material was collected by filtration to obtain 110 mg of (2S)-2-((4-((4-((1R,2E)-1,4-dihydroxybut-2-ene-1-yl)phenyl)ethynyl)benzoyl)(methyl)amino)-N-hydroxy-N',2-dimethyl-malonamide as a pale yellow solid.

$^1$H-NMR (400 MHz, CD$_3$OD) δ: 1.77 (3H, s), 2.79 (3H, s), 3.17 (3H, s), 4.02-4.14 (2H, m), 5.15-5.21 (1H, m), 5.84-5.90 (2H, m), 7.40 (2H, d, J=8.1 Hz), 7.51 (2H, d, J=8.3 Hz), 7.55 (2H, d, J=8.5 Hz), 7.60 (2H, d, J=8.5 Hz); MS (ESI): 488 [M+Na]$^+$, 464 [M-H]$^-$

INDUSTRIAL APPLICABILITY

The compound represented by general formula [1] or the salt thereof has a strong LpxC inhibitory effect and has strong antibacterial activity against Gram-negative bacteria including *Pseudomonas aeruginosa*, and is therefore useful as an antibacterial agent. In another aspect, the compound represented by general formula [1] or the salt thereof is excellent in safety and pharmacokinetics and is useful as an antibacterial agent.

The invention claimed is:
1. A compound represented by general formula [1]:

[Formula 1]

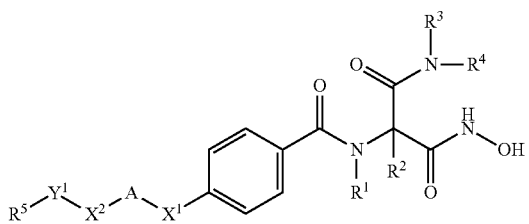

[1]

wherein

R$^1$ represents a hydrogen atom, an optionally substituted C$_{1-6}$ alkyl group, an optionally substituted C$_{3-8}$ cycloalkyl group or an optionally substituted C$_{1-6}$ alkoxy group;

R$^2$ represents a hydrogen atom, an optionally substituted C$_{1-6}$ alkyl group, an optionally substituted C$_{3-8}$ cycloalkyl group or an optionally substituted C$_{1-6}$ alkoxy group;

R$^3$ represents a hydrogen atom or an optionally substituted C$_{1-6}$ alkyl group;

R$^4$ represents a hydrogen atom, an optionally substituted C$_{1-6}$ alkyl group, an optionally substituted C$_{3-8}$ cycloalkyl group, an optionally substituted C$_{1-6}$ alkoxy group, an optionally substituted aromatic hydrocarbon group or an optionally substituted heterocyclic group;

X$^1$ represents an optionally substituted C$_{1-6}$ alkylene group, an optionally substituted C$_{2-6}$ alkenylene group or an optionally substituted C$_{2-6}$ alkynylene group;

A represents an optionally substituted C$_{3-8}$ cycloalkylene group or an optionally substituted divalent aromatic hydrocarbon group;

X$^2$ represents an optionally substituted C$_{1-6}$ alkylene group, an optionally substituted C$_{2-6}$ alkenylene group or an optionally substituted C$_{2-6}$ alkynylene group;

Y$^1$ represents an oxygen atom or a sulfur atom; and

R$^5$ represents a hydrogen atom, an optionally substituted C$_{1-6}$ alkyl group, an optionally substituted C$_{2-6}$ alkenyl group, an optionally substituted C$_{2-6}$ alkynyl group, an optionally substituted aromatic hydrocarbon group, an optionally substituted oxygen-containing heterocyclic group, a hydroxyl-protecting group or a thiol-protecting group, provided that when X$^2$ is CH(R$^6$) wherein R$^6$ represents a hydrogen atom or a methoxy group, R$^5$ means a group represented by a C$_{2-6}$ alkyl group optionally substituted by one or more groups selected from substituent group α, an optionally substituted C$_{2-6}$ alkenyl group, an optionally substituted C$_{1-6}$ alkynyl group, an optionally substituted aromatic hydrocarbon group, an optionally substituted oxygen-containing heterocyclic group, a hydroxyl-protecting group or a thiol-protecting group, wherein the substituent group α consists of: a halogen atom; a cyano group; a nitro group; an oxo group; an optionally substituted carbamoyl group; an optionally substituted C$_{2-6}$ alkenyl group; an optionally substituted C$_{2-6}$ alkynyl group; an optionally substituted C$_{3-8}$ cycloalkyl group; an optionally substituted C$_{1-6}$ alkoxy group; an optionally substituted aromatic hydrocarbon group; an optionally substituted aryloxy group; an optionally substituted arylthio group; an optionally substituted heterocyclic group; an optionally substituted heterocyclic oxy group; an optionally protected hydroxyl group; and an optionally protected carboxyl group;

or a salt thereof.

2. A compound represented by general formula [2]:

[Formula 2]

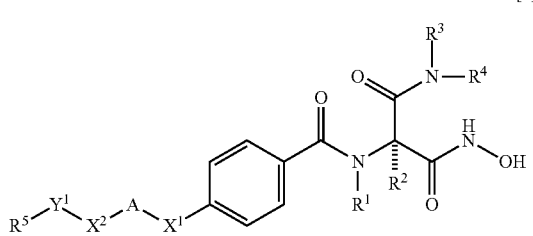

[2]

wherein

R$^1$ represents a hydrogen atom, an optionally substituted C$_{1-6}$ alkyl group, an optionally substituted C$_{3-8}$ cycloalkyl group or an optionally substituted C$_{1-6}$ alkoxy group;

R$^2$ represents a hydrogen atom, an optionally substituted C$_{1-6}$ alkyl group, an optionally substituted C$_{3-8}$ cycloalkyl group or an optionally substituted C$_{1-6}$ alkoxy group;

R$^3$ represents a hydrogen atom or an optionally substituted C$_{1-6}$ alkyl group;

R⁴ represents a hydrogen atom, an optionally substituted C₁₋₆ alkyl group, an optionally substituted C₃₋₈ cycloalkyl group, an optionally substituted C₁₋₆ alkoxy group, an optionally substituted aromatic hydrocarbon group or an optionally substituted heterocyclic group;

X¹ represents an optionally substituted C₁₋₆ alkylene group, an optionally substituted C₂₋₆ alkenylene group or an optionally substituted C₂₋₆ alkynylene group;

A represents an optionally substituted C₃₋₈ cycloalkylene group or an optionally substituted divalent aromatic hydrocarbon group;

X² represents an optionally substituted C₁₋₆ alkylene group, an optionally substituted C₂₋₆ alkenylene group or an optionally substituted C₂₋₆ alkynylene group;

Y¹ represents an oxygen atom or a sulfur atom; and

R⁵ represents a hydrogen atom, an optionally substituted C₁₋₆ alkyl group, an optionally substituted C₂₋₆ alkenyl group, an optionally substituted C₂₋₆ alkynyl group, an optionally substituted aromatic hydrocarbon group, an optionally substituted oxygen-containing heterocyclic group, a hydroxyl-protecting group or a thiol-protecting group, provided that when X² is CH(R⁶) wherein R⁶ represents a hydrogen atom or a methoxy group, R⁵ means a group represented by a C₂₋₆ alkyl group optionally substituted by one or more groups selected from substituent group α, an optionally substituted C₂₋₆ alkenyl group, an optionally substituted C₁₋₆ alkynyl group, an optionally substituted aromatic hydrocarbon group, an optionally substituted oxygen-containing heterocyclic group, a hydroxyl-protecting group or a thiol-protecting group, wherein the substituent group α consists of: a halogen atom; a cyano group; a nitro group; an oxo group; an optionally substituted carbamoyl group; an optionally substituted C₂₋₆ alkenyl group; an optionally substituted C₂₋₆ alkynyl group; an optionally substituted C₃₋₈ cycloalkyl group; an optionally substituted C₁₋₆ alkoxy group; an optionally substituted aromatic hydrocarbon group; an optionally substituted aryloxy group; an optionally substituted arylthio group; an optionally substituted heterocyclic group; an optionally substituted heterocyclic oxy group; an optionally protected hydroxyl group; and an optionally protected carboxyl group;

or a salt thereof.

3. The compound or a salt thereof according to claim 1, wherein R¹ is a hydrogen atom or an optionally substituted C₁₋₆ alkyl group.

4. The compound or a salt thereof according to claim 1, wherein R¹ is an optionally substituted C₁₋₆ alkyl group.

5. The compound or a salt thereof according to claim 1, wherein R² is a hydrogen atom or an optionally substituted C₁₋₆ alkyl group.

6. The compound or a salt thereof according to claim 1, wherein R² is an optionally substituted C₁₋₆ alkyl group.

7. The compound or a salt thereof according to claim 1, wherein R³ is a hydrogen atom, and R⁴ is an optionally substituted C₁₋₆ alkyl group.

8. The compound or a salt thereof according to claim 1, wherein X¹ is an optionally substituted C₂₋₆ alkynylene group.

9. The compound or a salt thereof according to claim 1, wherein A is an optionally substituted divalent aromatic hydrocarbon group.

10. The compound or a salt thereof according to claim 1, wherein Y¹ is an oxygen atom.

11. The compound or a salt thereof according to claim 1, wherein R⁵ is a hydrogen atom, an optionally substituted C₁₋₆ alkyl group, an optionally substituted C₂₋₆ alkenyl group, an optionally substituted C₂₋₆ alkynyl group, a hydroxyl-protecting group or a thiol-protecting group, provided that when X² is CH(R⁶) wherein R⁶ represents a hydrogen atom or a methoxy group, R⁵ is a C₂₋₆ alkyl group optionally substituted by one or more groups selected from substituent group α, an optionally substituted C₂₋₆ alkenyl group, an optionally substituted C₁₋₆ alkynyl group, a hydroxyl-protecting group or a thiol-protecting group, wherein the substituent group α consists of: a halogen atom; a cyano group; a nitro group; an oxo group; an optionally substituted carbamoyl group; an optionally substituted C₂₋₆ alkenyl group; an optionally substituted C₂₋₆ alkynyl group; an optionally substituted C₃₋₈ cycloalkyl group; an optionally substituted C₁₋₆ alkoxy group; an optionally substituted aromatic hydrocarbon group; an optionally substituted aryloxy group; an optionally substituted arylthio group; an optionally substituted heterocyclic group; an optionally substituted heterocyclic oxy group; an optionally protected hydroxyl group; and an optionally protected carboxyl group.

12. The compound or a salt thereof according to claim 1, wherein X² is a group represented by general formula [3]:

[Formula 3]

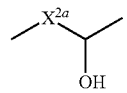

[3]

wherein X²ᵃ represents an optionally substituted C₁₋₅ alkylene group, provided that X²ᵃ is bonded to Y¹.

13. The compound or a salt thereof according to claim 1, wherein X² is a group represented by general formula [4]:

[Formula 4]

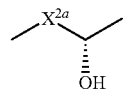

[4]

wherein X²ᵃ represents an optionally substituted C₁₋₅ alkylene group, provided that X²ᵃ is bonded to Y¹.

14. The compound or a salt thereof according to claim 1, wherein the compound is selected from
(2S)-2-((4-((4-(1,2-dihydroxyethyl)phenyl)ethynyl)benzoyl)(methyl)amino)-N-hydroxy-N',2-dimethylmalonamide,
(2S)—N-hydroxy-2-((4-((4-(3-hydroxy-2-(hydroxymethyl)propyl)phenyl)ethynyl)benzoyl)(methyl)amino)-N',2-dimethylmalonamide,
(2S)-2-((4-((4-((1R)-1,2-dihydroxyethyl)phenyl)ethynyl)benzoyl)(methyl)amino)-N-hydroxy-N',2-dimethylmalonamide,
(2S)-2-((4-((4-((1S)-1,2-dihydroxyethyl)phenyl)ethynyl)benzoyl)(methyl)amino)-N-hydroxy-N',2-dimethylmalonamide,
(2S)—N-hydroxy-2-((4-((4-((1S)-1-hydroxy-2-methoxyethyl)phenyl)ethynyl)benzoyl)(methyl)amino)-N',2-dimethylmalonamide, (2S)—N-hydroxy-2-((4-((4-((1S)-1-hydroxy-2-(2-hydroxyethoxy)ethyl)phenyl)ethynyl)benzoyl)(methyl)amino)-N',2-dimethylmalonamide, (2S)-2-((4-((4-((1R)-1,3-dihydroxypropyl)phenyl)ethynyl)benzoyl)(methyl)amino)-N-hydroxy-N',2-dimethylmalonamide, (2S)-2-((4-((4-((1S,2S)-1,2-dihydroxypropyl)phenyl)ethynyl)benzoyl)(methyl)amino)-N-hydroxy-N',2-dimethylmalonamide, (2S)-2-((4-((4-(1,4-dihydroxybutyl)phenyl)ethynyl)benzoyl)(methyl)amino)-N-hydroxy-N',2-dimethylmalonamide and (2S)—N-hydroxy-2-((4-((4-((1R)-1-hydroxy-3-methoxypropyl)phenyl)ethynyl)benzoyl)(methyl)amino)-N',2-dimethylmalonamide.

15. A compound selected from the group consisting of:

(2S)-2-((4-((4-(1,2-Dihydroxyethyl)phenyl)ethynyl)benzoyl)(methyl)amino)-N-hydroxy-N',2-dimethylmalonamide or a salt thereof;

(2S)—N-Hydroxy-2-((4-((4-(3-hydroxy-2-(hydroxymethyl)propyl)phenyl)ethynyl)benzoyl)(methyl)amino)-N',2-dimethylmalonamide or a salt thereof;

(2S)-2-((4-((4-((1R)-1,2-Dihydroxyethyl)phenyl)ethynyl)benzoyl)(methyl)amino)-N-hydroxy-N,2-dimethylmalonamide or a salt thereof;

(2S)-2-((4-((4-((1S)-1,2-Dihydroxyethyl)phenyl)ethynyl)benzoyl)(methyl)amino)-N-hydroxy-N',2-dimethylmalonamide or a salt thereof;

(2S)—N-Hydroxy-2-((4-((4-((1S)-1-hydroxy-2-methoxyethyl)phenyl)ethynyl)benzoyl)(methyl)amino)-N',2-dimethylmalonamide or a salt thereof;

(2S)—N-Hydroxy-2-((4-((4-((1S)-1-hydroxy-2-(2-hydroxyethoxy)ethyl)phenyl)ethynyl)benzoyl)(methyl)amino)-N',2-dimethylmalonamide or a salt thereof;

(2S)-2-((4-((4-((1R)-1,3-Dihydroxypropyl)phenyl)ethynyl)benzoyl)(methyl)amino)-N-hydroxy-N',2-dimethylmalonamide or a salt thereof;

(2S)-2-((4-((4-((1S,2S)-1,2-Dihydroxypropyl)phenyl)ethynyl)benzoyl)(methyl)amino)-N-hydroxy-N',2-dimethylmalonamide or a salt thereof;

(2S)-2-((4-((4-(1,4 Dihydroxybutyl)phenyl)ethynyl)benzoyl)(methyl)amino)-N-hydroxy-N',2-dimethylmalonamide or a salt thereof; and (2S)—N-Hydroxy-2-((4-((4-((1R)-1-hydroxy-3-methoxypropyl)phenyl)ethynyl)benzoyl)(methyl)amino)-N',2-dimethylmalonamide or a salt thereof.

16. An LpxC inhibitor comprising a compound or a salt thereof according to claim 1.

17. An antibacterial agent comprising a compound or a salt thereof according to claim 1.

18. (2S)-2-((4-((4-((1R)-1,2-Dihydroxyethyl)phenyl)ethynyl)benzoyl)(methyl)amino)-N-hydroxy-N',2-dimethylmalonamide or a salt thereof.

19. (2S)-2-((4-((4-((1S)-1,2-Dihydroxyethyl)phenyl)ethynyl)benzoyl)(methyl)amino)-N-hydroxy-N',2-dimethylmalonamide or a salt thereof.

20. (2S)-N-Hydroxy-2-((4-((4-((1S)-1-hydroxy-2-methoxyethyl)phenyl)ethynyl)benzoyl)(methyl)amino)-N',2-dimethylmalonamide or a salt thereof.

* * * * *